(12) United States Patent
Watson et al.

(10) Patent No.: US 12,123,012 B2
(45) Date of Patent: Oct. 22, 2024

(54) METHODS AND COMPOSITIONS FOR NUCLEIC ACID AND PROTEIN PAYLOAD DELIVERY

(71) Applicant: LIGANDAL, INC., San Francisco, CA (US)

(72) Inventors: Andre Ronald Watson, San Francisco, CA (US); Christian Foster, Oakland, CA (US)

(73) Assignee: LIGANDAL, INC., New York, NY (US)

( * ) Notice: Subject to any disclaimer, the term of this patent is extended or adjusted under 35 U.S.C. 154(b) by 0 days.

(21) Appl. No.: 17/104,552

(22) Filed: Nov. 25, 2020

(65) Prior Publication Data

US 2021/0324406 A1     Oct. 21, 2021

Related U.S. Application Data

(63) Continuation of application No. 15/842,820, filed on Dec. 14, 2017, now Pat. No. 10,975,388.

(60) Provisional application No. 62/517,346, filed on Jun. 9, 2017, provisional application No. 62/443,567, filed on Jan. 6, 2017, provisional application No. 62/443,522, filed on Jan. 6, 2017, provisional application No. 62/434,344, filed on Dec. 14, 2016.

(51) Int. Cl.

| | | |
|---|---|---|
| A61K 48/00 | (2006.01) |
| A61K 9/00 | (2006.01) |
| A61K 9/51 | (2006.01) |
| A61K 31/40 | (2006.01) |
| A61K 31/7105 | (2006.01) |
| A61K 47/34 | (2017.01) |
| A61K 47/42 | (2017.01) |
| A61K 47/54 | (2017.01) |
| A61K 47/64 | (2017.01) |
| A61K 47/68 | (2017.01) |
| A61P 3/10 | (2006.01) |
| A61P 35/00 | (2006.01) |
| A61P 37/00 | (2006.01) |
| B82Y 5/00 | (2011.01) |
| C12N 15/10 | (2006.01) |
| C12N 15/11 | (2006.01) |
| C12N 15/85 | (2006.01) |
| C12N 15/87 | (2006.01) |
| C12N 9/22 | (2006.01) |

(52) U.S. Cl.
CPC ............ *C12N 15/85* (2013.01); *A61K 9/0019* (2013.01); *A61K 9/0085* (2013.01); *A61K 9/5146* (2013.01); *A61K 31/40* (2013.01); *A61K 31/7105* (2013.01); *A61K 47/34* (2013.01); *A61K 47/42* (2013.01); *A61K 47/549* (2017.08); *A61K 47/64* (2017.08); *A61K 47/645* (2017.08); *A61K 47/6455* (2017.08); *A61K 47/6807* (2017.08); *A61K 48/0016* (2013.01); *A61K 48/0041* (2013.01); *A61K 48/0075* (2013.01); *A61P 3/10* (2018.01); *A61P 35/00* (2018.01); *A61P 37/00* (2018.01); *B82Y 5/00* (2013.01); *C12N 15/102* (2013.01); *C12N 15/111* (2013.01); *C12N 15/87* (2013.01); *C12N 9/22* (2013.01); *C12N 2310/14* (2013.01); *C12N 2310/20* (2017.05); *C12N 2310/3517* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 6,140,466 A | 10/2000 | Barbas et al. |
| 6,310,171 B1 | 10/2001 | Naito et al. |
| 6,376,248 B1 | 4/2002 | Hawley-Nelson et al. |
| 6,379,966 B2 | 4/2002 | Monahan et al. |
| 6,453,242 B1 | 9/2002 | Eisenberg et al. |
| 6,511,808 B2 | 1/2003 | Wolffe et al. |
| 6,805,904 B2 | 10/2004 | Anders et al. |
| 7,999,025 B2 | 8/2011 | Shumaker-Parry et al. |

(Continued)

FOREIGN PATENT DOCUMENTS

| | | |
|---|---|---|
| JP | 2011006447 A | 1/2011 |
| JP | 2012531467 A | 12/2012 |

(Continued)

OTHER PUBLICATIONS

Tal Tilayov, et al, Engineering Stem Cell Factor Ligands with Different c-Kit Agonistic Potencies, Molecules 2020, 25, 4850. (Year: 2020).*

(Continued)

*Primary Examiner* — Thomas S Heard
(74) *Attorney, Agent, or Firm* — Perkins Coie LLP

(57) ABSTRACT

Provided are methods and compositions for delivering a nucleic acid, protein, and/or ribonucleoprotein payload to a cell. Also provided are delivery molecules that include a peptide targeting ligand conjugated to a protein or nucleic acid payload (e.g., an siRNA molecule), or conjugated to a charged polymer polypeptide domain (e.g., poly-arginine such as 9R or a poly-histidine such as 6H, and the like). The targeting ligand provides for (i) targeted binding to a cell surface protein, and (ii) engagement of a long endosomal recycling pathway. As such, when the targeting ligand engages the intended cell surface protein, the delivery molecule enters the cell (e.g., via endocytosis) but is preferentially directed away from the lysosomal degradation pathway.

5 Claims, 147 Drawing Sheets

Specification includes a Sequence Listing.

(56) References Cited

U.S. PATENT DOCUMENTS

| | | |
|---|---|---|
| 8,323,618 B2 | 12/2012 | Bikram |
| 8,324,333 B2 | 12/2012 | Liu et al. |
| 8,389,485 B2 | 3/2013 | Czech et al. |
| 8,450,107 B1 | 5/2013 | Zhang et al. |
| 8,685,737 B2 | 4/2014 | Serber et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 9,308,267 B2 | 4/2016 | Payne et al. |
| 9,315,788 B2 | 4/2016 | Duchateau et al. |
| 9,315,828 B2 | 4/2016 | Takeuchi et al. |
| 9,326,940 B2 | 5/2016 | Lee et al. |
| 9,393,200 B2 | 7/2016 | Drasar et al. |
| 9,486,538 B2 | 11/2016 | Keil et al. |
| 9,504,651 B2 | 11/2016 | Maclachlan et al. |
| 9,504,747 B2 | 11/2016 | Baryza et al. |
| 9,533,047 B2 | 1/2017 | De Fougerolles et al. |
| 2003/0059767 A1 | 3/2003 | Barbas et al. |
| 2003/0108880 A1 | 6/2003 | Rebar et al. |
| 2004/0067503 A1 | 4/2004 | Tan et al. |
| 2004/0102606 A1 | 5/2004 | Balicki et al. |
| 2005/0053668 A1 | 3/2005 | Vail |
| 2005/0123600 A1 | 6/2005 | Trubetskoy et al. |
| 2006/0088599 A1 | 4/2006 | Prasad et al. |
| 2007/0026069 A1 | 2/2007 | Shastri et al. |
| 2007/0190155 A1 | 8/2007 | Leary et al. |
| 2007/0254842 A1 | 11/2007 | Bankiewicz |
| 2008/0312410 A1 | 12/2008 | Backer et al. |
| 2009/0030178 A1 | 1/2009 | Chang |
| 2009/0155289 A1 | 6/2009 | Roberts et al. |
| 2009/0220587 A1 | 9/2009 | Allon et al. |
| 2009/0233359 A1 | 9/2009 | Kwon |
| 2010/0015218 A1 | 1/2010 | Jadhav et al. |
| 2010/0196492 A1 | 8/2010 | Green et al. |
| 2010/0285111 A1 | 11/2010 | Torchilin et al. |
| 2010/0311168 A1 | 12/2010 | Samuel et al. |
| 2011/0077581 A1 | 3/2011 | Oyelere et al. |
| 2011/0145940 A1 | 6/2011 | Voytas et al. |
| 2011/0263835 A1 | 10/2011 | Ting et al. |
| 2012/0244224 A1 | 9/2012 | Biris et al. |
| 2013/0022538 A1 | 1/2013 | Rossi et al. |
| 2013/0137851 A1 | 5/2013 | Bishop et al. |
| 2013/0296285 A1 | 11/2013 | Alferiev et al. |
| 2014/0005379 A1 | 1/2014 | Gu |
| 2014/0068797 A1 | 3/2014 | Doudna et al. |
| 2014/0093575 A1 | 4/2014 | Hammond et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0242702 A1 | 8/2014 | Chen et al. |
| 2014/0248702 A1 | 9/2014 | Zhang et al. |
| 2014/0256046 A1 | 9/2014 | Zhang et al. |
| 2014/0273037 A1 | 9/2014 | Wu |
| 2014/0273226 A1 | 9/2014 | Wu |
| 2014/0273230 A1 | 9/2014 | Chen et al. |
| 2014/0273231 A1 | 9/2014 | Zhang et al. |
| 2014/0273232 A1 | 9/2014 | Zhang et al. |
| 2014/0273233 A1 | 9/2014 | Chen et al. |
| 2014/0273234 A1 | 9/2014 | Zhang et al. |
| 2014/0273235 A1 | 9/2014 | Voytas et al. |
| 2014/0287938 A1 | 9/2014 | Zhang et al. |
| 2014/0295556 A1 | 10/2014 | Joung et al. |
| 2014/0295557 A1 | 10/2014 | Joung et al. |
| 2014/0298547 A1 | 10/2014 | Sastry-Dent et al. |
| 2014/0304853 A1 | 10/2014 | Ainley et al. |
| 2014/0309487 A1 | 10/2014 | Lee et al. |
| 2014/0310828 A1 | 10/2014 | Lee et al. |
| 2014/0310830 A1 | 10/2014 | Zhang et al. |
| 2014/0315985 A1 | 10/2014 | May et al. |
| 2014/0335063 A1 | 11/2014 | Cannon et al. |
| 2014/0335620 A1 | 11/2014 | Zhang et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0349400 A1 | 11/2014 | Jakimo et al. |
| 2014/0349405 A1 | 11/2014 | Sontheimer et al. |
| 2014/0356867 A1 | 12/2014 | Peter et al. |
| 2014/0356956 A1 | 12/2014 | Church et al. |
| 2014/0356958 A1 | 12/2014 | Mali et al. |
| 2014/0356959 A1 | 12/2014 | Church et al. |
| 2014/0357523 A1 | 12/2014 | Zeiner et al. |
| 2014/0357530 A1 | 12/2014 | Zhang et al. |
| 2014/0364333 A1 | 12/2014 | Wu et al. |
| 2014/0377868 A1 | 12/2014 | Joung et al. |
| 2015/0166983 A1 | 6/2015 | Liu et al. |
| 2015/0174267 A1 | 6/2015 | Castaigne |
| 2015/0232883 A1 | 8/2015 | Dahlman et al. |
| 2015/0374840 A1 | 12/2015 | Rosendahl |
| 2016/0208243 A1 | 7/2016 | Zhang et al. |
| 2016/0230189 A1 | 8/2016 | Kotha et al. |
| 2016/0237455 A1 | 8/2016 | Glucksmann et al. |
| 2016/0263047 A1 | 9/2016 | Kaufman |

FOREIGN PATENT DOCUMENTS

| | | |
|---|---|---|
| JP | 2013506628 A | 2/2013 |
| WO | 199610038 A1 | 4/1996 |
| WO | 2000042219 | 7/2000 |
| WO | 200066629 A1 | 11/2000 |
| WO | 2002026209 | 4/2002 |
| WO | 2002042459 | 5/2002 |
| WO | 2002099084 | 12/2002 |
| WO | 2003062455 | 7/2003 |
| WO | 2003080809 | 10/2003 |
| WO | 2005014791 A2 | 2/2005 |
| WO | 2005084190 A2 | 9/2005 |
| WO | 2005123142 A1 | 12/2005 |
| WO | 2006101782 A2 | 9/2006 |
| WO | 2007109354 A2 | 9/2007 |
| WO | 2008021207 A2 | 2/2008 |
| WO | 2009042186 A2 | 4/2009 |
| WO | 2009054985 A1 | 4/2009 |
| WO | 2009083738 A2 | 7/2009 |
| WO | 2010054401 A1 | 5/2010 |
| WO | 2010065123 A1 | 6/2010 |
| WO | 2011000095 A1 | 1/2011 |
| WO | 2011041897 A1 | 4/2011 |
| WO | 2011096408 A1 | 8/2011 |
| WO | 2013058812 A1 | 4/2013 |
| WO | 2014093701 A1 | 6/2014 |
| WO | 2015042585 A1 | 3/2015 |
| WO | 2015088445 A1 | 6/2015 |
| WO | 2016081029 A1 | 5/2016 |

OTHER PUBLICATIONS

Kim et al., "LHRH Receptor-Mediated Delivery of siRNA Using Polyelectrolyte Complex Micelles Self-Assembled from siRNA-PEG-LHRH Conjugate and PEI," Bioconjugate Chem., 2008, vol. 19, pp. 2156-2162.

IP Office China, First Office Action and Search Report for Chinese Application No. 201780085854.6, Mail Date: Jul. 29, 2022. 8 pages.

IP Office Japan, Office Action dated Dec. 27, 2021 for Patent Application No. 2019-531743, 10 pages.

IP Office Russia, Office Action dated Jul. 30, 2021 for Application No. 2019121992, 15 pages.

(56) References Cited

OTHER PUBLICATIONS

Akinc, et al., (2008) "A combinatorial library of lipid-like materials for delivery of RNAi therapeutics"; Nature Biotechnology, 26(5); pp. 561-569.
Auer , et al., (2013) "Highly efficient CRISPR/Cas9-mediated knock-in in zebrafish by homology-independent DNA repair", Genome Research 24; pp. 142-153.
Bechara & Sagan , "Cell-penetrating peptides: 20 years later, where do we stand?," FEBS Letters 587 (2013) 1693-1702 (Year: 2013).
Beerli and Barbas, (2002) "Engineering polydactyl zinc-finger transcription factors"; Nat Biotechnol 20; pp. 135-141.
Briner, et al., (2014) "Guide RNA functional modules direct Cas9 activity and orthogonality"; Mol Cell. 56(2); pp. 333-339.
Burstein, et al., (2017) "New CRISPR-Cas systems from uncultivated microbes"; Nature. 542(7640); pp. 237-241. Epub Dec. 22, 2016.
Carroll, et al., (2006) "Design, construction and in vitro testing of zinc finger nucleases"; Nature Protocols 1(3); pp. 1329-1341.
Chen, et al., (2013) "Efficient genome editing in Caenorhabditis elegans by CRISPR-targeted homologous recombination"; Nucleic Acids Res. 41 (20):e19; pp. 1-6.
Cheng, et al., (2013) "Multiplexed activation of endogenous genes by CRISPR-on, an RNA-guided transcriptional activator system"; Cell Res. 23(10); pp. 1163-1171.
Cho, et al., (2013) "Heritable gene knockout in Caenorhabditis elegans by direct injection of Cas9-sgRNA ribonucleoproteins"; Genetics. 195(3); pp. 1177-1180.
Chou, et al., (2011) "Strategies for the Intracellular Delivery of Nanoparticles"; Chem Soc Rev, vol. 40, pp. 233-245.
Chu, et al., (2015) "Increasing the efficiency of homology-directed repair for CRISPR-Cas9-induced precise gene editing in mammalian cells"; Nat Biotechnol. 33(5); pp. 543-548.
Chylinski, et al., (2013) "The tracrRNA and Cas9 families of type II CRISPR-Cas immunity systems"; RNA Biol.I 0(5); pp. 726-737.
DiCarlo, et al., (2013) "Genome engineering in *Saccharomyces cerevisiae* using CRISPR-Cas systems"; Nucleic Acids Res. 41 (7); pp. 4336-4343.
Dickinson, et al., (2013) "Engineering the Caenorhabditis elegans genome using Cas9-triggered homologous recombination"; Nat Methods 10(10); pp. 1028-1034.
Douglas, et al., (2006) "Effects of alginate inclusion on the vector properties of chitosan-based nanoparticles"; Journal of Controlled Release, vol. 115, pp. 354-361.
Dreier, et al., (2000) "Insights into the molecular recognition of the 5'-GNN-3' family of DNA sequences by zinc finger domains"; J Mol Biol 303; pp. 489-502.
Dreier, et al., (2001) "Development of zinc finger domains for recognition of the 5'-ANN-3' family of DNA sequences and their use in the construction of artificial transcription factors"; J Biol Chem 276(31); pp. 29466-29478.
Dreier, et al., (2005) "Development of zinc finger domains for recognition of the 5'-CNN-3' family DNA sequences and their use in the construction of artificial transcription factors"; J Biol Chem 280(42); pp. 35588-35597.
Durai, et al., (2005) "Zinc finger nucleases: custom-designed molecular scissors for genome engineering of plant and mammalian cells"; Nucleic Acids Res 33; pp. 5978-5990.
Ebina, et al., (2013) "Harnessing the CR1SPR/Cas9 system to disrupt latent HIV-1 provirus"; Sci Rep. 3:2510; pp. 1-7.
Fahmy, T.M., et al., "Targeted for drug delivery", Materials Today, Elsevier, Amsterdam, NL, vol. 8, No. 8, Aug. 1, 2005 (Aug. 1, 2005), pp. 18-26.
Foster, et al., (2015) "Fluorescent dye incorporation causes weakened gene association and intracellular aggregate formation in nonviral carriers"; J Gene Med. 17(3-5); pp. 69-79.
Fujii, et al., (2013) "Efficient generation of large-scale genome-modified mice using gRNA and CAS9 endonuclease."; Nucleic Acids Res. 41 (20):e187; pp. 1-9.
Gao, et al., (2016) "DNA-guided genome editing using the Natronobacterium gregoryi Argonaute"; Nat Biotechnol. 34(7); pp. 768-773.

Goodman, et al., (1996) "B-arrestin acts as a clathrin adaptor in endocytosis of the beta2-adrenergic receptor"; Nature. 383(6599); pp. 447-450.
Guan, et al., (2002) "Heritable endogenous gene regulation in plants with designed poly dactyl zinc finger transcription factors"; Proc Natl Acad Sci USA 99; pp. 13296-13301.
Harmar, (2001) "Family-B G-protein-coupled receptors"; Genome Biology vol. 2 No 12; pp. 1-10.
Heitz, F., et al. (2009) "Twenty years of cell-penetrating peptides: from molecular mechanisms to therapeutics," British journal of pharmacology, 2009, V. 157, N. 2, p. 195-206.
Heyes, et al., (2005) "Cationic lipid saturation influences intracellular delivery of encapsulated nucleic acids"; J. Control Release, 107; pp. 276-287.
Hofland, (2015) "Enhancing ADCs to Target Diseased Cells and Deliver Payloads", ADC Review: Journal of Antibody-Drug Conjugates; Feb. 4, 2015; pp. 1-6: available online at https://adcreview.com/news/enhancing-adc-target-diseased-cells-deliver-payloads/.
Hou, et al., (2013) "Efficient genome engineering in human pluripotent stem cells using Cas9 from Neisseria meningitides"; Proc Natl Acad Sci USA. 110(39); pp. 15644-15649.
Hu, et al., "Heritable gene-targeting with gRNA/Cas9 in rats"; Cell Res. 23(11); pp. 1322-1325.
Jamieson, et al., (2003) "Drug discovery with engineered zinc-finger proteins"; Nature Rev Drug Discov 2; pp. 361-368.
Jiang, et al., (2013) "Demonstration of CRISPR/Cas9/sgRNA-mediated targeted gene modification in *Arabidopsis*, tobacco, sorghum and rice"; Nucleic Acids Res. 41 (20):e188.
Jinek, et al., (2012) "A programmable dual-RNA-guided DNA endonuclease in adaptive bacterial immunity"; Science 337(6096); pp. 816-821.
Jinek, et al., (2013) "RNA-programmed genome editing in human cells"; Elife.2:e00471; pp. 1-9.
Juliano, R.L., et al., "Receptors, endocytosis, and trafficking: the biological basis of targeted delivery of antisense and siRNA oligonucleotides", Journal of Drug Targeting, vol. 21, No. 1, Nov. 19, 2012 (Nov. 19, 2012), pp. 27-43.
Kawai, S., et al. (2010) "Transformation of *Saccharomyces cerevisiae* and other fungi: methods and possible underlying mechanism", Bioengineered bugs, 2010, V. 1, N. 6, p. 395-403.
Kim, S.H., et al., "LHRH Receptor-Mediated Delivery of siRNA Using Polyelectrolyte Complex Micelles Self-Assembled from siRNA-PEG-LHRH Conjugate and PEI", Bioconjugate Chemistry, American Chemical Society, vol. 19, 2156-62, Nov. 2008.
Kumar, et al., , (2007) "Transvascular delivery of small interferingRNA to the central nervous system"; Nature. 448 (7149); pp. 39-43.
Larsen, et al., , (2012) "Using the Epigenetic Code to Promote the Unpackaging and Transcriptional Activation of DNA Polyplexes for Gene Delivery"; Molecular Pharmaceutics, vol. 9, pp. 1041-1051.
Larson, et al., , (2013) "CRISPR interference (CRISPRi) for sequence-specific control of gene expression"; Nat Protoc. 8(11); 2180-2196.
Lee, et al., "A fabricated siRNA nanoparticle for ultra-long gene silencing in vivo."; Advanced Functional Materials, vol. 23, Issue 28; Jul. 26, 2013; pp. 3488-3493.
Lee, Sang-Kyung, et al., "Cell-Specific siRNA Delivery by Peptides and Antibodies", Isotope Labeling of Biomolecules—Applications, Jan. 1, 2012 (Jan. 1, 2012), Elsevier, US, vol. 502, pp. 91-122.
Liao, et al., "Enhancement of efficiencies of the cellular uptake and gene silencing of chitosan/siRNA complexes via the inclusion of a negatively charged poly(y-glutamic acid)"; Biomaterials, 2010, vol. 31, pp. 8780-8788.
Liu, et al., (2002) "Validated zinc finger protein designs for all 16 GNN DNA triplet targets"; J Biol Chem 277; pp. 3850-3856.
Love, et al., (2010) "Lipid-like materials for low-dose, in vivo gene silencing"; PNAS 107; pp. 1864-1869.
Ma, et al., (2013) "A guide RNA sequence design platform for the CRISPR/Cas9 system for model organism genomes"; Biomed Res Int.2013:270805; pp. 1-4.
Mahon, et al., (2010) "Combinatorial approach to determine functional group effects on lipidoid-mediated siRNA delivery"; Bioconjug Chem. 21; pp. 1448-1454.
Makarov A, et al., (2015) "An updated evolutionary classification of CRISPR-Cas systems"; Nat Rev Microbiol. 13(11); pp. 722-736.

(56) References Cited

OTHER PUBLICATIONS

Mali, et al., (2013) "Cas9 as a versatile tool for engineering biology"; Nat Methods. 10(10); pp. 957-963.
McGovern, et al., (2014) "Molecular Mechanisms Underlying Beta-Arrestin-Dependent Chemotaxis and Actin-Cytoskeletal Reorganization"; Handb Exp Pharmacol.219; pp. 341-359.
McNeer, et al., (2013) "Systemic delivery of triplex-forming PNA and donor DNA by nanoparticles mediates site-specific genome editing of human hematopoietic cells in vivo"; Gene Therapy 20(6); pp. 658-669.
Miyata, et al., "Enhanced transfection with silica-coated polyplexes loading plasmid DNA"; Biomaterials, Mar. 20, 2010, vol. 31, No. 17, pp. 4764-4770.
Nakayama, et al., (2013) "Enhanced transfection with silica-coated polyplexes loading plasmid DNA"; Genesis. 51(12); pp. 835-843.
Nikitenko, N.A., et al., "Nonviral Delivery Methods and Therapeutic Application of Small Interfering RNA", Acta Naturae (Russian Version), vol. 5, 36-56 (2013).
Opanasopit, et al., , "The development of poly-L-arginine-coated liposomes for gene delivery"; Int J Nanomedicine,, vol. 6; Oct. 7, 2011; pp. 2245-2252.
Ordiz, et al., (2002) "Regulation of transgene expression in plants with polydactyl zinc finger transcription factors"; Proc Natl Acad Sci USA 99; pp. 13290-13295.
Pabo, et al., (2001) Design and selection of novel Cys2His2 zinc finger proteins; Ann Rev Biochem 70; pp. 313-340.
Pandit, et al., "Multilayered Nanoparticles for Gene Delivery Used to Reprogram Human Foreskin Fibroblasts to Neurospheres"; Tissue Engineering, Part C, vol. 21, No. 8, Apr. 17, 2015, pp. 786-794.
Pandit, et al., "Supplementary Data, Multilayered Nanoparticles for Gene Delivery Used to Reprogram Human Foreskin Fibroblasts to Neurospheres"; Tissue Engineering, Part C, vol. 21, No. 8, Apr. 17, 2015, pp. 1-8.
Pattanayak, et al., (2013) "High-throughput profiling of off-target DNA cleavage reveals RNA-programmed Cas9 nuclease specificity"; Nat Biotechnol.31(9); pp. 839-843.
Peng, (2011) "Mechanisms of cellular uptake and intracellular trafficking with chitosan/DNA/poly(y-glutamic acid) complexes as a gene delivery vector"; Biomaterials, vol. 32, pp. 239-248.
Porteus and Carroll, (2005) "Gene targeting using zinc finger nucleases"; Nat Biotechnol 23; pp. 967-973.
Poyner and Hay, (2012) "Secretin family (Class B) G protein-coupled receptors—from molecular to clinical perspectives"; British Journal of Pharmacology 166; pp. 1-3.
Qi, et al., (2013) "Repurposing CRISPR as an RNA-guided platform for sequence-specific control of gene expression"; Cell. 152(5); pp. 1173-1183.
Ramakrishna, et al., (2014) "Gene disruption by cell-penetrating peptide-mediated delivery of Cas9 protein and guide RNA"; Journal, Genome Res 24(6), pp. 1-28.
Ran, et al., (2013) "Double nicking by RNA-guided CRISPR Cas9 for enhanced genome editing specificity"; Cell. 154(6); pp. 1380-1389.
Ran, et al., (2013) "Genome engineering using the CR1SPR-Cas9 system"; Nat Protoc.8(11); pp. 2281-2308.
Reill, et al., "Histone H3 tail peptides and poly(ethylenimine) have synergistic effects for gene delivery"; Mal Pharm., vol. 9, No. 5, Apr. 25, 2012, pp. 1031-1040.
Robert, et al., (2015) "Pharmacological inhibition of DNA-PK stimulates Cas9-mediated genome editing"; Genome Med. 7:93; pp. 1-11.
Ross, et al., (2015) "Histone-targeted Polyplexes Avoid Endosomal Escape and Enter the Nucleus During Postmitotic Redistribution of ER Membranes"; Mal Ther Nucleic Acids. 4:e226. pp. 1-13.
Ross, et al., (2015) "Importin-4 Regulates Gene Delivery by Enhancing Nuclear Retention and Chromatin Deposition by Polyplexes"; Mal Pharm. 12(12); pp. 4488-4897.
Sanjana, et al., (2012) A transcription activator-like effector toolbox for genome engineering Nature Protocols, 7; pp. 171-192.

Schiffelers, R.M., et al., "Cancer siRNA therapy 1-12 by tumor selective delivery with ligand-targeted sterically stabilized nanoparticle", Nucleic Acids Research, vol. 32, No. 19, Oct. 28, 2004 (Oct. 28, 2004), pp. e149-e149.
Schroeder, et al., (2010) "Lipid-based nanotherapeutics for siRNA delivery"; J Intern Med. 267; pp. 9-21.
Segal and Barbas, (2001) "Custom DNA-binding proteins come of age: polydactyl zinc-finger proteins"; Curr Opin Biotechnol 12; pp. 632-637.
Segal, (2002) "The use of zinc finger peptides to study the role of specific factor binding sites in the chromatin environment"; Methods 26; pp. 76-83.
Segal, et al., (2003) "Evaluation of a modular strategy for the construction of novel polydactyl zinc finger DNA-binding proteins"; Biochemistry 42; pp. 2137-2148.
Semple, et al., (2010) "Rational design of cationic lipids for siRNA delivery"; Nature Biotechnology, 28; pp. 172-176.
Shmakov, et al., (2015) "Discovery and Functional Characterization of Diverse Class 2 CRISPR-Cas Systems"; Mol Cell. 60(3); pp. 385-397.
Siegw Art, et al., (2011) "Combinatorial synthesis of chemically diverse core-shell nanoparticles for intracellular delivery"; Proc Natl Acad Sci USA. 108(32); pp. 12996-3001.
Siu, Fai Fiu, et al., "Structure of the human glucagon class BG-protein coupled receptor," Nature 499:444-451 (2013).
Smith, et al., (2017) "In situ programming of leukaemia-specific T cells using synthetic DNA nanocarriers"; Nat Nanotechnol. (8):813-820.
Srinivasarao, M., et al., "Principles in the design of ligand-targeted cancer therapeutics and imaging agents", Nature reviews Drug discovery, 2015, V. 14, N. 3, p. 203-219.
Sumo, et al., (2012) "Smart multilayered assembly for biocompatible siRNA delivery featuring dissolvable silica, endosome-dismpting polycation, and detachable PEG"; ACS Nano. 6(8); pp. 6693-6705.
Tyrrell, et al., (2012) "Multilayered Nanoparticles For Controlled Release of Paclitaxel Formed by Near-Critical Micellization of Triblock Copolymers"; Marcomolecules, vol. 45, pp. 4809-4817.
Upadhyay, et al., (2013) "RNA-guided genome editing for target gene mutations in wheat"; G3 (Bethesda) 3(12); pp. 2233-2238.
Walsh, et al., (2013) "A variant CRISPR-Cas9 system adds versatility to genome engineering"; ProcNatlAcadSci USA. 110(39);pp. 15514-15515.
Wang, et al., "Influence of the polyanion on the physico-chemical properties and biological activities ofpolyanion/DNA/polycation ternary polyplexes"; Acta Biomater, vol. 8, No. 8; Apr. 27, 2012; pp. 3014-3026.
Wang, et al., (2013) "One-step generation of mice carrying mutations in multiple genes by CRISPR/Cas-mediated genome engineering"; Cell. 153(4); pp. 910-918.
Watson, et al., "Optimizing Polymeric Nanoparticle Core Designs for Gene Delivery"; Bioengineering Conference NEBEC), 2013 39th Annual Northeast, Apr. 5-7, 2013, Syracuse, New York.
Wolfe, et al., (2000) "DNA recognition by Cys2His2 zinc finger proteins"; Ann Rev Biophys Biomol Struct 29; pp. 183-212.
Woodle, M.C., et al., "Nanoparticles deliver RNAi therapy", Materials Today, Elsevier, Amsterdam, NL, vol. 8, No. 8, Aug. 1, 2005 (Aug. 1, 2005), pp. 34-41.
Xie, et al., (2013) "RNA-Guided Genome Editing in Plants Using a CRISPR-Cas System"; Mal Plant, vol. 6, No. 6; pp. 1975-1983.
Yang, et al., (2013) "One-step generation of mice carrying reporter and conditional alleles by CRISPR/Cas-mediated genome engineering"; Cell 154(6); pp. 1370-1379.
Zetsche, et al., (2015) "Cpfl is a single RN A-guided endonuclease of a class 2 CRISPR-Cas system"; Cell, 163(3); pp. 7597-7671.
Zhang, et al., (1997) "A central role for beta-arrestins and clathrin-coated vesicle-mediated endocytosis in beta2-adrenergic receptor resensitization. Differential regulation of receptor resensitization in two distinct cell types"; J Biol Chem.272(43); pp. 27005-27014.
Zhao, M., et al. (2004) "Intracellular cargo delivery using tat peptide and derivatives", Medicinal research reviews, 2004, V. 24, N. 1, p. 1-12.

(56) References Cited

OTHER PUBLICATIONS

Zhou, J., et al. (2009) "Preparation and PEGylation of exendin-4 peptide secreted from yeast *Pichia pastoris*", European Journal of Pharmaceutics and biopharmaceutics, 2009, V. 72, N. 2, pp. 412-417.
EPO, European Search Report for Application No. 14846422.5, Dated Apr. 18, 2017.
EPO, partial European Search Report for Application No. 17882004.9, Dec. 10, 2020.
EPO, Extended European Search Report for Application No. 17882004.9, 14 pages, mail date Mar. 15, 2021.
International Search Report for PCT/US2014/057000 dated Jan. 14, 2015.
USPTO, International Search Report and Written Opinion for International Application No. PCT/US17/66541 dated Mar. 8, 2018, 11 pages.
IP Office Russia, Search Report for Application No. 2019121992, mail date Jan. 26, 2021.
IP Office Russia, Office Action with English translation for Application No. 2019121992, mail date Apr. 22, 2021.
IP Office China, "Second Office Action", for Chinese Application No. 201780085854.6, Feb. 23, 2023, 13 pages with English translation.
IP Office Israel, "Office Action", for Israeli Application No. 267034, Mail date: Sep. 19, 2022.
IP Office Israel, "Office Action #2", for Application No. 267034, Aug. 8, 2023, 3 pages.
IP Office Japan, "Second Office Action", for Japanese Application No. 2019-531743, Mail date Oct. 31, 2022, with English translation.
IP Office Korea, "Notice of Preliminary Rejection", for Application No. 10-2019-7020171, May 15, 2023, 11 pages with English translation.
IP Office China, "Decision of Rejection", for Application No. 201780085854.6, Mail Date: Sep. 7, 2023, 9 pages (English translation).
EPO, Exam Report, for Application No. 17882004.9, Mail Date: Nov. 21, 2023; 8 pages.
IP Office Japan, Notice of Reasons for Rejection for Application No. 2023-117292. Mail date: Apr. 1, 2024. 3 pages with English translation.

\* cited by examiner

Figure 1
A
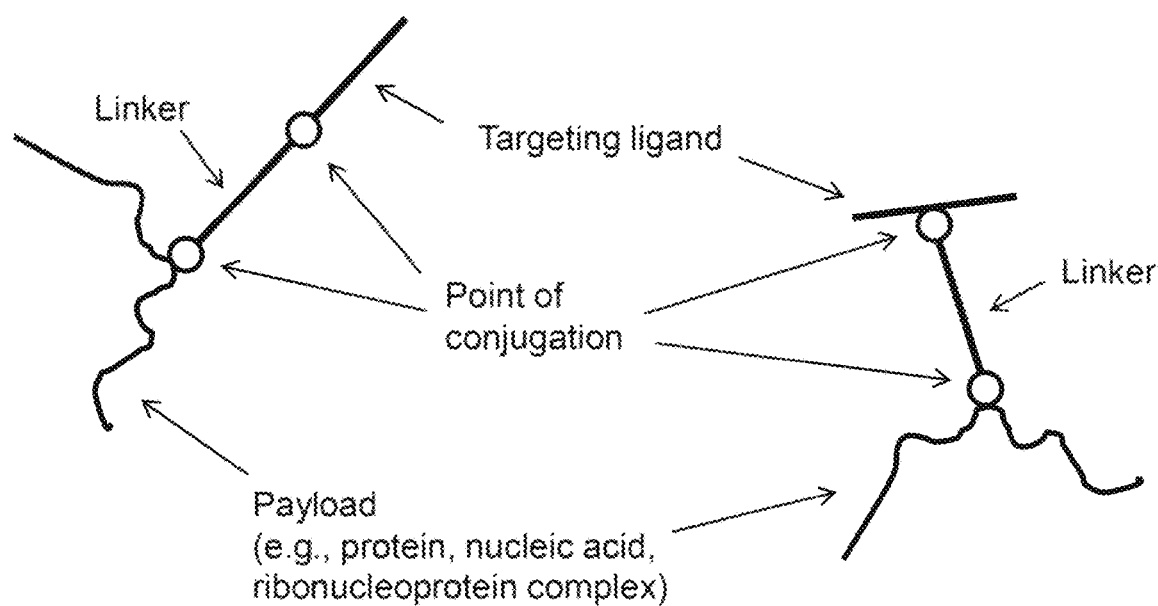
B
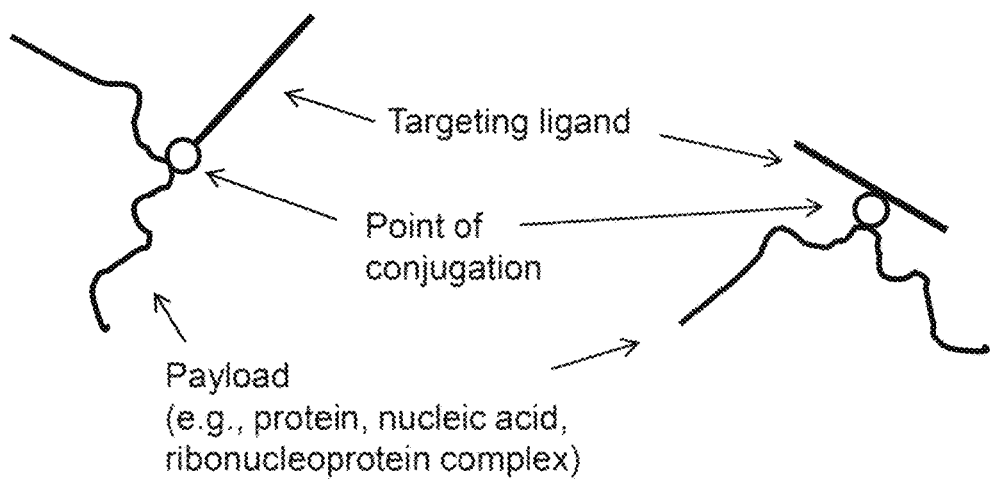

Figure 1
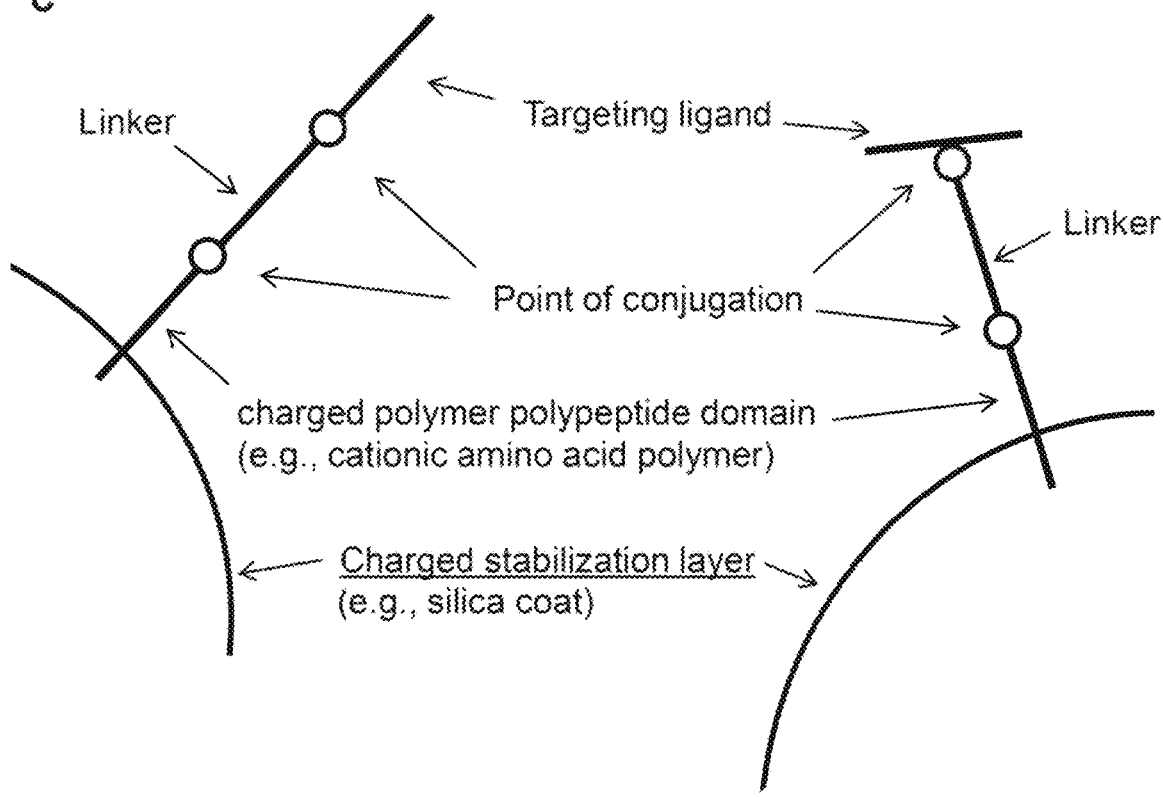
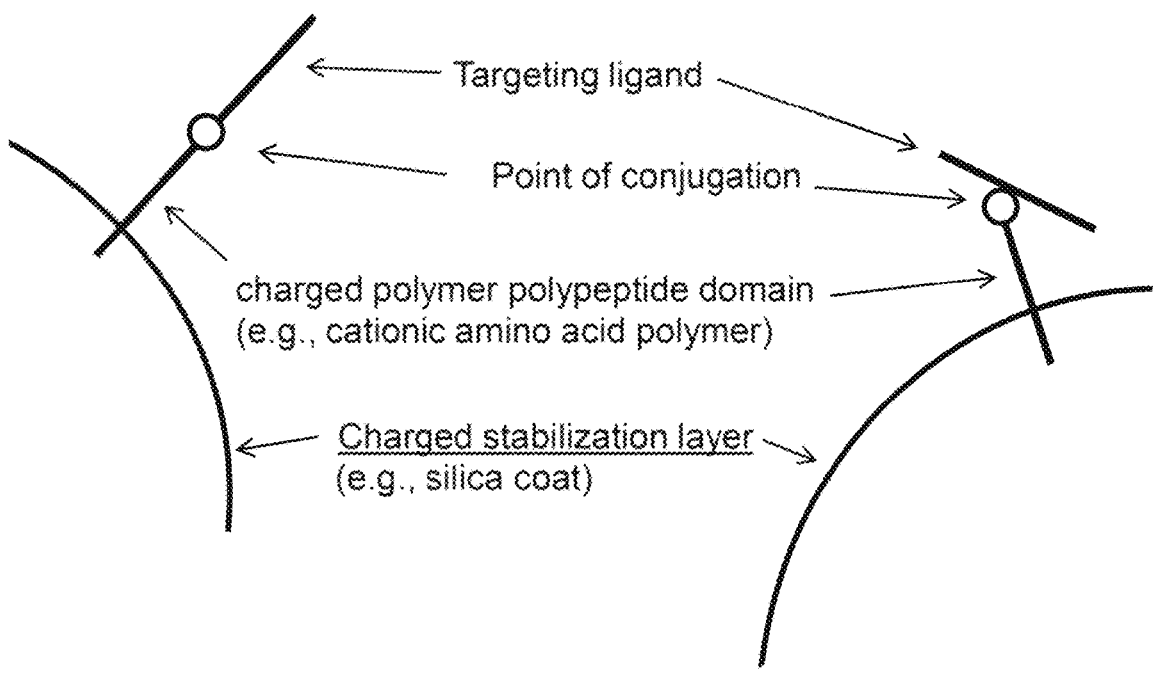

Figure 1
E
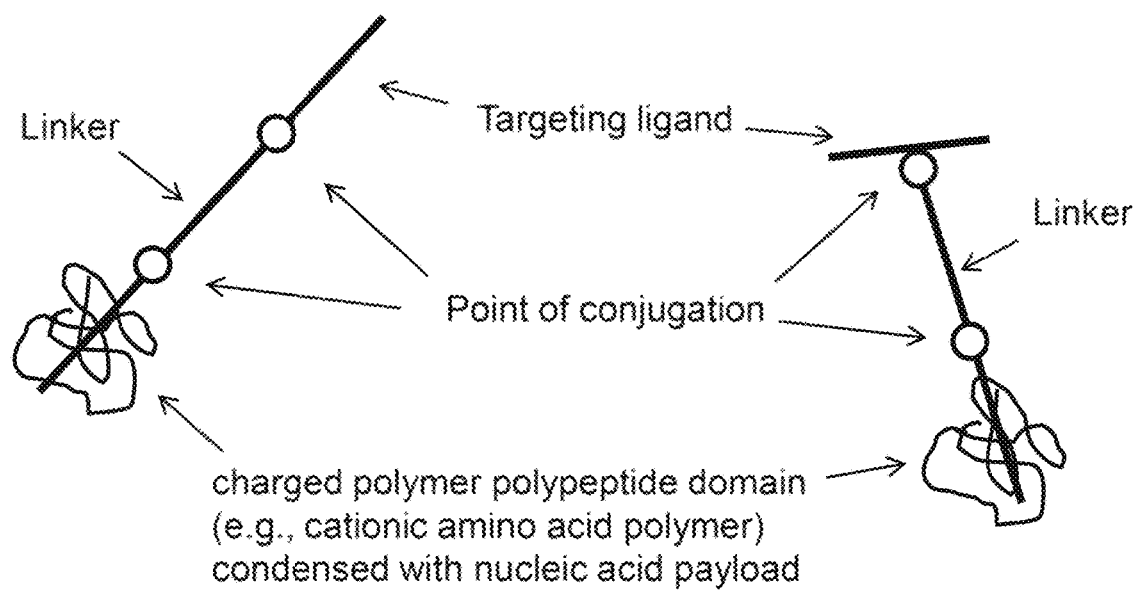
F
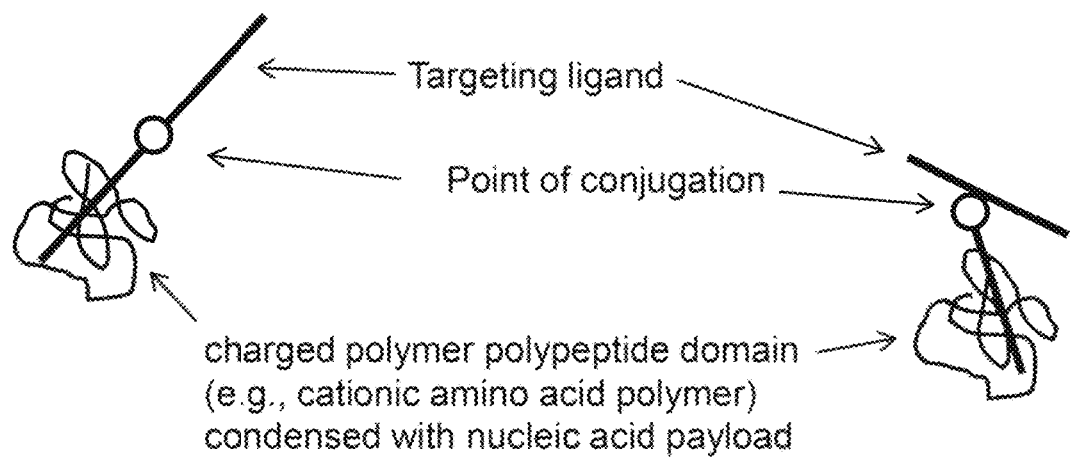

B

D

Figure 8
a)
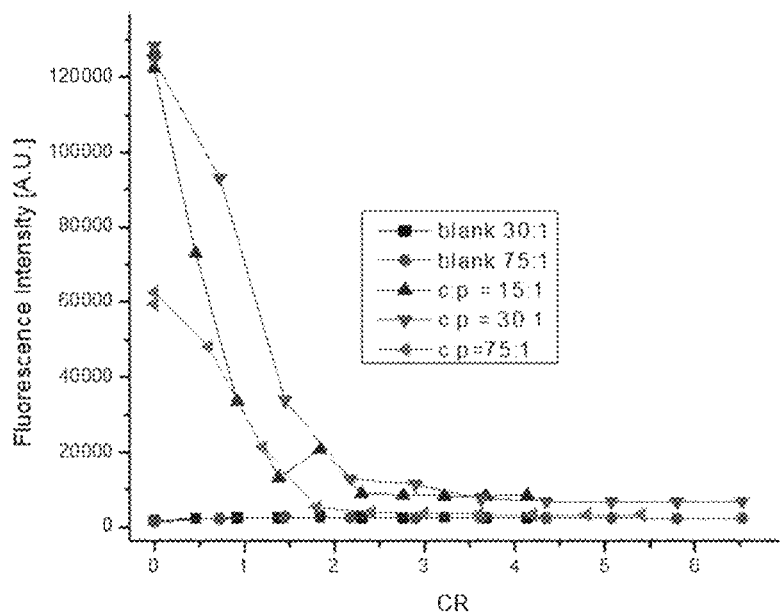
b)
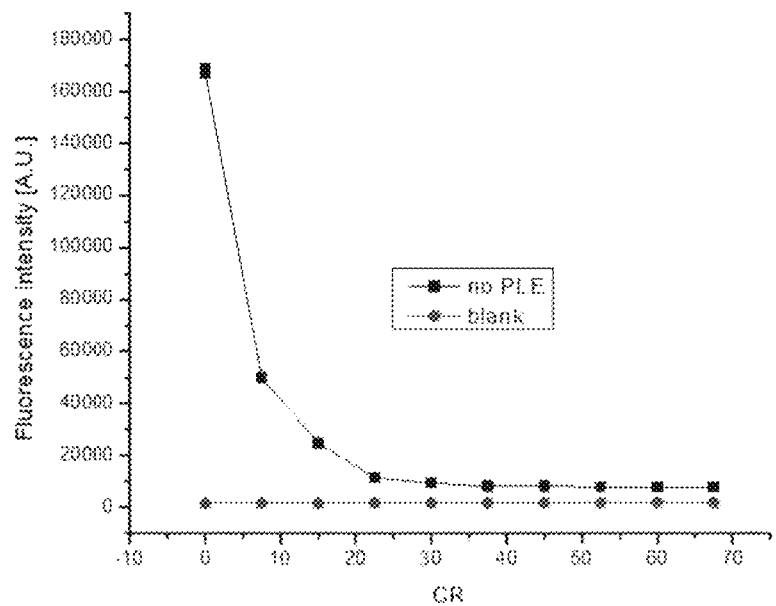

Figure 19
a)
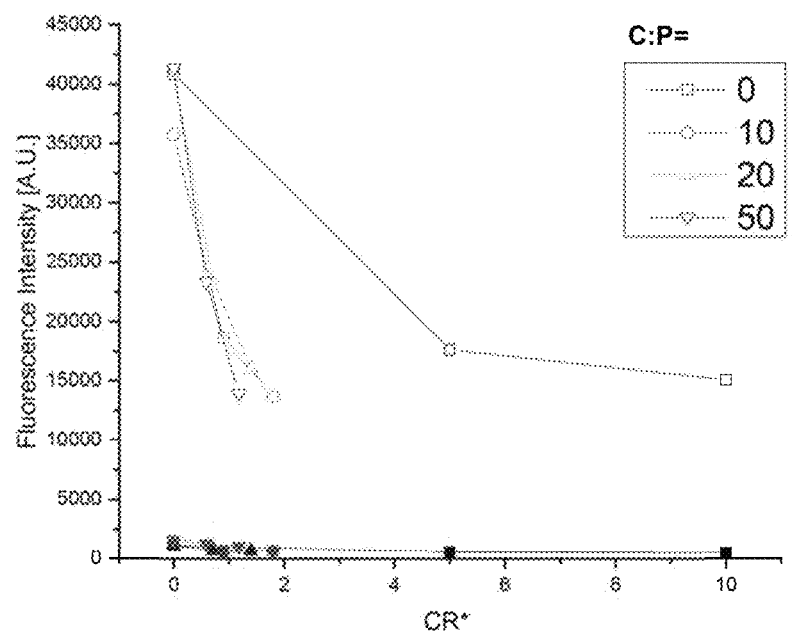
b)
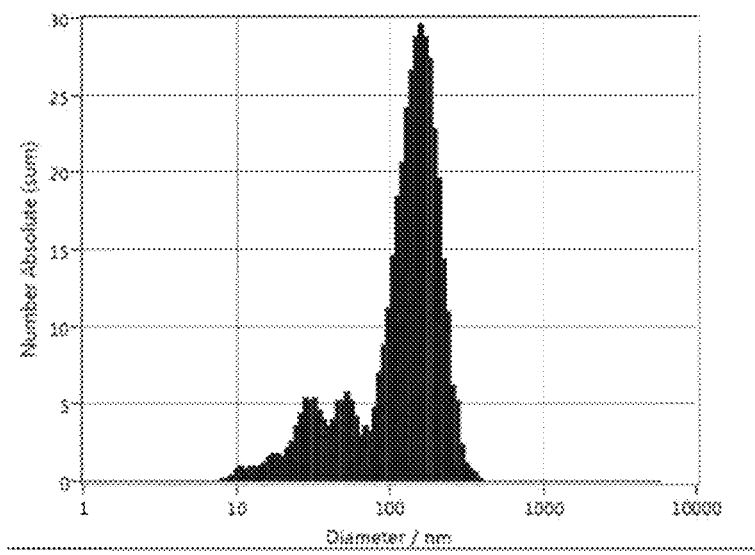

Figure 21
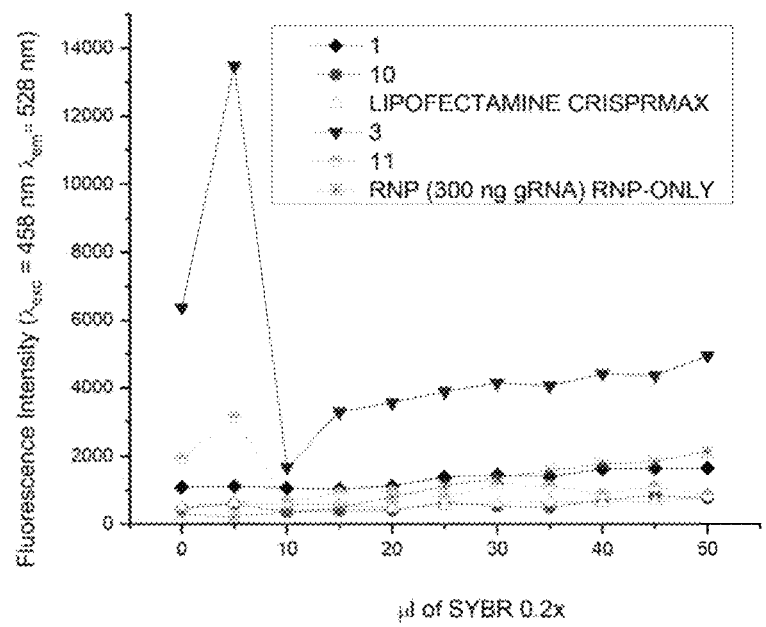
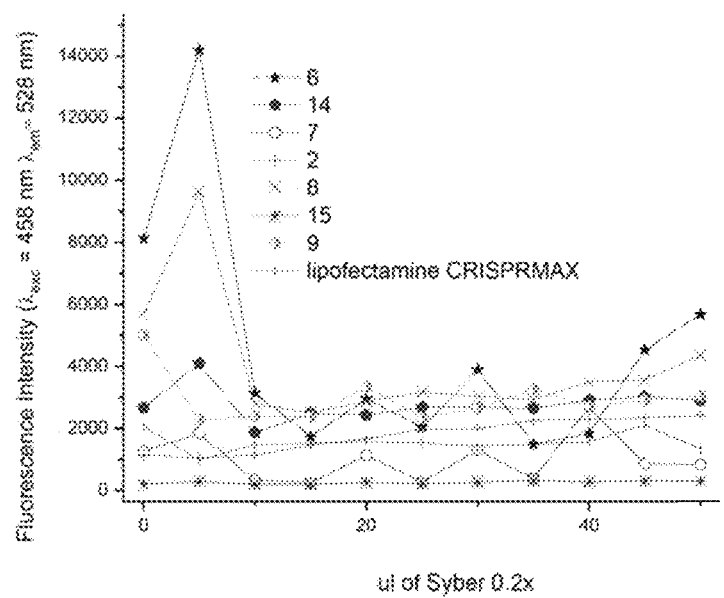

Figure 22
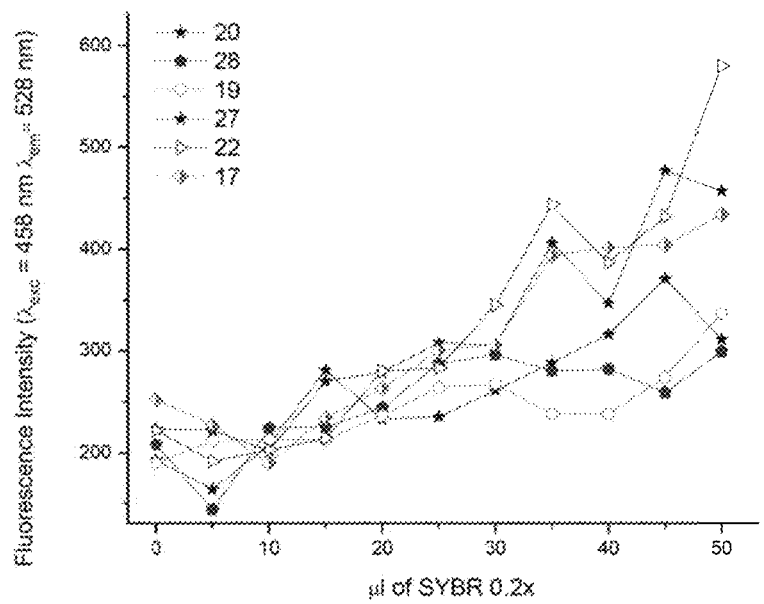
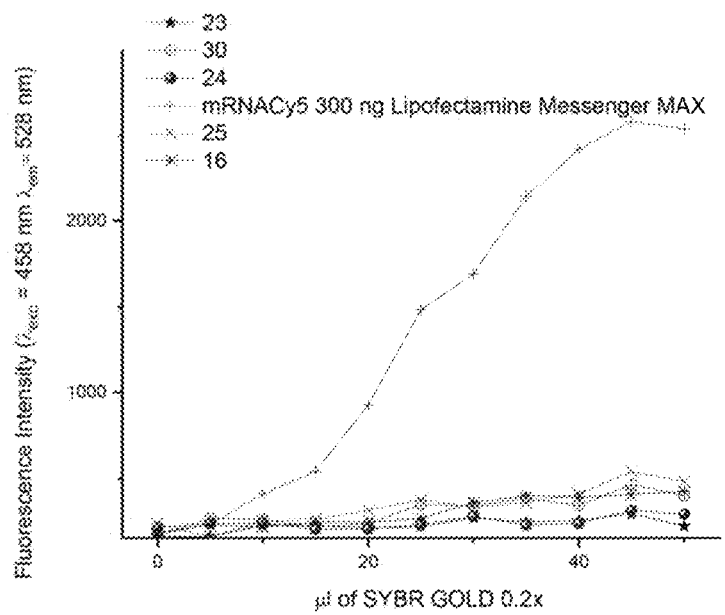

Figure 23
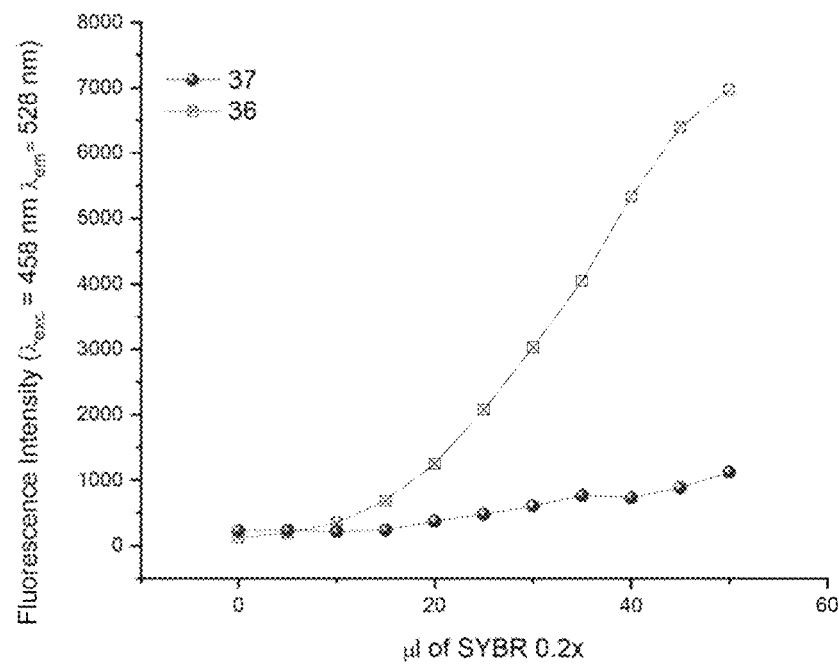
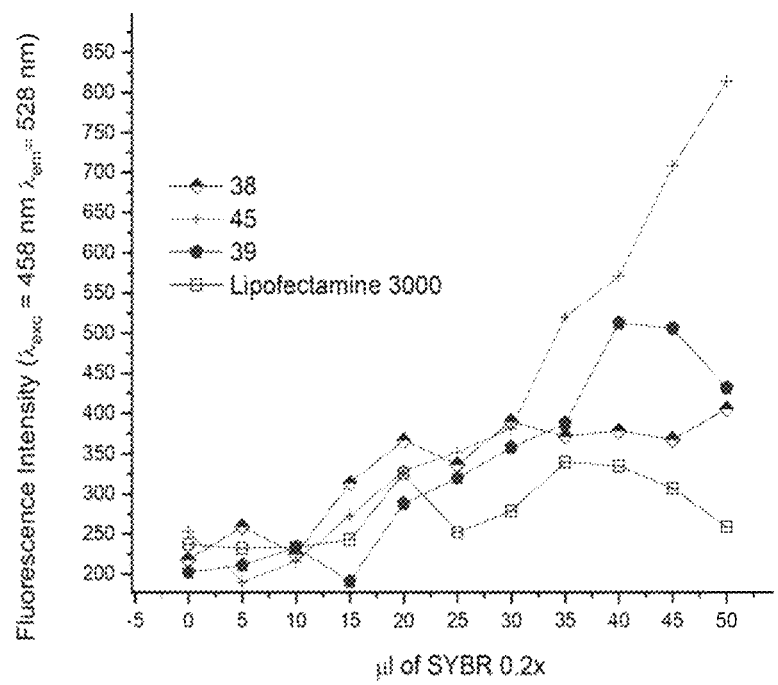

A

FIGURE 34 (Cont. 1)
B
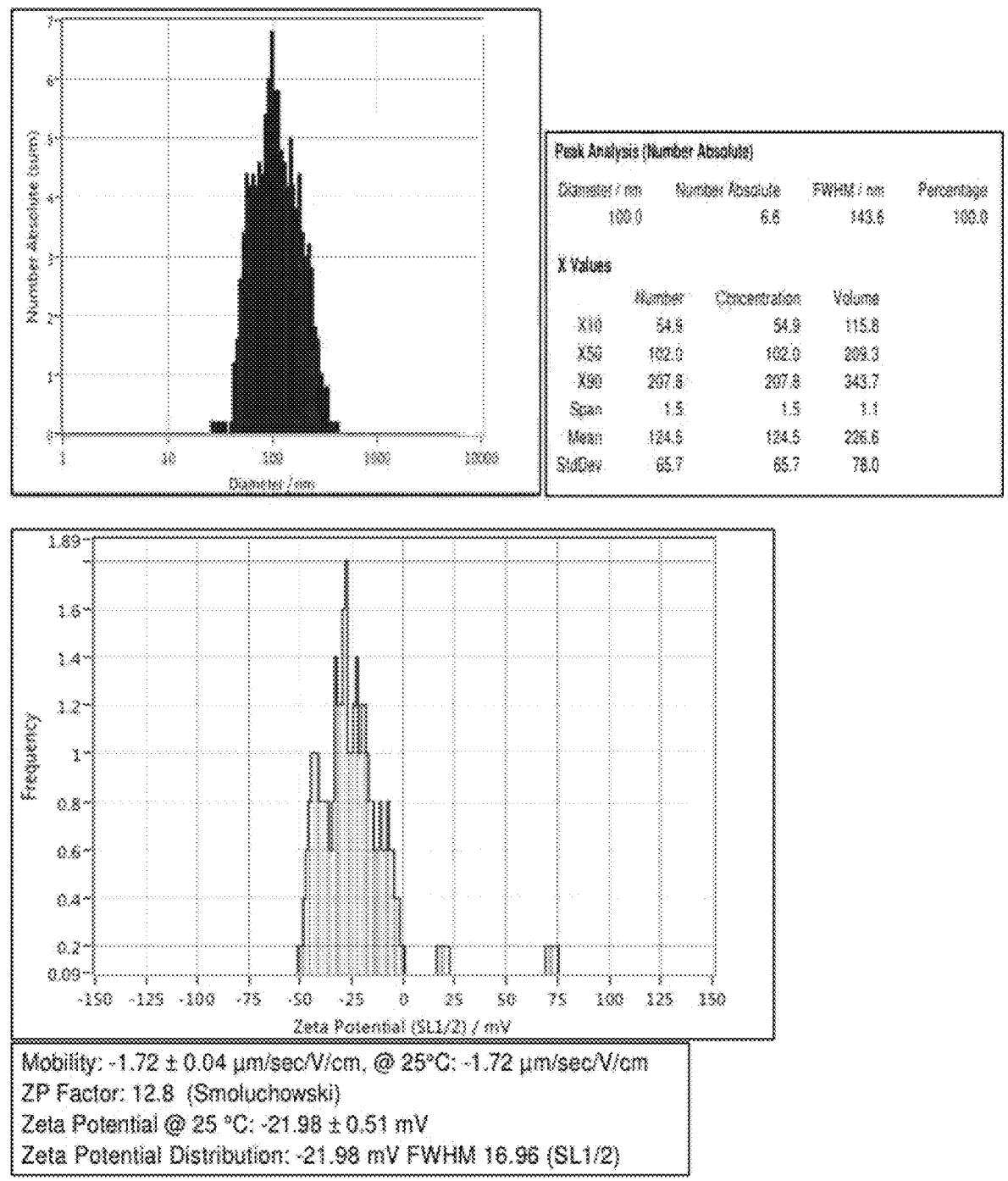

FIGURE 34 (Cont. 2)
C  Ligandal ligand catalog # ESELLg_mESEL_(4GS)2_9R_N
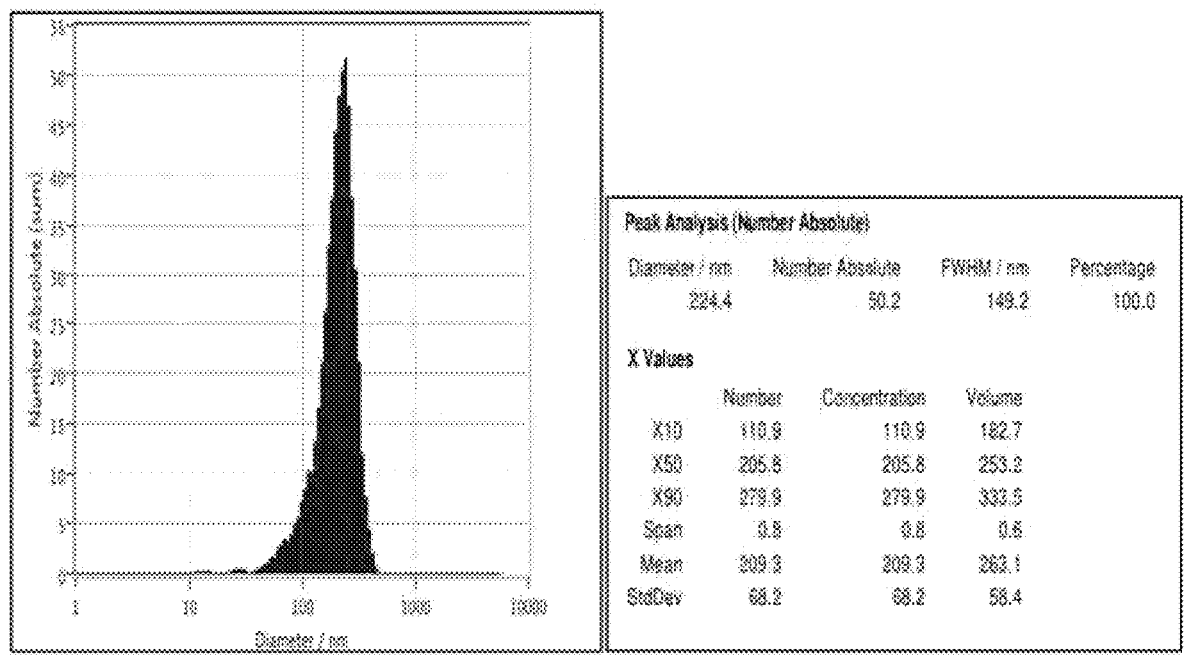
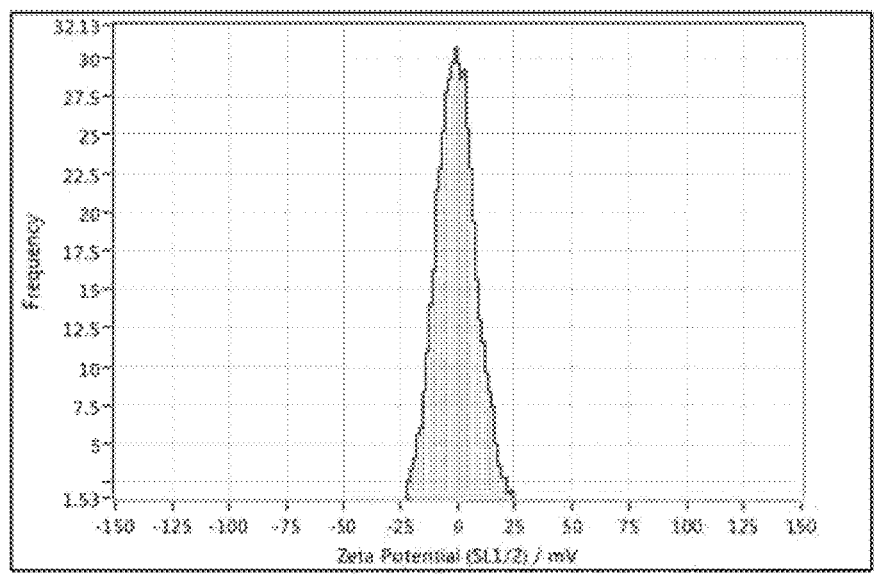

Figure 36  HSC.001.001
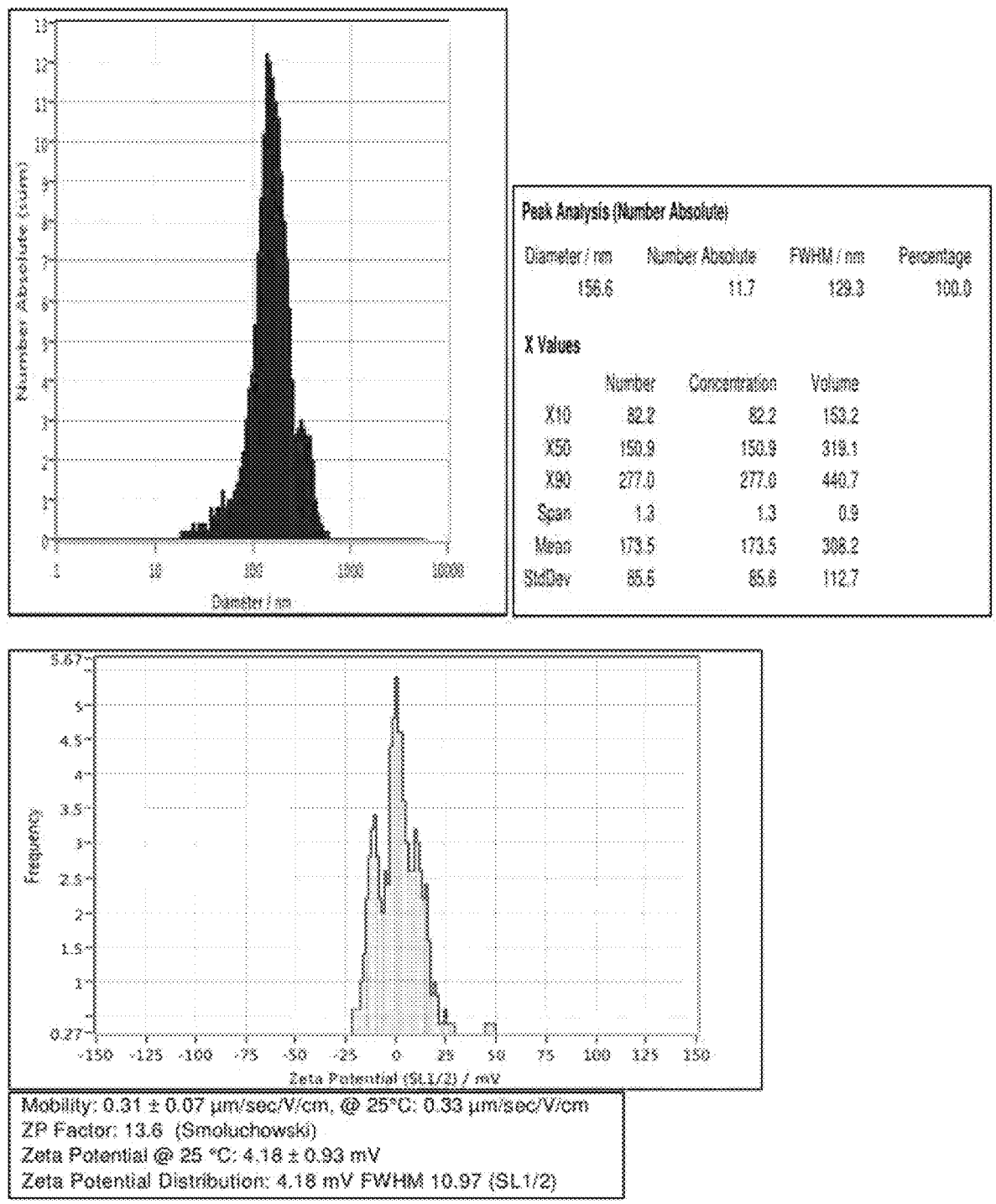

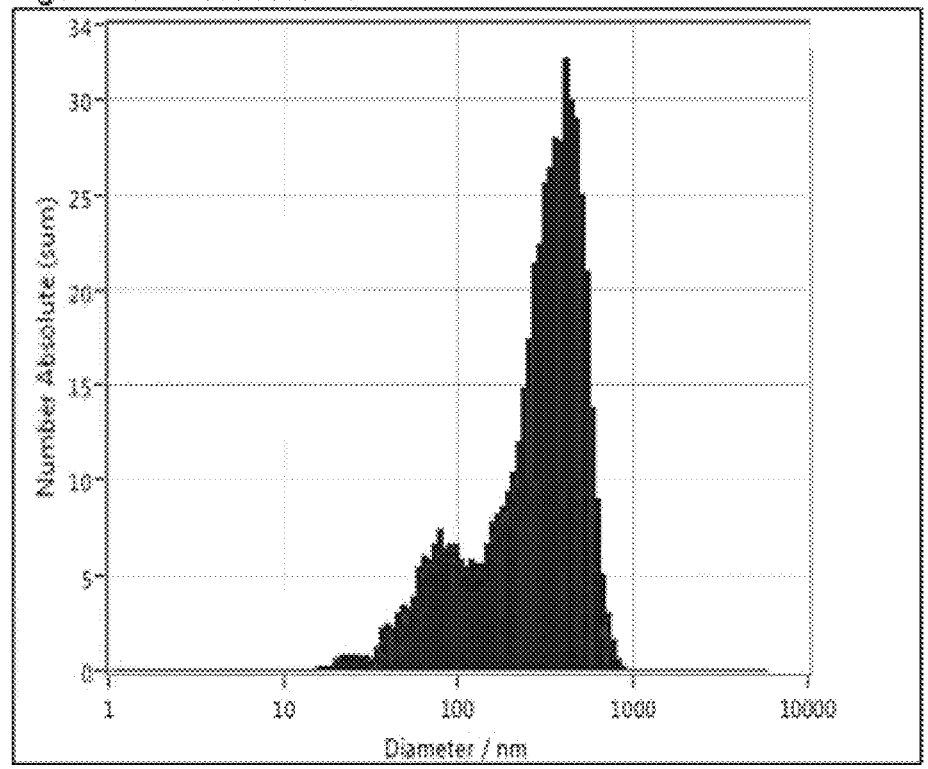

Figure 38  HSC.002.01
Targeting Ligand - ESELLg_mESEL_(4GS)2_9R_N
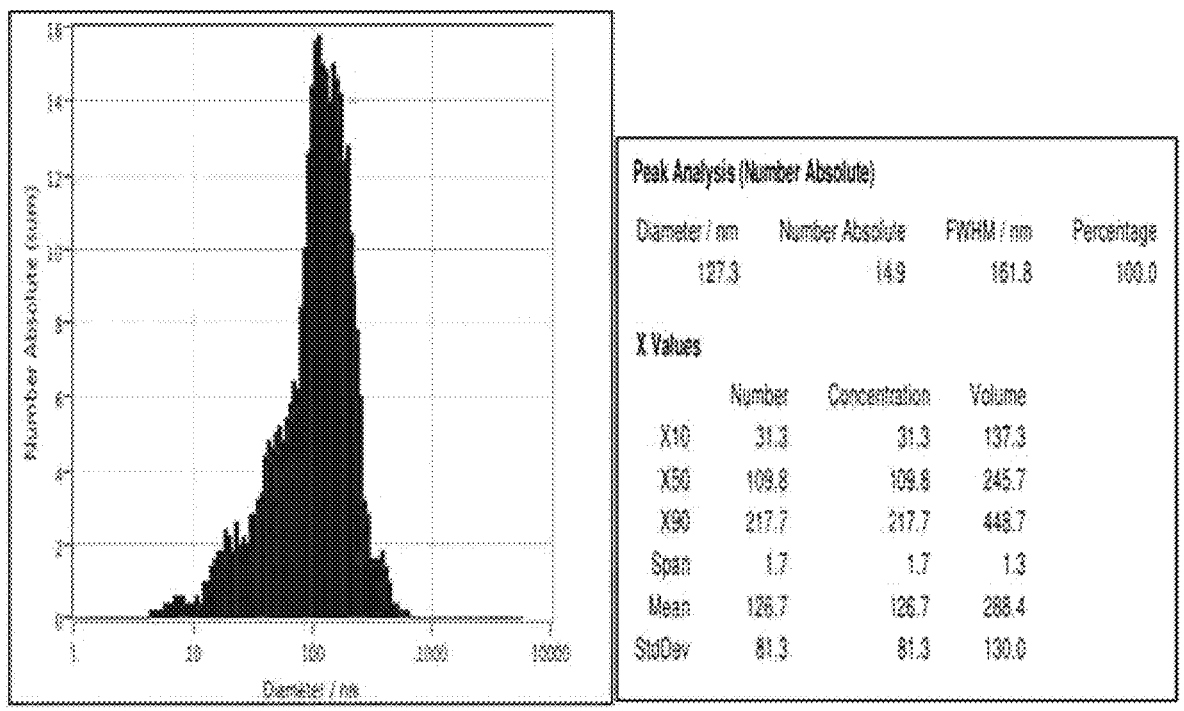
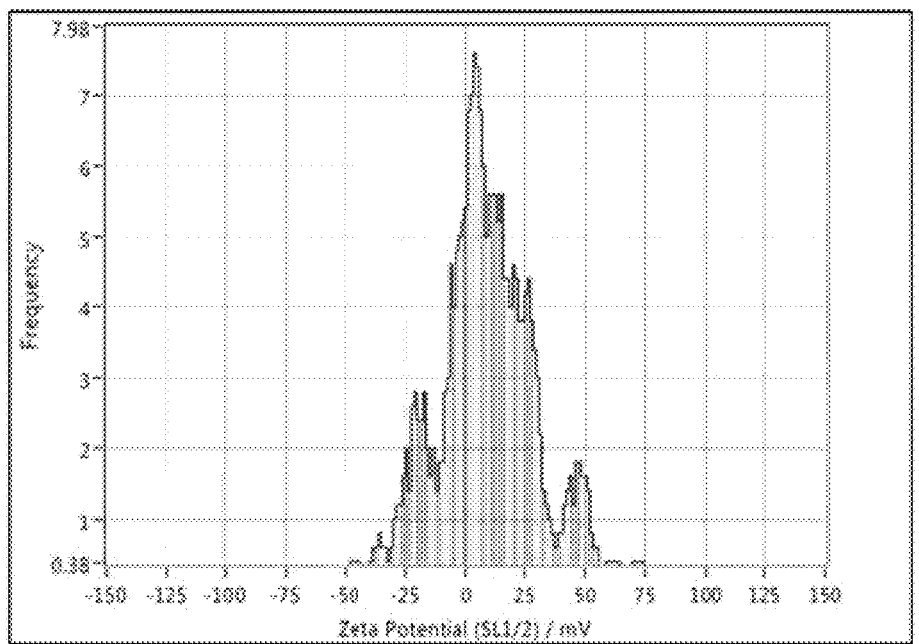
Mobility: 0.88 ± 0.05 μm/sec/V/cm, @ 25°C: 0.85 μm/sec/V/cm
ZP Factor: 12.5 (Smoluchowski)
Zeta Potential @ 25 °C: 10.90 ± 0.58 mV
Zeta Potential Distribution: 10.90 mV FWHM 22.10 (SL1/2)

Figure 39  HSC.002.02
Targeting Ligand - ESELLg_mESEL_(4GS)2_9R_C
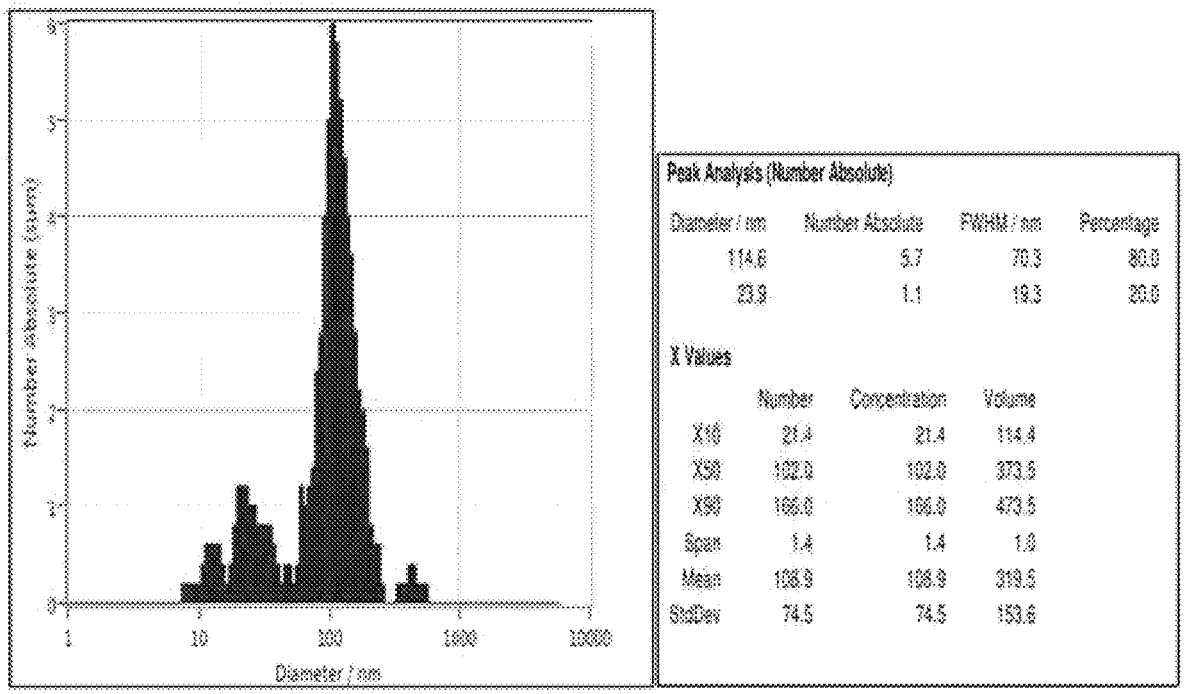
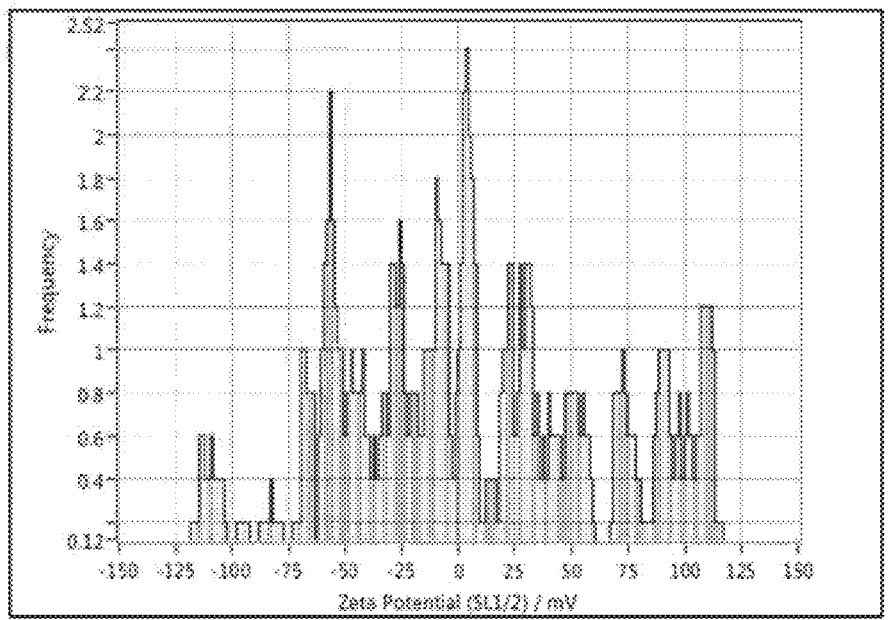
Zeta Potential @ 25 °C: -7.10 ± 0.30 mV
Zeta Potential Distribution: -7.10 mV FWHM 6.49 (SL1/2)
Concentration: 6.7E+7 Particles / mL
Dilution Factor: 1
Original Concentration: 6.7E+7 Particles / cm³

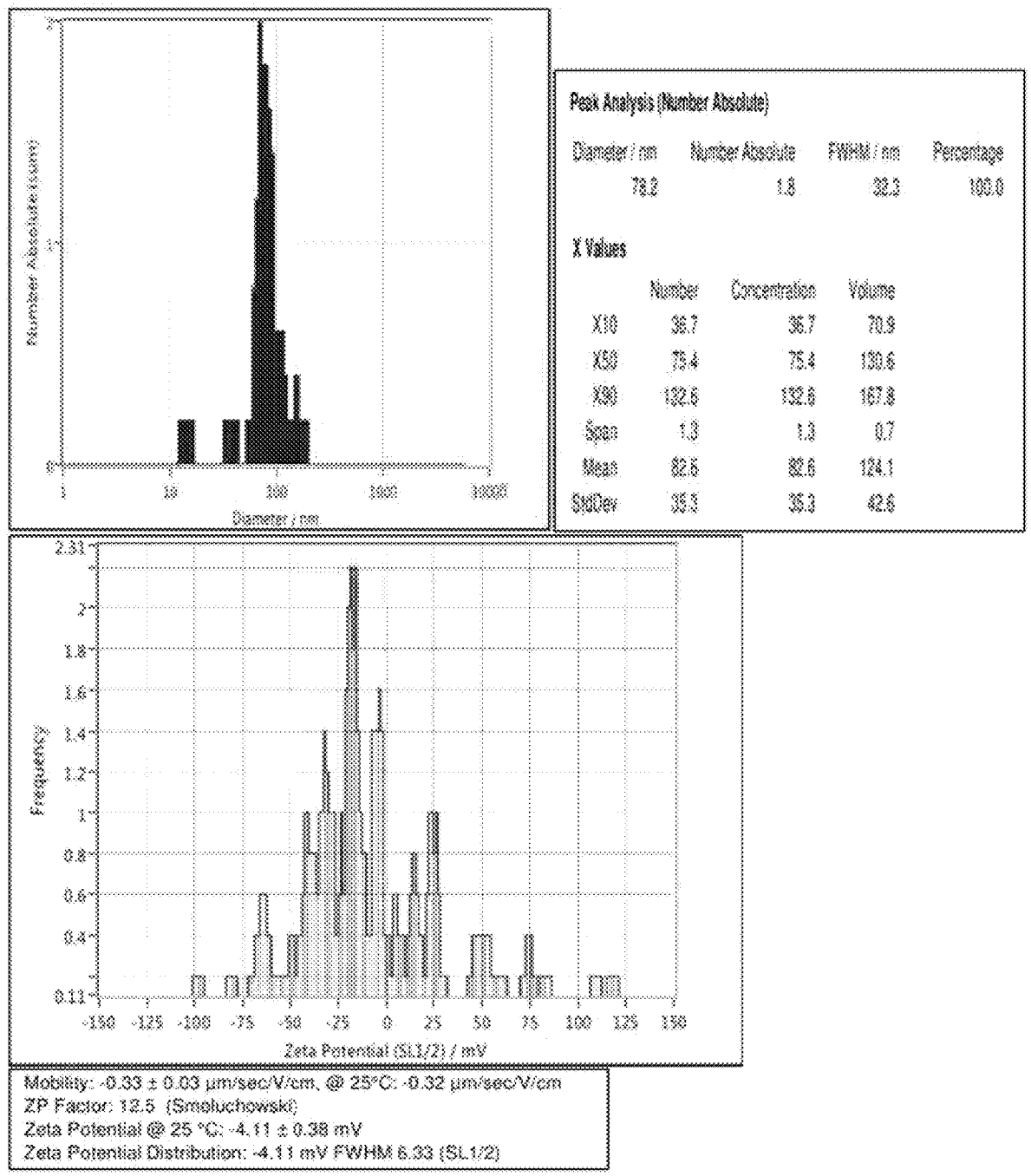
Figure 40 HSC.002.03
Targeting Ligand - CD45_mSiglec_(4GS)2_9R_C

Figure 41  HSC.002.004
Targeting Ligand – Cy5mRNA-SiO2-PEG
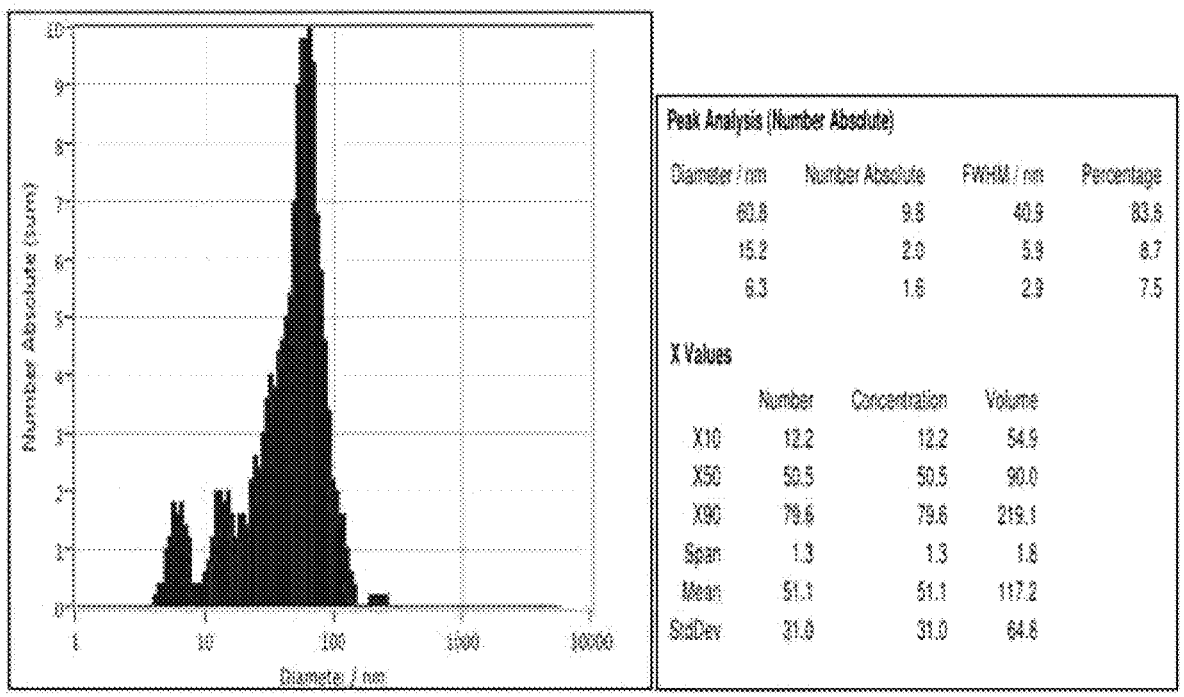
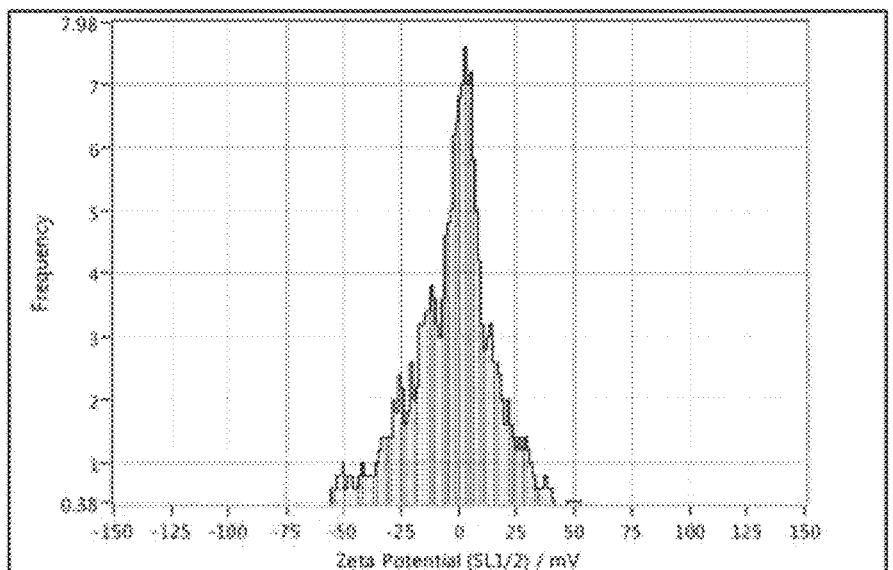

Figure 42   BLOOD.002.88
            Targeting Ligand - CD45_mSiglec_(4GS)2_9R_C
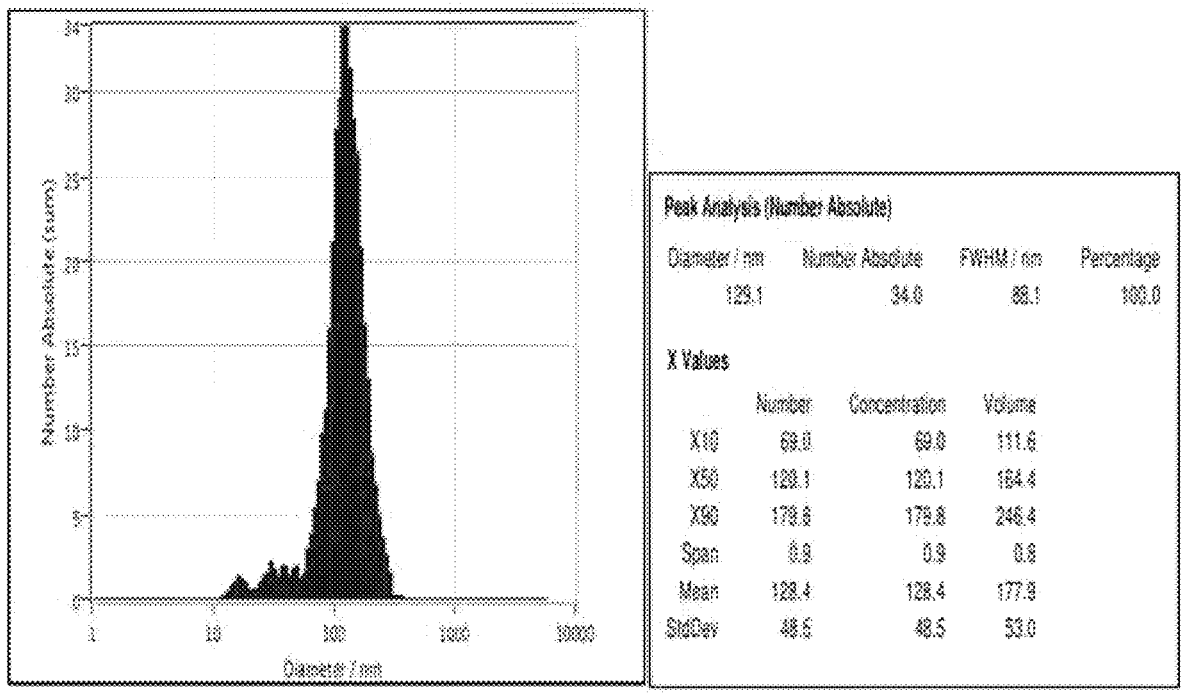
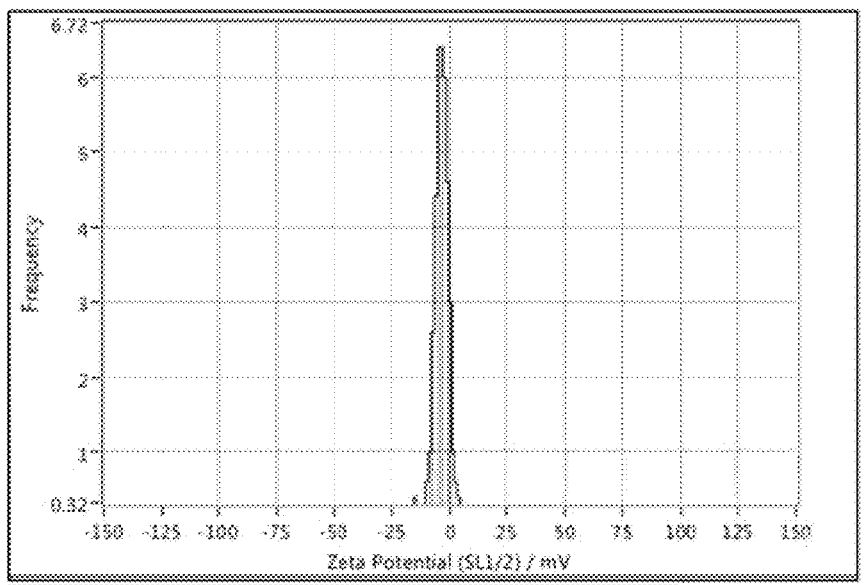

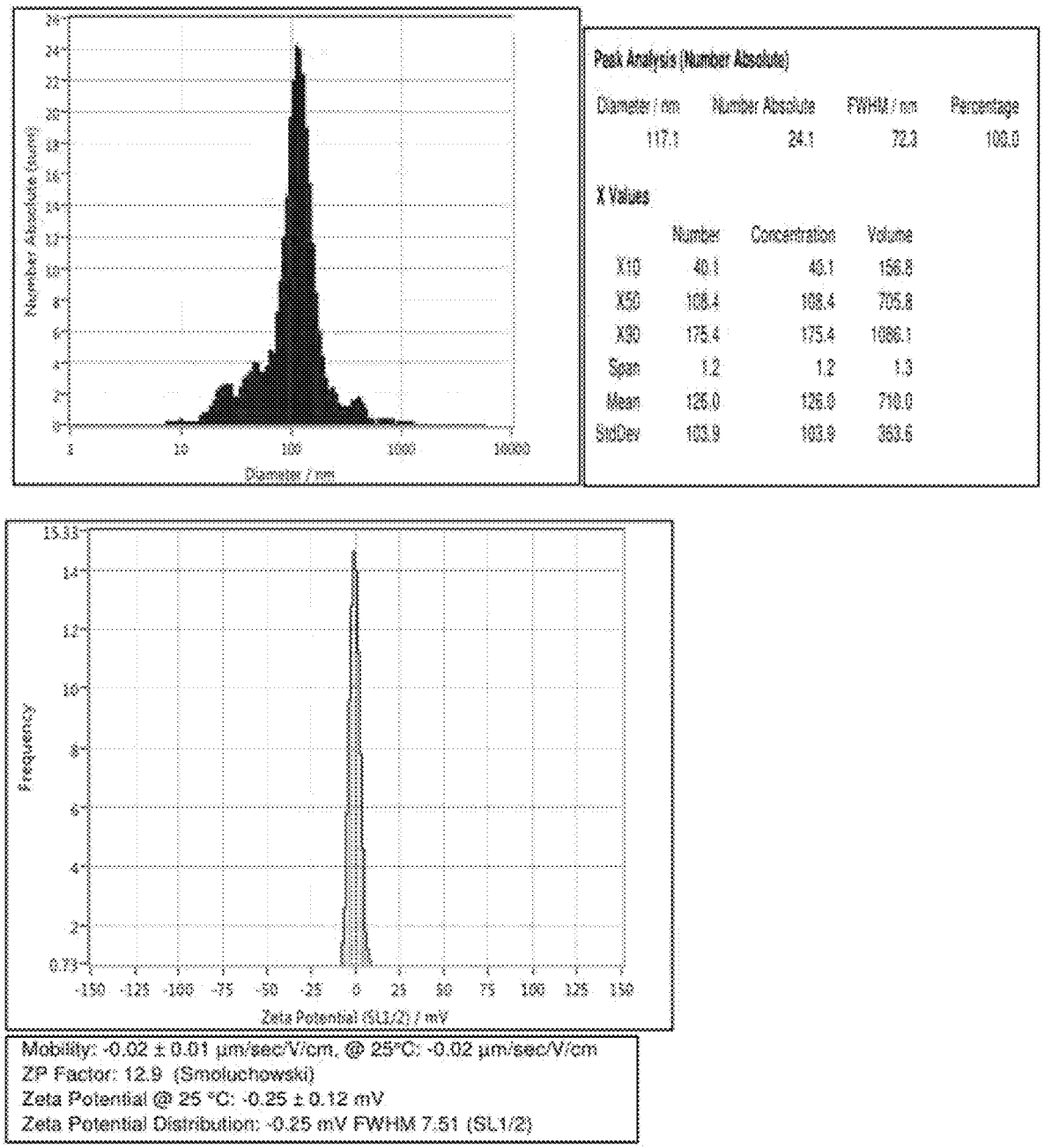
Figure 43  BLOOD.002.89
Targeting Ligand - CD45_mSiglec_(4GS)2_9R_C

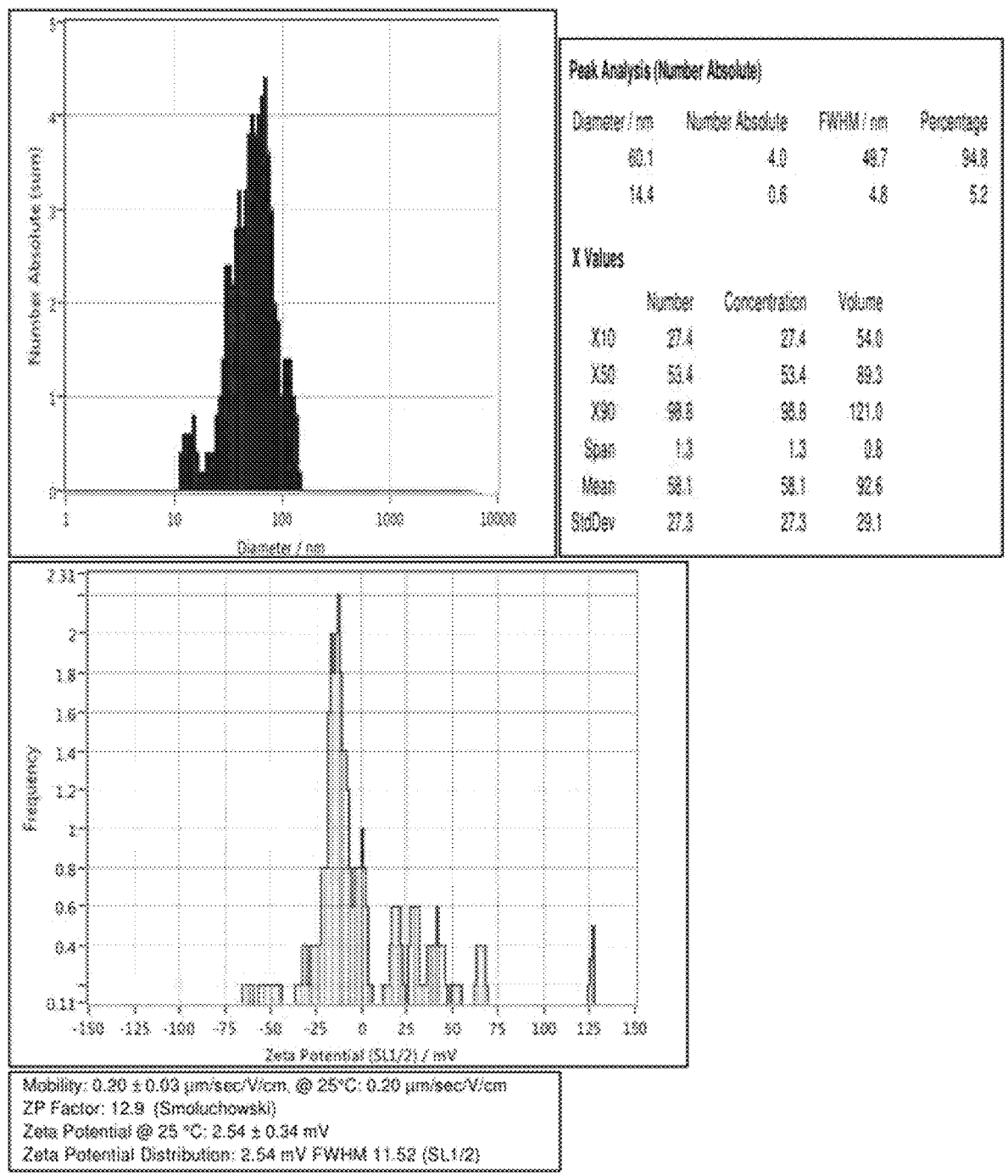
Figure 44 BLOOD.002.90 PLK30_PEG113

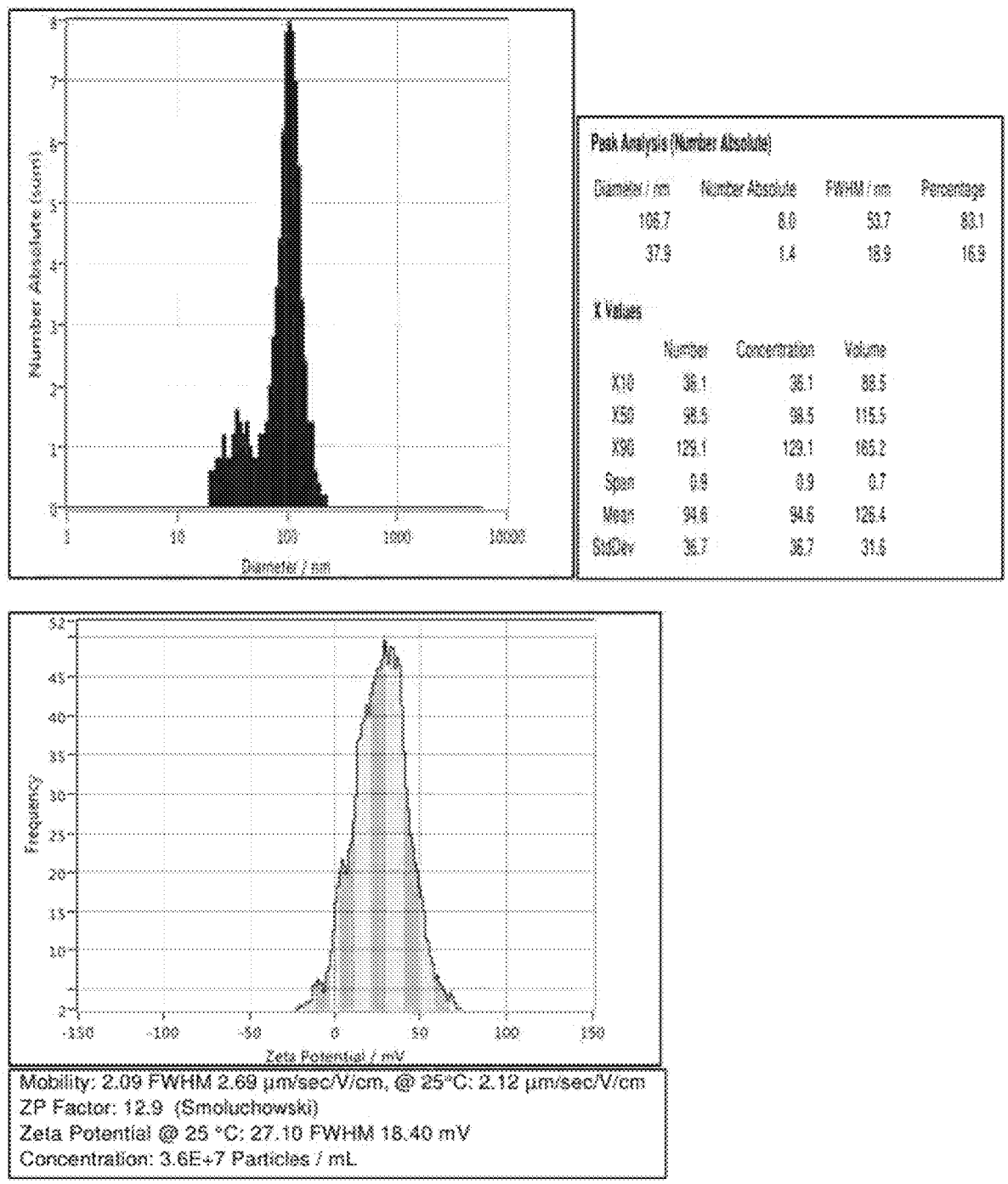
Figure 45  BLOOD.002.91
PLR50

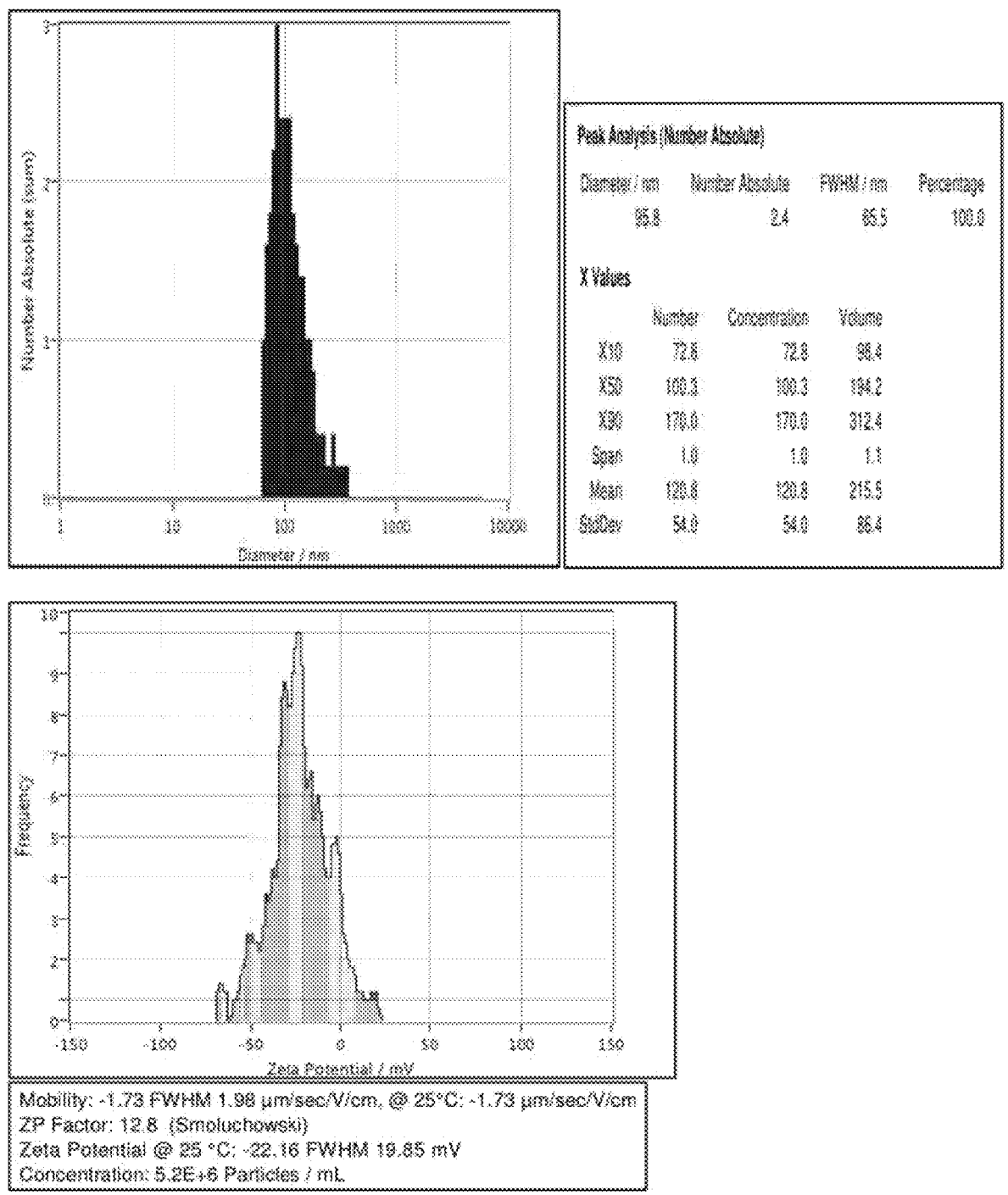
Figure 46  BLOOD.002.92
Targeting Ligand - CD45_mSiglec_(4GS)2_9R_C

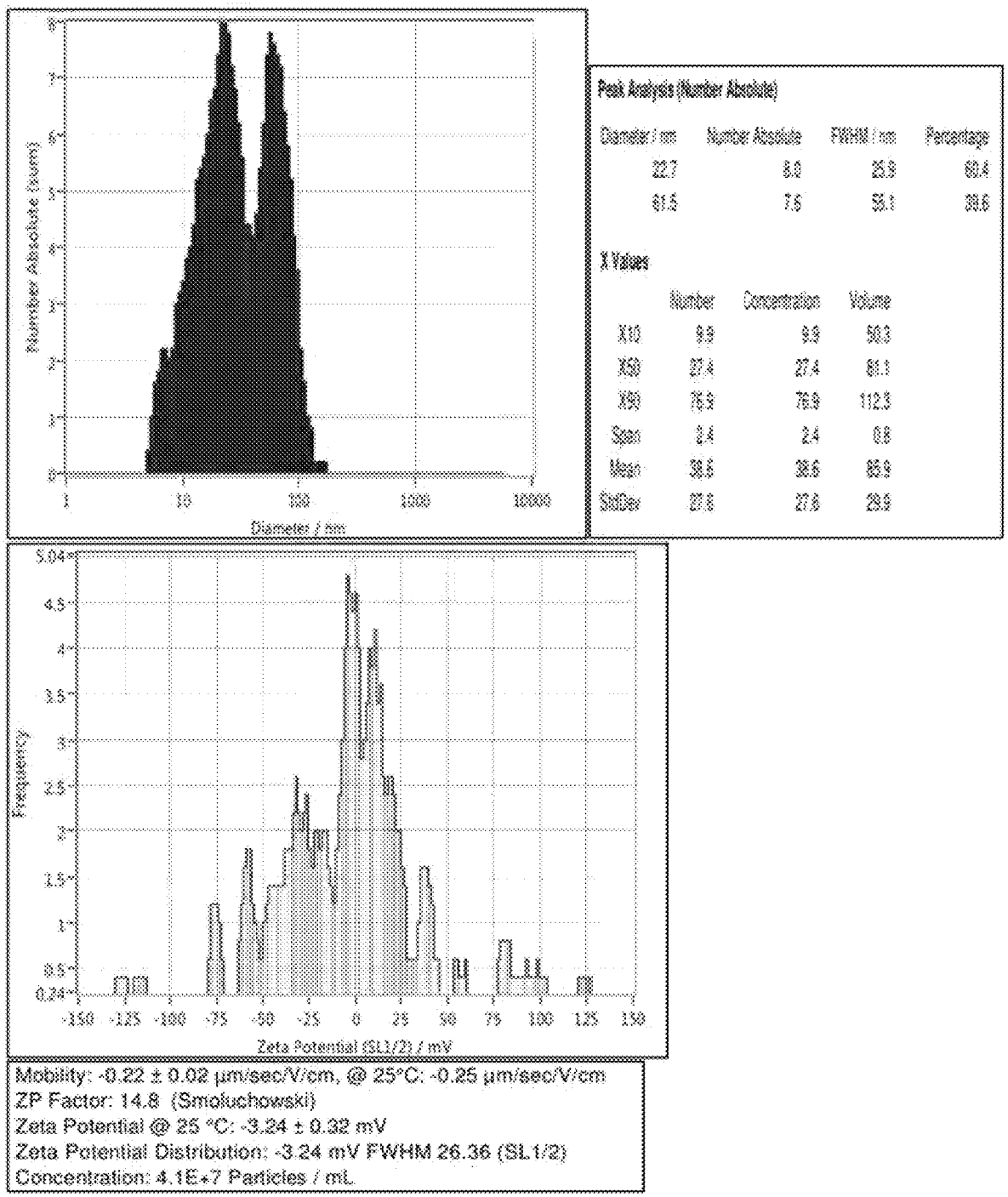
Figure 47 TCELL.001.1.CRISPR1
Poly(L-Arginine) n=10

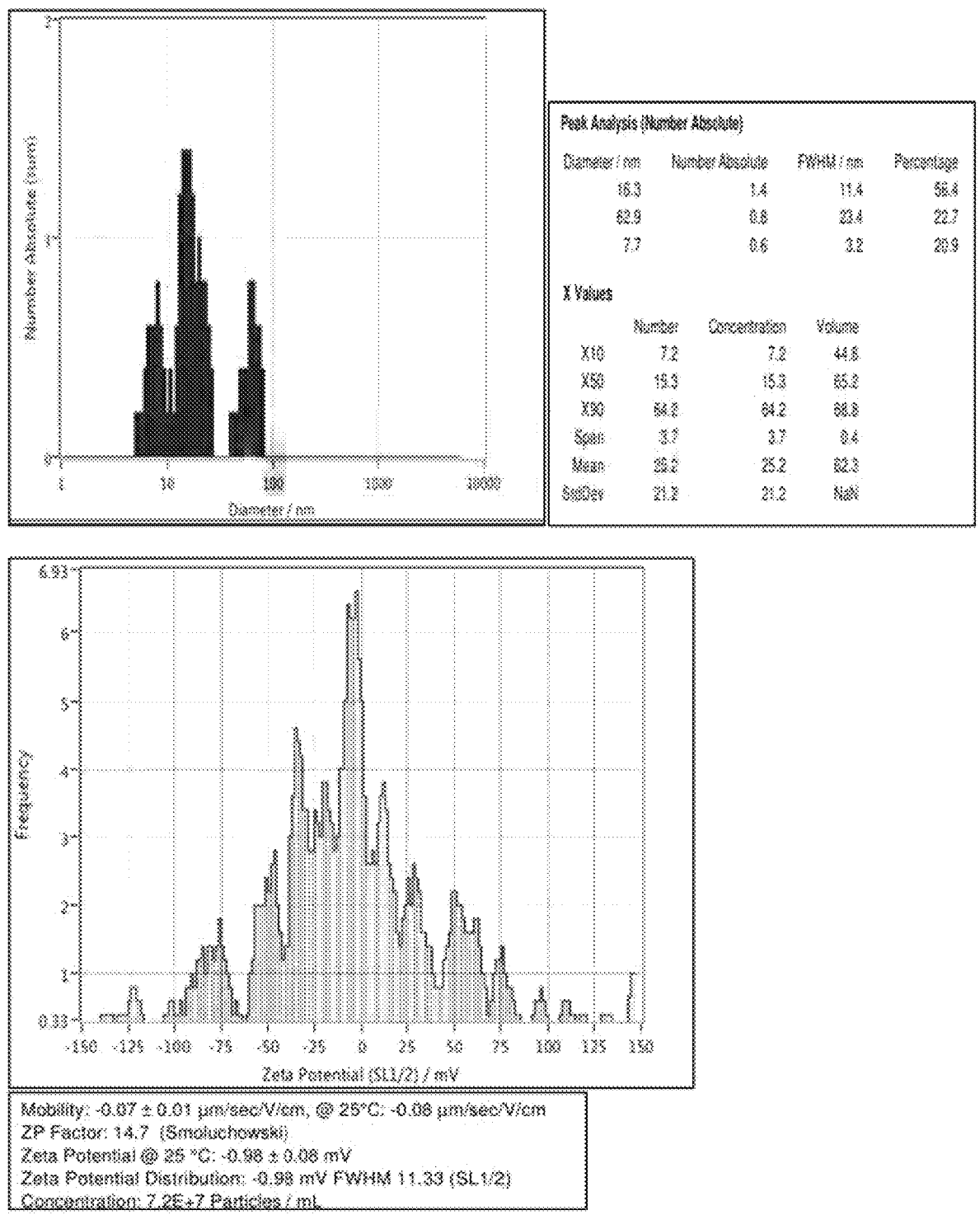
Figure 48  TCELL.001.3.CRISPR2
Targeting Ligand - CD45_mSiglec_(4GS)2_9R_C

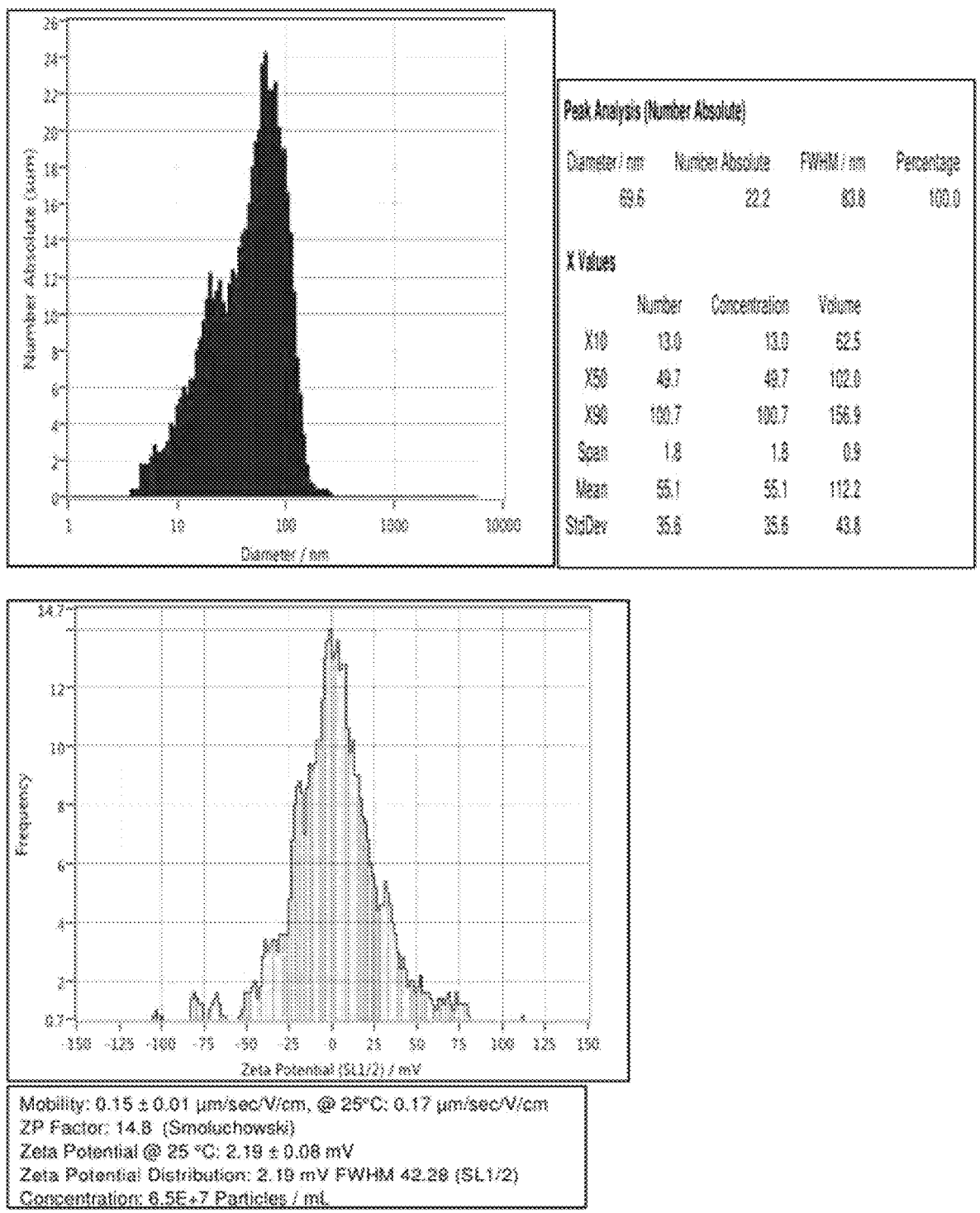
Figure 49 TCELL.001.13.CRISPR12
Targeting Ligand - IL2R_mIL2_(4GS)2_9R_N Figure 50 TCELL.001.14.CRISPR13
Targeting Ligand - IL2R_mIL2_(4GS)2_9R_C
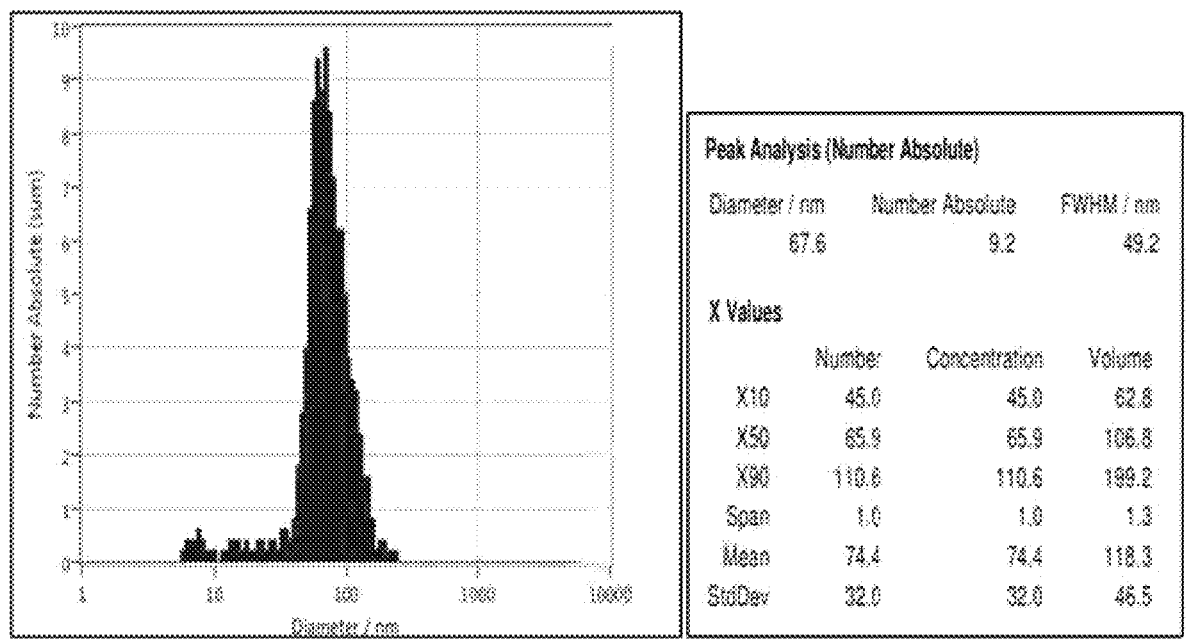
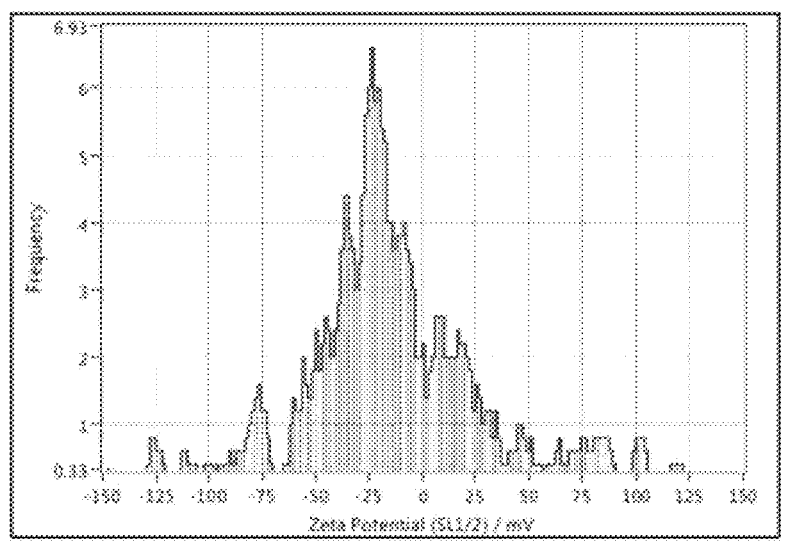
Mobility: -0.63 ± 0.01 µm/sec/V/cm, @ 25°C: -0.73 µm/sec/V/cm
ZP Factor: 14.9 (Smoluchowski)
Zeta Potential @ 25 °C: -9.37 ± 0.16 mV
Zeta Potential Distribution: -9.37 mV FWHM 27.63 (SL1/2)
Concentration: 3.5E+7 Particles / mL

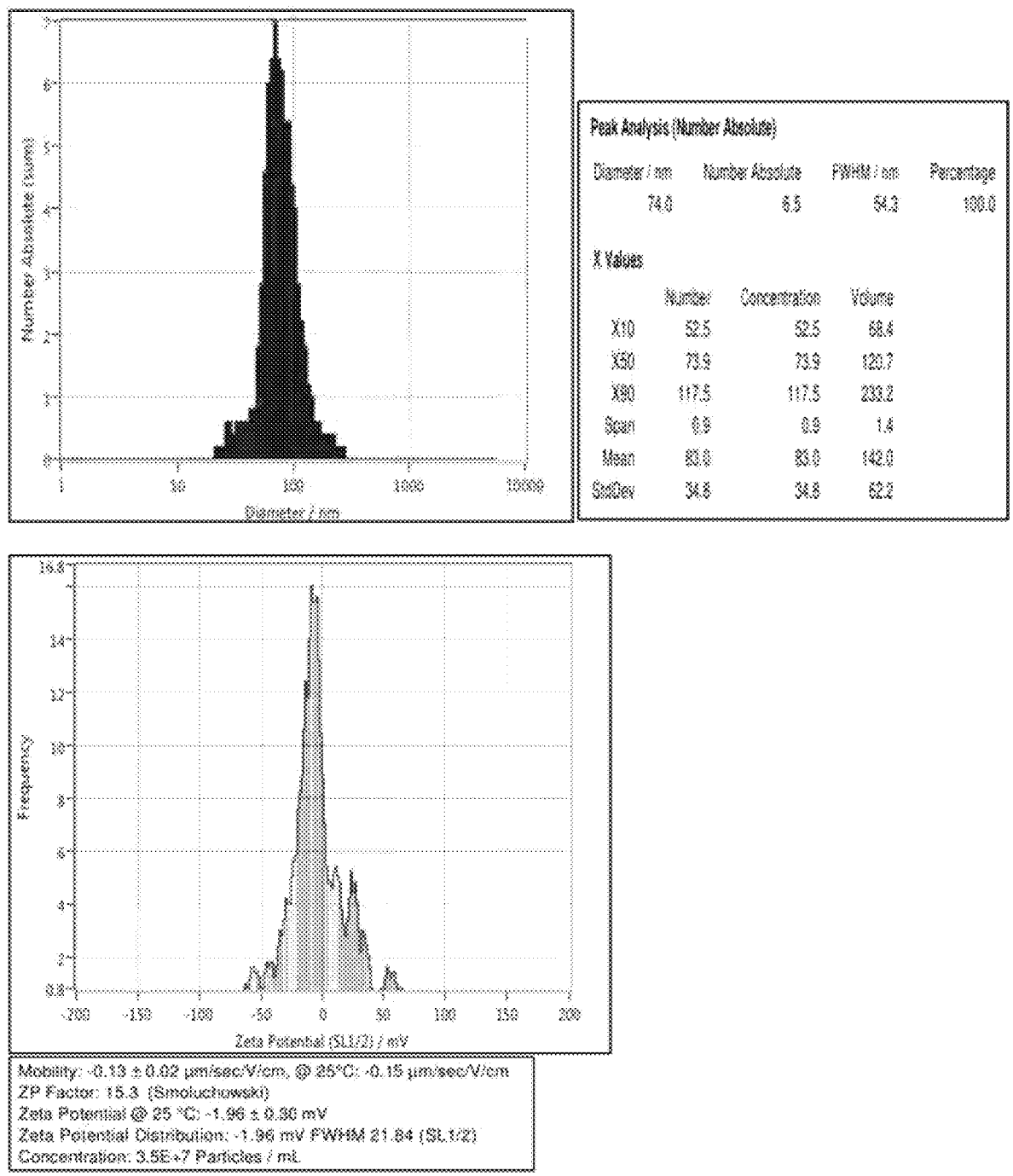
Figure 51 TCELL.001.16.MRNA1 Poly(L-Arginine) n=10

Figure 52   TCELL.001.18.MRNA2
Targeting Ligand - CD45_mSiglec_(4GS)2_9R_C
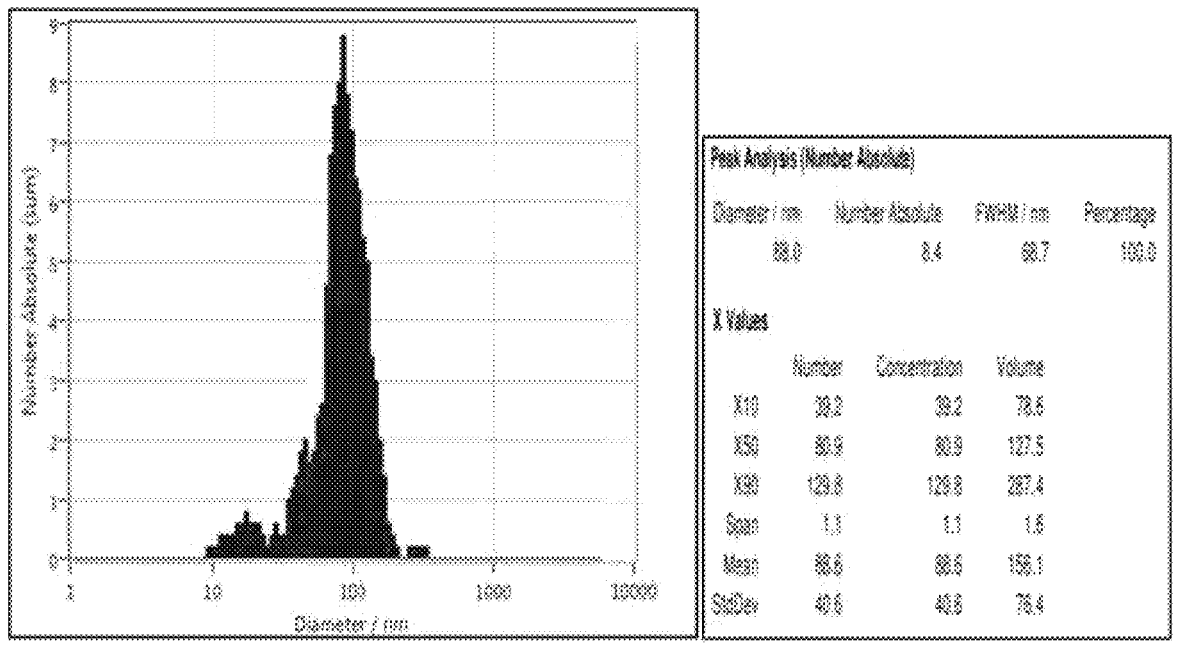
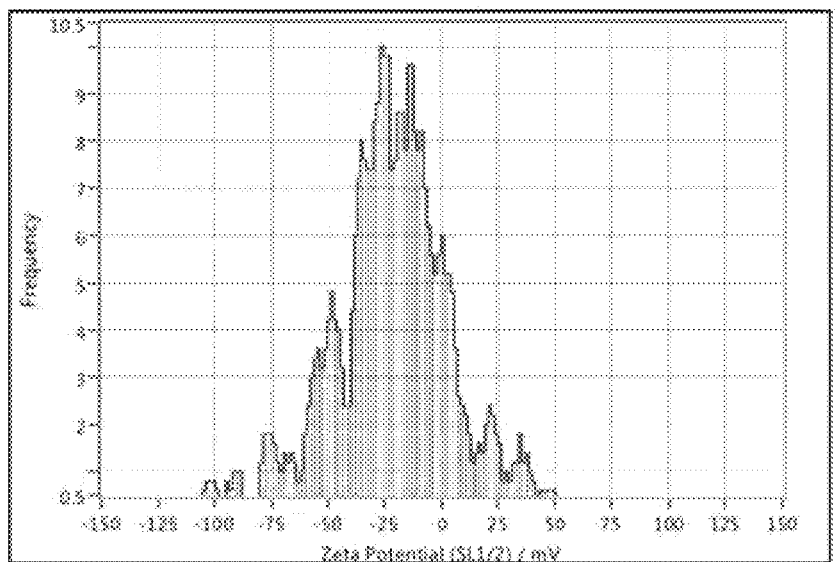
Mobility: -1.36 ± 0.01 µm/sec/V/cm, @ 25°C: -1.58 µm/sec/V/cm
ZP Factor: 14.9 (Smoluchowski)
Zeta Potential @ 25 °C: -20.26 ± 0.15 mV
Zeta Potential Distribution: -20.26 mV FWHM 20.45 (SL1/2)
Concentration: 2.0E+7 Particles / mL

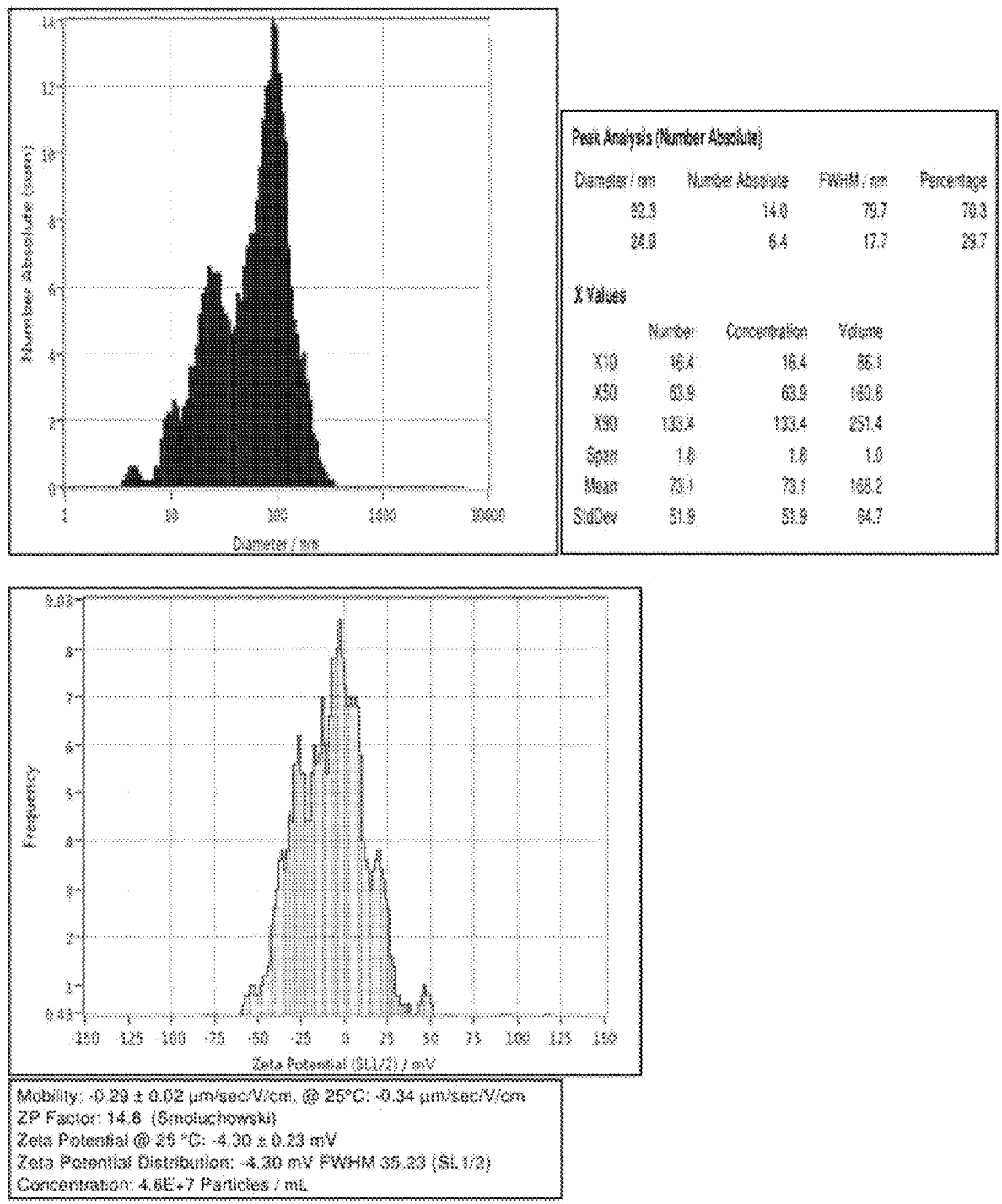
Figure 53  TCELL.001.28.MRNA12
Targeting Ligand - IL2R_mIL2_(4GS)2_9R_N Figure 54  TCELL.001.29.MRNA13
Targeting Ligand - IL2R_mIL2_(4GS)2_9R_C
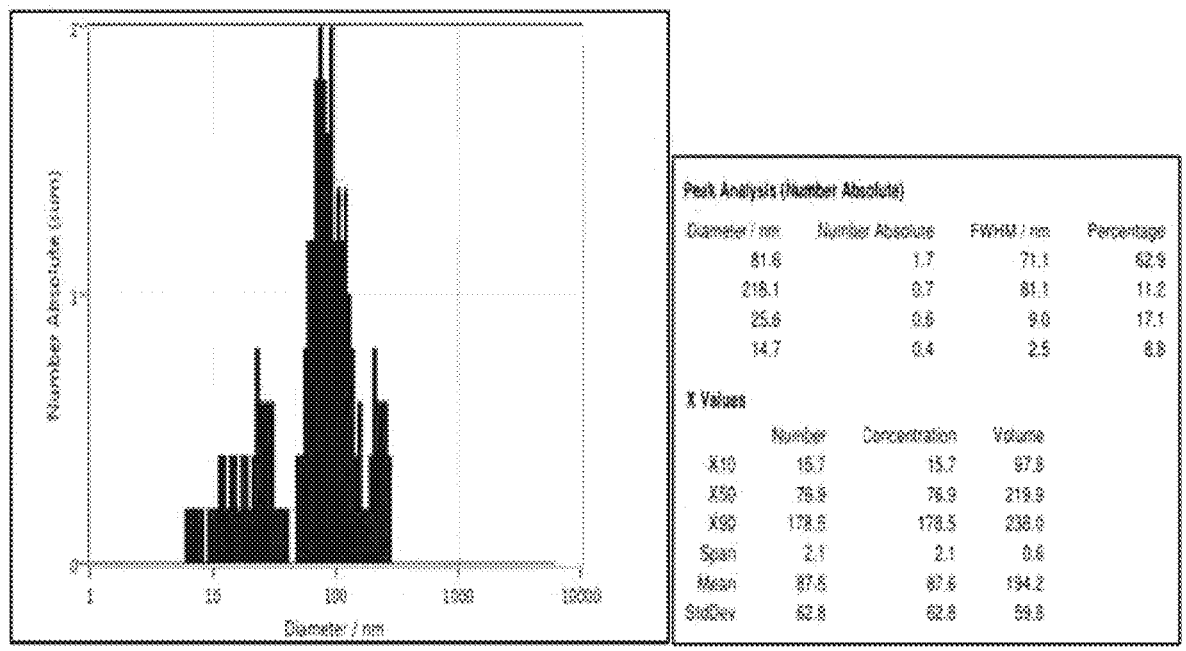
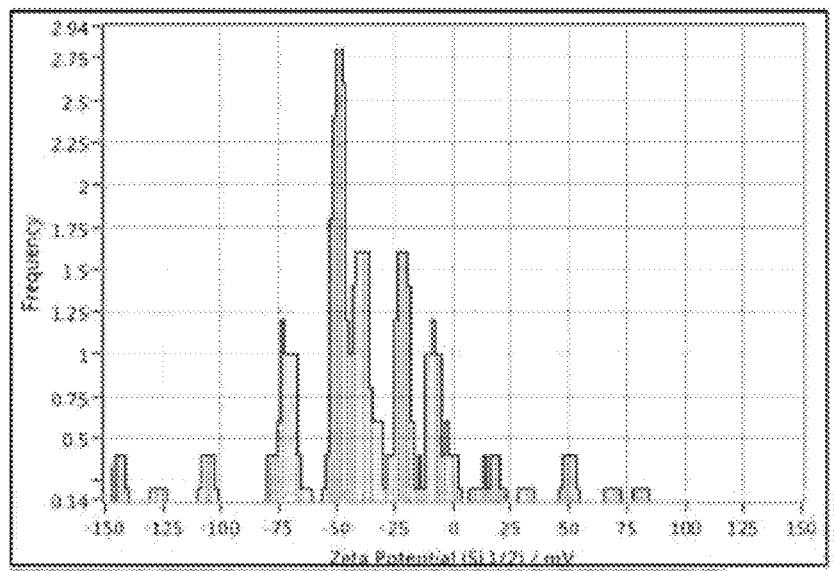

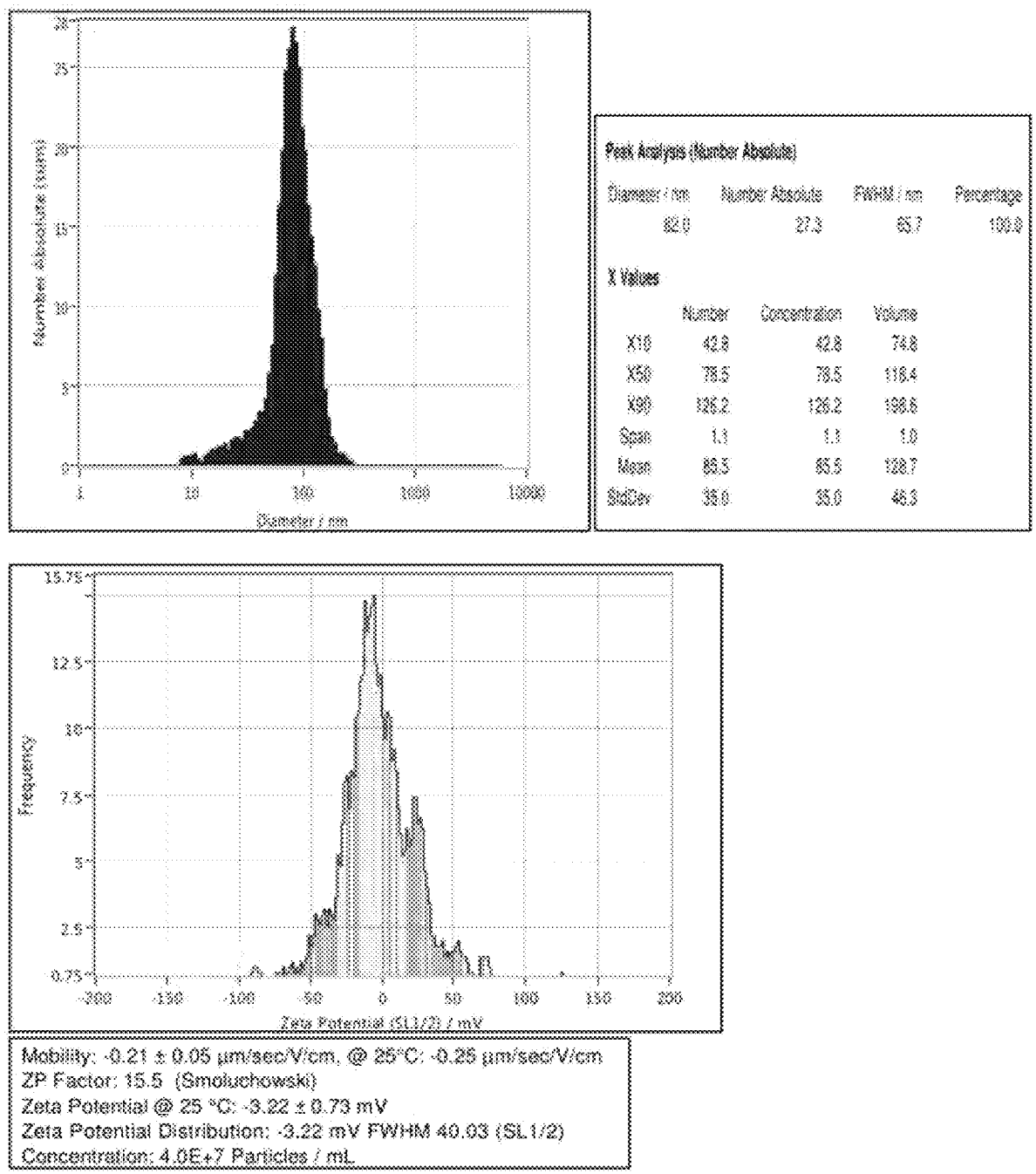
Figure 55  TCELL.001.31.PDNA1
Poly(L-Arginine) n=10

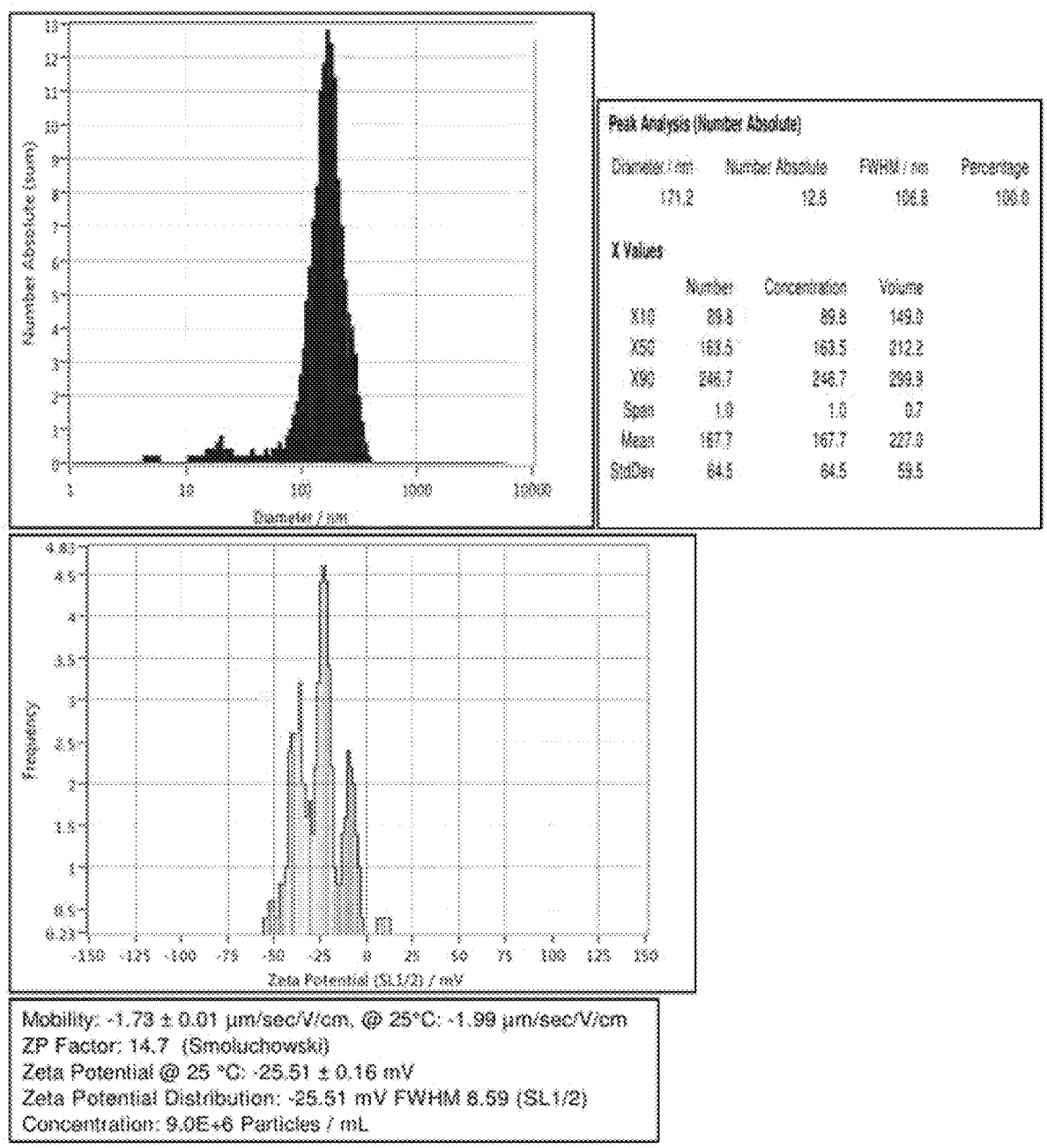
Figure 56 TCELL.001.33.PDNA2
Targeting Ligand - CD45_mSiglec_(4GS)2_9R_C

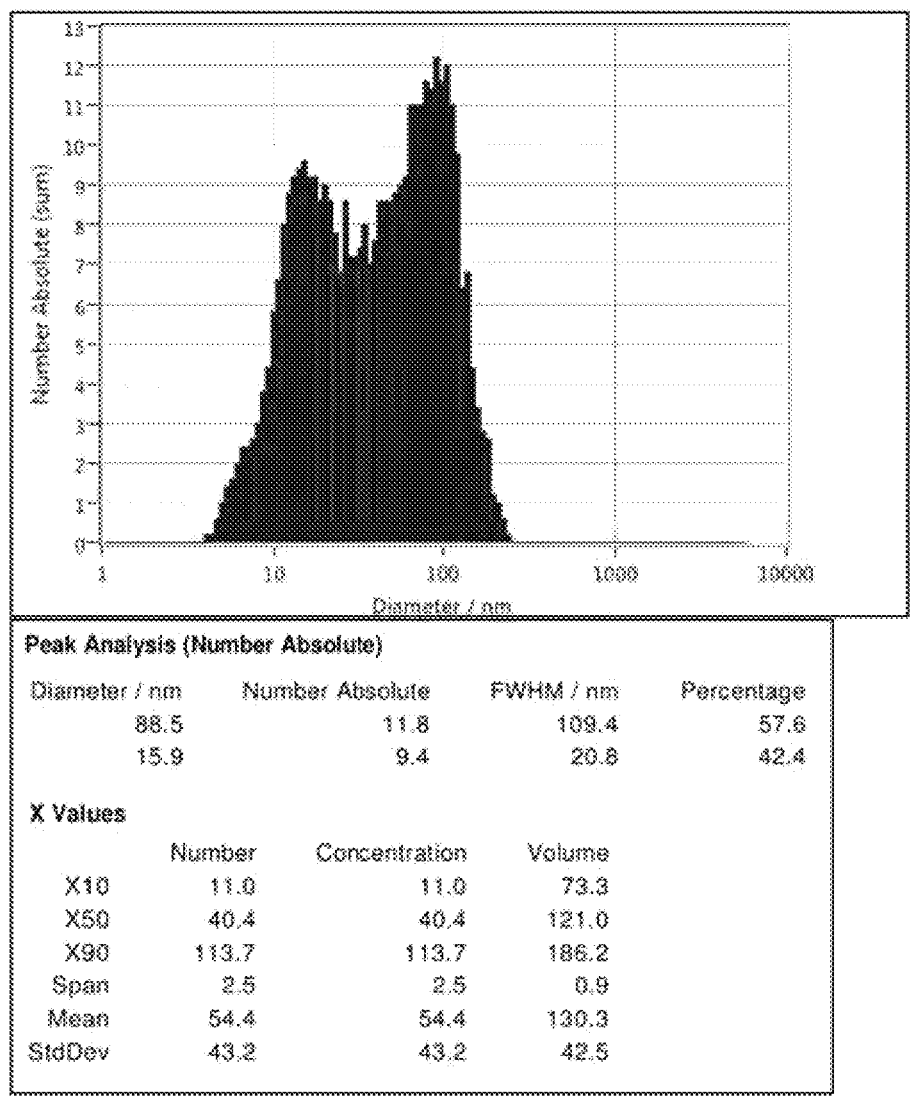
Figure 57 TCELL_001.43.pDNA12
Targeting Ligand - IL2R_mIL2_(4GS)2_9R_N

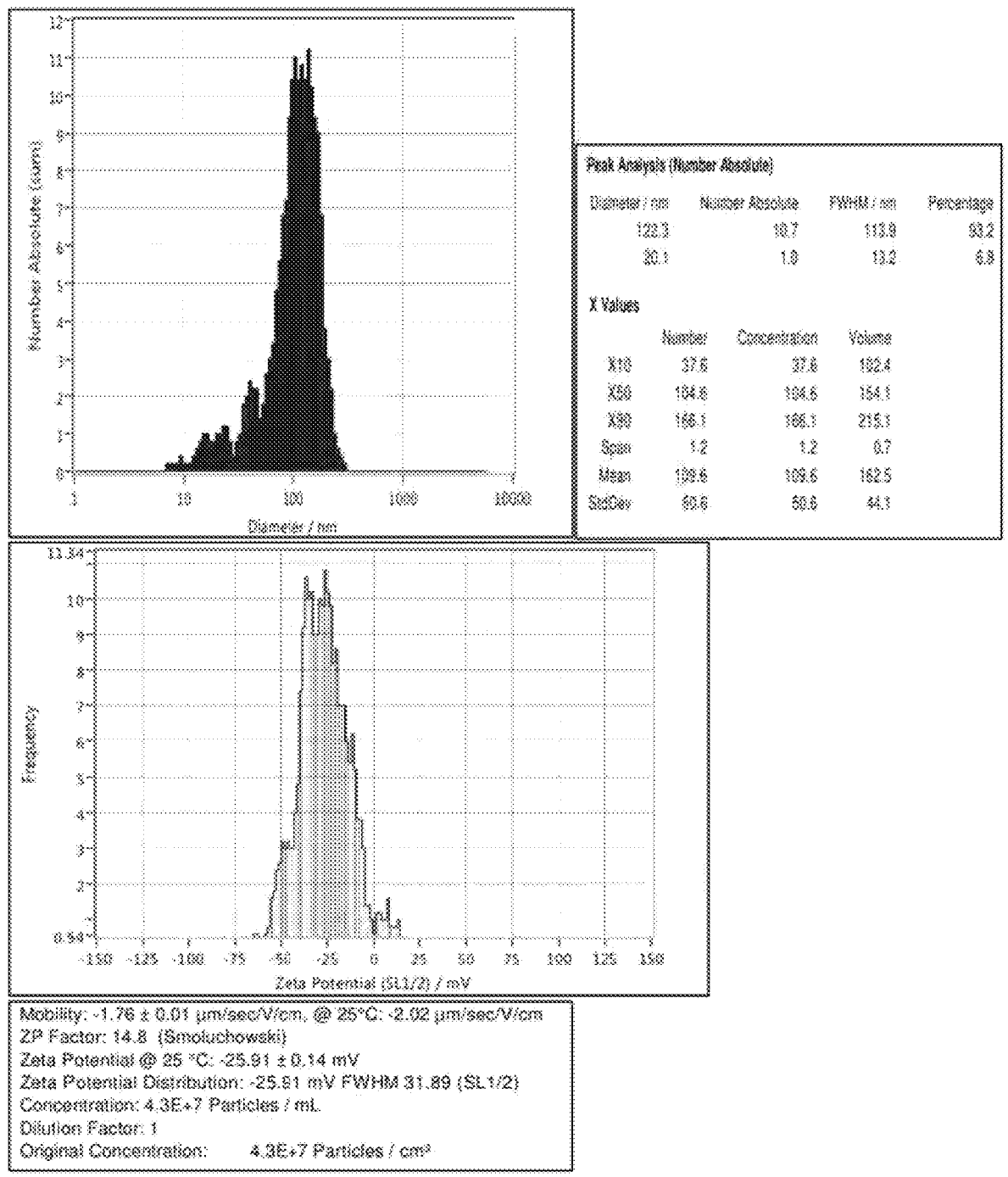
Figure 58  TCELL.001.44.pDNA13
Targeting Ligand - IL2R_mIL2_(4GS)2_9R_C Figure 59 TCELL.001.46.SIRNA1
Poly(L-Arginine) n=10
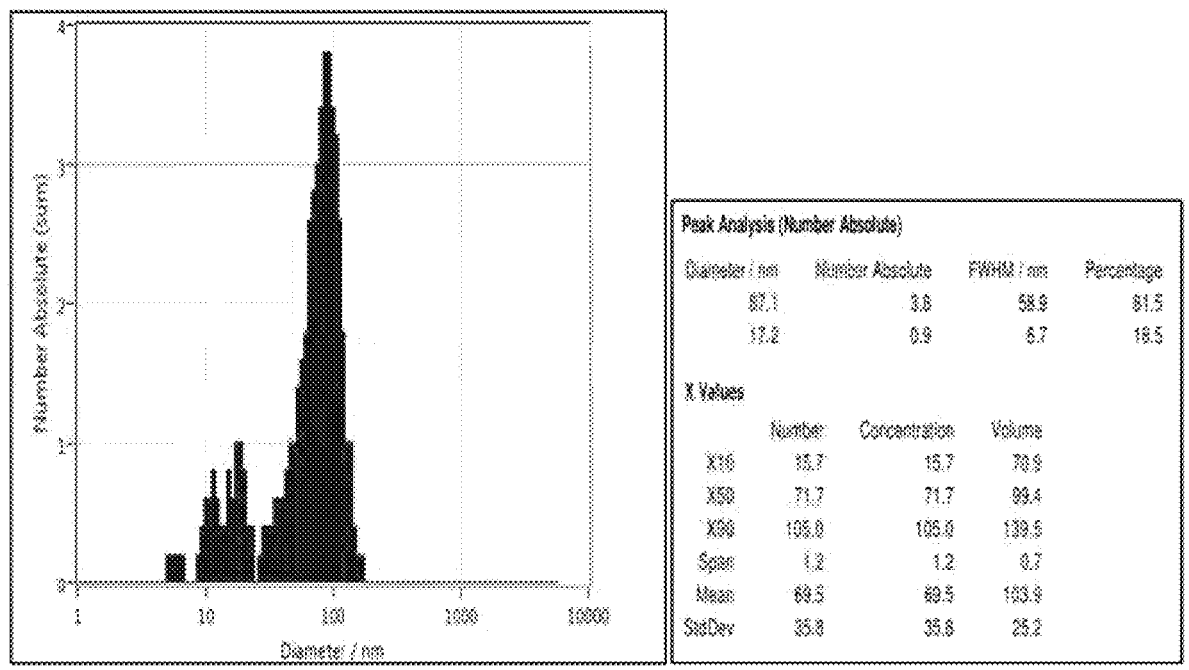
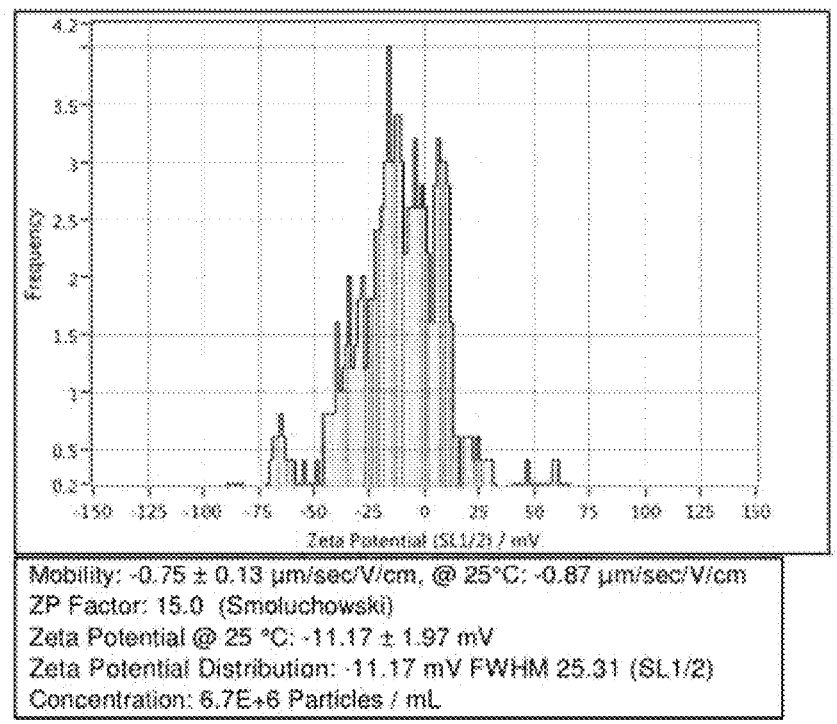
Mobility: -0.75 ± 0.13 μm/sec/V/cm, @ 25°C; -0.87 μm/sec/V/cm
ZP Factor: 15.0 (Smoluchowski)
Zeta Potential @ 25 °C: -11.17 ± 1.97 mV
Zeta Potential Distribution: -11.17 mV FWHM 25.31 (SL1/2)
Concentration: 6.7E+6 Particles / mL

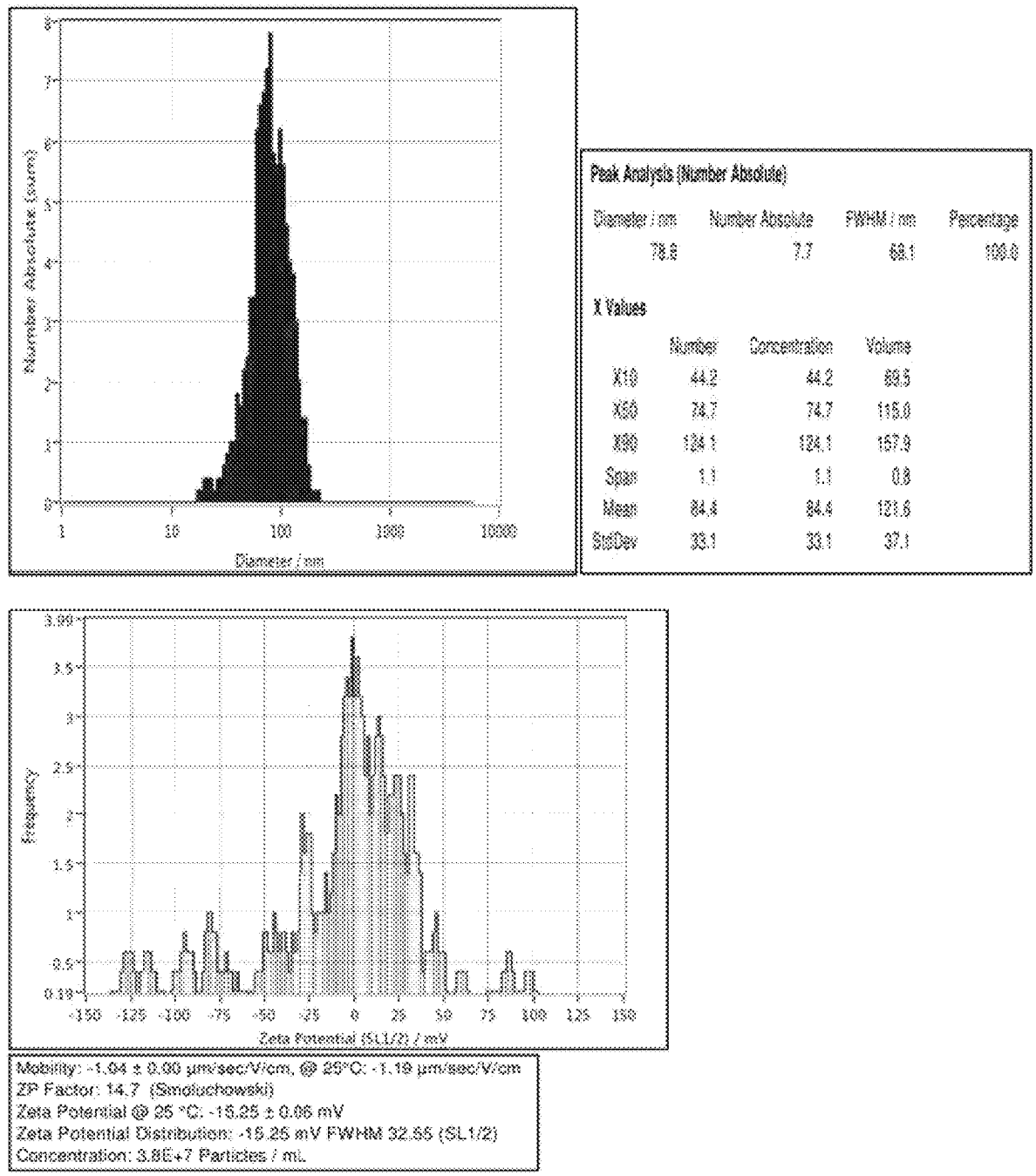
Figure 60 TCELL.001.48.SIRNA2
Targeting Ligand - CD45_mSiglec_(4GS)2_9R_C Figure 61 TCELL.001.58
Targeting Ligand - IL2R_mIL2_(4GS)2_9R_N
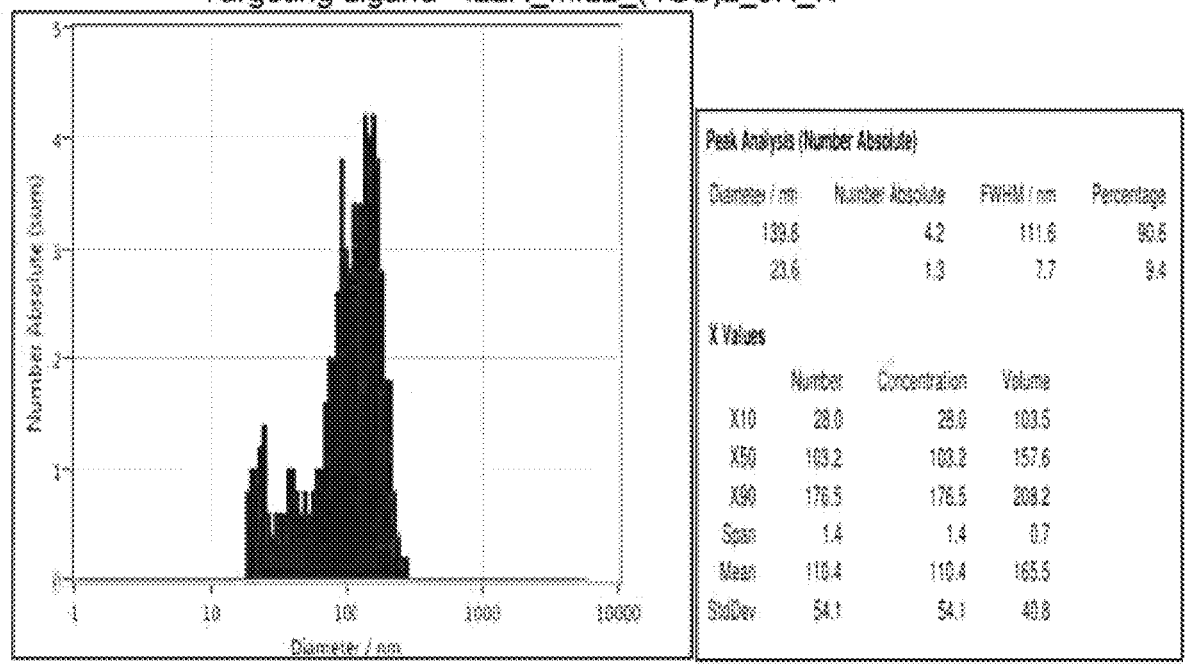
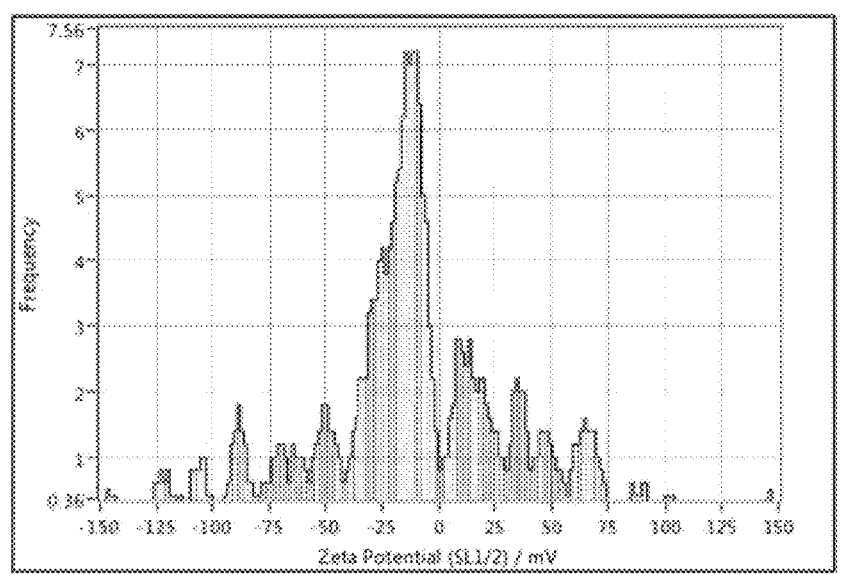
Mobility: -0.68 ± 0.01 µm/sec/V/cm, @ 25°C: -0.79 µm/sec/V/cm
ZP Factor: 14.9 (Smoluchowski)
Zeta Potential @ 25 °C: -10.09 ± 0.12 mV
Zeta Potential Distribution: -10.09 mV FWHM 21.02 (SL1/2)
Concentration: 1.6E+7 Particles / mL

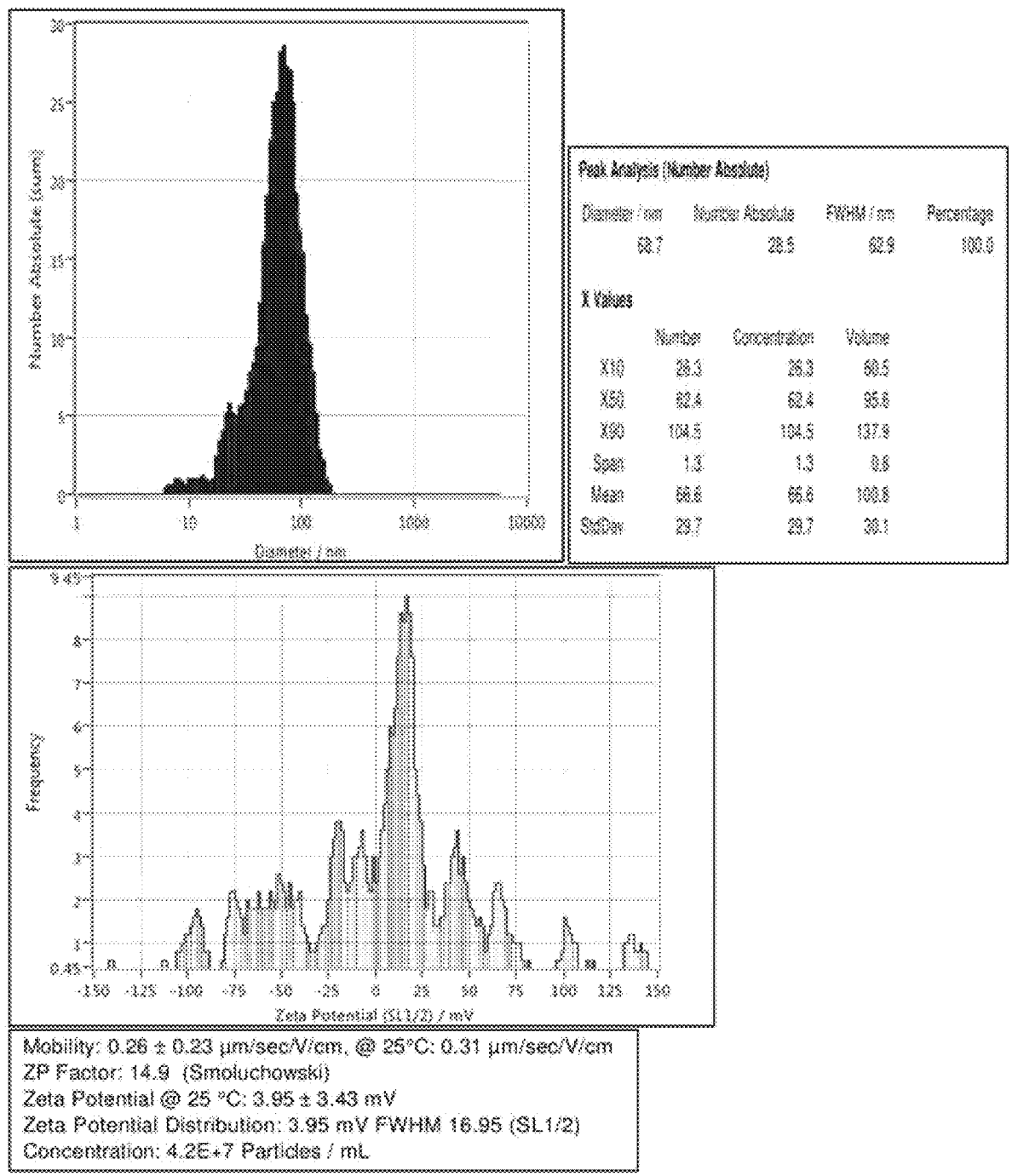
Figure 62  TCELL.001.59
Targeting Ligand - IL2R_mIL2_(4GS)2_9R_C

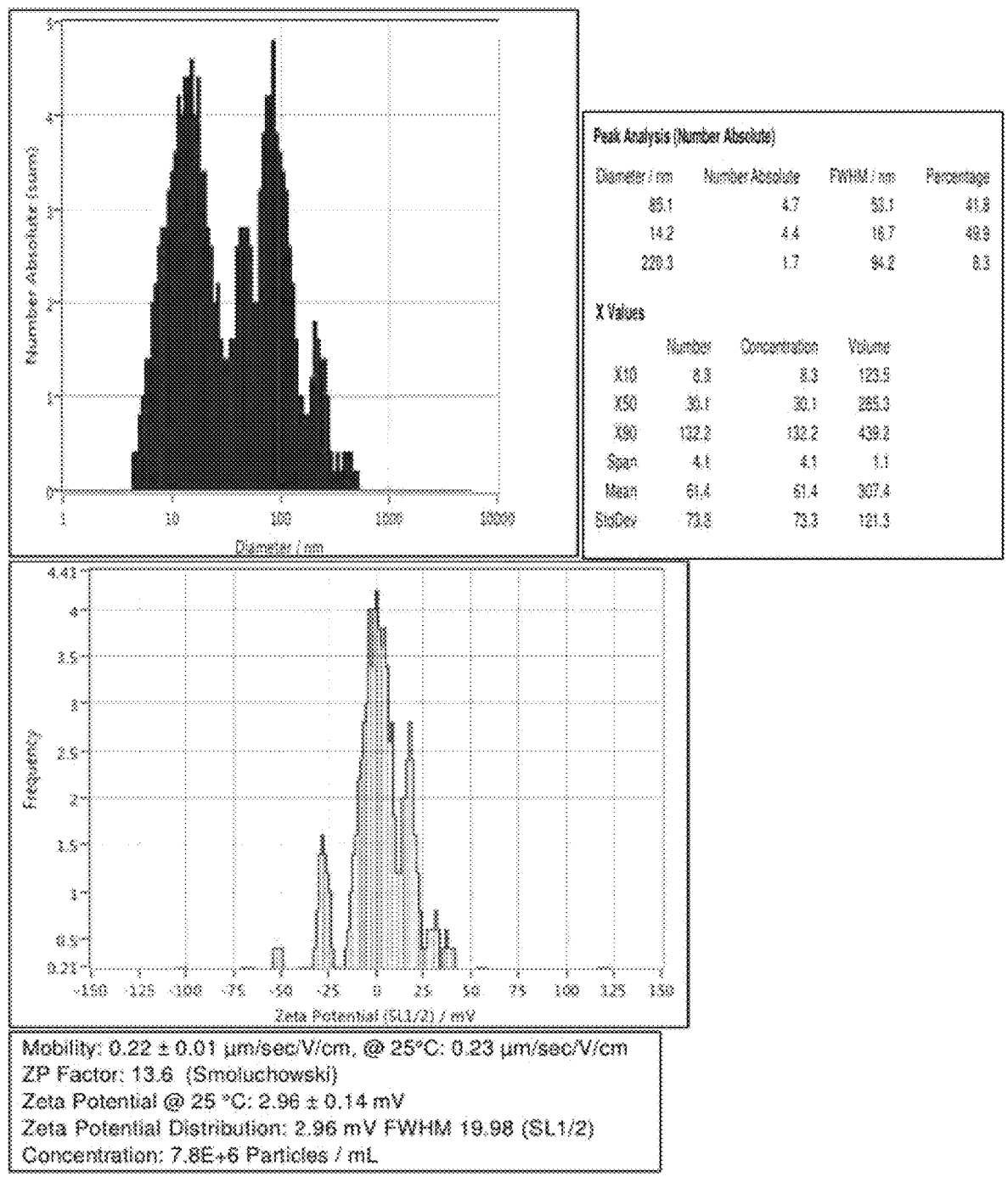
Figure 63. CYNOBM.002.82 Poly(L-Arginine) n=50

Figure 64 CYNOBM.002.83
Targeting Ligand - IL2R_mIL2_(4GS)2_9R_N
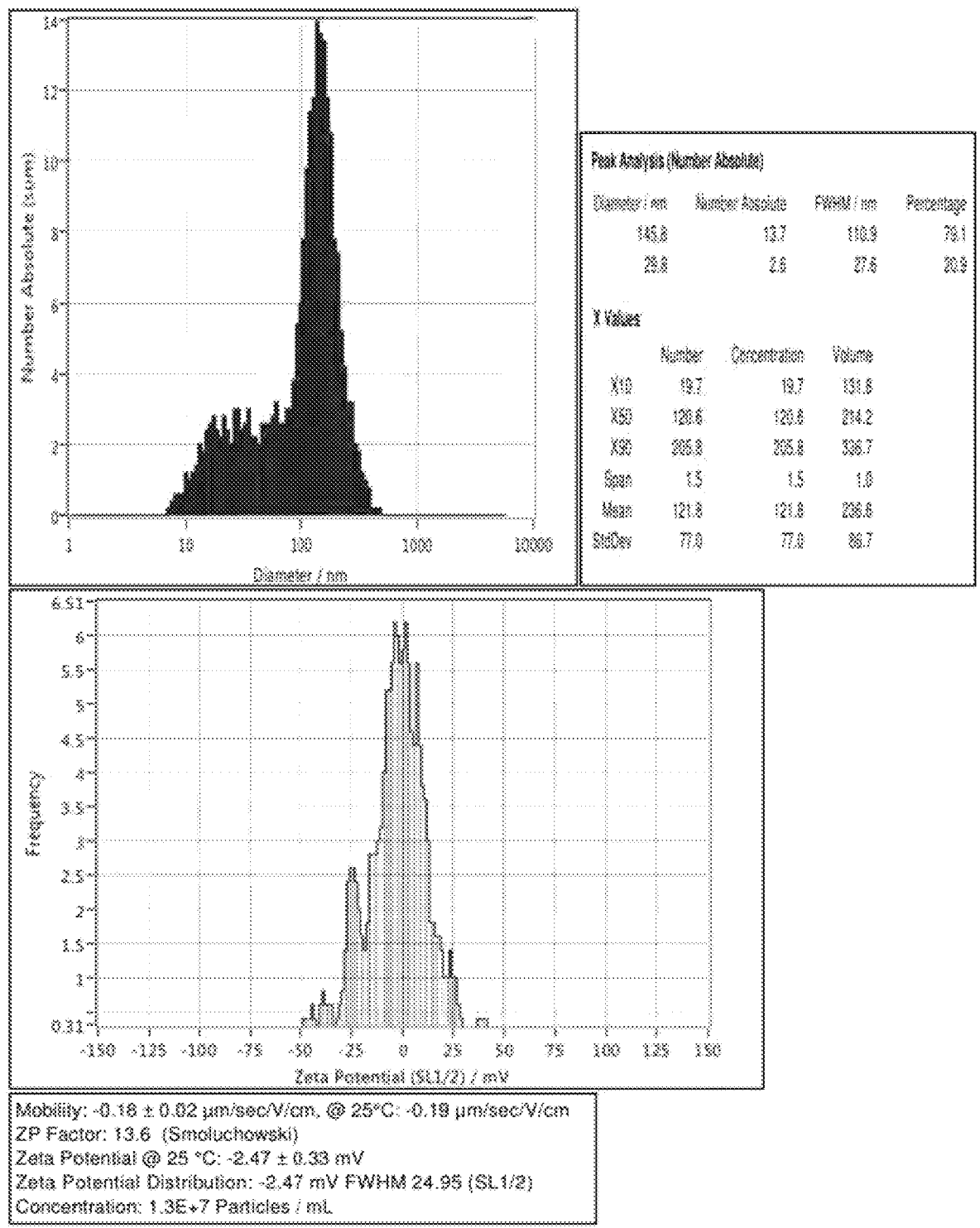

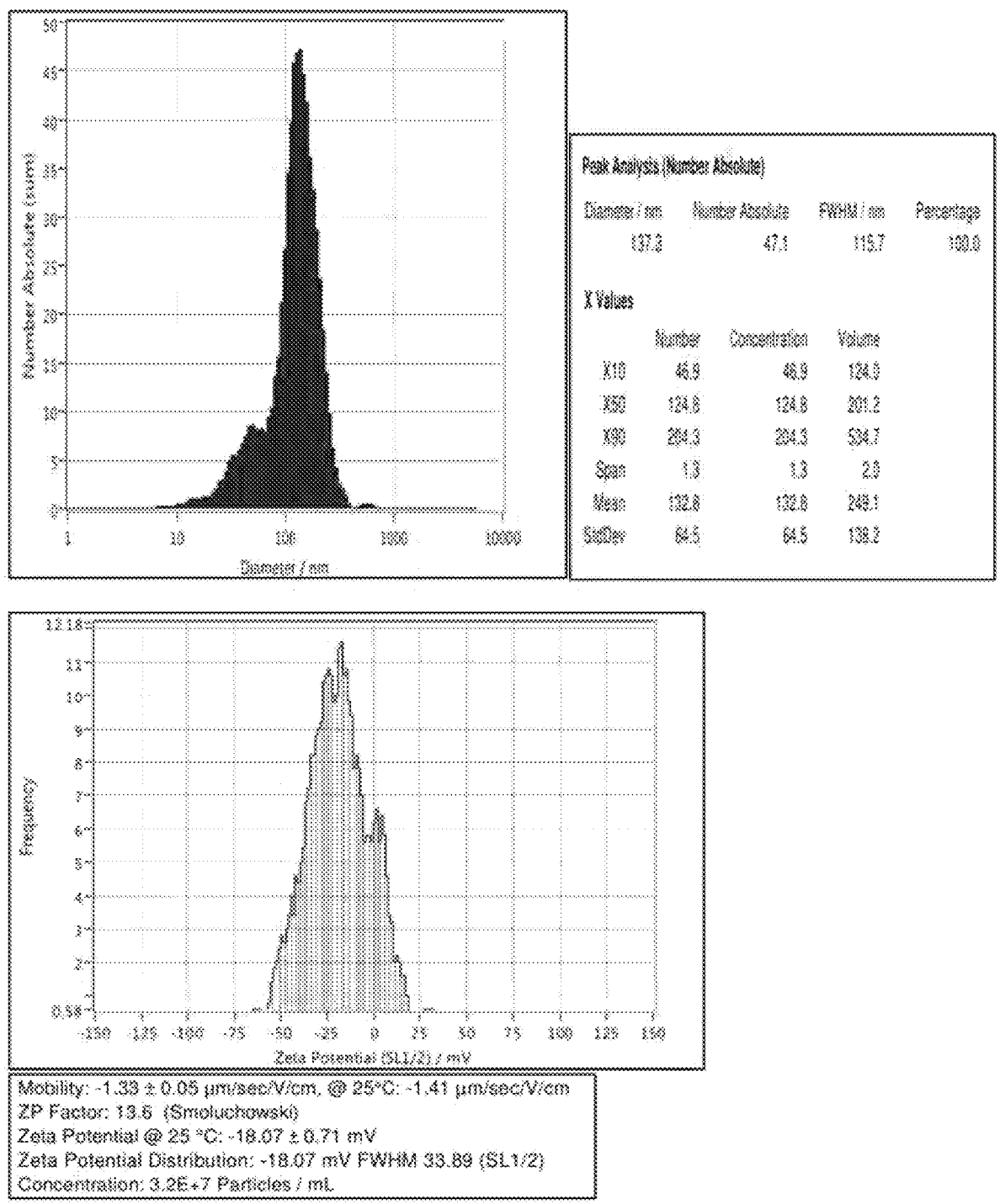
Figure 65 CYNOBM.002.84
Targeting Ligand - ESELLg_mESEL_(4GS)2_9R_N

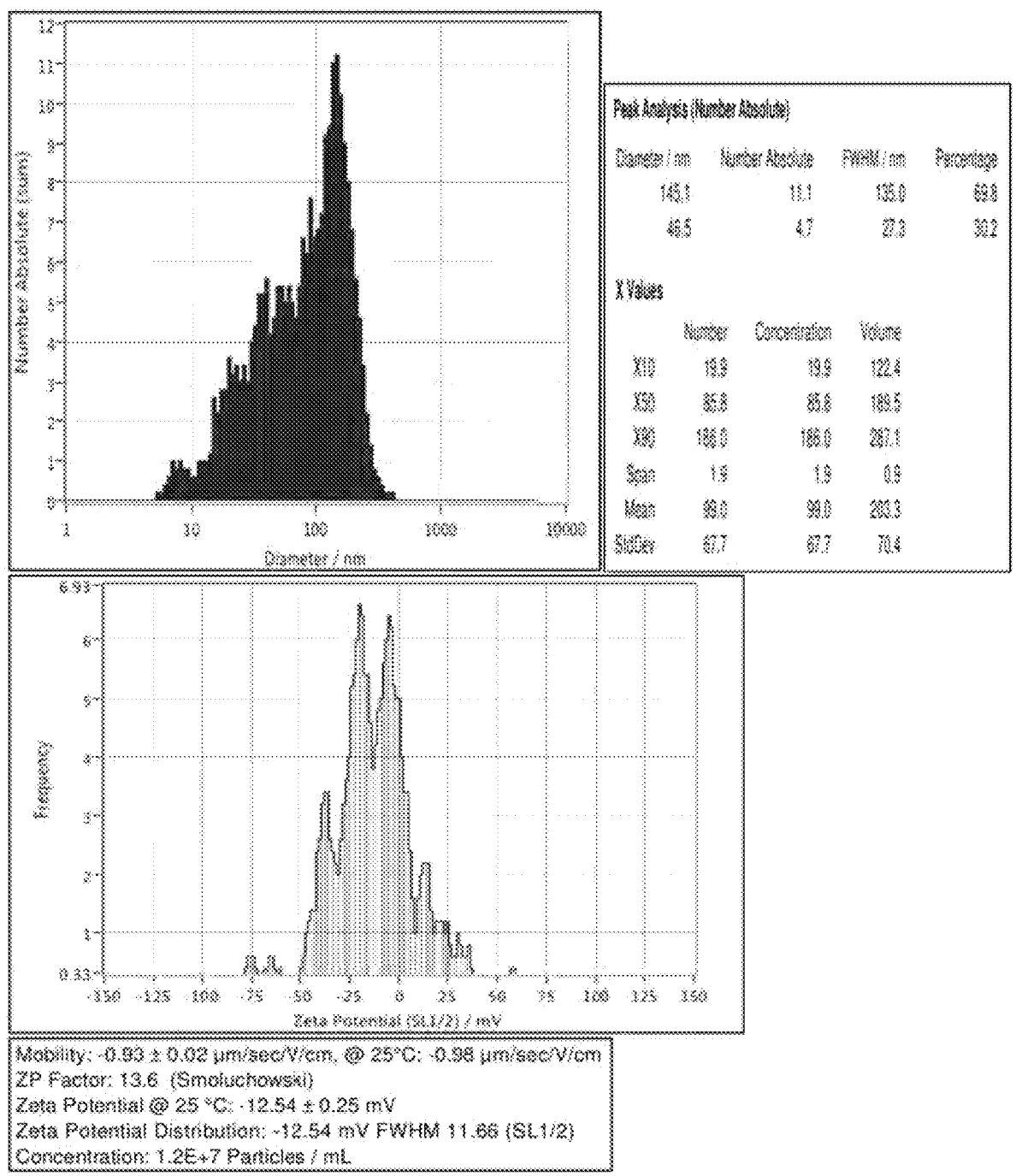
Figure 66  CYNOBM.002.85
Targeting Ligand - cKit_mSCF_(4GS)2_9R_N

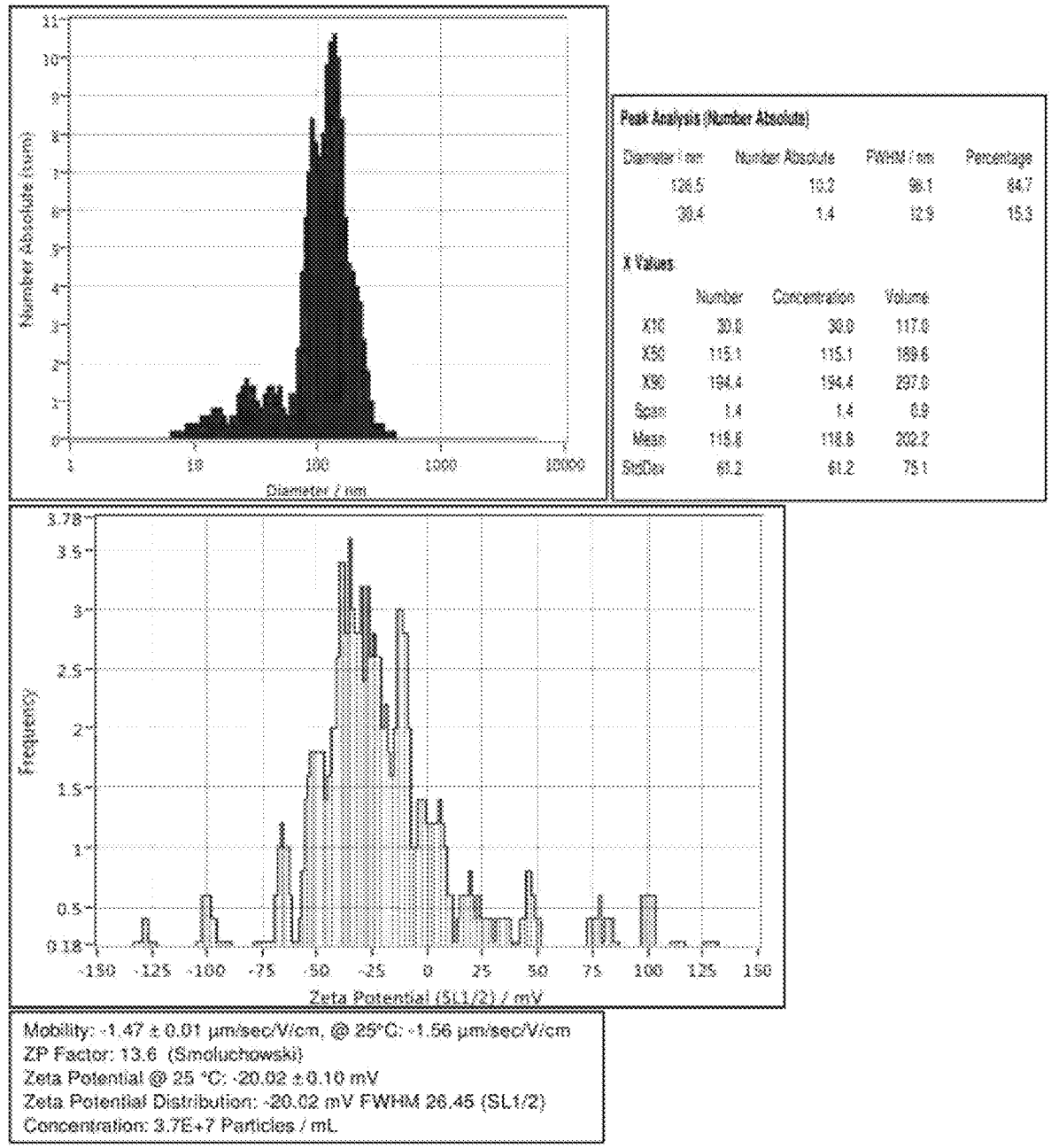
Figure 67 CYNOBM.002.86
Targeting Ligands - IL2R_mIL2_(4GS)2_9R_N, ESELLg_mESEL_(4GS)2_9R_N, cKit_mSCF_(4GS)2_9R_N Figure 68 CYNOBM.002.76
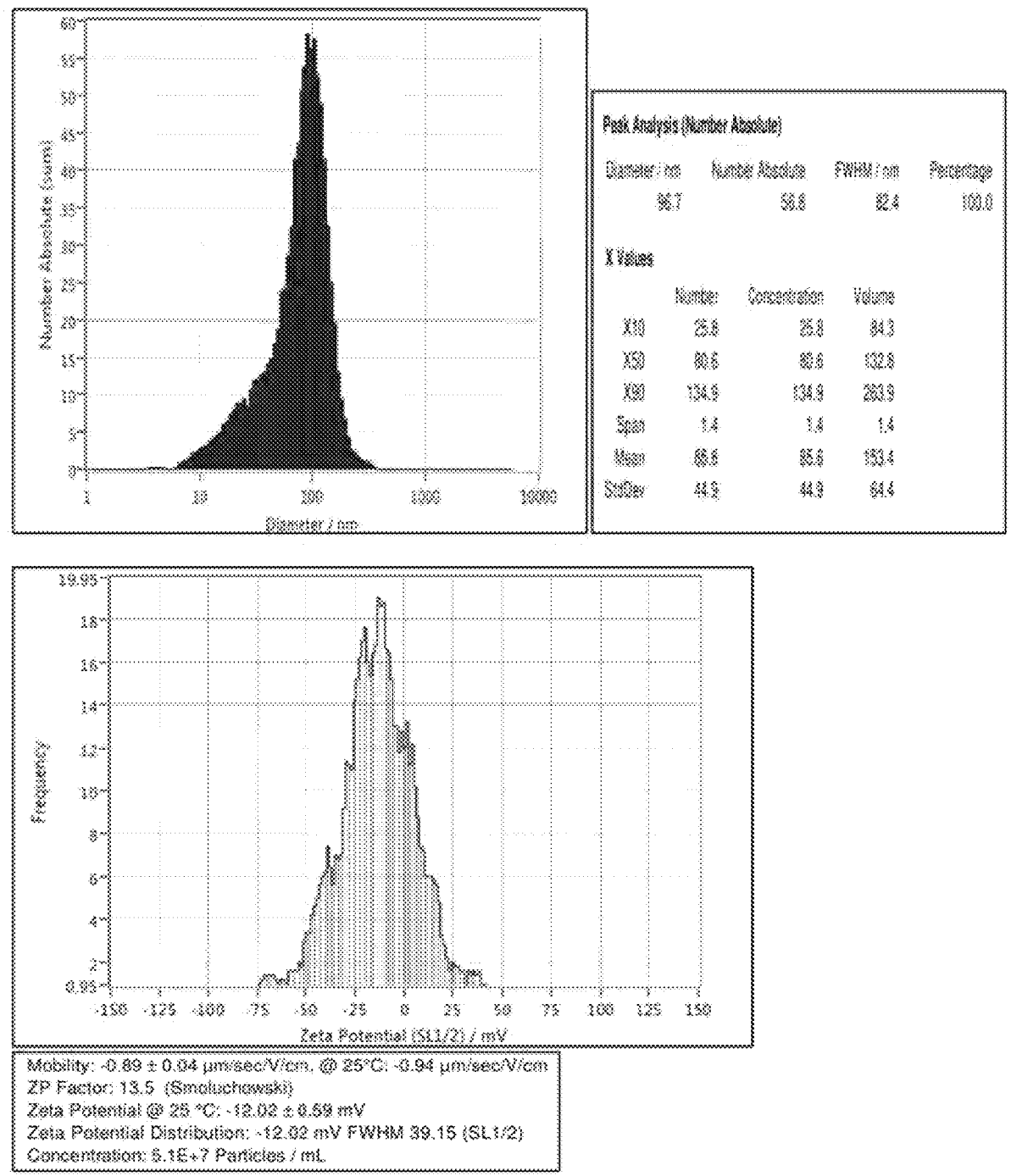

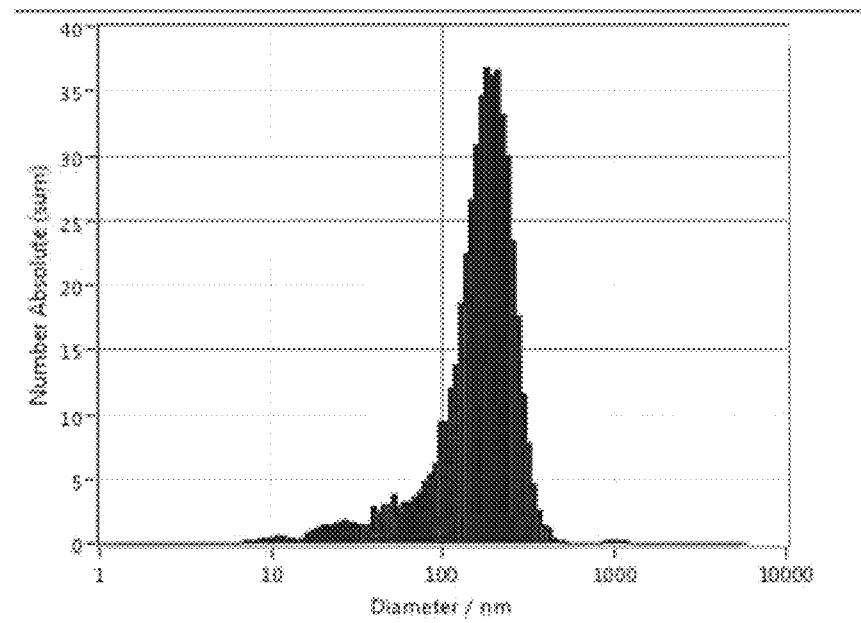
Figure 69 CYNOBM.002.77 Targeting Ligand - IL2R_mIL2_(4GS)2_9R_N

Figure 70   CYNOBM.002.78
Targeting Ligand - ESELLg_mESEL_(4GS)2_9R_N
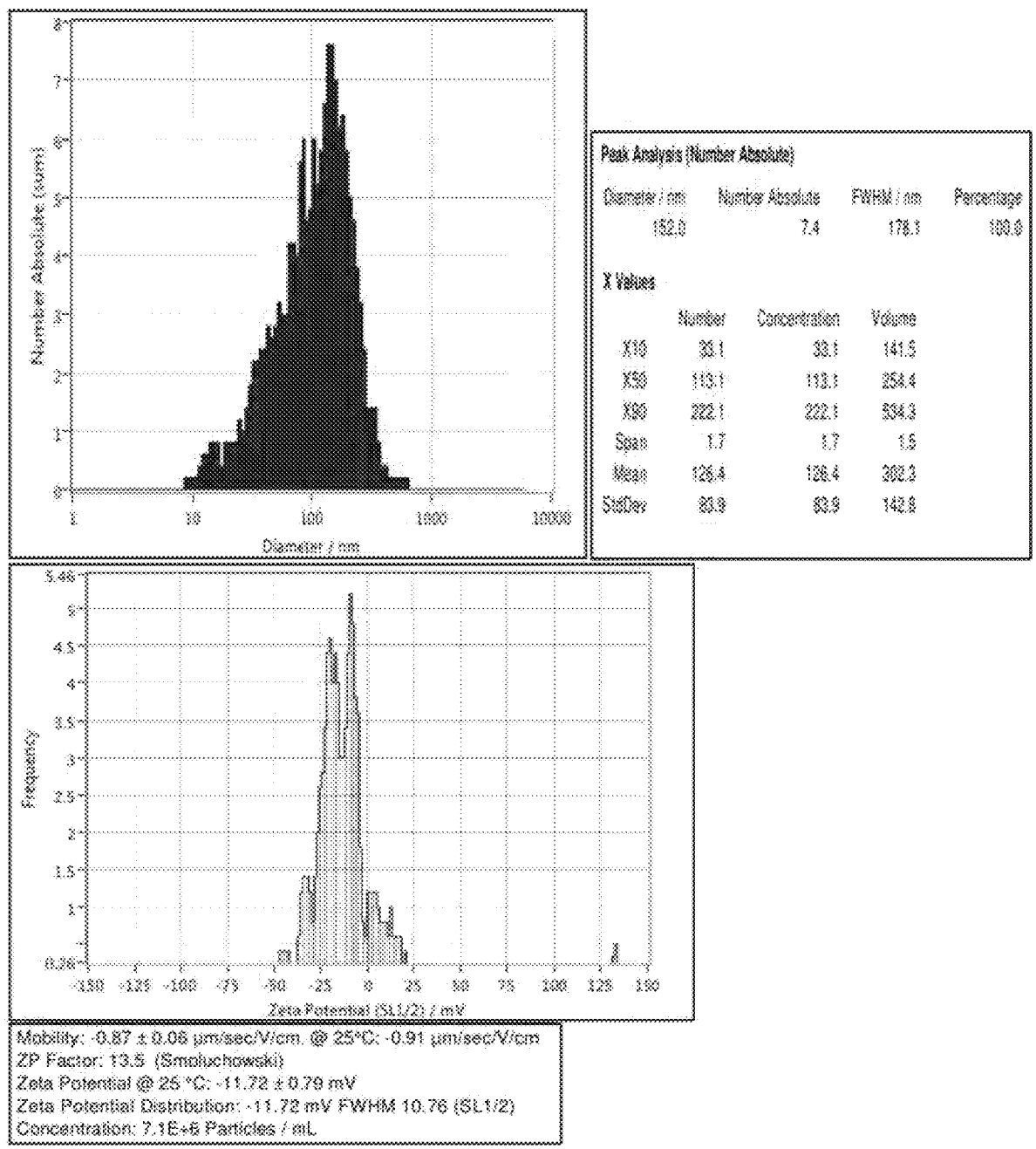

Figure 71   CYNOBM.002.79
            Targeting Ligand - SCF_mcKit_(4GS)2_9R_N
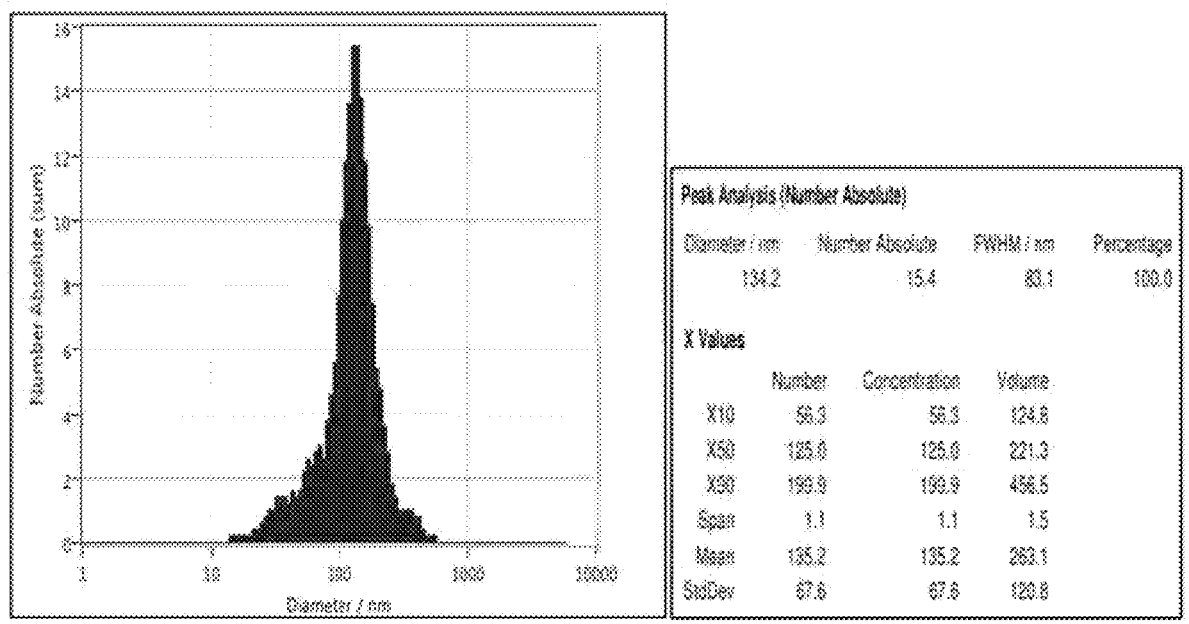
Figure 72   CYNOBM.002.80
            Targeting Ligand - cKit_mSCF_(4GS)2_9R_N
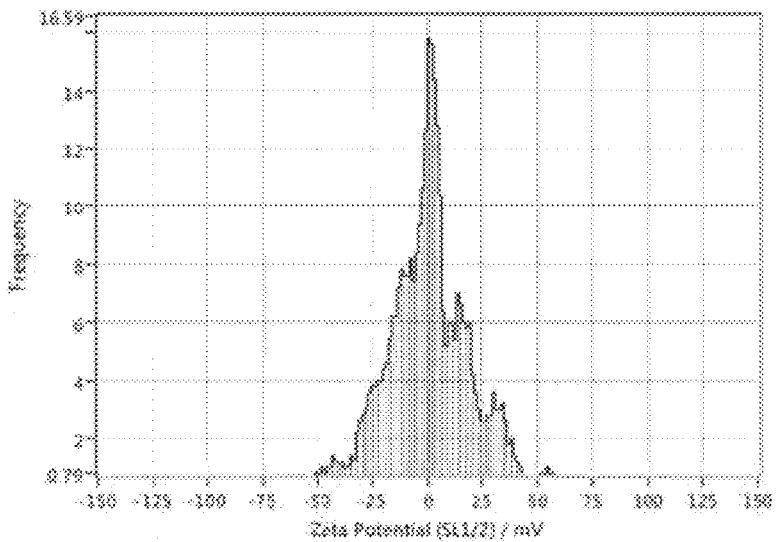

Figure 73 CynoBM.002 Untransfected Control
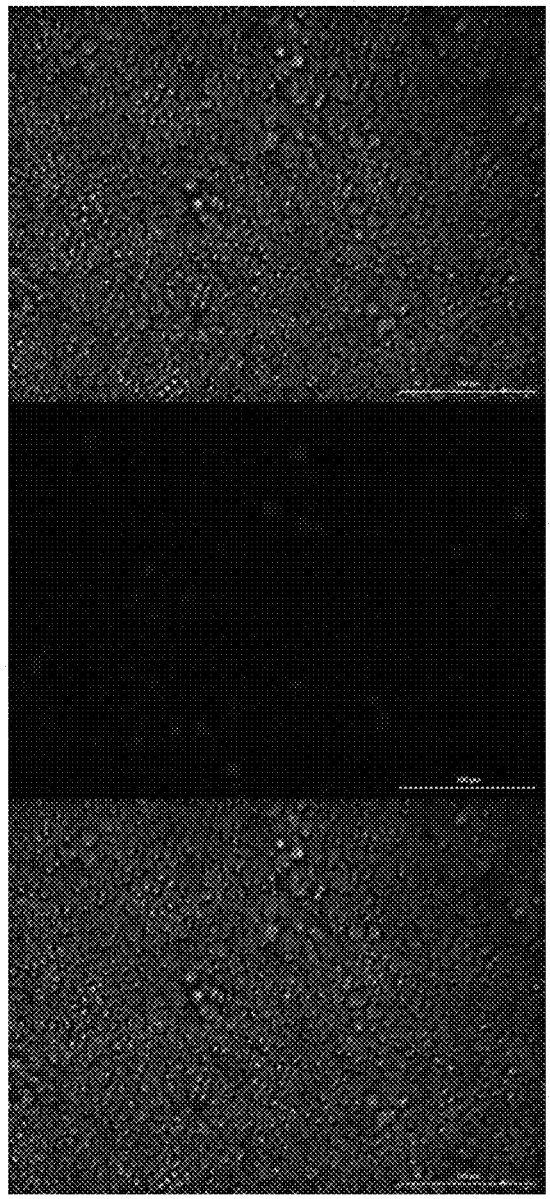

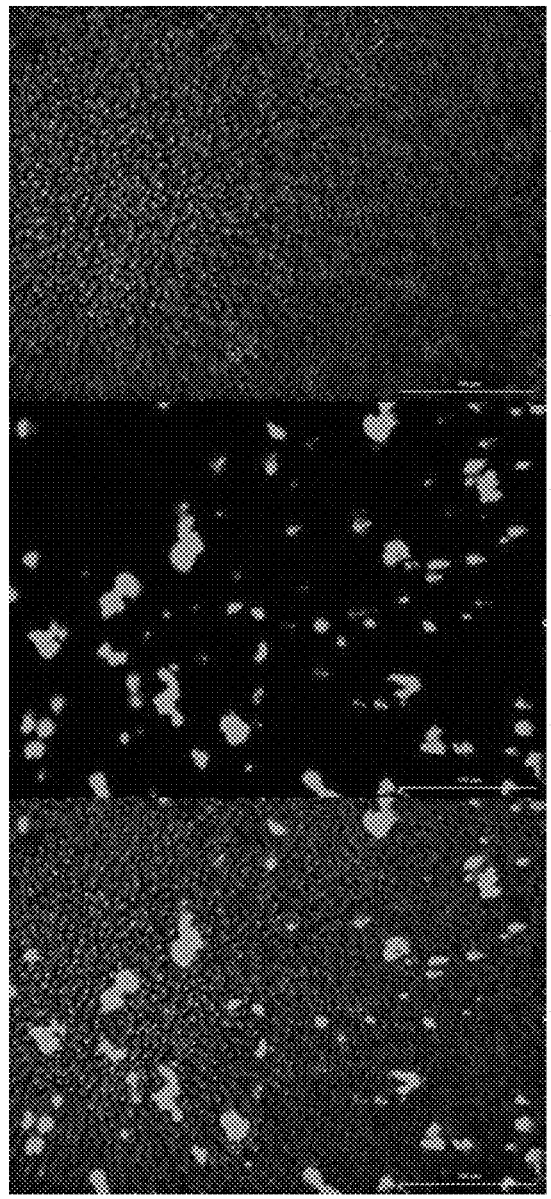
Figure 74CynoBM.002 Lipofectamine CRISPRMAX

Figure 75 CynoBM.002 EGFP-RNP & Cy5 mRNA Only
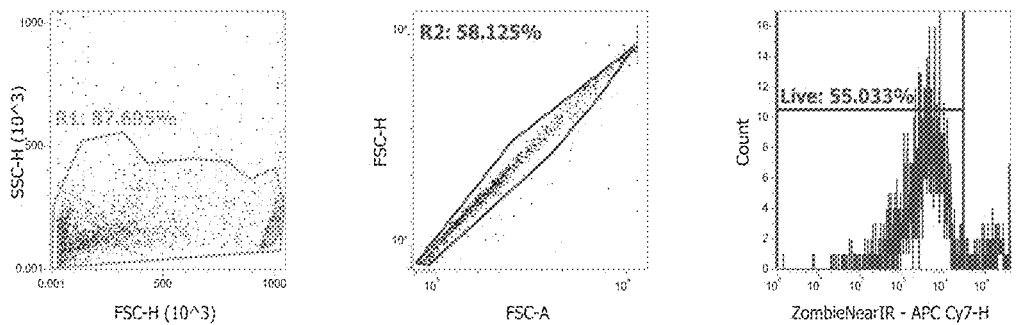
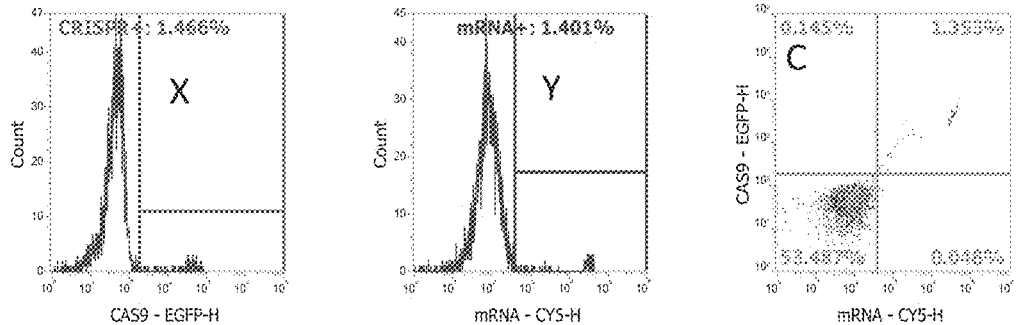
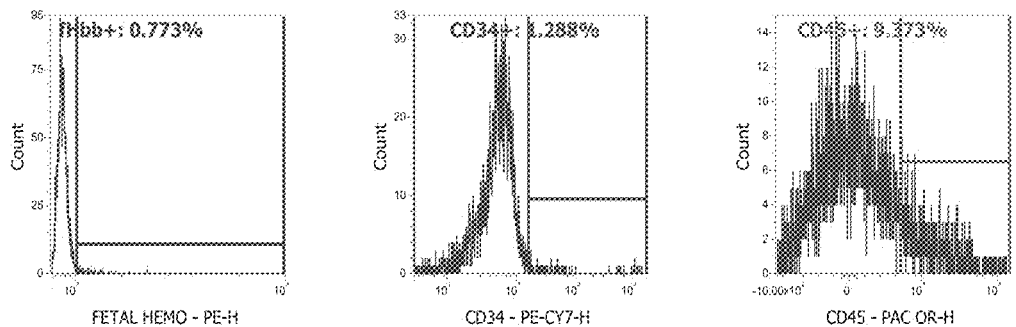
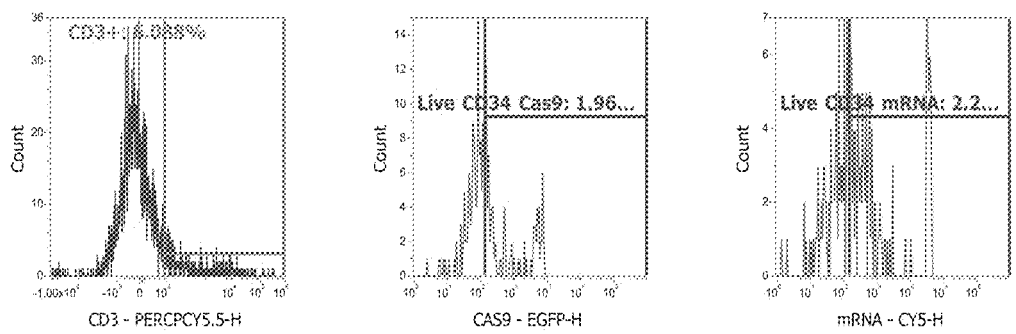

Figure 76   CynoBM.002.82
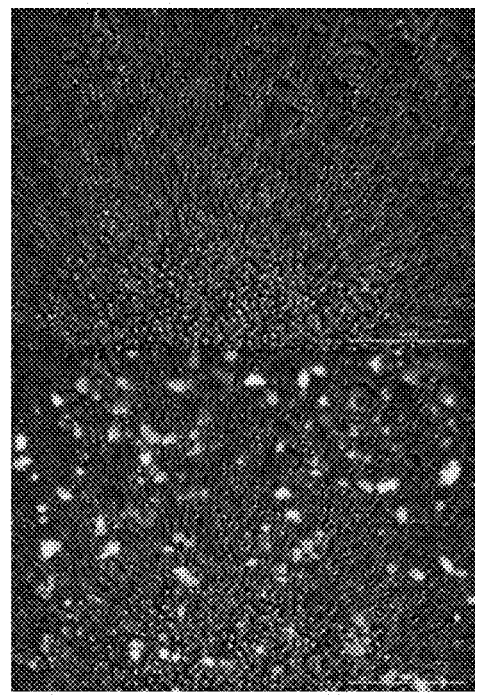

Figure 76 (cont. 1)
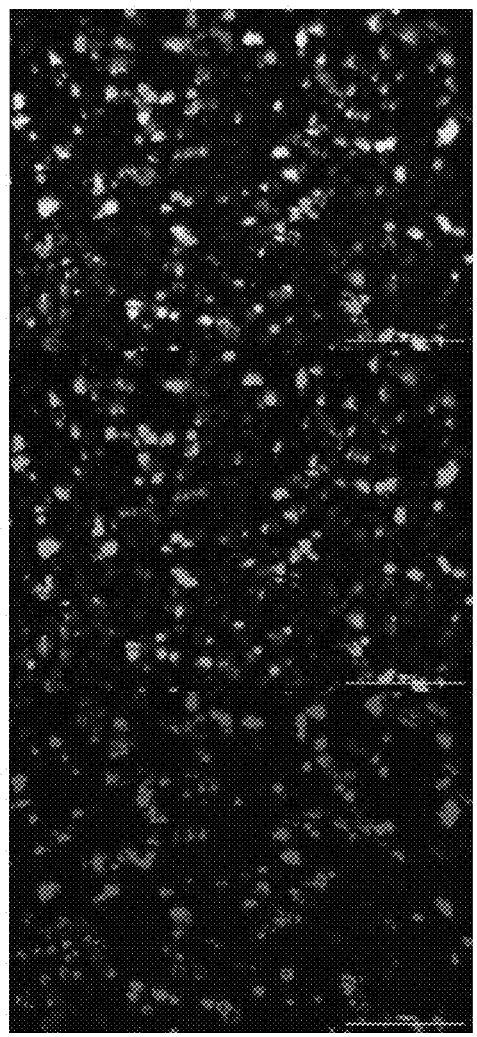

Figure 76 (cont. 2)
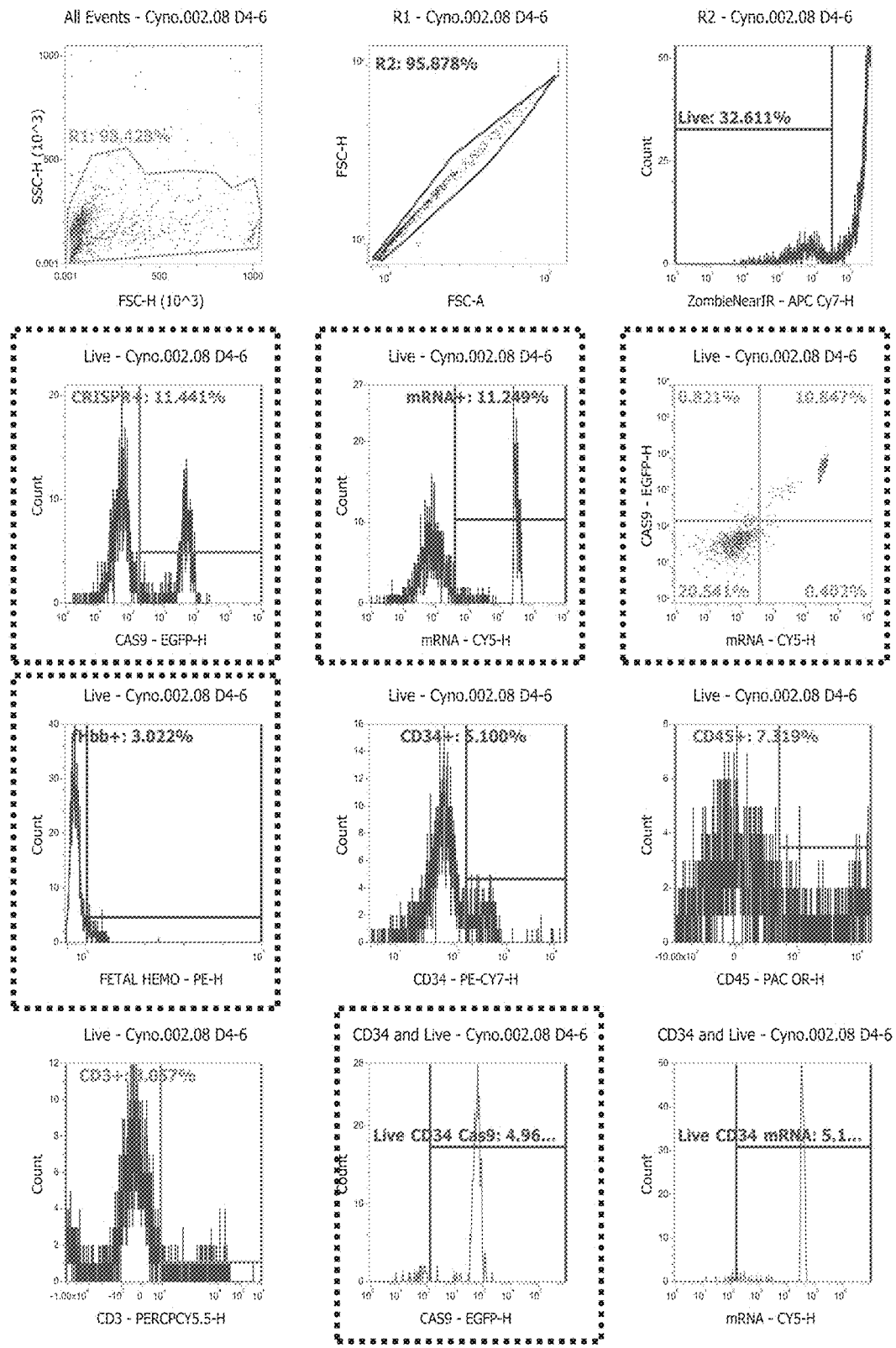

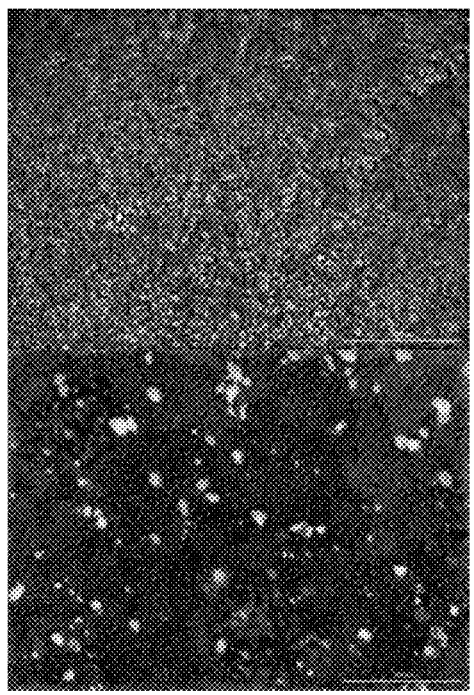
Figure 77 CynoBM.002.83

Figure 77 (cont. 1)
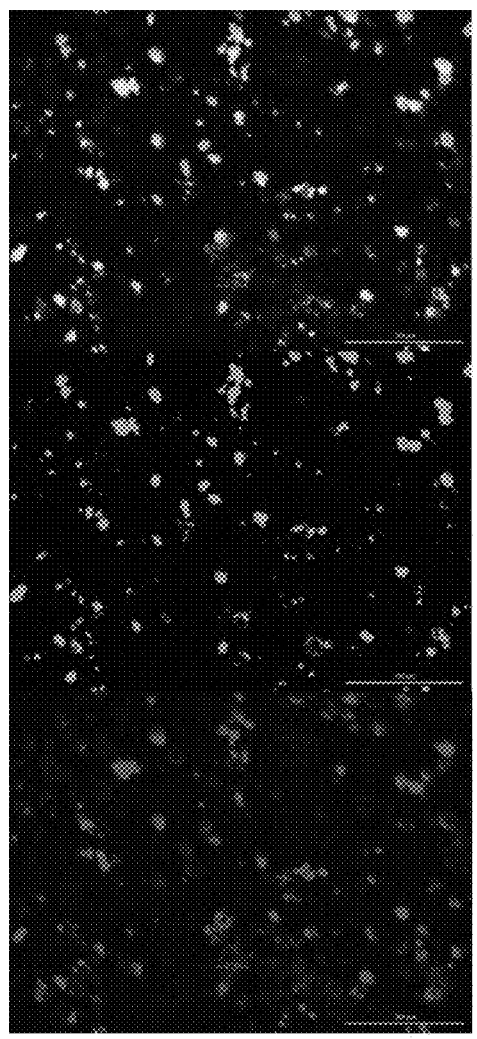

Figure 77 (cont. 2)
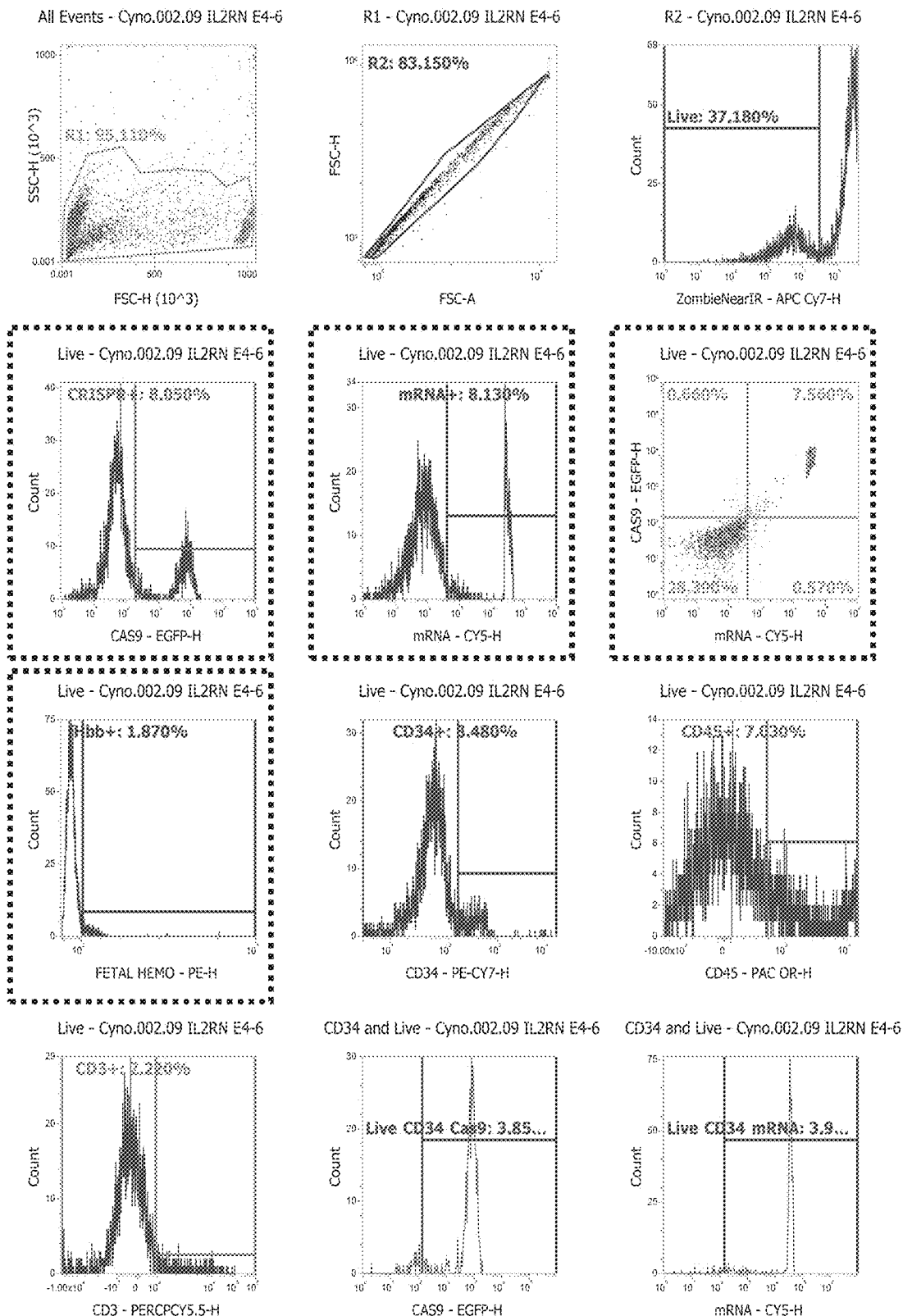

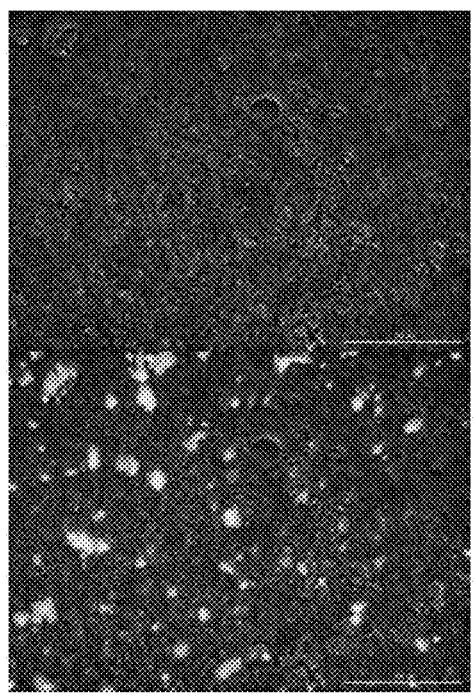
Figure 78  CynoBM.002.84

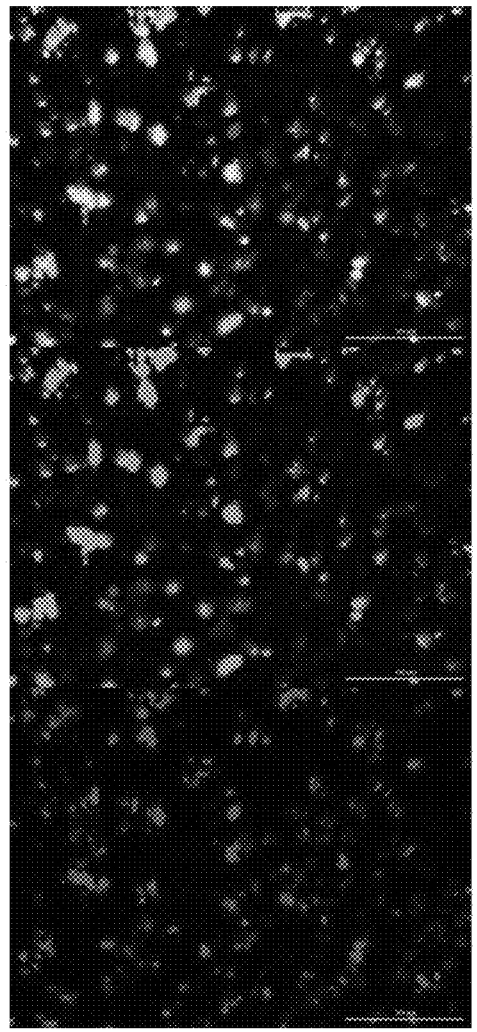
Figure 78 (cont. 1)

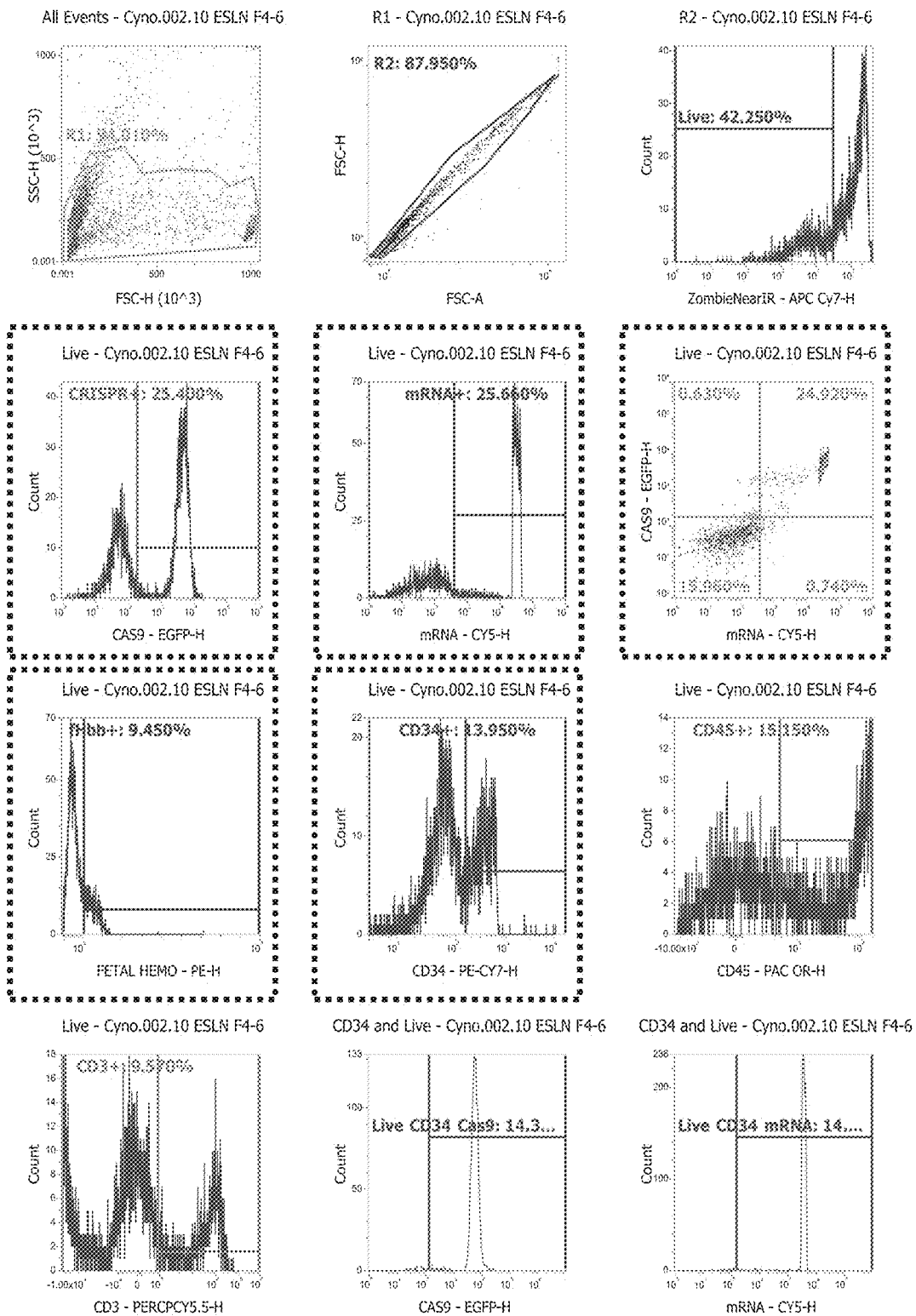
Figure 78 (cont. 2)

Figure 79 CynoBM.002.85
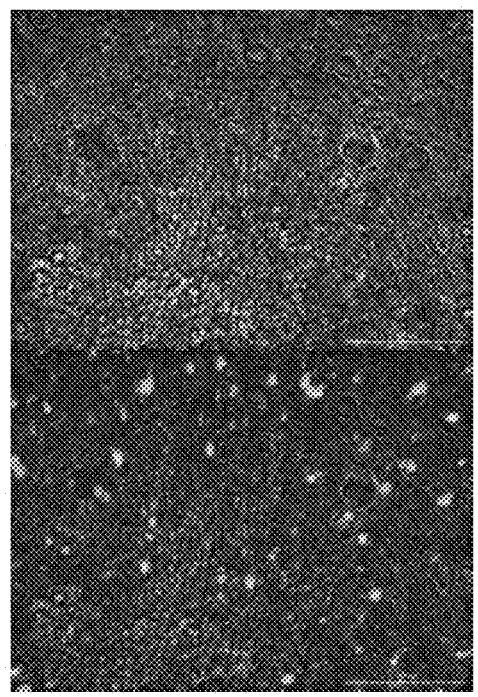

Figure 79 (cont. 1)
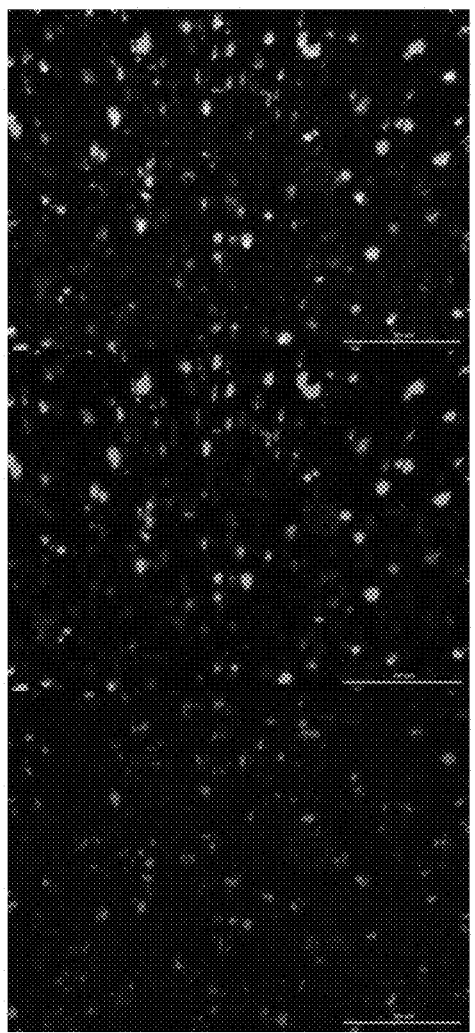

Figure 79 (cont. 2)
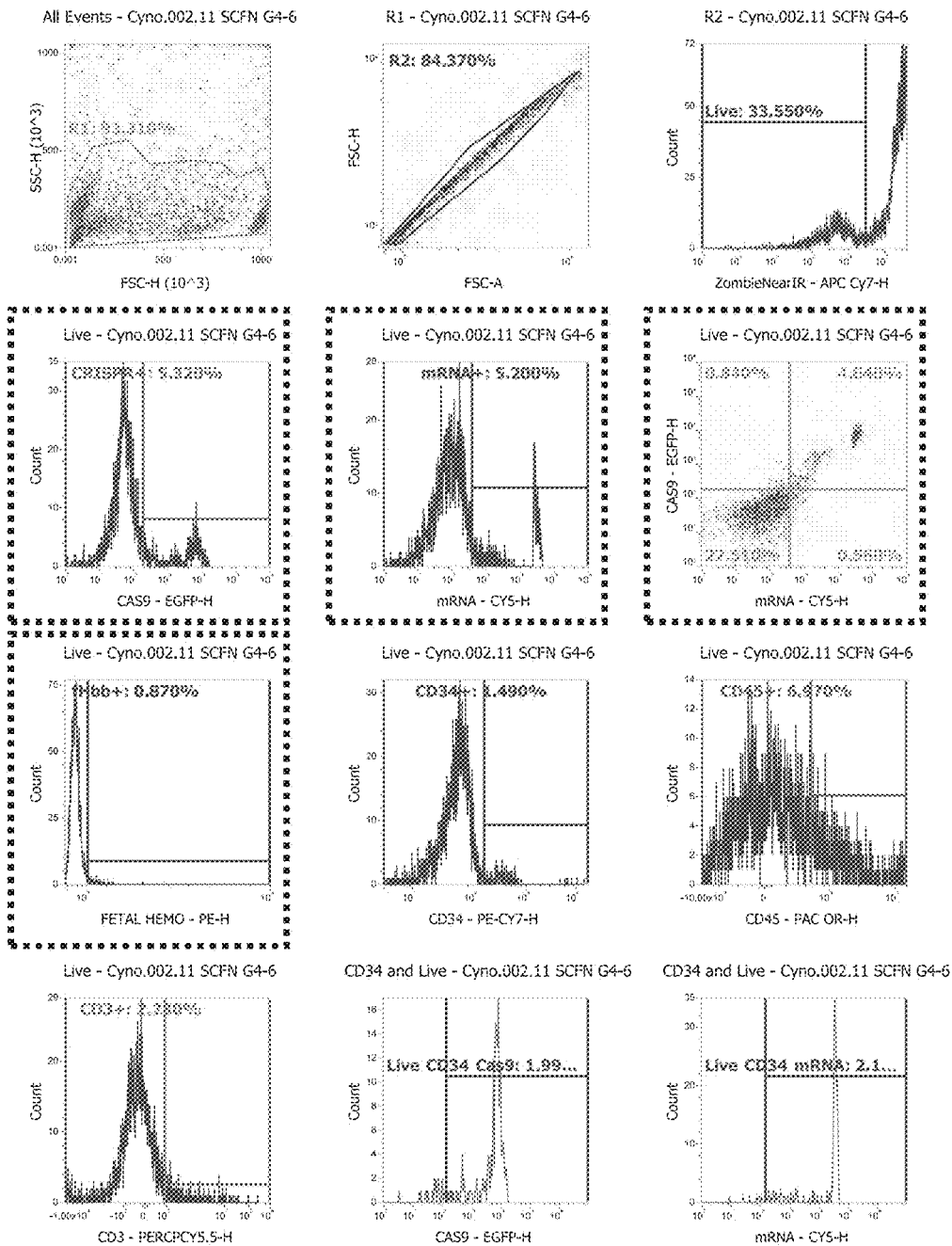

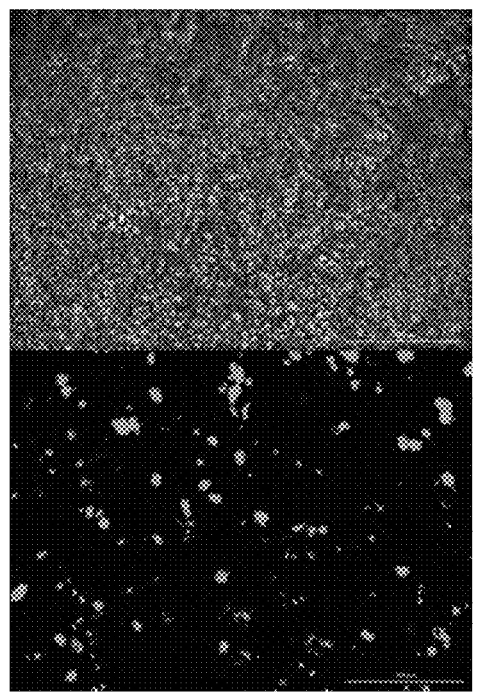
Figure 80  CynoBM.002.86

Figure 80 (cont. 1)
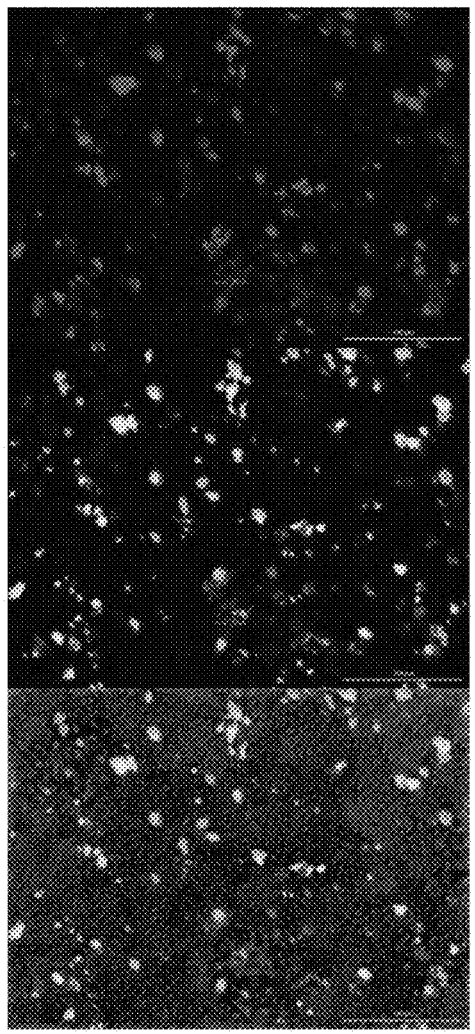

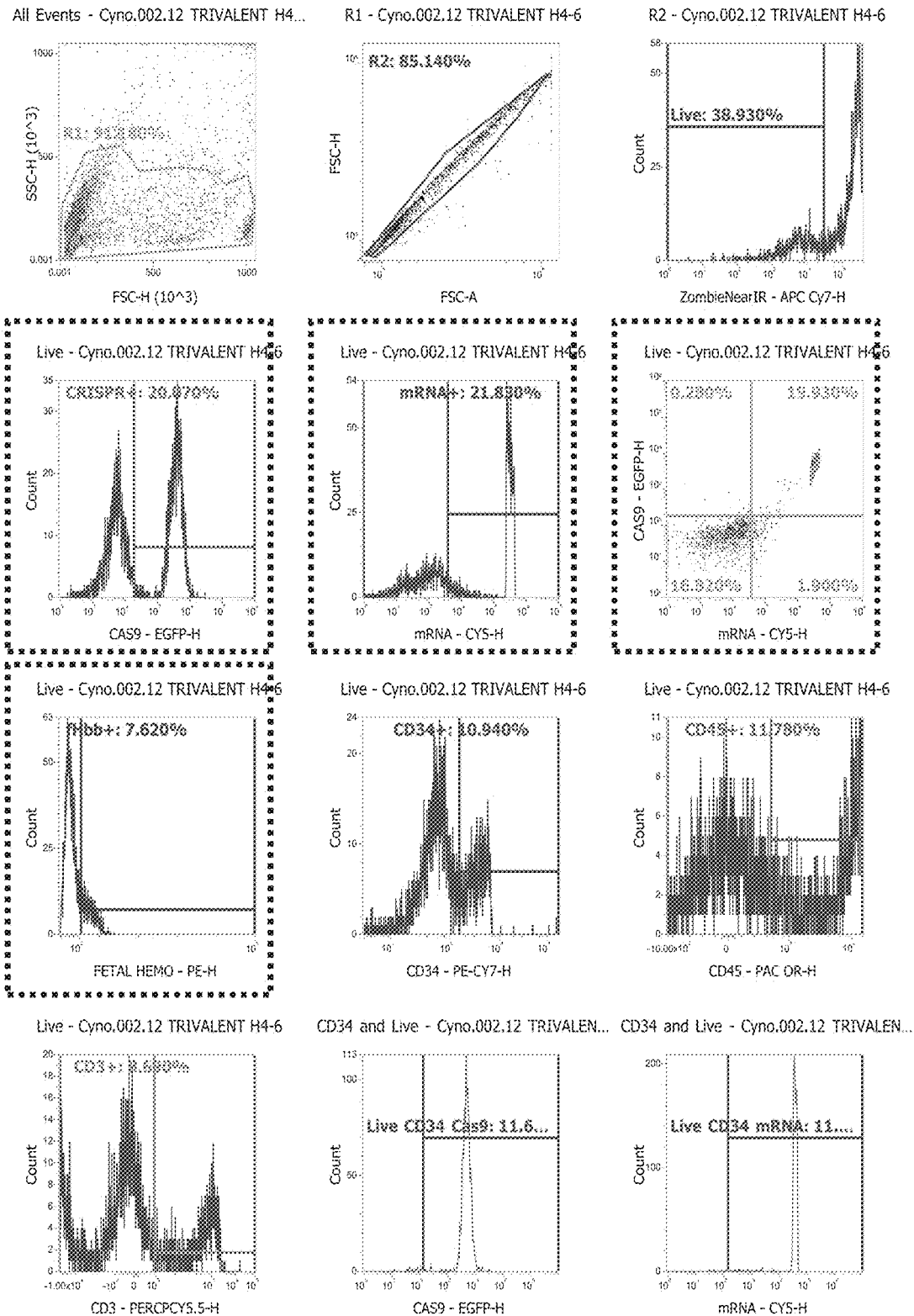
Figure 80 (cont. 2)

Figure 81 CynoBM.002.75
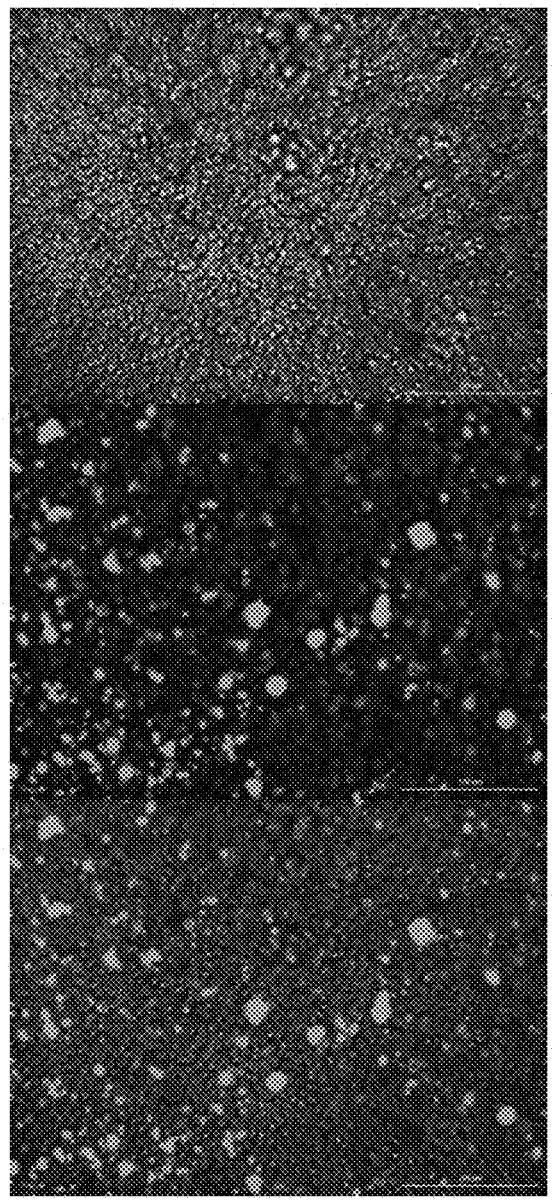

Figure 82 CynoBM.002.76
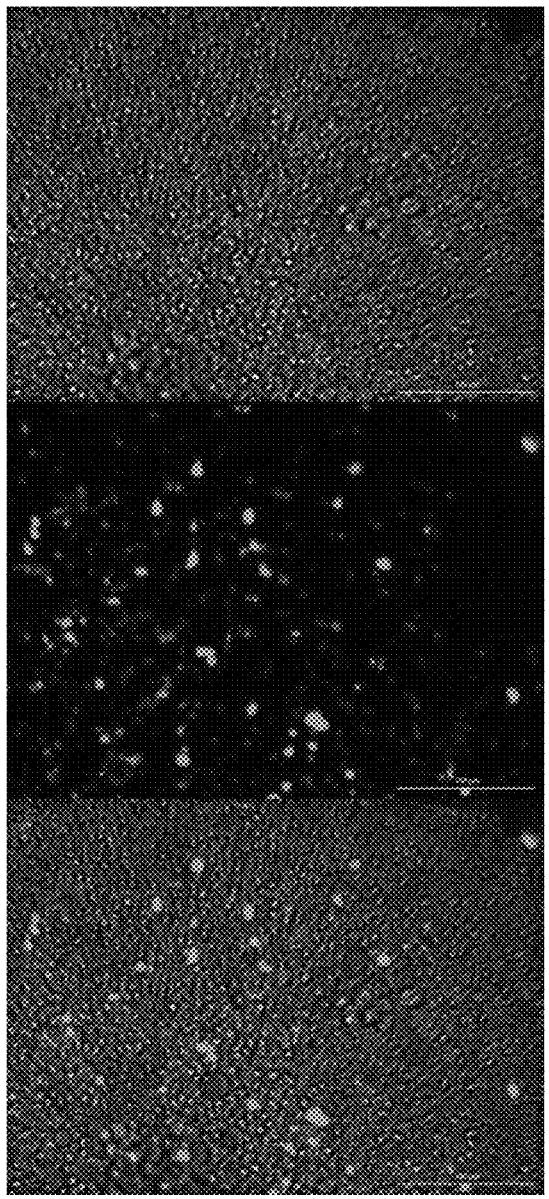

Figure 83 CynoBM.002.77
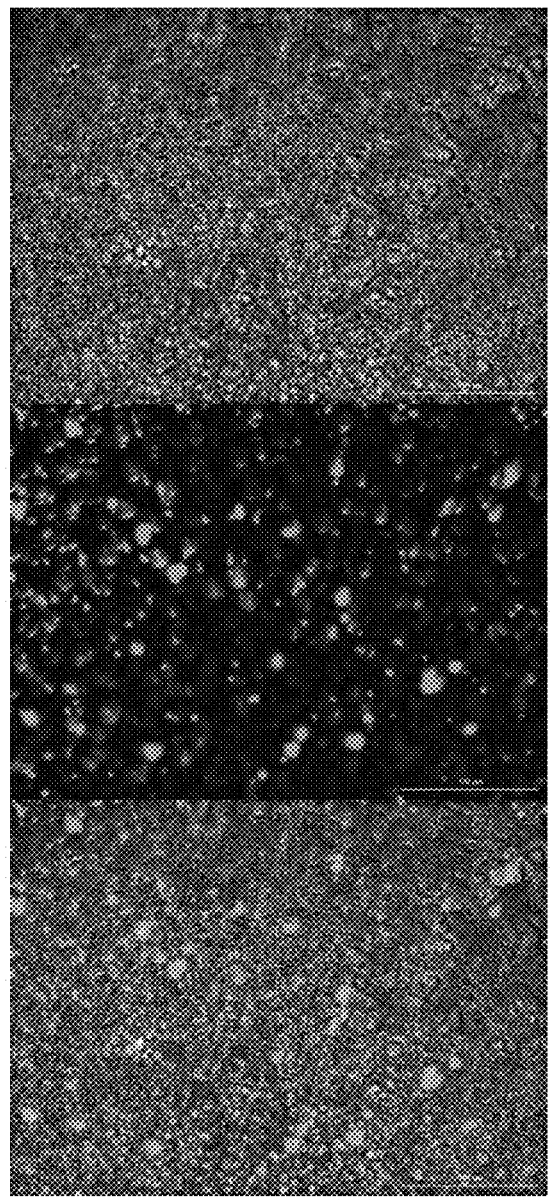

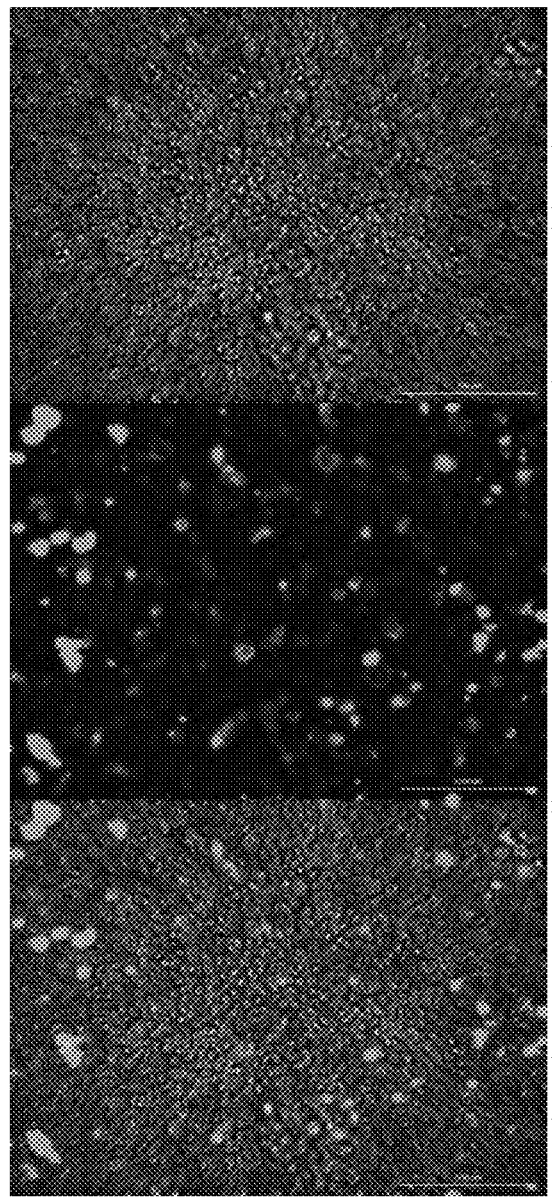
Figure 84 CynoBM.002.78

Figure 85 CynoBM.002.79
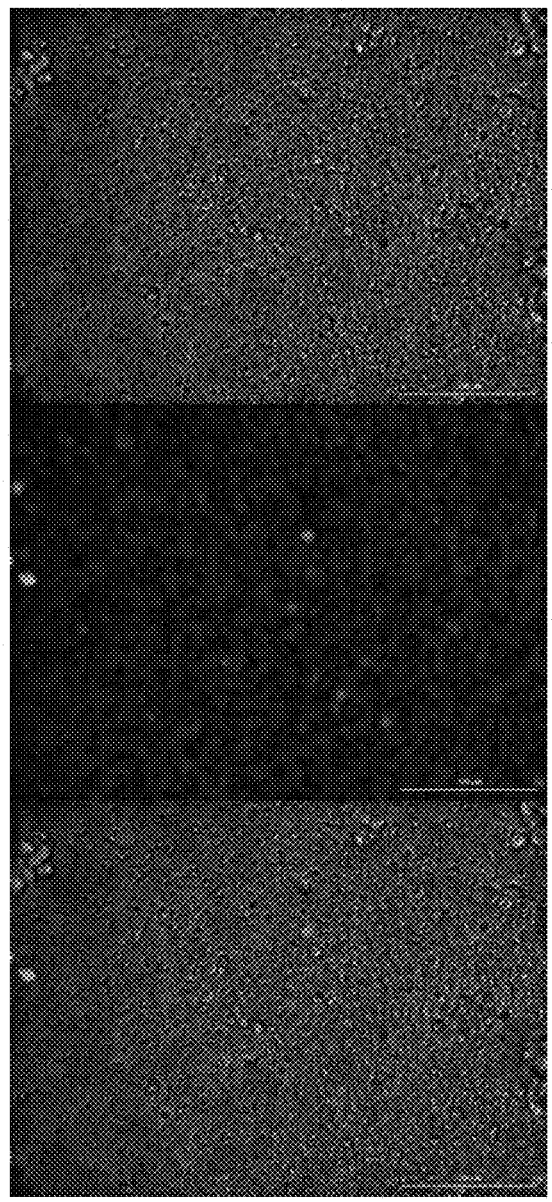

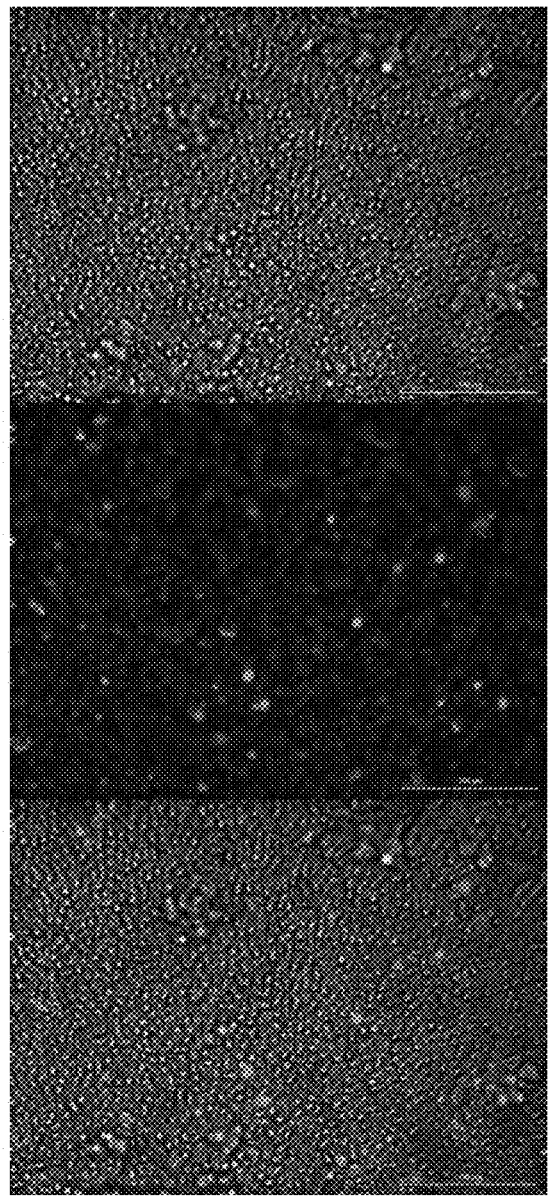
Figure 86 CynoBM.002.80

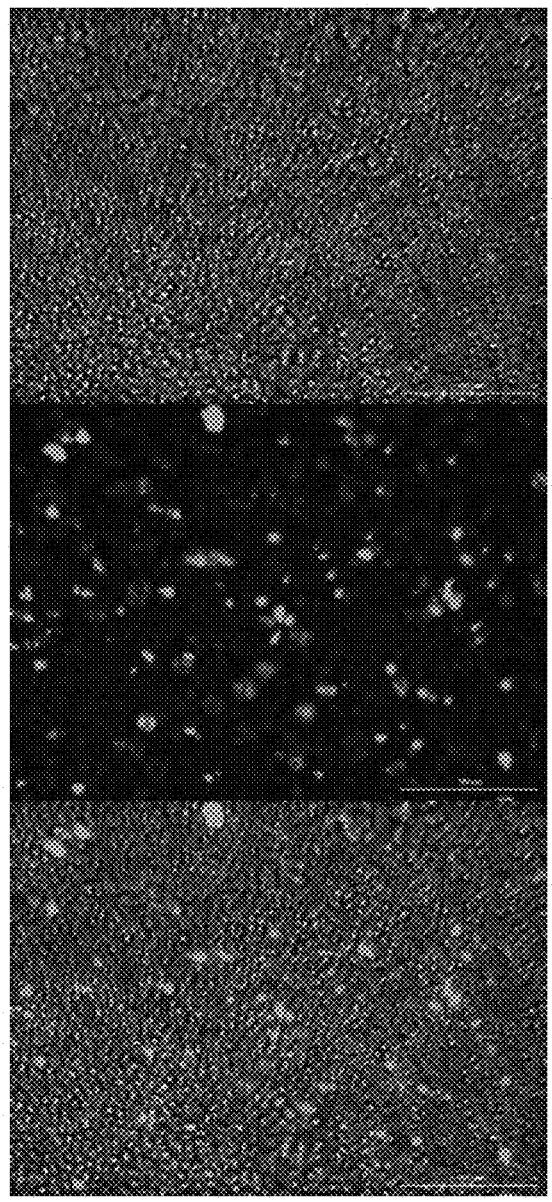
Figure 87 CynoBM.002.81

Figure 88 CynoBM.002 EGFP-RNP Only
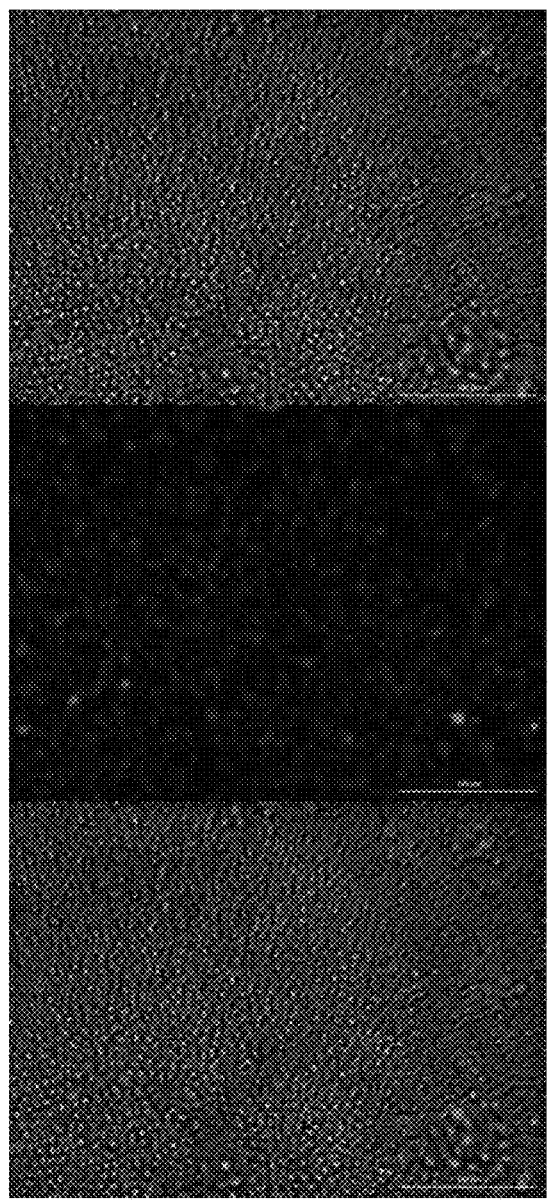

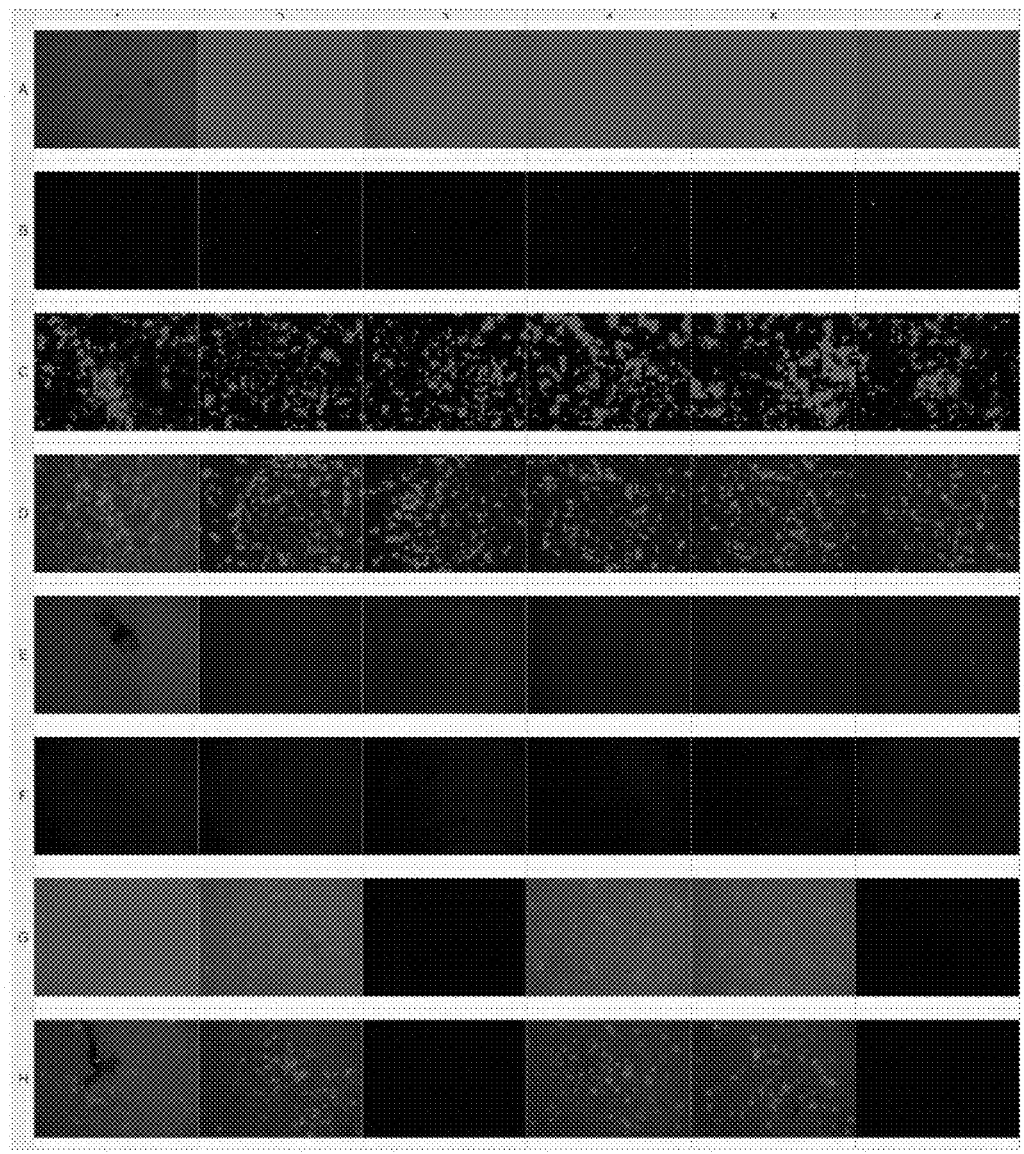
Figure 89 HSC.004 High-Content Screening

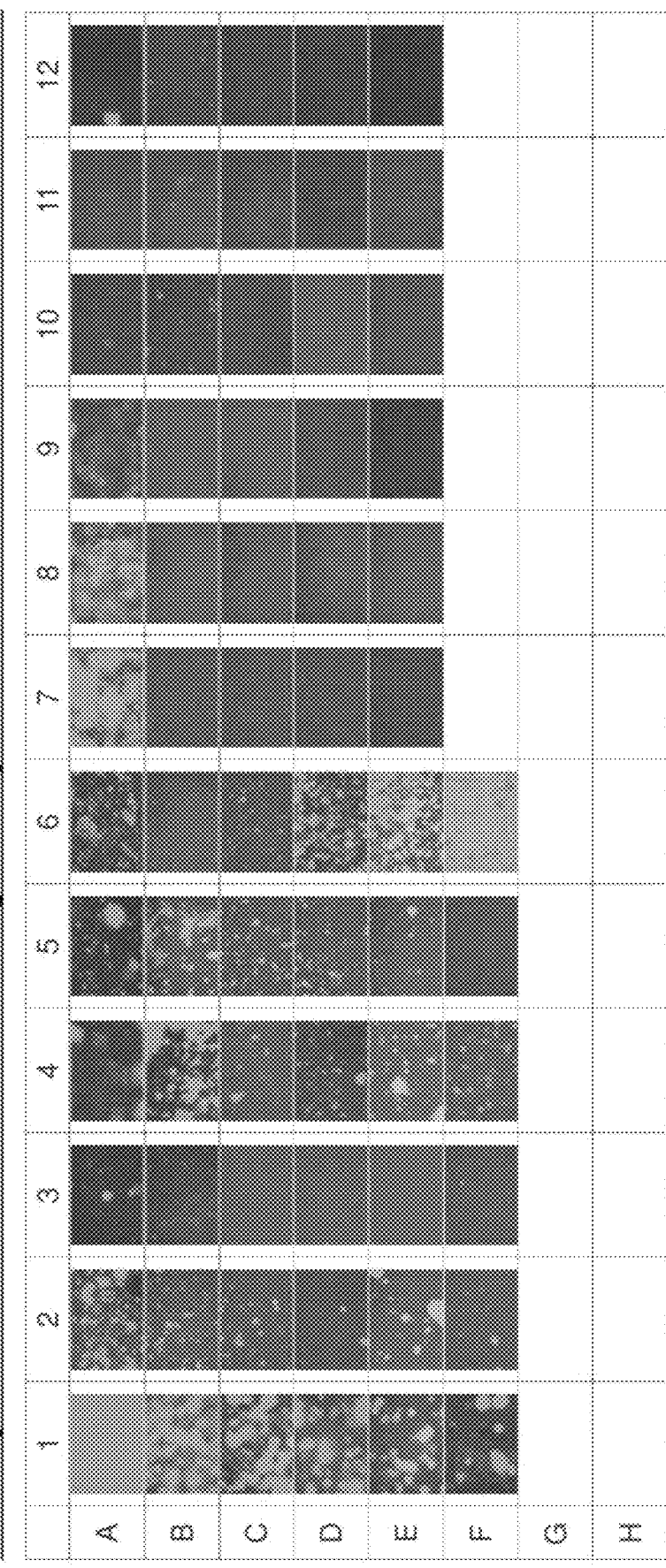
Figure 90 TCELL.001 High-Content Screening Picture [DAPI 377,447+GFP 469,525+Bright Field]

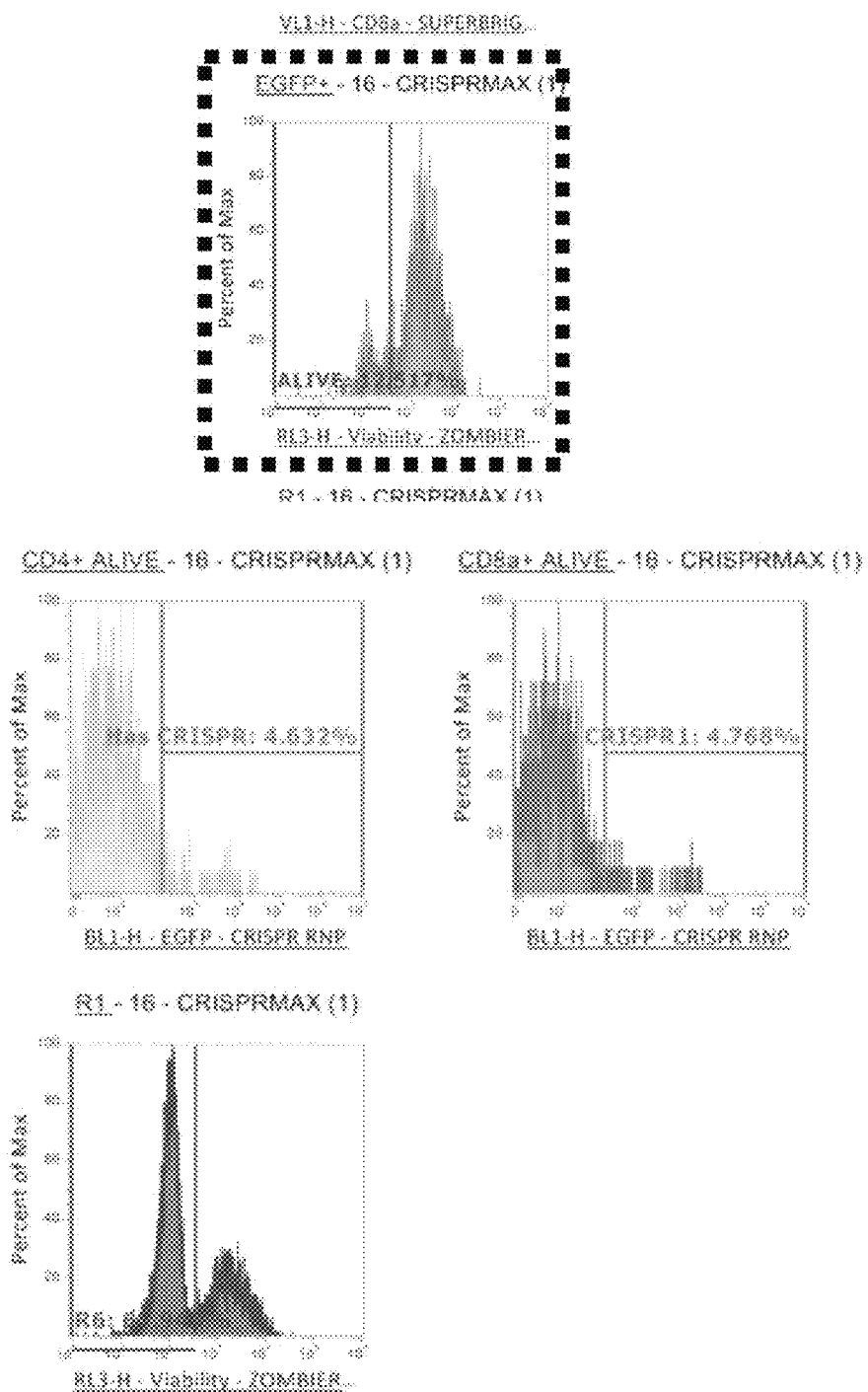
Figure 91 TCELL.001 Lipofectamine CRISPRMAX

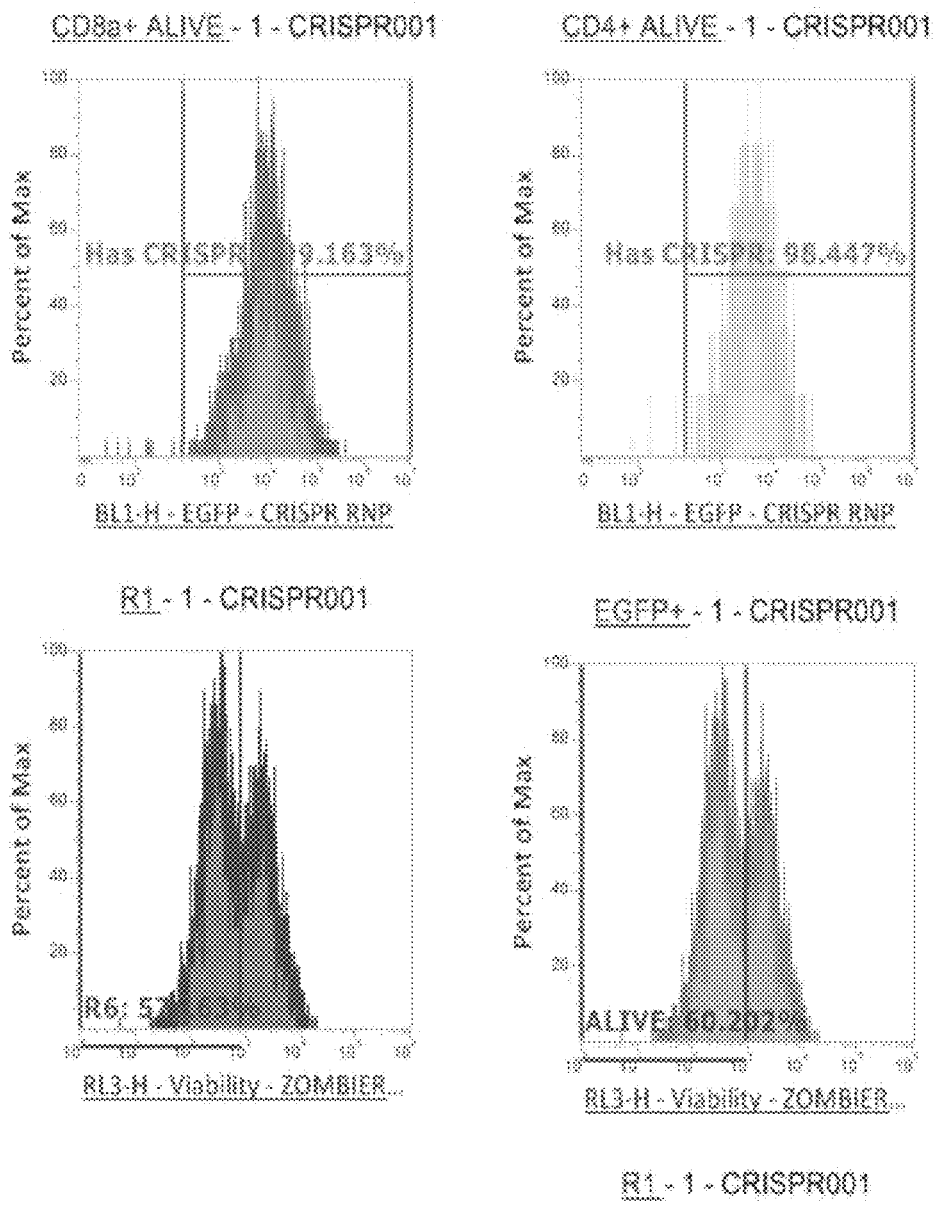
Figure 92 TCELL.001.1

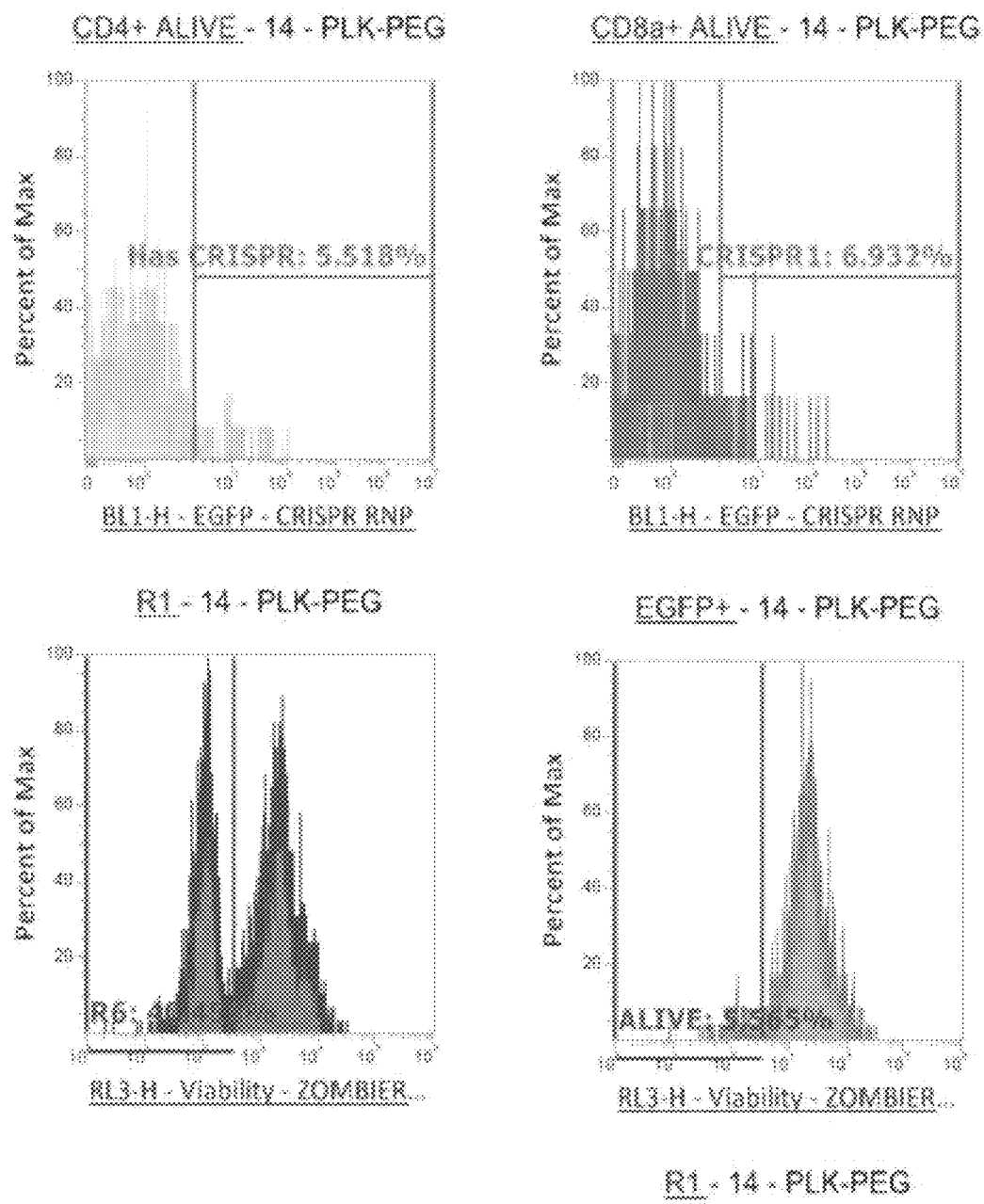

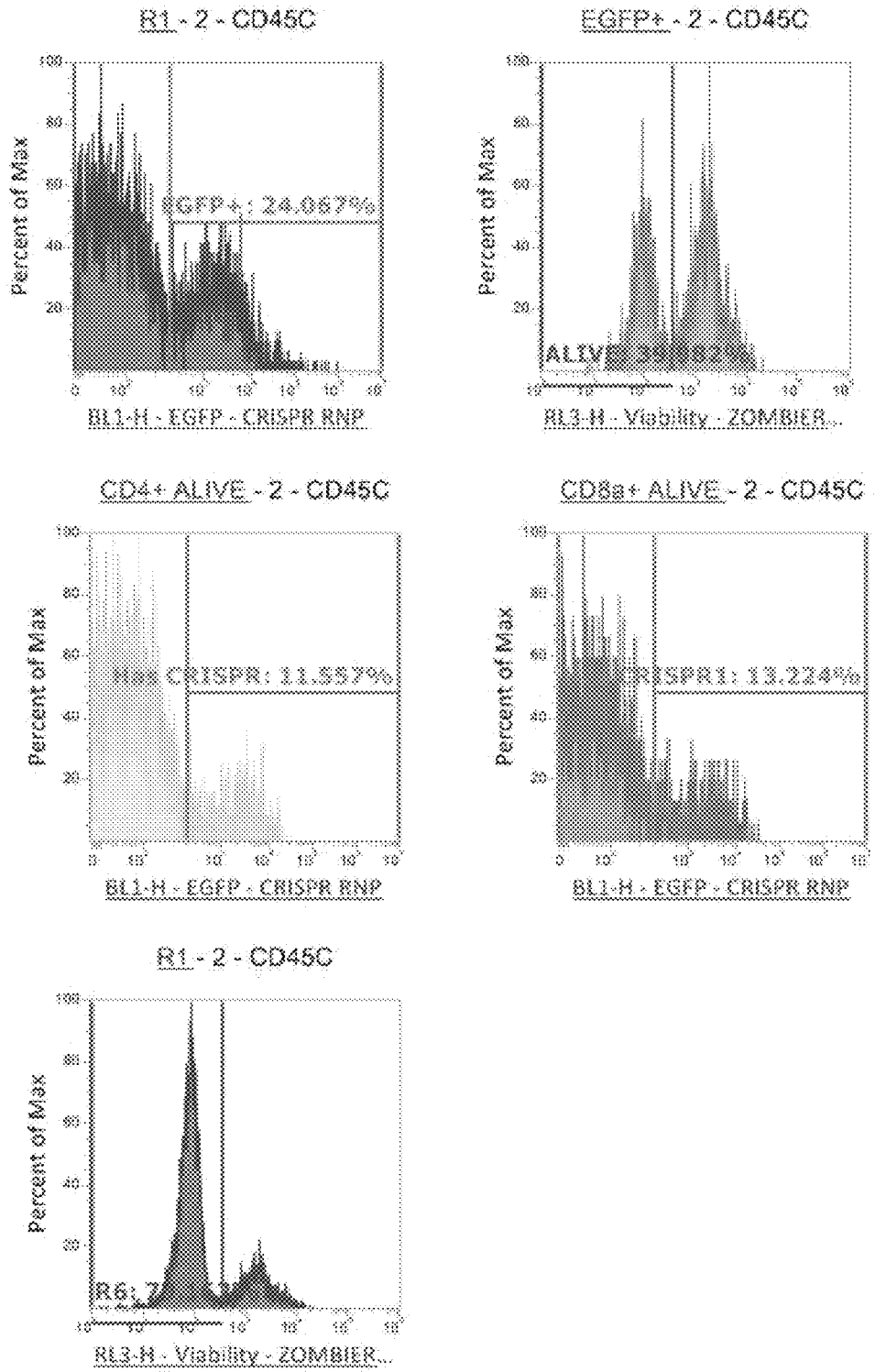

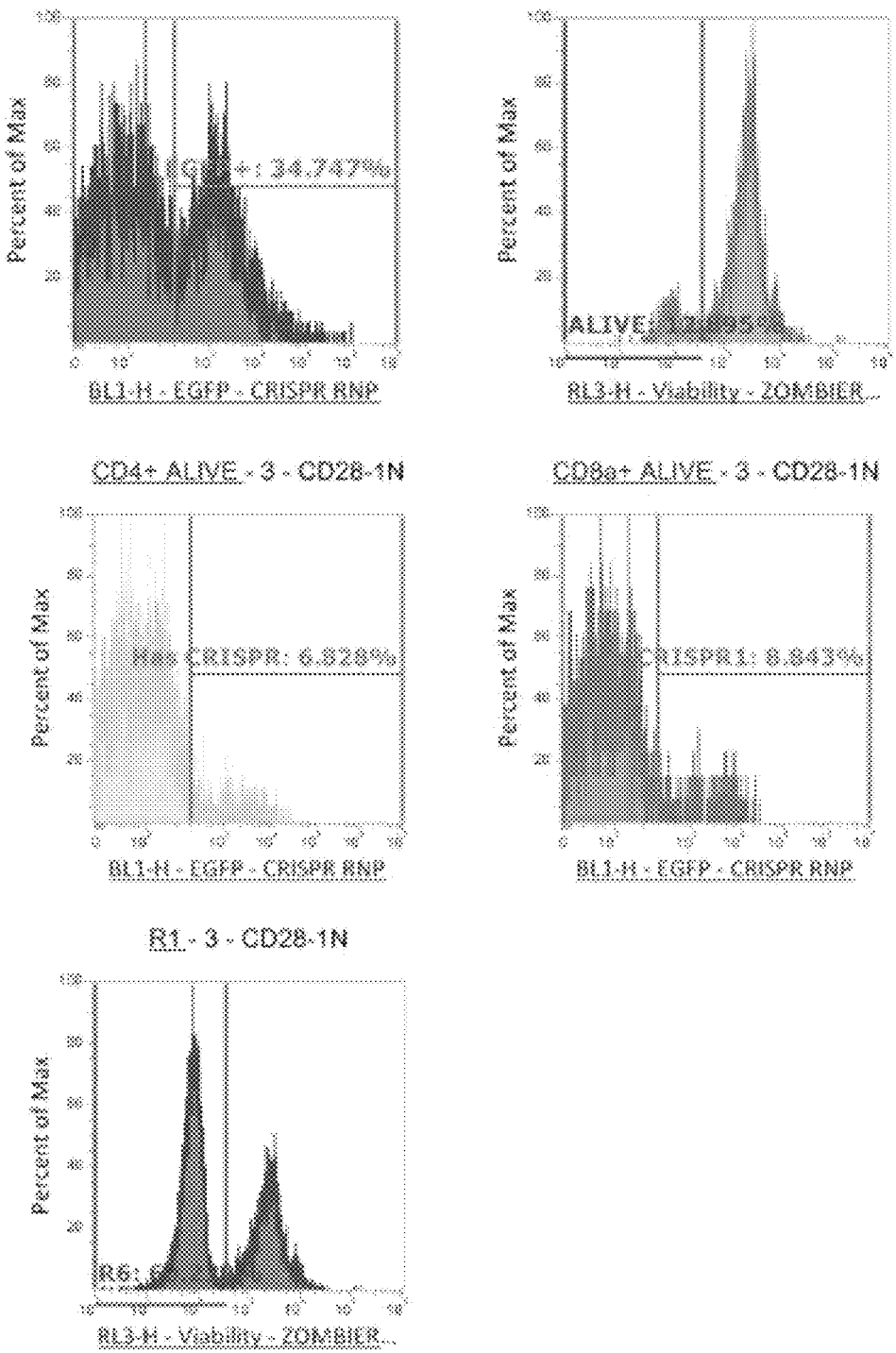
Figure 95 TCell.001.4

Figure 96 TCell.001.5
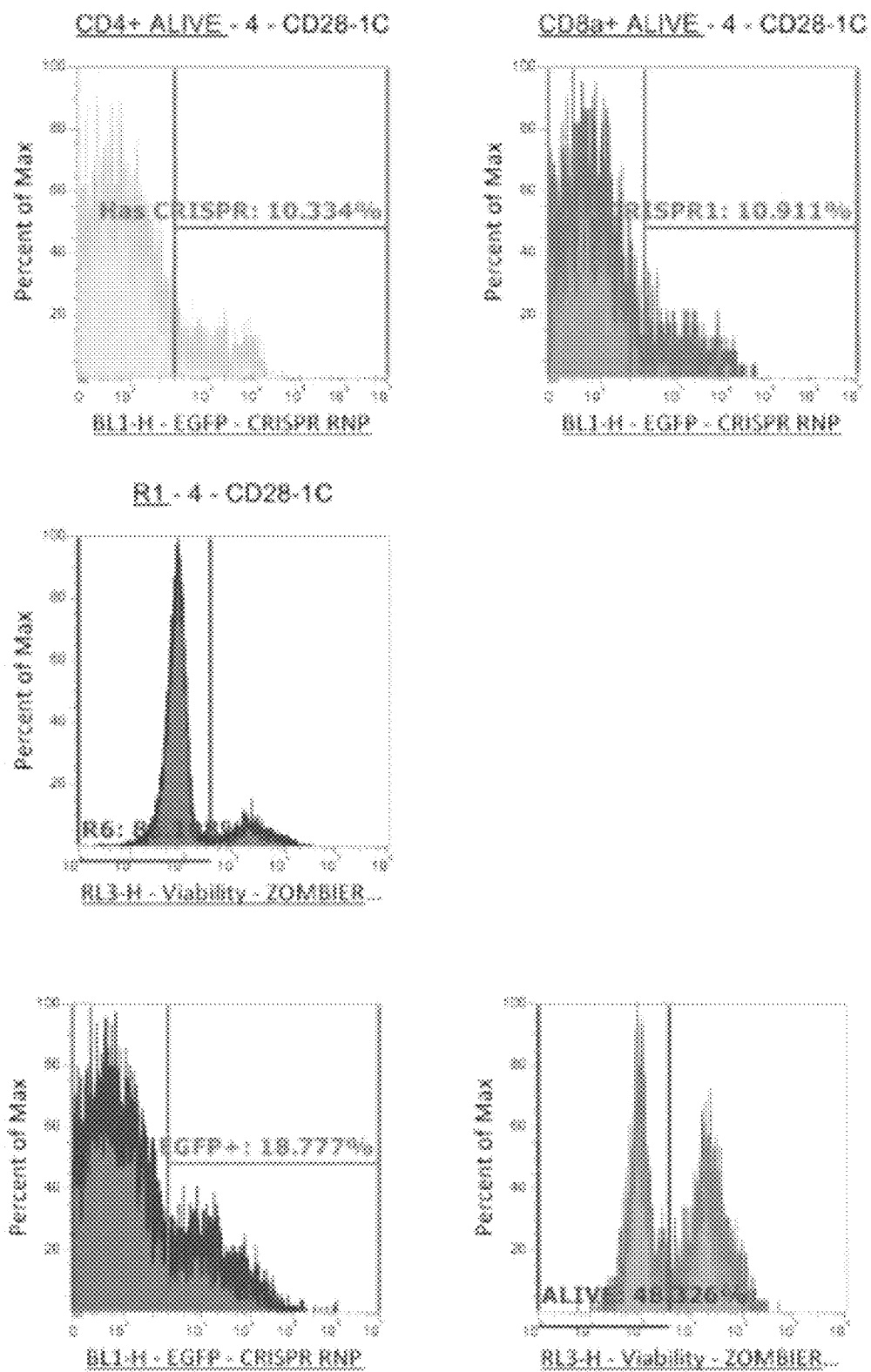

Figure 97 TCell.001.6
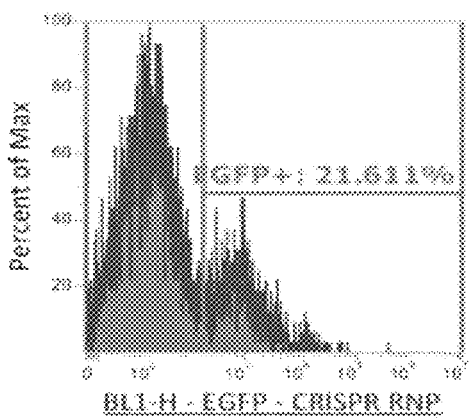
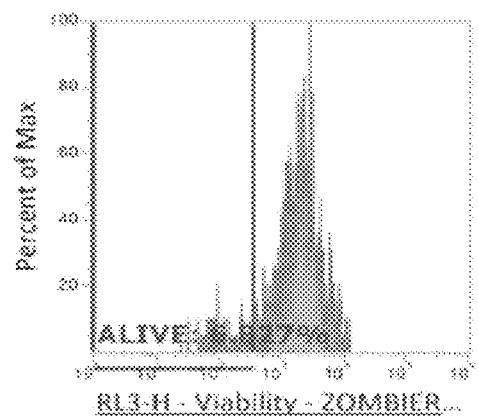
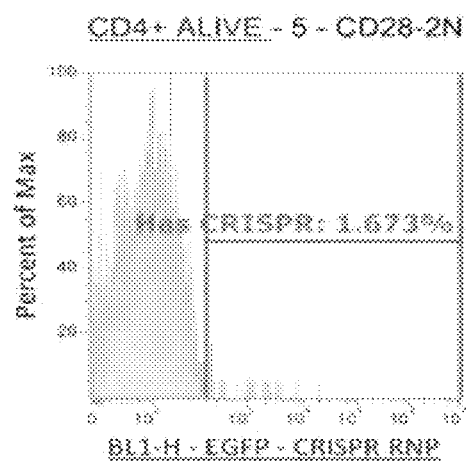
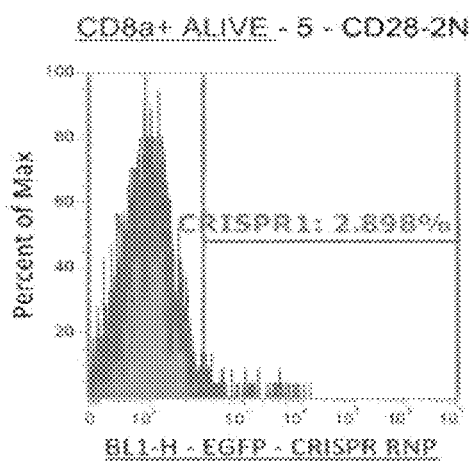
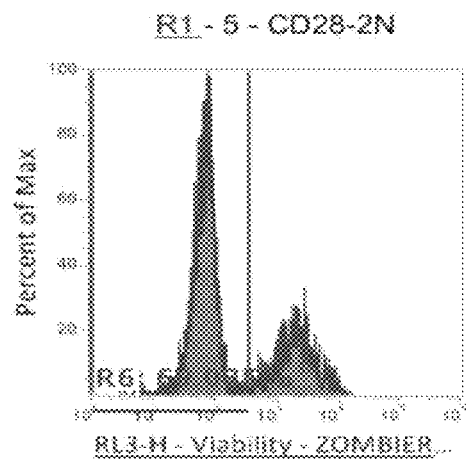

Figure 98 TCell.001.7
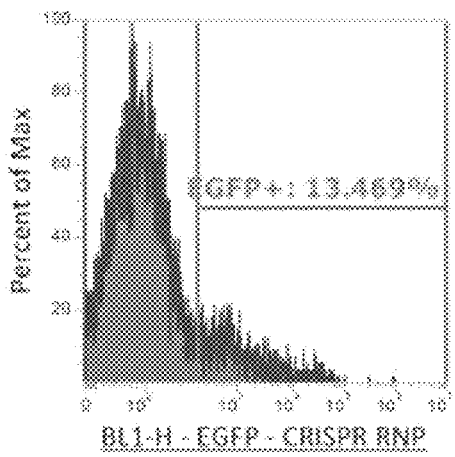
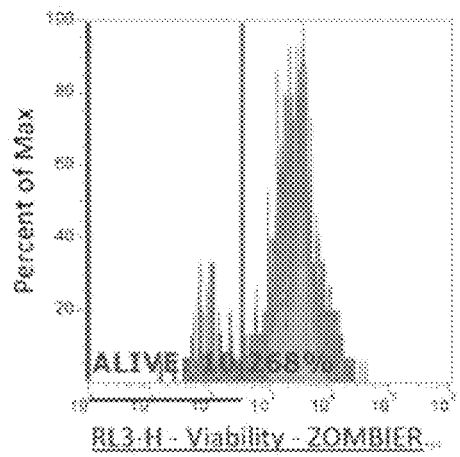
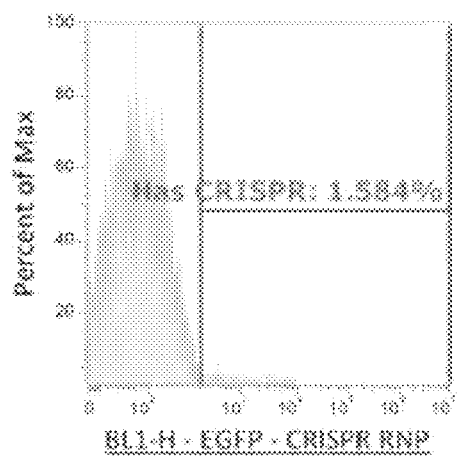
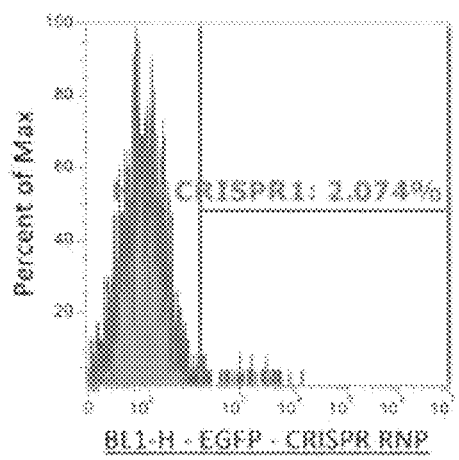
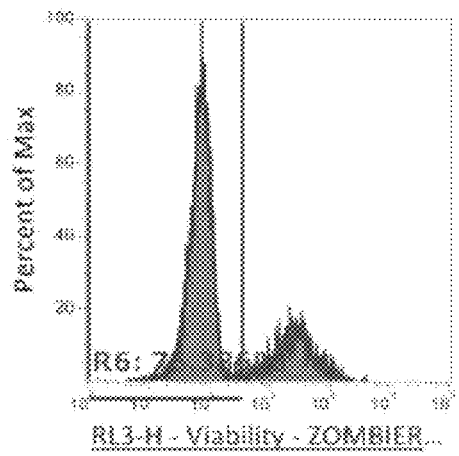

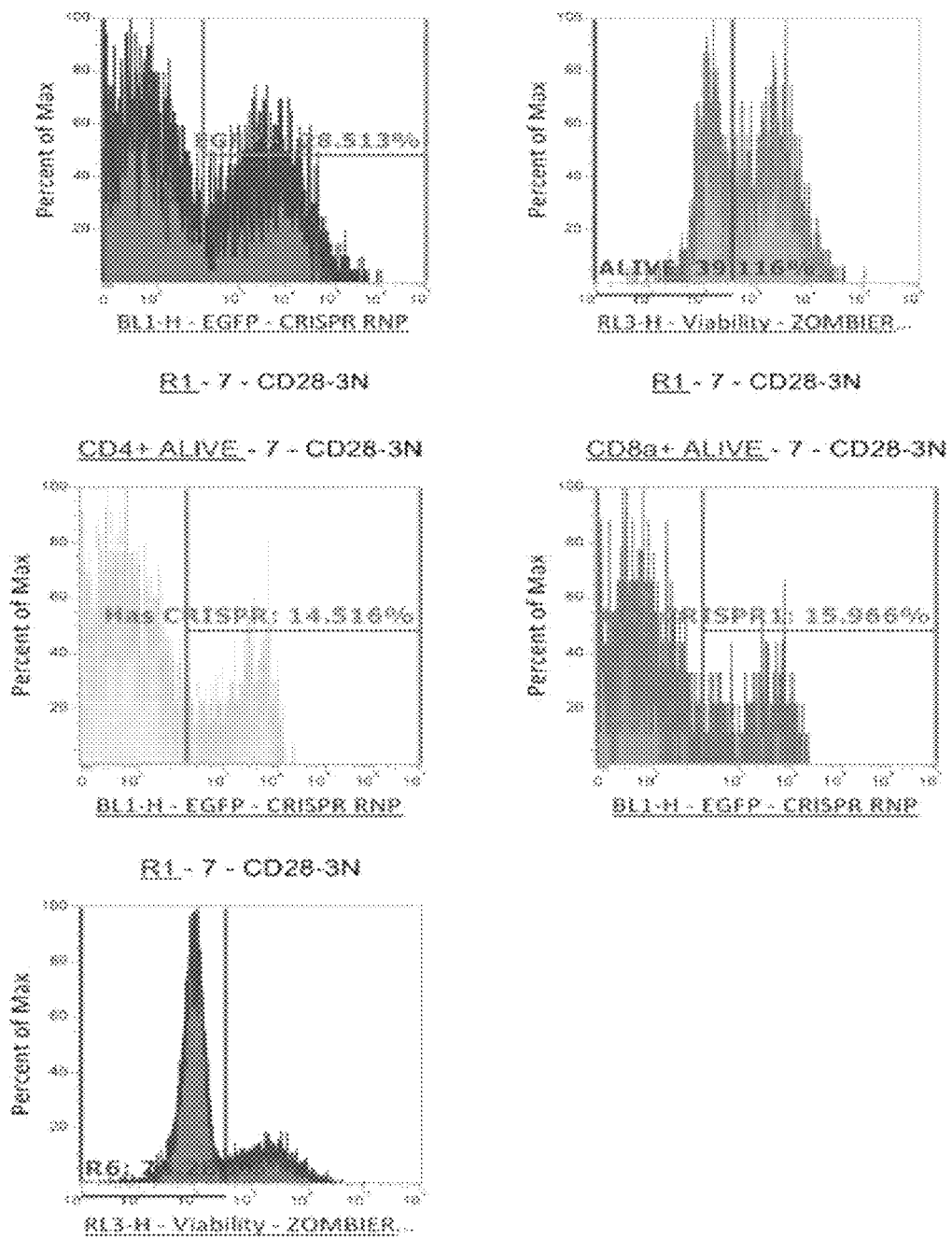

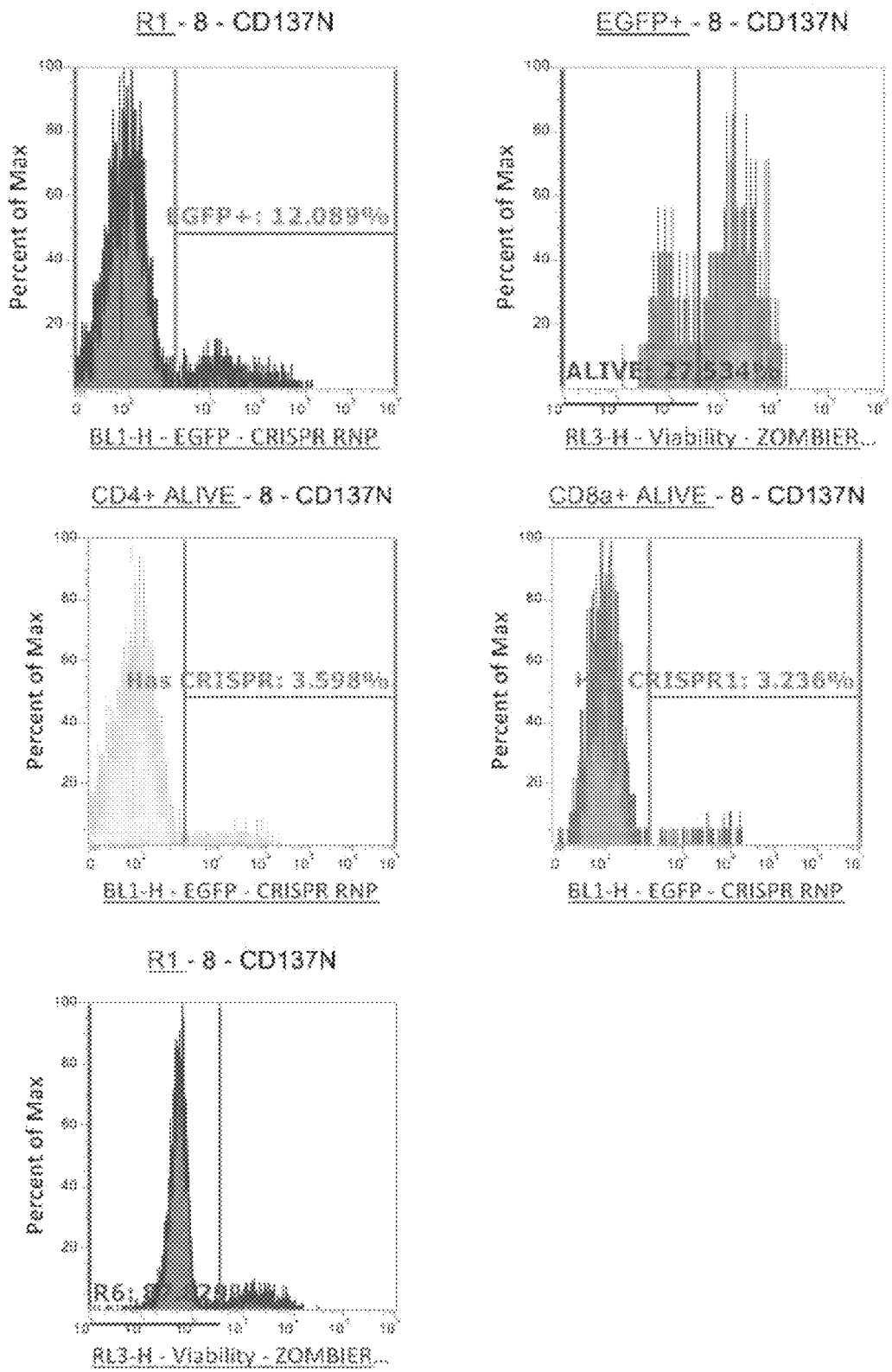
Figure 100 TCell.001.9

Figure 101 TCell.001.10
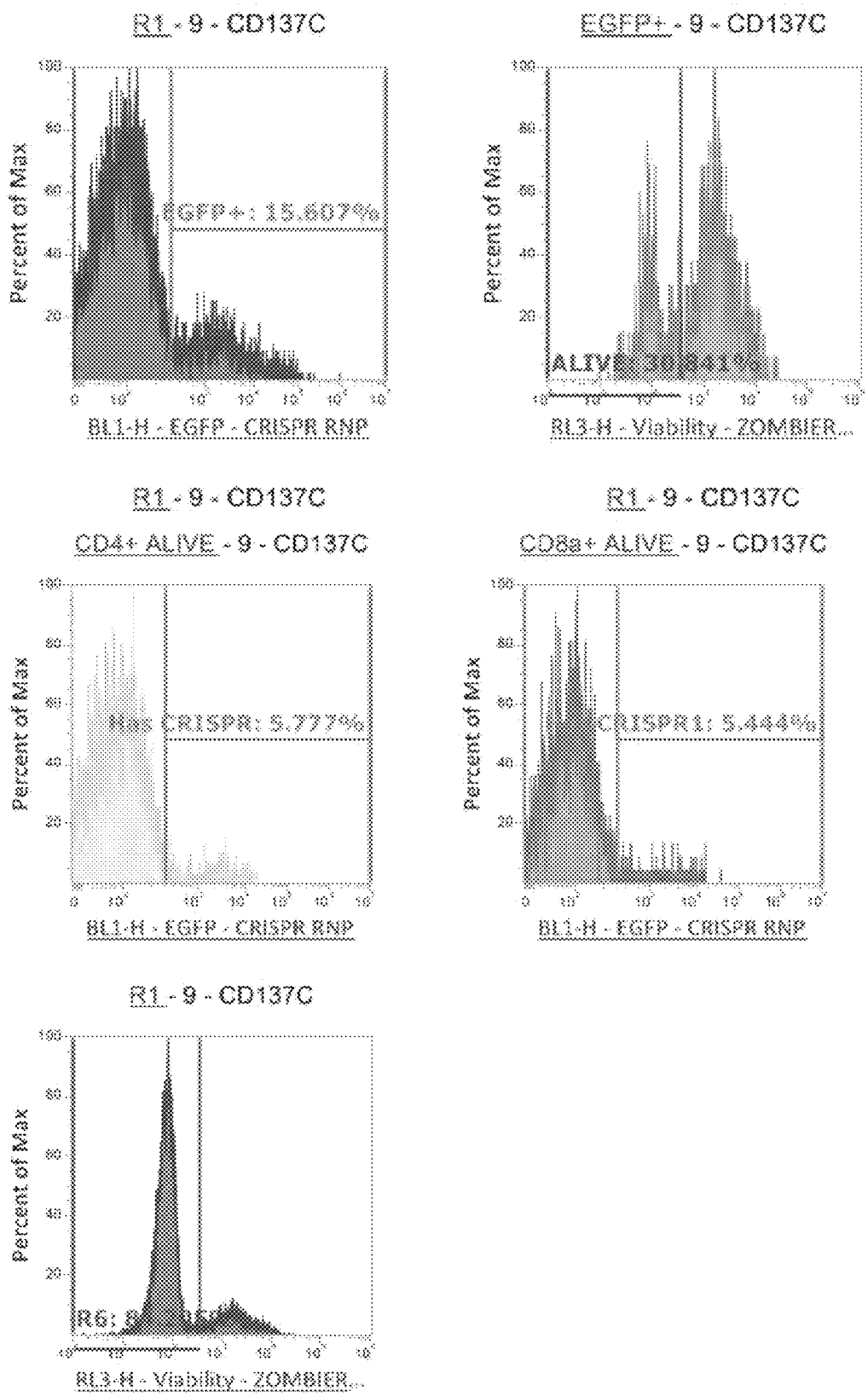

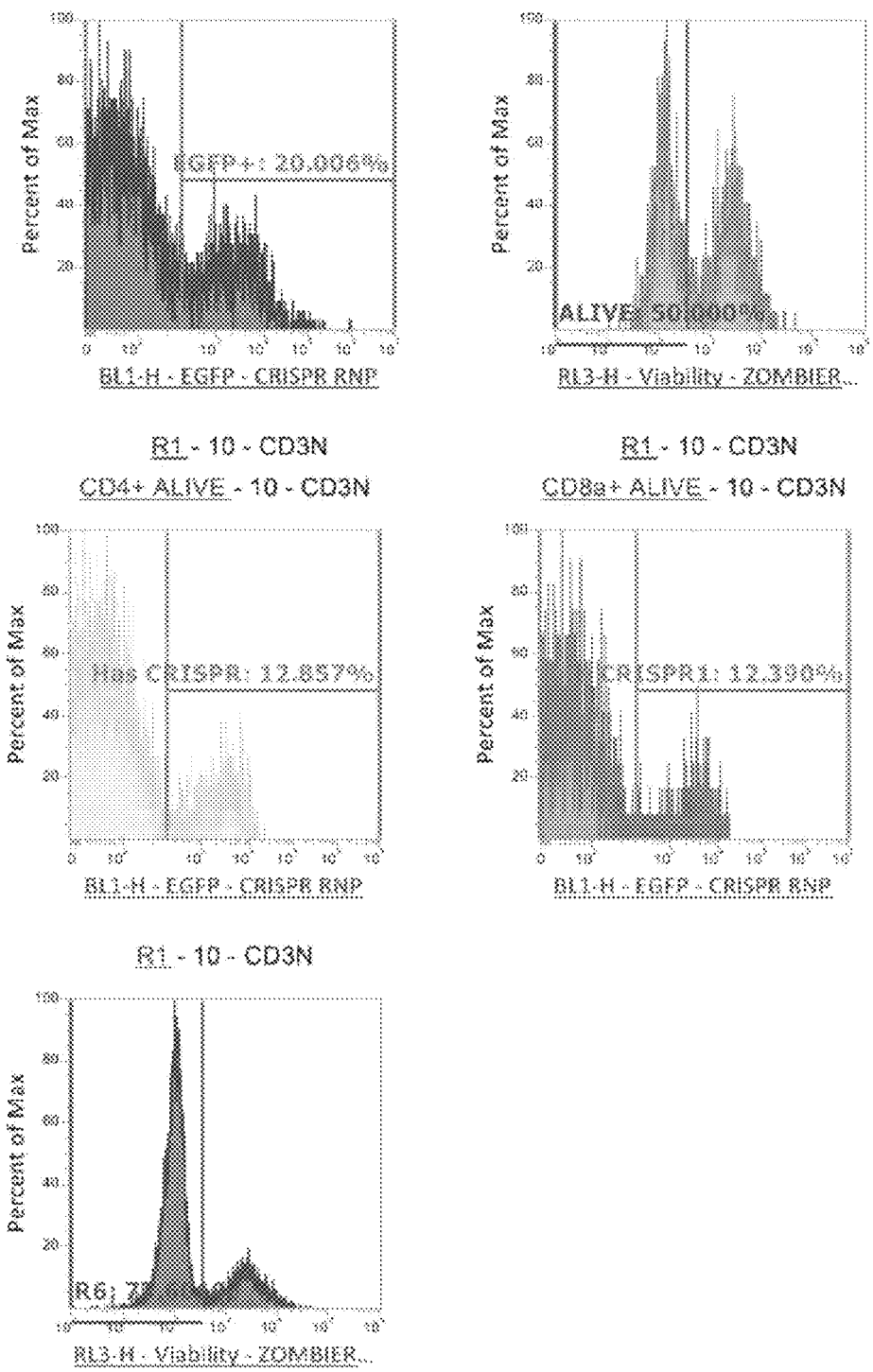
Figure 102 TCell.001.11

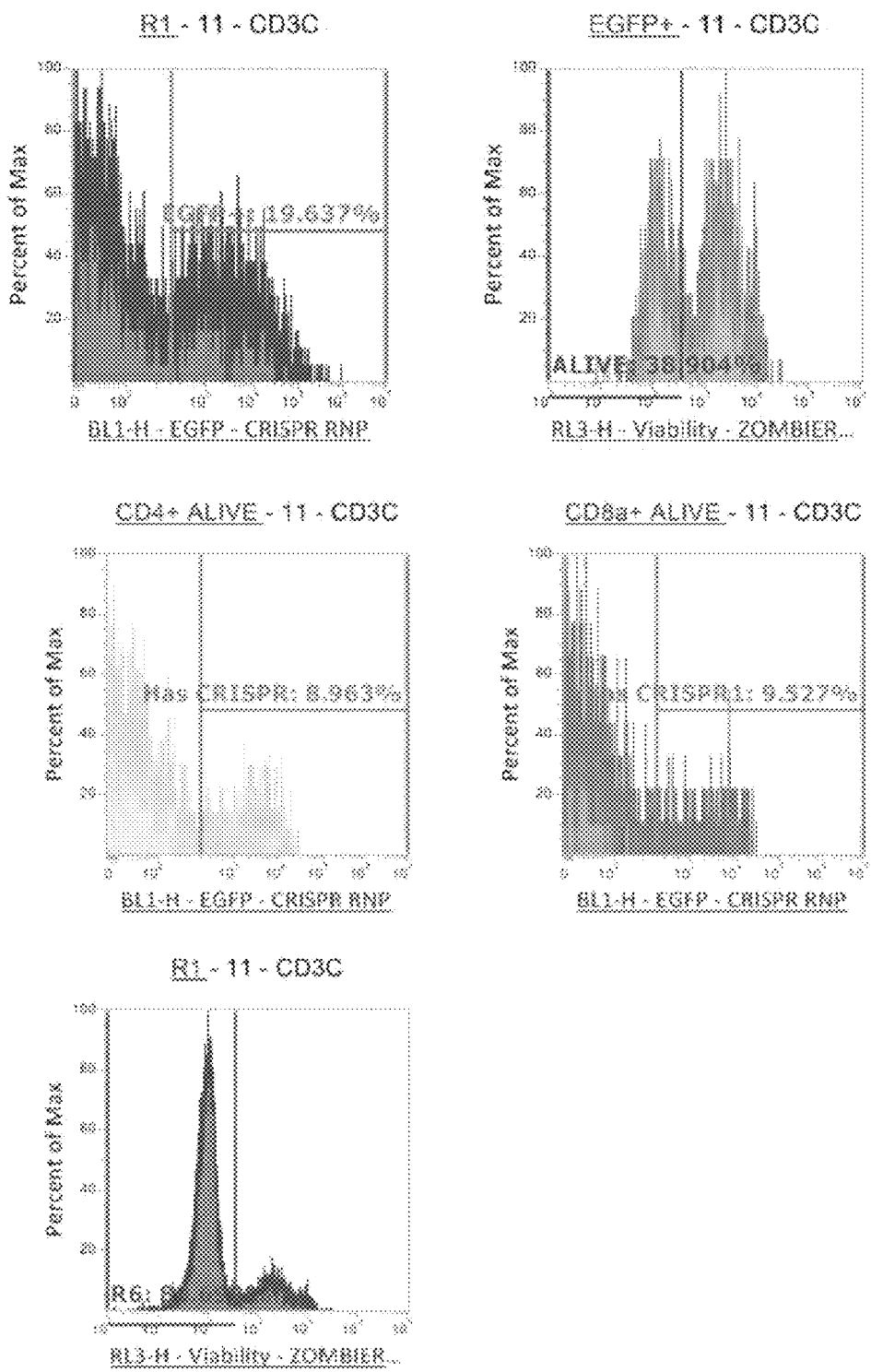
Figure 103  TCell.001.12

Figure 104  TCell.001.13
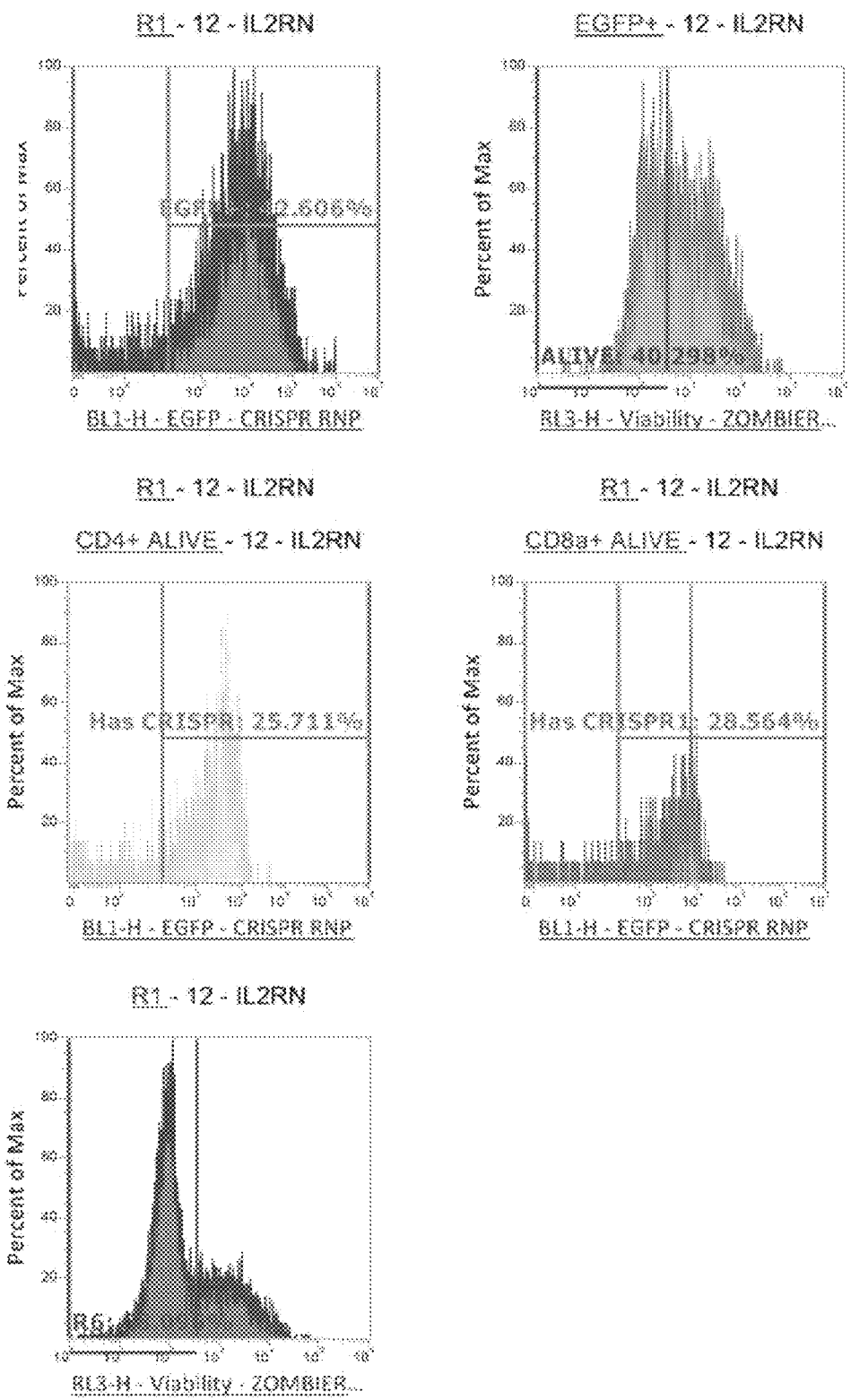

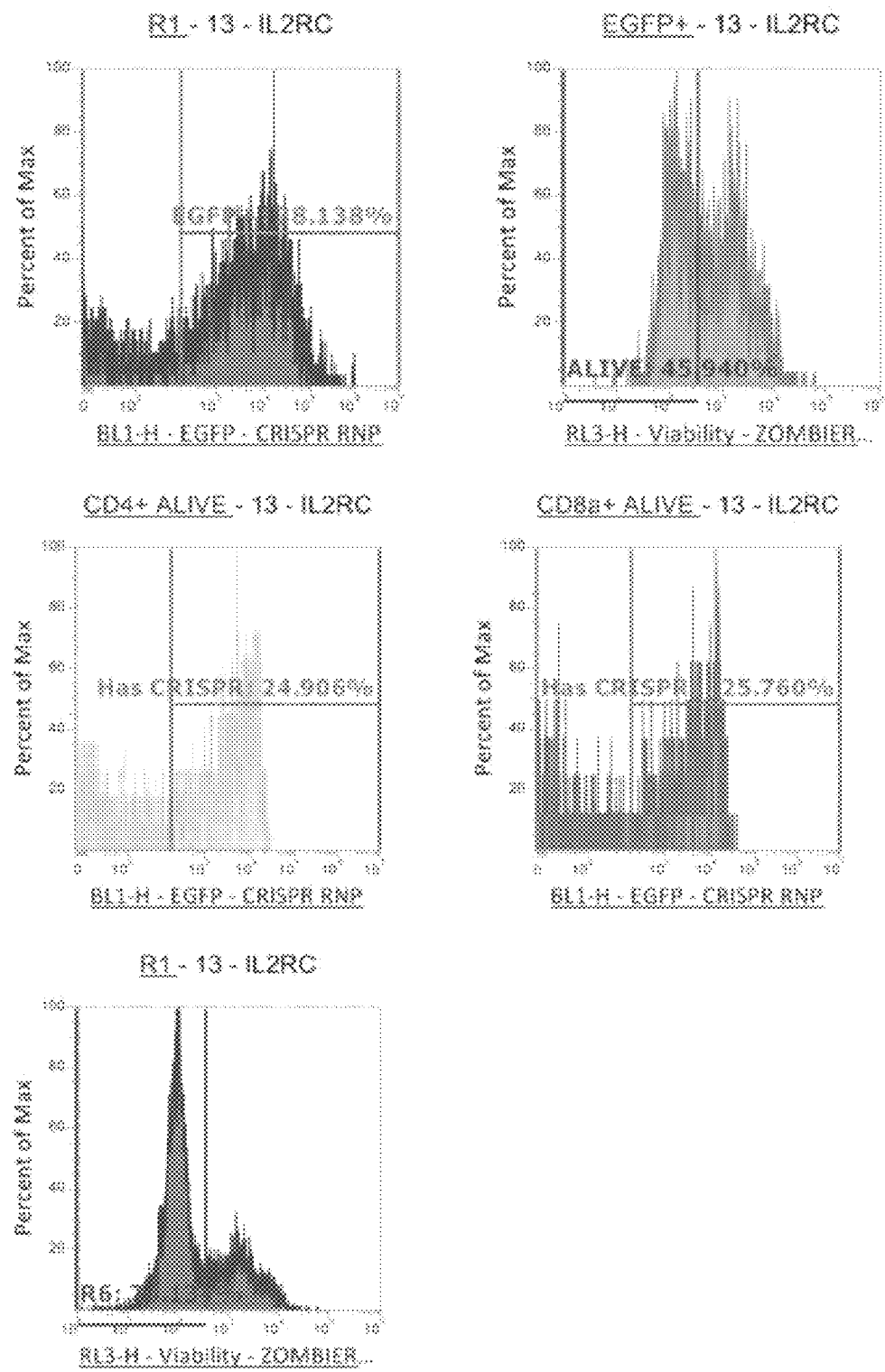
Figure 105 TCell.001.14

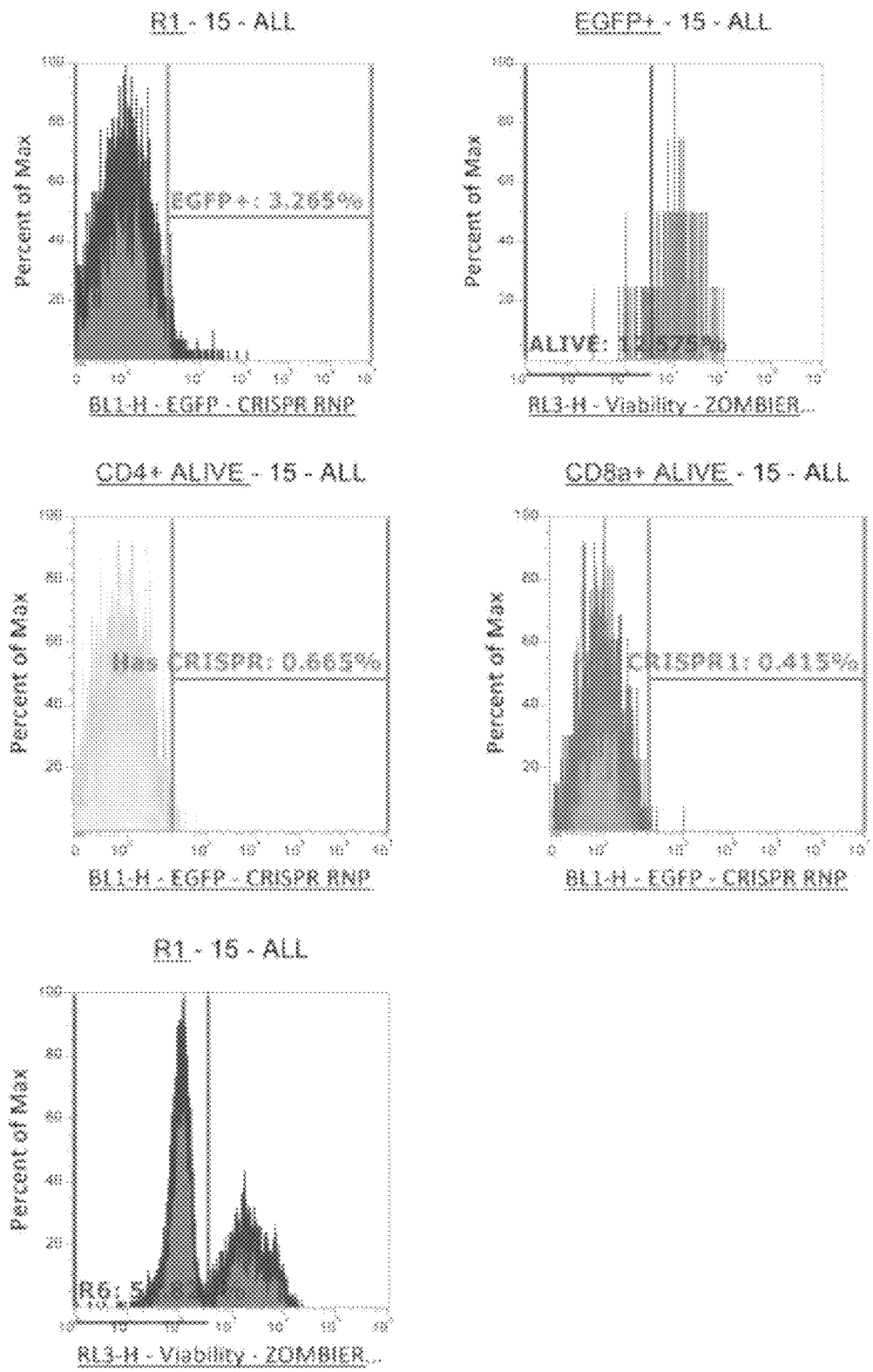
Figure 106 TCell.001.15

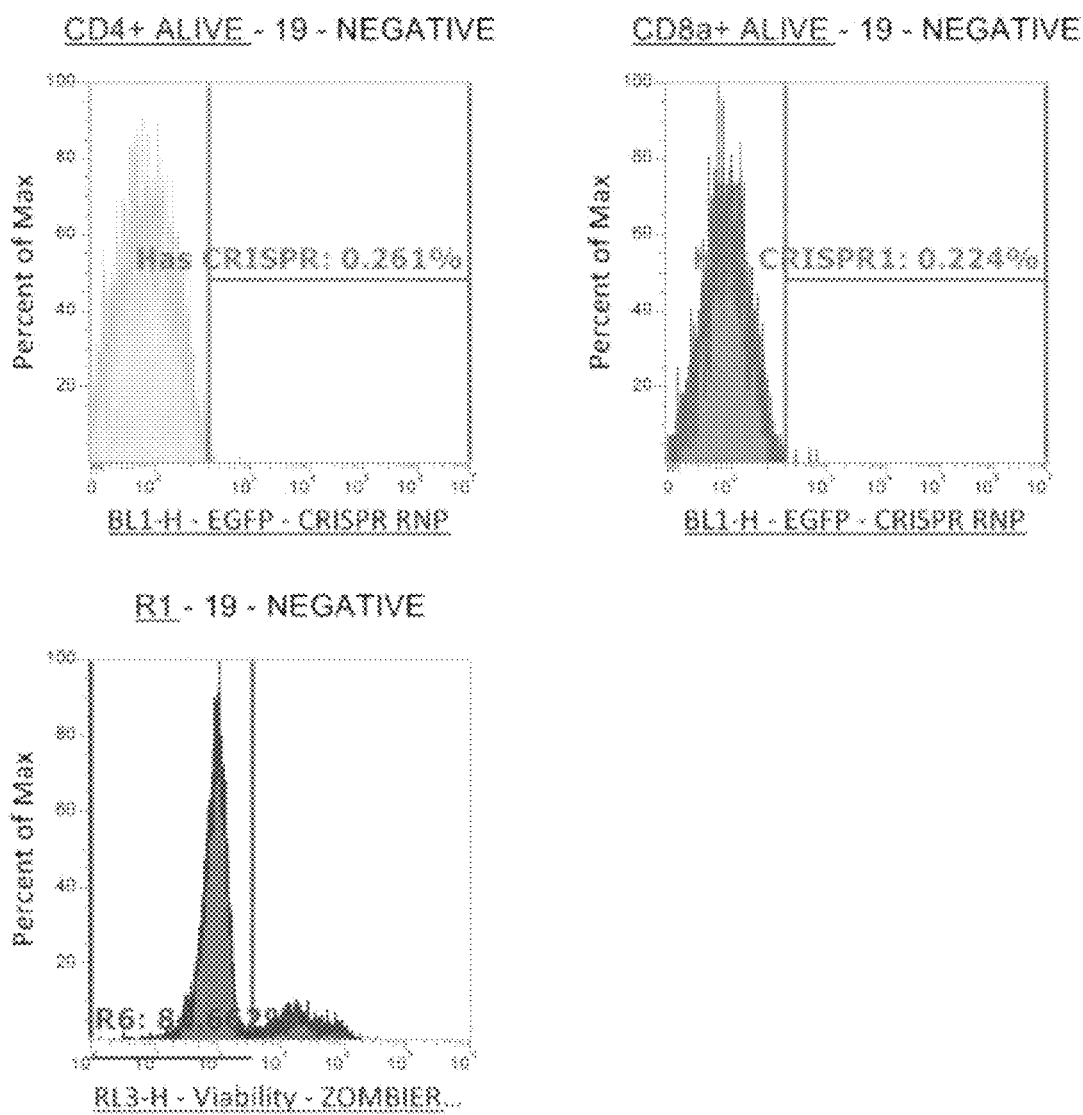
Figure 107 TCELL.001 Negative Controls

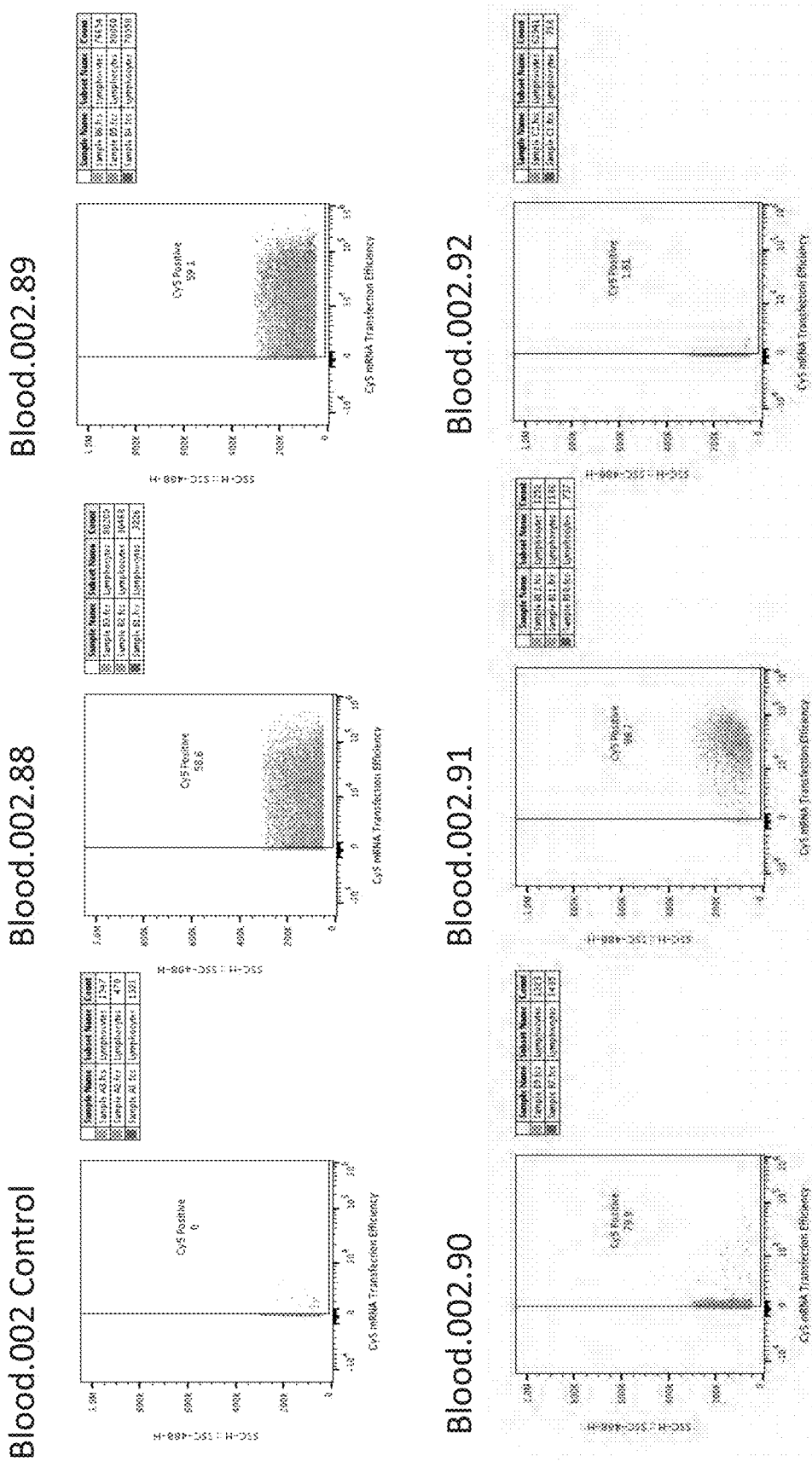
Figure 108 Blood.002

Figure 109 TCELL.001.27
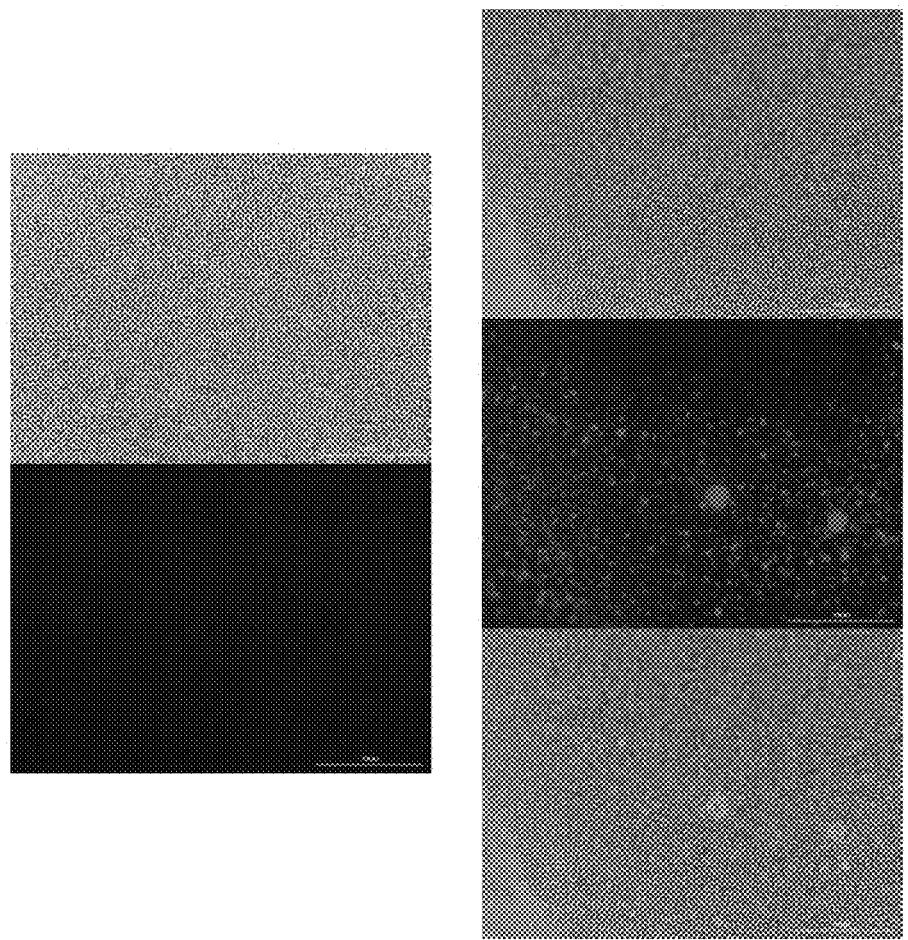

Figure 110 (cont.)
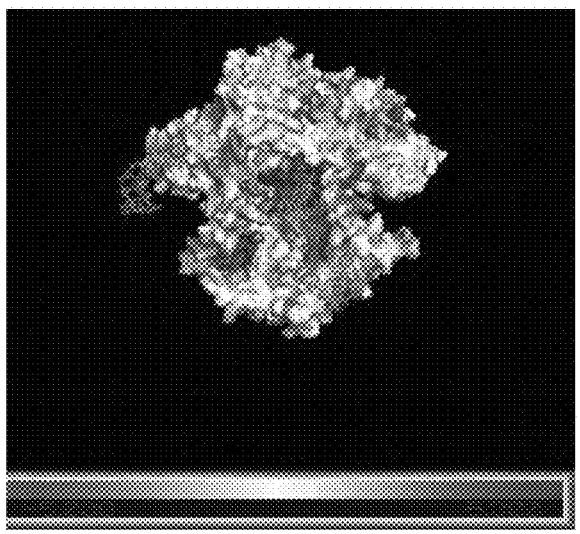
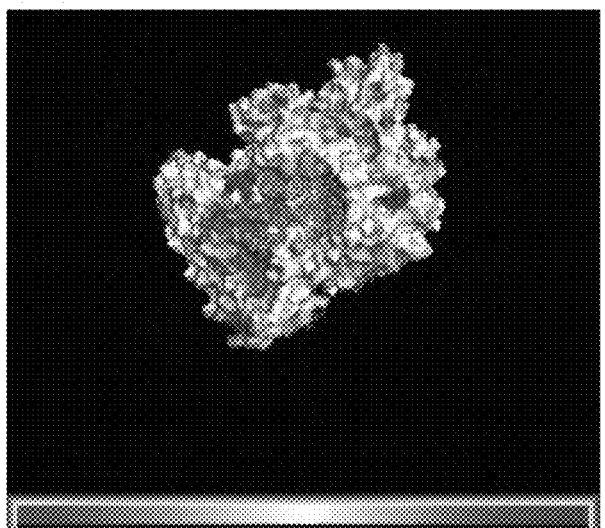
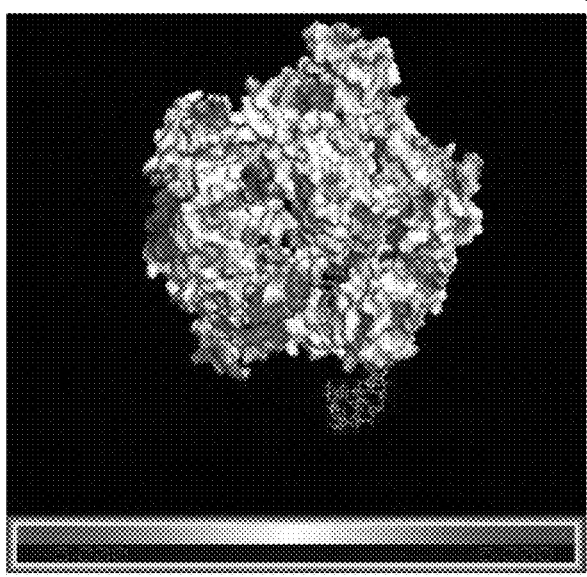

- Chain B interleukin-2 receptor alpha chain
- B 3 CYS
- B 4 ASP
- B 5 ASP
- B 6 ASP
- A 33 ASN
- A 34 PRO
- A 35 LYS
- A 36 LEU
- A 37 THR
- A 38 ARG
- A 39 MET
- A 40 LEU
- A 41 THR
- A 42 PHE
- A 43 LYS
- A 44 PHE
- A 45 TYR
- B 25 MET
- B 26 LEU
- B 27 ASN
- B 28 CYS
- B 29 GLU

Figure 120

Converged to a structure in which the strand heavily interacts with the linker residues.

For residues 71 to 94 there are hydrophobic residues that stabilize the helix by interacting with two other helices in KIT. Hydrophobic residues are shown in red:

SNYSIIDKLVNIVDDLVECVKENS

Sequence was changed to remove the hydrophobic residues and replaced with amino isobutyric acid (Aib) which helps induce helical folds.

SNYS  IDK  LVNIV  DD  LVECVKENS

KIT7194_AIB1: SNYS AibADK AibANAibA DD AibAEAibAKENS

METHODS AND COMPOSITIONS FOR NUCLEIC ACID AND PROTEIN PAYLOAD DELIVERY

CROSS-REFERENCE

This application is a continuation of U.S. application Ser. No. 15/842,820, filed Dec. 14, 2017, which claims the benefit of U.S. Provisional Patent Application No. 62/434,344, filed Dec. 14, 2016, of U.S. Provisional Patent Application No. 62/517,346, filed Jun. 9, 2017, of U.S. Provisional Patent Application No. 62/443,567, filed Jan. 6, 2017, and of U.S. Provisional Patent Application No. 62/443,522, filed Jan. 6, 2017, all of which applications are incorporated herein by reference in their entirety.

INCORPORATION BY REFERENCE OF SEQUENCE LISTING PROVIDED AS A TEXT FILE

A Sequence Listing is provided herewith as a text file, "LGDL-003 SeqList_ST25.txt" created on Dec. 14, 2017 and having a size of 54 KB. The contents of the text file are incorporated by reference herein in their entirety.

INTRODUCTION

Despite recent progress in the field of ligand-targeted therapeutics, methods for delivery of intracellularly-active payloads, e.g., nucleic acid therapeutics for gene therapy applications, remain limited. A primary hurdle is the ability to create a matching targeting ligand for a given therapeutic application involving the shuttling of an intracellularly-active payload to its appropriate intracellular microenvironment. Some research has been conducted with the aim of creating high-affinity targeting techniques for bare nucleic acid (e.g. chemically modified siRNA molecules covalently bound to N-acetylgalactosamine (GalNAc) for liver targeting), or nanoparticle-based drug/gene delivery (e.g., prostate-specific membrane antigen (PSMA)-targeted docetaxel nanoparticles). However, currently available methods do not take into account many of the considerations involved in the effective, targeted delivery of nucleic acid, protein, and/or ribonucleoprotein payload to a cell. The present disclosure addresses these concerns and provides related advantages.

SUMMARY

Provided are methods and compositions for delivering a nucleic acid, protein, and/or ribonucleoprotein payload to a cell. Also provided are delivery molecules that include a peptide targeting ligand conjugated to a protein or nucleic acid payload (e.g., an siRNA molecule), or conjugated to a charged polymer polypeptide domain (e.g., poly-arginine such as 9R or a poly-histidine such as 6H, and the like). The targeting ligand provides for (i) targeted binding to a cell surface protein, and (ii) engagement of a long endosomal recycling pathway. As such, when the targeting ligand engages the intended cell surface protein, the delivery molecule enters the cell (e.g., via endocytosis) but is preferentially directed away from the lysosomal degradation pathway. In some cases, the targeting ligand provides for targeted binding to a cell surface protein, but does not necessarily provide for engagement of a long endosomal recycling pathway.

In some cases when the targeting ligand is conjugated to a charged polymer polypeptide domain, the charged polymer polypeptide domain interacts with (e.g., is condensed with) a nucleic acid payload such as an siRNA, or a plasmid DNA, or mRNA. In some cases when the targeting ligand is conjugated to a charged polymer polypeptide domain, the charged polymer polypeptide domain interacts with (e.g., is condensed with) a protein payload. In some cases, the charged polymer polypeptide domain of a subject delivery molecule interacts with a payload (e.g., nucleic acid and/or protein) and is present in a composition with an anionic polymer (e.g., the delivery molecule can be condensed with both a payload and an anionic polymer).

In some cases when the targeting ligand is conjugated to a charged polymer polypeptide domain, the charged polymer polypeptide domain interacts, e.g., electrostatically, with a charged stabilization layer (such as a silica, peptoid, polycysteine, or calcium phosphate coating) of a nanoparticle.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1 (panels A-F) provides schematic drawings of example configurations of a subject delivery molecule. Note that the targeting ligand can be conjugated at the N- or C-terminus (left of each panel), but can also be conjugated at an internal position (right of each panel). The molecules in panels A, C, and E include a linker while those of panels B, D, and F do not. (panels A-B) delivery molecules that include a targeting ligand conjugated to a payload. (panels C-D) delivery molecules that include a targeting ligand conjugated to a charged polymer polypeptide domain that is interacting electrostatically with a charged stabilization layer of a nanoparticle. (panels E-F) delivery molecules that include a targeting ligand conjugated to a charged polymer polypeptide domain that is condensed with a nucleic acid payload.

FIG. 2, panel A provides an example of a conjugation strategy of Exendin-4 (1-39) [Cys11] (SEQ ID NO: 2), conjugated to a nucleic acid, protein or ribonucleoprotein with a reducibly-cleavable disulfide bond. FIG. 2, panel B provides an example of a conjugation strategy of Exendin-4 (1-39) [Cys11], conjugated to a nucleic acid, protein or ribonucleoprotein with an amine-reactive bond. FIG. 2, panel C provides an example of a conjugation strategy of Exendin-4 (1-39) [Cys11], conjugated via a reducibly-cleavable disulfide bond to a linker, which is conjugated to a nucleic acid, protein or ribonucleoprotein (via an amine-reactive domain). FIG. 2, panel D provides an example of a conjugation strategy of Exendin-4 (1-39) [Cys11], conjugated via a reducibly-cleavable disulfide bond to a linker, which is conjugated to a charged polymer polypeptide domain (a 9R sequence is depicted), which then coats a nanoparticle surface by interacting electrostatically with the charged stabilization layer (e.g., silica, peptoid, polycysteine, or calcium phosphate coating) of the nanoparticle.

FIG. 8 provides condensation curves on nanoparticles with payload: VWF-EGFP pDNA with peptide nucleic acid (PNA) Binding Site.

FIG. 19 provides condensation curves on nanoparticles with payload: NLS-Cas9-EGFP RNP complexed to HBB gRNA.

FIG. 22 provides data collected when using nanoparticles with Cy5 EGFP mRNA as payload.

FIG. 36 provides data related to project HSC.001.001 (see Table 4).

FIG. 37 provides data related to project HSC.001.002 (see Table 4).

FIG. 38 provides data related to project HSC.002.01 (Targeting Ligand—ESELLg_mESEL_(4GS)2_9R_N) (see Table 4).

FIG. 39 provides data related to project HSC.002.02 (Targeting Ligand—ESELLg_mESEL_(4GS)2_9R_C) (see Table 4).

FIG. 40 provides data related to project HSC.002.03 (Targeting Ligand—CD45_mSiglec_(4GS)2_9R_C) (see Table 4).

FIG. 41 provides data related to project HSC.002.04 (Targeting Ligand—Cy5mRNA-SiO2-PEG) (see Table 4).

FIG. 42 provides data related to project BLOOD.002.88 (Targeting Ligand—CD45_mSiglec_(4GS)2_9R_C) (see Table 4).

FIG. 43 provides data related to project BLOOD.002.89 (Targeting Ligand—CD45_mSiglec_(4GS)2_9R_C) (see Table 4).

FIG. 44 provides data related to project BLOOD.002.90 (see Table 4).

FIG. 45 provides data related to project BLOOD.002.91 (PLR50) (see Table 4).

FIG. 46 provides data related to project BLOOD.002.92 (Targeting Ligand—CD45_mSiglec_(4GS)2_9R_C) (see Table 4).

FIG. 47 provides data related to project TCELL.001.1 (see Table 4).

FIG. 48 provides data related to project TCELL.001.3 (see Table 4).

FIG. 49 provides data related to project TCELL.001.13 (see Table 4).

FIG. 50 provides data related to project TCELL.001.14 (see Table 4).

FIG. 51 provides data related to project TCELL.001.16 (see Table 4).

FIG. 52 provides data related to project TCELL.001.18 (see Table 4).

FIG. 53 provides data related to project TCELL.001.28 (see Table 4).

FIG. 54 provides data related to project TCELL.001.29 (see Table 4).

FIG. 55 provides data related to project TCELL.001.31 (see Table 4).

FIG. 56 provides data related to project TCELL.001.33 (see Table 4).

FIG. 57 provides data related to project TCELL.001.43 (see Table 4).

FIG. 58 provides data related to project TCELL.001.44 (see Table 4).

FIG. 59 provides data related to project TCELL.001.46 (see Table 4).

FIG. 60 provides data related to project TCELL.001.48 (see Table 4).

FIG. 61 provides data related to project TCELL.001.58 (see Table 4).

FIG. 62 provides data related to project TCELL.001.59 (see Table 4).

FIG. 63 provides data related to project CYN-OBM.002.82 (see Table 4).

FIG. 64 provides data related to project CYN-OBM.002.83 (see Table 4).

FIG. 65 provides data related to project CYN-OBM.002.84 (see Table 4).

FIG. 66 provides data related to project CYN-OBM.002.85 (see Table 4).

FIG. 67 provides data related to project CYN-OBM.002.86 (see Table 4).

FIG. 68 provides data related to project CYN-OBM.002.76 (see Table 4).

FIG. 69 provides data related to project CYN-OBM.002.77 (see Table 4).

FIG. 70 provides data related to project CYN-OBM.002.78 (see Table 4).

FIG. 71 provides data related to project CYN-OBM.002.79 (see Table 4).

FIG. 72 provides data related to project CYN-OBM.002.80 (see Table 4).

FIG. 75 provides data related to project CynoBM.002 RNP-Only controls (see Table 4).

FIG. 76 provides data related to project CynoBM.002.82 (see Table 4).

FIG. 77 provides data related to project CynoBM.002.83 (see Table 4).

FIG. 78 provides data related to project CYN-OBM.002.84 (see Table 4).

FIG. 79 provides data related to project CynoBM.002.85 (see Table 4).

FIG. 80 provides data related to project CynoBM.002.86 (see Table 4).

FIG. 88 provides qualitative images of CynoBM.002 RNP-Only controls.

FIG. 89 provides data related to project HSC.004 (see Table 4) high-content screening.

FIG. 90 provides data related to project TCELL.001 (see Table 4) high-content screening.

FIG. 91 provides data related to project TCELL.001 (see Table 4) lipofectamine CRISPRMAX controls.

FIG. 92 provides data related to project TCell.001.1 (see Table 4).

FIG. 93 provides data related to project TCell.001.2 (see Table 4).

FIG. 94 provides data related to project TCell.001.3 (see Table 4).

FIG. 95 provides data related to project TCell.001.4 (see Table 4).

FIG. 96 provides data related to project TCell.001.5 (see Table 4).

FIG. 97 provides data related to project TCell.001.6 (see Table 4).

FIG. 98 provides data related to project TCell.001.7 (see Table 4).

FIG. 99 provides data related to project TCell.001.8 (see Table 4).

FIG. 100 provides data related to project TCell.001.9 (see Table 4).

FIG. 101 provides data related to project TCell.001.10 (see Table 4).

FIG. 102 provides data related to project TCell.001.11 (see Table 4).

FIG. 103 provides data related to project TCell.001.12 (see Table 4).

FIG. 104 provides data related to project TCell.001.13 (see Table 4).

FIG. 105 provides data related to project TCell.001.14 (see Table 4).

FIG. 106 provides data related to project TCell.001.15 (see Table 4).

FIG. 107 provides data related to negative controls for project TCell.001 (see Table 4).

FIG. 108 provides data related to project Blood.002 (see Table 4).

FIG. 109 provides data related to project TCell.001.27 (see Table 4).

Figure 119:
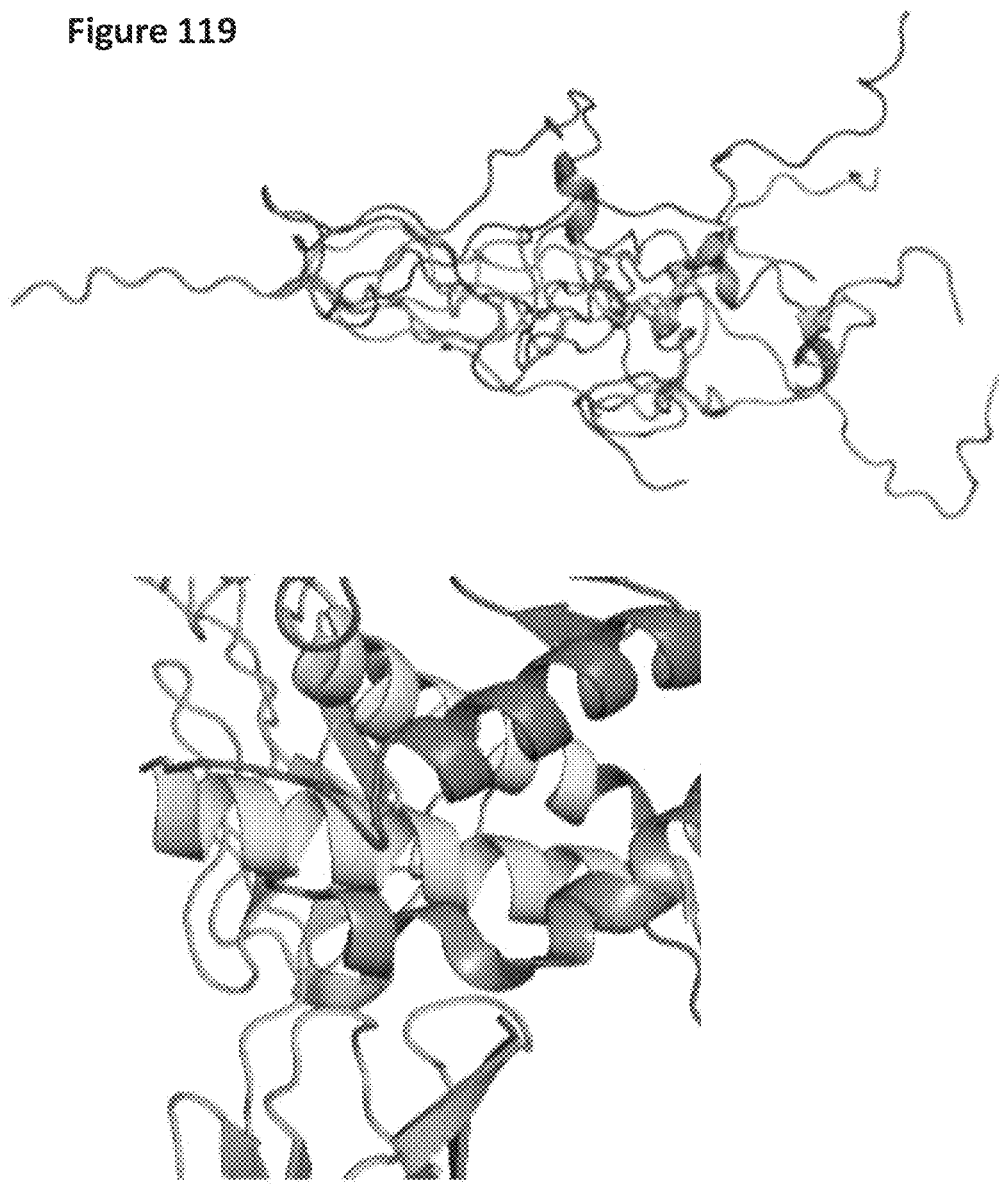

FIG. 119 provides example images generated during rational design of a cKit Receptor Fragment.

FIG. 120 provides example images generated during rational design of a cKit Receptor Fragment.

Figure 121:
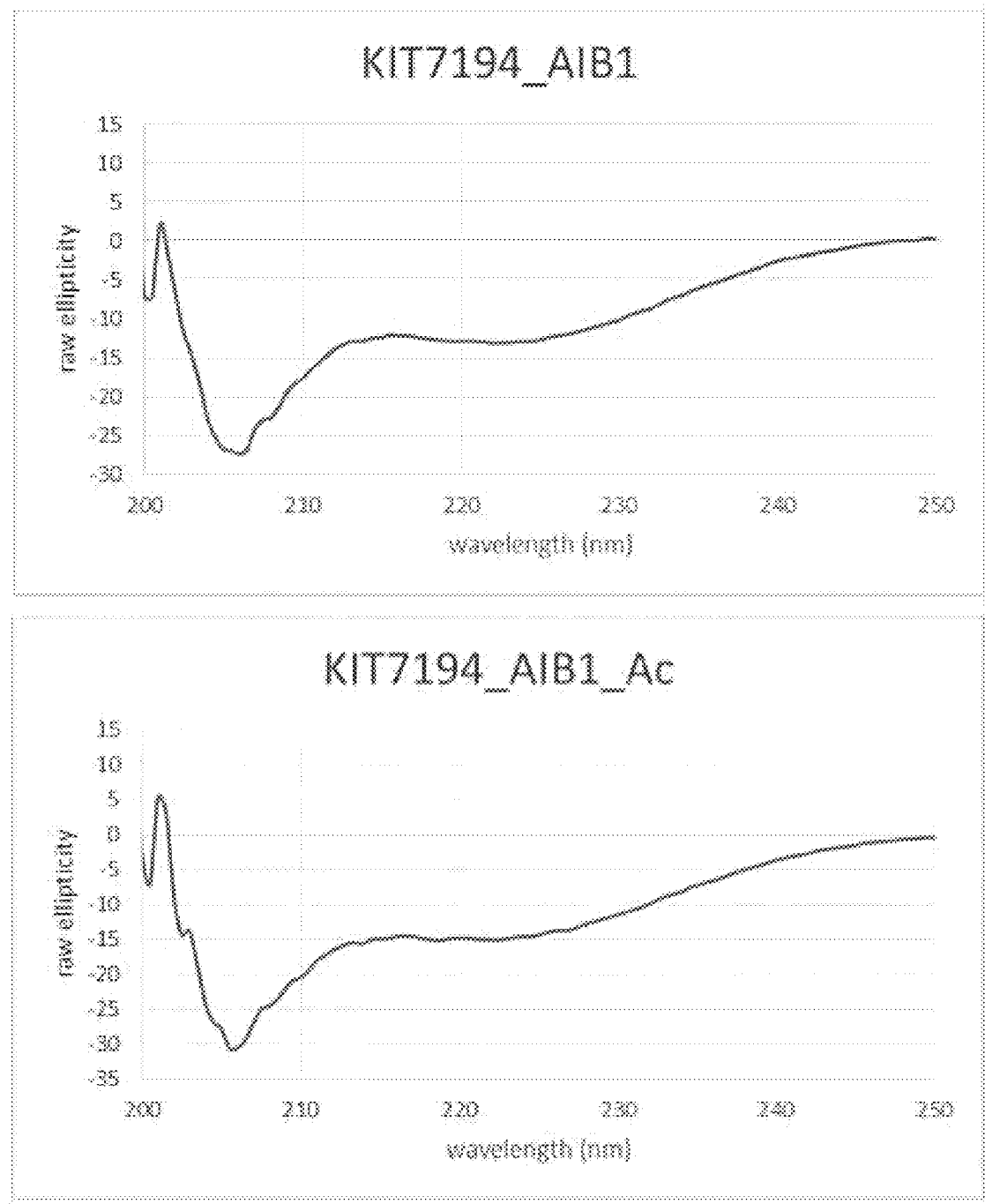

FIG. 121 provides circular dichroism data from analyzing the rationally designed cKit Receptor Fragment.

Figure 122:
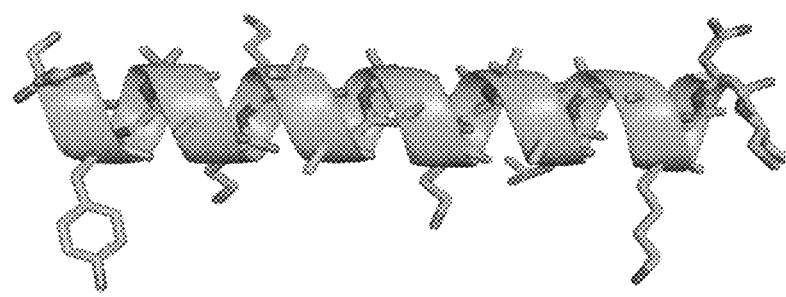

FIG. 122 depicts modeling of the stabilized conformation of the rationally designed cKit Receptor Fragment.

Figure 123:
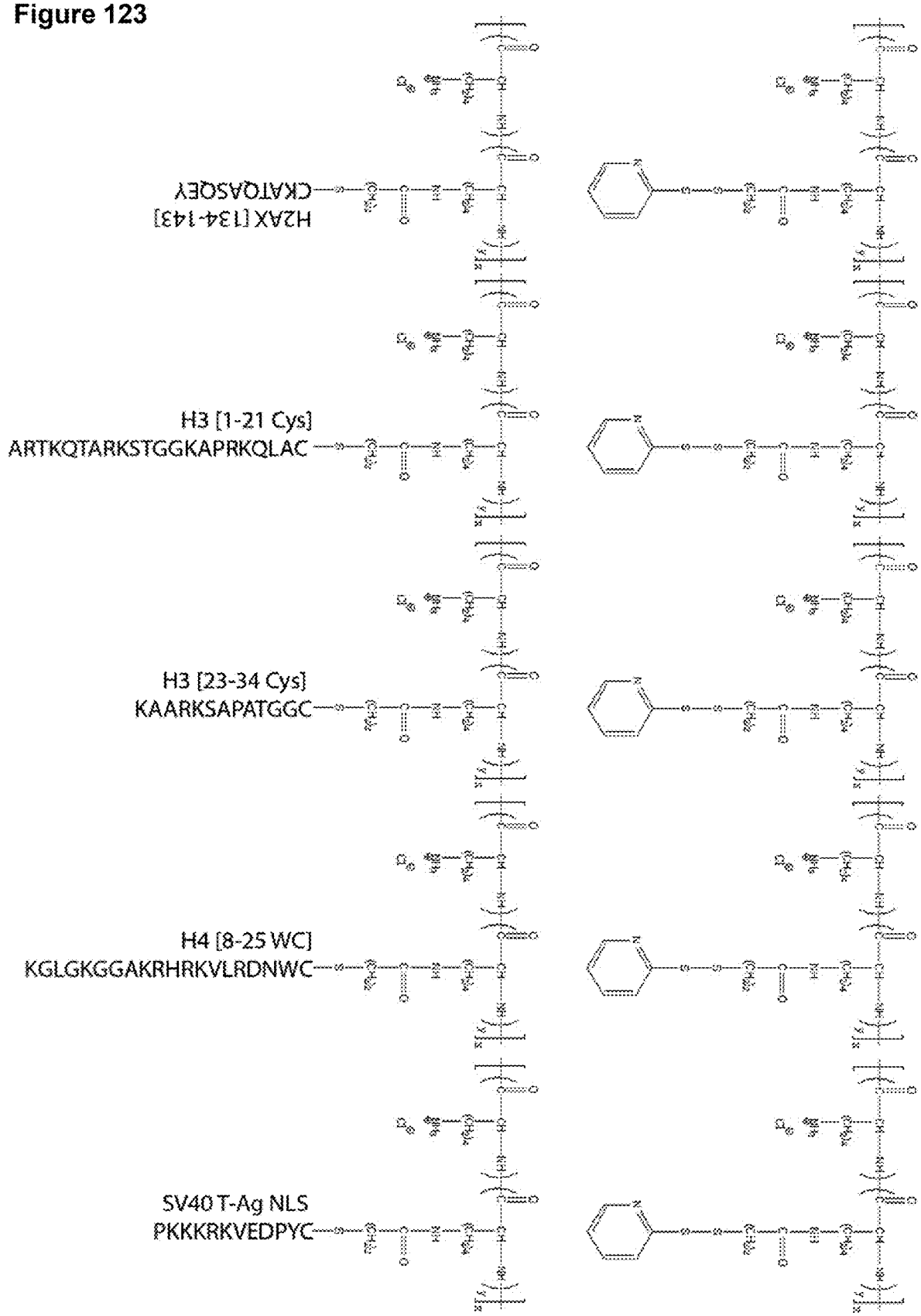

FIG. 123 depicts an example of a branched histone structure in which HTPs are conjugated to the side chains of a cationic polymer backbone. The polymer on the right represents the precursor backbone molecule and the molecule on the left is an example of a segment of a branched structure.

DETAILED DESCRIPTION

As summarized above, provided are methods and compositions for delivering a nucleic acid, protein, and/or ribonucleoprotein payload to a cell. The provided delivery molecules include a peptide targeting ligand conjugated to a protein or nucleic acid payload (e.g., an siRNA molecule), or conjugated to a charged polymer polypeptide domain (e.g., poly-arginine such as 9R or a poly-histidine such as 6H, and the like). The targeting ligand provides for (i) targeted binding to a cell surface protein, and (ii) engagement of a long endosomal recycling pathway.

Before the present methods and compositions are described, it is to be understood that this invention is not limited to the particular methods or compositions described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order that is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the endonuclease" includes reference to one or more endonucleases and equivalents thereof, known to those skilled in the art, and so forth. It is further noted that the claims may be drafted to exclude any element, e.g., any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication. Further, the dates of publication provided may be different from the actual publication dates which may need to be independently confirmed.

Methods and Compositions

Once endocytosed, transmembrane cell surface proteins can return to the cell surface by at least two different routes: directly from sorting endosomes via the "short cycle" or indirectly traversing the perinuclear recycling endosomes that constitute the "long cycle." Thus, from the endosomal compartment, at least three diverse pathways diverge to different destinations: lysosomes (degradative pathway), perinuclear recycling compartment ('long cycle'; or 'long', 'indirect', or 'slow' endosomal recycling pathway), or directly to the plasma membrane ('short cycle'; or 'short, 'direct', or 'fast' endosomal recycling pathway). Until now attention has not been given to the combined roles of (a) binding affinity, (b) signaling bias/functional selectivity, and (c) specific endosomal sorting pathways, in selecting for an appropriate targeting ligand for mediating effective delivery and, e.g., expression of a nucleic acid within a cell.

Figure 2:
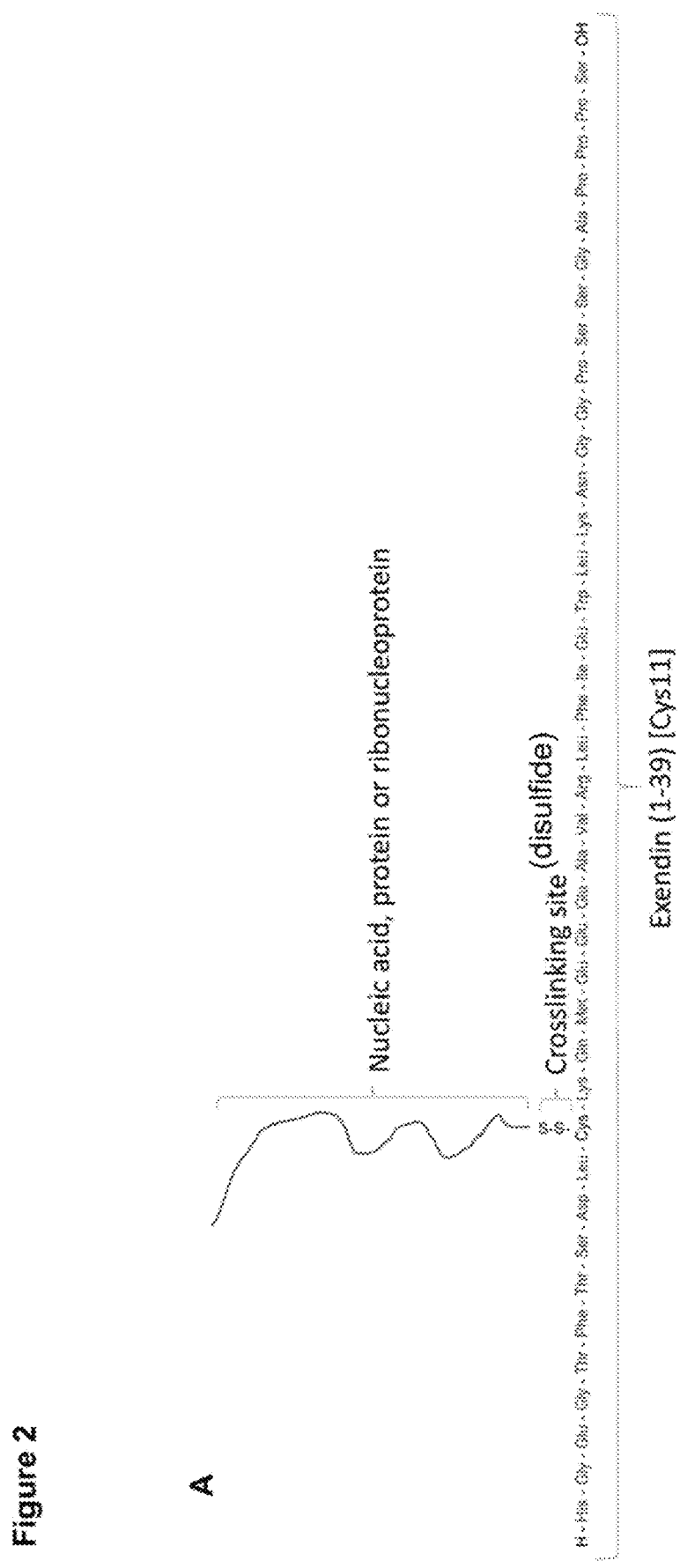
FIG. 2 (panels A-D) provides schematic drawings of example configurations of a subject delivery molecule. The targeting ligand depicted is Exendin (with a S11C substitution), see SEQ ID NO: 2). Examples are shown with different conjugation chemistry, with and without a linker, and with conjugation (via a linker) to a charged polymer polypeptide domain that is interacting electrostatically with a charged stabilization layer of a nanoparticle ("anionic nanoparticle surface").
Figure 2:
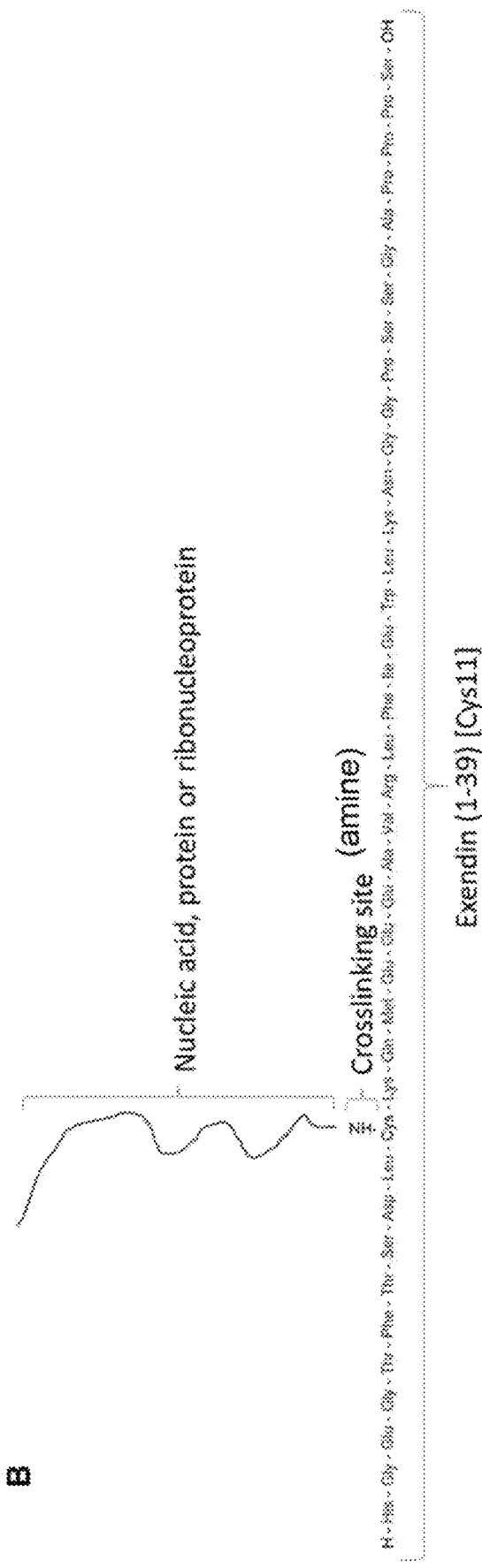
Figure 2:
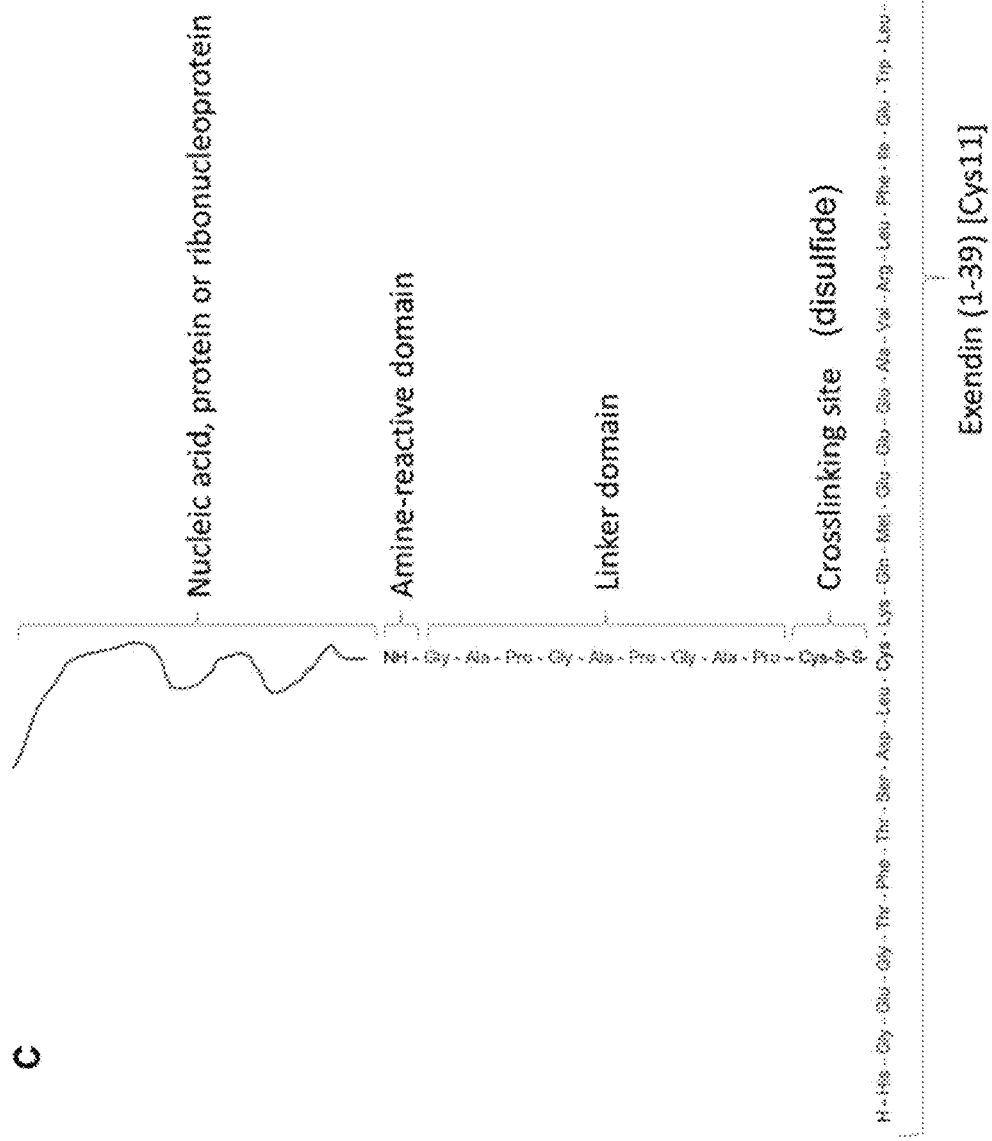
Figure 2:
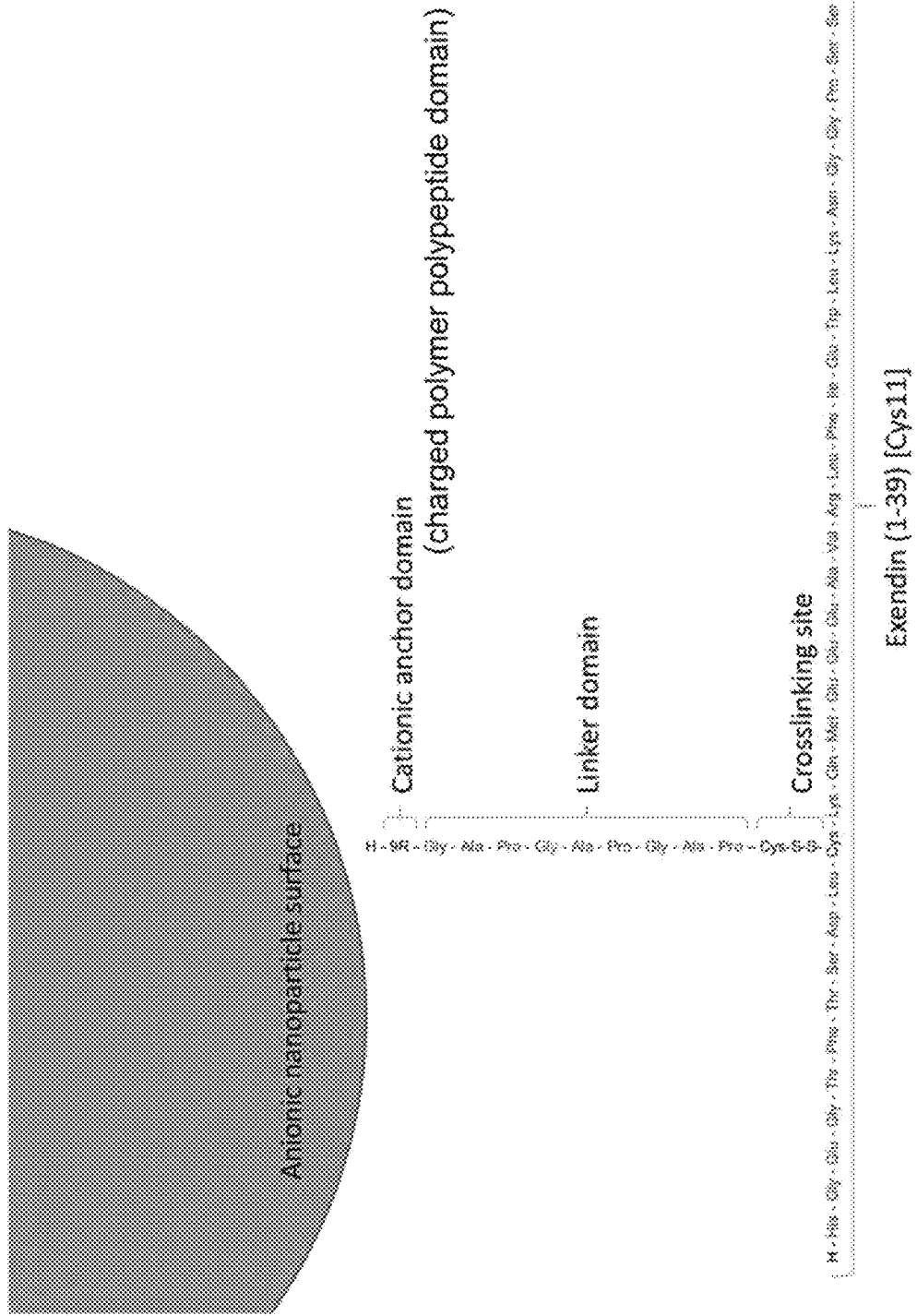

Provided are delivery molecules that include a peptide targeting ligand conjugated to a protein or nucleic acid payload, or conjugated to a charged polymer polypeptide domain. The targeting ligand provides for (i) targeted binding to a cell surface protein, and (ii) engagement of a long endosomal recycling pathway. In some cases when the targeting ligand is conjugated to a charged polymer polypeptide domain, the charged polymer polypeptide domain interacts with (e.g., is condensed with) a nucleic acid payload. In some cases the targeting ligand is conjugated via an intervening linker. Refer to FIG. 1 and FIG. 2 for examples of different possible conjugation strategies (i.e., different possible arrangements of the components of a subject delivery molecule). In some cases, the targeting ligand provides for targeted binding to a cell surface protein, but does not necessarily provide for engagement of a long endosomal recycling pathway. Thus, also provided are delivery molecules that include a peptide targeting ligand conjugated to a protein or nucleic acid payload, or conjugated to a charged polymer polypeptide domain, where the targeting ligand provides for targeted binding to a cell surface protein (but does not necessarily provide for engagement of a long endosomal recycling pathway).

In some cases, the delivery molecules disclosed herein are designed such that a nucleic acid or protein payload reaches its extracellular target (e.g., by providing targeted biding to a cell surface protein) and is preferentially not destroyed within lysosomes or sequestered into 'short' endosomal recycling endosomes. Instead, delivery molecules of the disclosure can provide for engagement of the 'long' (indirect/slow) endosomal recycling pathway, which can allow for endosomal escape and/or or endosomal fusion with an organelle.

For example, in some cases, β-arrestin is engaged to mediate cleavage of seven-transmembrane GPCRs (McGovern et al., Handb Exp Pharmacol. 2014; 219:341-59; Goodman et al., Nature. 1996 Oct. 3; 383(6599):447-50; Zhang et al., J Biol Chem. 1997 Oct. 24; 272(43):27005-14) and/or single-transmembrane receptor tyrosine kinases (RTKs) from the actin cytoskeleton (e.g., during endocytosis), triggering the desired endosomal sorting pathway. Thus, in some embodiments the targeting ligand of a delivery molecule of the disclosure provides for engagement of β-arrestin upon binding to the cell surface protein (e.g., to provide for signaling bias and to promote internalization via endocytosis following orthosteric binding).

Targeting Ligand

A variety of targeting ligands can be used as part of a subject delivery molecule, and numerous different targeting ligands are envisioned. In some embodiments the targeting ligand is a fragment (e.g., a binding domain) of a wild type protein. For example, the peptide targeting ligand of a subject delivery molecule can have a length of from 4-50 amino acids (e.g., from 4-40, 4-35, 4-30, 4-25, 4-20, 4-15, 5-50, 5-40, 5-35, 5-30, 5-25, 5-20, 5-15, 7-50, 7-40, 7-35, 7-30, 7-25, 7-20, 7-15, 8-50, 8-40, 8-35, 8-30, 8-25, 8-20, or 8-15 amino acids). The targeting ligand can be a fragment of a wild type protein, but in some cases has a mutation (e.g., insertion, deletion, substitution) relative to the wild type amino acid sequence (i.e., a mutation relative to a corresponding wild type protein sequence). For example, a targeting ligand can include a mutation that increases or decreases binding affinity with a target cell surface protein.

In some cases, a targeting ligand can include a mutation that adds a cysteine residue, which can facilitate strategies for conjugation to a linker, a protein or nucleic acid payload, and/or a charged polymer polypeptide domain. For example, cysteine can be used for crosslinking (conjugation) to nucleic acids (e.g., siRNA) and proteins via sulfhydryl chemistry (e.g., a disulfide bond) and/or amine-reactive chemistry.

In some cases, a targeting ligand includes an internal cysteine residue. In some cases, a targeting ligand includes a cysteine residue at the N- and/or C-terminus. In some cases, in order to include a cysteine residue, a targeting ligand is mutated (e.g., insertion or substitution) relative to a corresponding wild type sequence. As such, any of the targeting ligands described herein can be modified with any of the above insertions and/or substitutions using a cysteine residue (e.g., internal, N-terminal, C-terminal insertion of or substitution with a cysteine residue).

By "corresponding" wild type sequence is meant a wild type sequence from which the subject sequence was or could have been derived (e.g., a wild type protein sequence having high sequence identity to the sequence of interest). For example, for a targeting ligand that has one or more mutations (e.g., substitution, insertion) but is otherwise highly similar to a wild type sequence, the amino acid sequence to which it is most similar may be considered to be a corresponding wild type amino acid sequence.

A corresponding wild type protein/sequence does not have to be 100% identical (e.g., can be 85% or more identical, 90% or more identical, 95% or more identical, 98% or more identical, 99% or more identical, etc.)(outside of the position(s) that is modified), but the targeting ligand and corresponding wild type protein (e.g., fragment of a wild protein) can bind to the intended cell surface protein, and retain enough sequence identity (outside of the region that is modified) that they can be considered homologous. The amino acid sequence of a "corresponding" wild type protein sequence can be identified/evaluated using any convenient method (e.g., using any convenient sequence comparison/alignment software such as BLAST, MUSCLE, T-COFFEE, etc.).

Examples of targeting ligands that can be used as part of a subject delivery molecule include, but are not limited to, those listed in Table 1. Examples of targeting ligands that can be used as part of a subject delivery molecule include, but are not limited to, those listed in Table 2 (many of the sequences listed in Table 2 include the targeting ligand (e.g., SNRWLDVK for row 2) conjugated to a cationic polypeptide domain, e.g., 9R, 6R, etc., via a linker (e.g., GGGGSGGGGS). Examples of amino acid sequences that can be included in a targeting ligand include, but are not limited to: NPKLTRMLTFKFY (SEQ ID NO: xx) (IL2), TSVGKYPNTGYYGD (SEQ ID NO: xx) (CD3), SNRWLDVK (Siglec), EKFILKVRPAFKAV (SEQ ID NO: xx) (SCF); EKFILKVRPAFKAV (SEQ ID NO: xx) (SCF), EKFILKVRPAFKAV (SEQ ID NO: xx) (SCF), SNYSIDKLVNIVDDLVECVKENS (SEQ ID NO: xx) (cKit), and Ac-SNYSAibADKAibANAibADDAibAEAibAKENS (SEQ ID NO: xx) (cKit). Thus in some cases a targeting ligand includes an amino acid sequence that has 85% or more (e.g., 90% or more, 95% or more, 98% or more, 99% or more, or 100%) sequence identity with NPKLTRMLTFKFY (SEQ ID NO: xx) (IL2), TSVGKYPNTGYYGD (SEQ ID NO: xx) (CD3), SNRWLDVK (Siglec), EKFILKVRPAFKAV (SEQ ID NO: xx) (SCF); EKFILKVRPAFKAV (SEQ ID NO: xx) (SCF), EKFILKVRPAFKAV (SEQ ID NO: xx) (SCF), or SNYSIDKLVNIVDDLVECVKENS (SEQ ID NO: xx) (cKit).

97% or more, 98% or more, 99% or more, 99.5% or more, or 100% sequence identity) with the amino acid sequence set forth in any one of SEQ ID NOs: 1-12.

The terms "targets" and "targeted binding" are used herein to refer to specific binding. The terms "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides, a ligand specifically binds to a particular receptor relative to other available receptors). In some embodiments, the affinity of one molecule for another molecule to which it specifically binds is characterized by a $K_d$ (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity correlates with a lower $K_d$.

In some cases, the targeting ligand provides for targeted binding to a cell surface protein selected from a family B G-protein coupled receptor (GPCR), a receptor tyrosine kinase (RTK), a cell surface glycoprotein, and a cell-cell

TABLE 1

Examples of Targeting ligands

| Cell Surface Protein | Targeting Ligand | Sequence | SEQ ID NO: |
|---|---|---|---|
| Family B GPCR | Exendin | HGEGTFTSDLSKQMEEEAVRLFIEWLKNGGPSSGAPPPS | 1 |
| | Exendin (S11C) | HGEGTFTSDLCKQMEEEAVRLFIEWLKNGGPSSGAPPPS | 2 |
| FGF receptor | FGF fragment | KRLYCKNGGFFLRIHPDGRVDGVREKSDPHIKLQLQAEERGVVSIKGVCANRYLAMKEDGRLLASKCVTDECFFFERLESNNYNTY | 3 |
| | FGF fragment | KNGGFFLRIHPDGRVDGVREKS | 4 |
| | FGF fragment | HFKDPK | 5 |
| | FGF fragment | LESNNYNT | 6 |
| | E-selectin | MIASQFLSALTLVLLIKESGA | 7 |
| | L-selectin | MVFPWRCEGTYWGSRNILKLWVWTLLCCDFLIHHGTHC | 8 |
| | | MIFPWKCQSTQRDLVVNIFKLWGWTMLCCDFLAHHGTDC | 9 |
| | | MIFPWKCQSTQRDLVVNIFKLWGWTMLCC | 10 |
| transferrin receptor | Transferrin ligand | THRPPMWSPVWP | 11 |
| α5β1 integrin | α5β1 ligand | RRETAWA | 12 |
| | α5β1 ligand | RGD | |

A targeting ligand of a subject delivery molecule can include the amino acid sequence RGD and/or an amino acid sequence having 85% or more sequence identity (e.g., 90% or more, 95% or more, 97% or more, 98% or more, 99% or more, 99.5% or more, or 100% sequence identity) with the amino acid sequence set forth in any one of SEQ ID NOs: 1-12. In some cases, a targeting ligand of a subject delivery molecule includes the amino acid sequence RGD and/or the amino acid sequence set forth in any one of SEQ ID NOs: 1-12. In some embodiments, a targeting ligand of a subject delivery molecule can include a cysteine (internal, C-terminal, or N-terminal), and can also include the amino acid sequence RGD and/or an amino acid sequence having 85% or more sequence identity (e.g., 90% or more, 95% or more, adhesion molecule. Consideration of a ligand's spatial arrangement upon receptor docking can be used to accomplish the appropriate desired functional selectivity and endosomal sorting biases, e.g., so that the structure function relationship between the ligand and the target is not disrupted due to the conjugation of the targeting ligand to the payload or charged polymer polypeptide domain. For example, conjugation to a nucleic acid, protein, ribonucleoprotein, or charged polymer polypeptide domain could potentially interfere with the binding cleft(s).

Thus, in some cases, where a crystal structure of a desired target (cell surface protein) bound to its ligand is available (or where such a structure is available for a related protein), one can use 3D structure modeling and sequence threading to visualize sites of interaction between the ligand and the target. This can facilitate, e.g., selection of internal sites for placement of substitutions and/or insertions (e.g., of a cysteine residue).

As an example, in some cases, the targeting ligand provides for binding to a family B G protein coupled receptor (GPCR) (also known as the 'secretin-family'). In some cases, the targeting ligand provides for binding to both an allosteric-affinity domain and an orthosteric domain of the family B GPCR to provide for the targeted binding and the engagement of long endosomal recycling pathways, respectively (see e.g., the examples section below as well as FIG. 3 and FIG. 4).

G-protein-coupled receptors (GPCRs) share a common molecular architecture (with seven putative transmembrane segments) and a common signaling mechanism, in that they interact with G proteins (heterotrimeric GTPases) to regulate the synthesis of intracellular second messengers such as cyclic AMP, inositol phosphates, diacylglycerol and calcium ions. Family B (the secretin-receptor family or 'family 2') of the GPCRs is a small but structurally and functionally diverse group of proteins that includes receptors for polypeptide hormones and molecules thought to mediate intercellular interactions at the plasma membrane (see e.g., Harmar et al., Genome Biol. 2001; 2(12):REVIEWS3013). There have been important advances in structural biology as relates to members of the secretin-receptor family, including the publication of several crystal structures of their N-termini, with or without bound ligands, which work has expanded the understanding of ligand binding and provides a useful platform for structure-based ligand design (see e.g., Poyner et al., Br J Pharmacol. 2012 May; 166(1):1-3).

For example, one may desire to use a subject delivery molecule to target the pancreatic cell surface protein GLP1R (e.g., to target β-islets) using the Exendin-4 ligand, or a derivative thereof. In such a case, an amino acid for cysteine substitution and/or insertion (e.g., for conjugation to a nucleic acid payload) can be identified by aligning the Exendin-4 amino acid sequence, which is HGEGTFTSDL-SKQMEEEAVRLFIEWLKNGGPSSGAPPPS (SEQ ID NO. 1), to crystal structures of glucagon-GCGR (4ERS) and GLP1-GLP1R-ECD complex (PDB: 3IOL), using PDB 3 dimensional renderings, which may be rotated in 3D space in order to anticipate the direction that a cross-linked complex must face in order not to disrupt the two binding clefts (see e.g., the examples section below as well as FIG. 3 and FIG. 4). When a desirable cross-linking site (e.g., site for substitution/insertion of a cysteine residue) of a targeting ligand (that targets a family B GPCR) is sufficiently orthogonal to the two binding clefts of the corresponding receptor, high-affinity binding may occur as well as concomitant long endosomal recycling pathway sequestration (e.g., for optimal payload release).

In some cases, a subject delivery molecule includes a targeting ligand that includes an amino acid sequence having 85% or more (e.g., 90% or more, 95% or more, 98% or more, 99% or more, or 100%) identity to the exendin-4 amino acid sequence (SEQ ID NO: 1). In some such cases, the targeting ligand includes a cysteine substitution or insertion at one or more of positions corresponding to L10, S11, and K12 of the amino acid sequence set forth in SEQ ID NO: 1. In some cases, the targeting ligand includes a cysteine substitution or insertion at a position corresponding to S11 of the amino acid sequence set forth in SEQ ID NO: 1. In some cases, a subject delivery molecule includes a targeting ligand that includes an amino acid sequence having the exendin-4 amino acid sequence (SEQ ID NO: 1).

As another example, in some cases a targeting ligand according to the present disclosure provides for binding to a receptor tyrosine kinase (RTK) such as fibroblast growth factor (FGF) receptor (FGFR). Thus in some cases the targeting ligand is a fragment of an FGF (i.e., comprises an amino acid sequence of an FGF). In some cases, the targeting ligand binds to a segment of the RTK that is occupied during orthosteric binding (e.g., see the examples section below). In some cases, the targeting ligand binds to a heparin-affinity domain of the RTK. In some cases, the targeting ligand provides for targeted binding to an FGF receptor and comprises an amino acid sequence having 85% or more sequence identity (e.g., 90% or more, 95% or more, 97% or more, 98% or more, 99% or more, 99.5% or more, or 100% sequence identity) with the amino acid sequence KNGGFFLRIHPDGRVDGVREKS (SEQ ID NO: 4). In some cases, the targeting ligand provides for targeted binding to an FGF receptor and comprises the amino acid sequence set forth as SEQ ID NO: 4.

In some cases, small domains (e.g., 5-40 amino acids in length) that occupy the orthosteric site of the RTK may be used to engage endocytotic pathways relating to nuclear sorting of the RTK (e.g., FGFR) without engagement of cell-proliferative and proto-oncogenic signaling cascades, which can be endemic to the natural growth factor ligands. For example, the truncated bFGF (tbFGF) peptide (a.a.30-115), contains a bFGF receptor binding site and a part of a heparin-binding site, and this peptide can effectively bind to FGFRs on a cell surface, without stimulating cell proliferation. The sequences of tbFGF are KRLYCKNGGFFL-RIHPDGRVDGVREKSDPHIKLQL-QAEERGVVSIKGVCANRYLAMKEDGRLLASKCVTD ECFFFERLESNNYNTY (SEQ ID NO: 13) (see, e.g., Cai et al., Int J Pharm. 2011 Apr. 15; 408(1-2):173-82).

In some cases, the targeting ligand provides for targeted binding to an FGF receptor and comprises the amino acid sequence HFKDPK (SEQ ID NO: 5) (see, e.g., the examples section below). In some cases, the targeting ligand provides for targeted binding to an FGF receptor, and comprises the amino acid sequence LESNNYNT (SEQ ID NO: 6) (see, e.g., the examples section below).

In some cases, a targeting ligand according to the present disclosure provides for targeted binding to a cell surface glycoprotein. In some cases, the targeting ligand provides for targeted binding to a cell-cell adhesion molecule. For example, in some cases, the targeting ligand provides for targeted binding to CD34, which is a cell surface glycoprotein that functions as a cell-cell adhesion factor, and which is protein found on hematopoietic stem cells (e.g., of the bone marrow). In some cases, the targeting ligand is a fragment of a selectin such as E-selectin, L-selectin, or P-selectin (e.g., a signal peptide found in the first 40 amino acids of a selectin). In some cases a subject targeting ligand includes sushi domains of a selectin (e.g., E-selectin, L-selectin, P-selectin).

In some cases, the targeting ligand comprises an amino acid sequence having 85% or more sequence identity (e.g., 90% or more, 95% or more, 97% or more, 98% or more, 99% or more, 99.5% or more, or 100% sequence identity) with the amino acid sequence MIASQFLSALTLVL-LIKESGA (SEQ ID NO: 7). In some cases, the targeting ligand comprises the amino acid sequence set forth as SEQ ID NO: 7. In some cases, the targeting ligand comprises an amino acid sequence having 85% or more sequence identity (e.g., 90% or more, 95% or more, 97% or more, 98% or more, 99% or more, 99.5% or more, or 100% sequence identity) with the amino acid sequence MVFPWRCEGTYWGSRNILKLWVWTLLCCDF-LIHHGTHC (SEQ ID NO: 8). In some cases, the targeting ligand comprises the amino acid sequence set forth as SEQ ID NO: 8. In some cases, targeting ligand comprises an amino acid sequence having 85% or more sequence identity (e.g., 90% or more, 95% or more, 97% or more, 98% or more, 99% or more, 99.5% or more, or 100% sequence identity) with the amino acid sequence MIFPWKCQSTQRDLWNIFKLWGWTMLCCD-FLAHHGTDC (SEQ ID NO: 9). In some cases, targeting ligand comprises the amino acid sequence set forth as SEQ ID NO: 9. In some cases, targeting ligand comprises an amino acid sequence having 85% or more sequence identity (e.g., 90% or more, 95% or more, 97% or more, 98% or more, 99% or more, 99.5% or more, or 100% sequence identity) with the amino acid sequence MIFPWKCQSTQRDLWNIFKLWGWTMLCC (SEQ ID NO: 10). In some cases, targeting ligand comprises the amino acid sequence set forth as SEQ ID NO: 10.

Fragments of selectins that can be used as a subject targeting ligand (e.g., a signal peptide found in the first 40 amino acids of a selectin) can in some cases attain strong binding to specifically-modified sialomucins, e.g., various Sialyl Lewis$^x$ modifications/O-sialylation of extracellular CD34 can lead to differential affinity for P-selectin, L-selectin and E-selectin to bone marrow, lymph, spleen and tonsillar compartments. Conversely, in some cases a targeting ligand can be an extracellular portion of CD34. In some such cases, modifications of sialylation of the ligand can be utilized to differentially target the targeting ligand to various selectins.

In some cases, a targeting ligand according to the present disclosure provides for targeted binding to a transferrin receptor. In some such cases, the targeting ligand comprises an amino acid sequence having 85% or more sequence identity (e.g., 90% or more, 95% or more, 97% or more, 98% or more, 99% or more, 99.5% or more, or 100% sequence identity) with the amino acid sequence THRPPMWSPVWP (SEQ ID NO: 11). In some cases, targeting ligand comprises the amino acid sequence set forth as SEQ ID NO: 11.

In some cases, a targeting ligand according to the present disclosure provides for targeted binding to an integrin (e.g., α5β1 integrin). In some such cases, the targeting ligand comprises an amino acid sequence having 85% or more sequence identity (e.g., 90% or more, 95% or more, 97% or more, 98% or more, 99% or more, 99.5% or more, or 100% sequence identity) with the amino acid sequence RRETAWA (SEQ ID NO: 12). In some cases, targeting ligand comprises the amino acid sequence set forth as SEQ ID NO: 12. In some cases, the targeting ligand comprises the amino acid sequence RGD.

Also provided are delivery molecules with two different peptide sequences that together constitute a targeting ligand. For example, in some cases a targeting ligand is bivalent (e.g., heterobivalent). In some cases, cell-penetrating peptides and/or heparin sulfate proteoglycan binding ligands are used as heterobivalent endocytotic triggers along with any of the targeting ligands of this disclosure. A heterobivalent targeting ligand can include an affinity sequence from one of targeting ligand and an orthosteric binding sequence (e.g., one known to engage a desired endocytic trafficking pathway) from a different targeting ligand.

Conjugation Partner/Payload
Nucleic Acid Payload

In some embodiments, a targeting ligand of a delivery molecule of the disclosure is conjugated to a nucleic acid payload (see e.g., FIG. 1, panels A-B). In some embodiments, a delivery molecule of the disclosure is condensed with (interacts electrostatically with) a nucleic acid payload. The nucleic acid payload can be any nucleic acid of interest, e.g., the nucleic acid payload can be linear or circular, and can be a plasmid, a viral genome, an RNA, a DNA, etc. In some cases, the nucleic payload is an RNAi agent or a DNA template encoding an RNAi agent, where the RNAi agent can be, e.g., an shRNA or an siRNA. In some cases, the nucleic acid payload is an siRNA molecule. In some embodiments, a targeting ligand of a delivery molecule of the disclosure is conjugated to a protein payload, and in some cases the targeting ligand is conjugated to a ribonucleoprotein complex (e.g., via conjugation to the protein component or to the RNA component of the complex). Conjugation can be accomplished by any convenient technique and many different conjugation chemistries will be known to one of ordinary skill in the art. In some cases the conjugation is via sulfhydryl chemistry (e.g., a disulfide bond). In some cases the conjugation is accomplished using amine-reactive chemistry. In some cases, a targeting ligand includes a cysteine residue and is conjugated to the nucleic acid payload via the cysteine residue.

The term "nucleic acid payload" encompasses modified nucleic acids. Likewise, the terms "RNAi agent" and "siRNA" encompass modified nucleic acids. For example, the nucleic acid molecule can be a mimetic, can include a modified sugar backbone, one or more modified internucleoside linkages (e.g., one or more phosphorothioate and/or heteroatom internucleoside linkages), one or more modified bases, and the like. A subject nucleic acid payload (e.g., an siRNA) can have a morpholino backbone structure. In some case, a subject nucleic acid payload (e.g., an siRNA) can have one or more locked nucleic acids (LNAs). Suitable sugar substituent groups include methoxy (—O—CH$_3$), aminopropoxy (—OCH$_2$CH$_2$CH$_2$NH$_2$), allyl (—CH$_2$—CH=CH$_2$), —O— allyl (—O—CH$_2$—CH=CH$_2$) and fluoro (F). 2'-sugar substituent groups may be in the arabino (up) position or ribo (down) position. Suitable base modifications include synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2 (3H)-one), carbazole cytidine (2H-pyrimido(4,5-b)indol-2-one), pyridoindole cytidine (H-pyrido(3',2':4,5)pyrrolo(2,3-d)pyrimidin-2-one).

In some cases, a nucleic acid payload can include a conjugate moiety (e.g., one that enhances the activity, cellular distribution or cellular uptake of the oligonucleotide). These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject nucleic acid.

Charged Polymer Polypeptide Domain

In some case a targeting ligand of a subject delivery molecule is conjugated to a charged polymer polypeptide domain (a cationic anchoring domain) (see e.g., FIG. 1, panels C-F). Charged polymer polypeptide domains can include repeating cationic residues (e.g., arginine, lysine, histidine). In some cases, a cationic anchoring domain has a length in a range of from 3 to 30 amino acids (e.g., from 3-28, 3-25, 3-24, 3-20, 4-30, 4-28, 4-25, 4-24, or 4-20 amino acids; or e.g., from 4-15, 4-12, 5-30, 5-28, 5-25, 5-20, 5-15, 5-12 amino acids). In some cases, a cationic anchoring domain has a length in a range of from 4 to 24 amino acids. Suitable examples of a charged polymer polypeptide domain include, but are not limited to: RRRRRRRRR (9R)(SEQ ID NO: 15) and HHHHHH (6H)(SEQ ID NO: 16).

A charged polymer polypeptide domain (a cationic anchoring domain) can be any convenient cationic charged domain. For example, such a domain can be a histone tail peptide (HTP). In some cases a charged polymer polypeptide domain includes a histone and/or histone tail peptide (e.g., a cationic polypeptide can be a histone and/or histone tail peptide). In some cases a charged polymer polypeptide domain includes an NLS-containing peptide (e.g., a cationic polypeptide can be an NLS-containing peptide). In some cases a charged polymer polypeptide domain includes a peptide that includes a mitochondrial localization signal (e.g., a cationic polypeptide can be a peptide that includes a mitochondrial localization signal).

In some cases, a charged polymer polypeptide domain of a subject delivery molecule is used as a way for the delivery molecular to interact with (e.g., interact electrostatically, e.g., for condensation) the payload (e.g., nucleic acid payload and/or protein payload).

In some cases, a charged polymer polypeptide domain of a subject delivery molecule is used as an anchor to coat the surface of a nanoparticle with the delivery molecule, e.g., so that the targeting ligand is used to target the nanoparticle to a desired cell/cell surface protein (see e.g., FIG. 1, panels C-D). Thus, in some cases, the charged polymer polypeptide domain interacts electrostatically with a charged stabilization layer of a nanoparticle. For example, in some cases a nanoparticle includes a core (e.g., including a nucleic acid, protein, and/or ribonucleoprotein complex payload) that is surrounded by a stabilization layer (e.g., a silica, peptoid, polycysteine, or calcium phosphate coating). In some cases, the stabilization layer has a negative charge and a positively charged polymer polypeptide domain can therefore interact with the stabilization layer, effectively anchoring the delivery molecule to the nanoparticle and coating the nanoparticle surface with a subject targeting ligand (see, e.g., FIG. 1, panels C and D). Conjugation can be accomplished by any convenient technique and many different conjugation chemistries will be known to one of ordinary skill in the art. In some cases the conjugation is via sulfhydryl chemistry (e.g., a disulfide bond). In some cases the conjugation is accomplished using amine-reactive chemistry. In some cases, the targeting ligand and the charged polymer polypeptide domain are conjugated by virtue of being part of the same polypeptide.

In some cases a charged polymer polypeptide domain (cationic) can include a polymer selected from: poly(arginine)(PR), poly(lysine)(PK), poly(histidine)(PH), poly(ornithine), poly(citrulline), and a combination thereof. In some cases a given cationic amino acid polymer can include a mix of arginine, lysine, histidine, ornithine, and citrulline residues (in any convenient combination). Polymers can be present as a polymer of L-isomers or D-isomers, where D-isomers are more stable in a target cell because they take longer to degrade. Thus, inclusion of D-isomer poly(amino acids) delays degradation (and subsequent payload release). The payload release rate can therefore be controlled and is proportional to the ratio of polymers of D-isomers to polymers of L-isomers, where a higher ratio of D-isomer to L-isomer increases duration of payload release (i.e., decreases release rate). In other words, the relative amounts of D- and L-isomers can modulate the release kinetics and enzymatic susceptibility to degradation and payload release.

In some cases a cationic polymer includes D-isomers and L-isomers of an cationic amino acid polymer (e.g., poly (arginine)(PR), poly(lysine)(PK), poly(histidine)(PH), poly (ornithine), poly(citrulline)). In some cases the D- to L-isomer ratio is in a range of from 10:1-1:10 (e.g., from 8:1-1:10, 6:1-1:10, 4:1-1:10, 3:1-1:10, 2:1-1:10, 1:1-1:10, 10:1-1:8, 8:1-1:8, 6:1-1:8, 4:1-1:8, 3:1-1:8, 2:1-1:8, 1:1-1:8, 10:1-1:6, 8:1-1:6, 6:1-1:6, 4:1-1:6, 3:1-1:6, 2:1-1:6, 1:1-1:6, 10:1-1:4, 8:1-1:4, 6:1-1:4, 4:1-1:4, 3:1-1:4, 2:1-1:4, 1:1-1:4, 10:1-1:3, 8:1-1:3, 6:1-1:3, 4:1-1:3, 3:1-1:3, 2:1-1:3, 1:1-1:3, 10:1-1:2, 8:1-1:2, 6:1-1:2, 4:1-1:2, 3:1-1:2, 2:1-1:2, 1:1-1:2, 10:1-1:1, 8:1-1:1, 6:1-1:1, 4:1-1:1, 3:1-1:1, or 2:1-1:1).

Thus, in some cases a cationic polymer includes a first cationic polymer (e.g., amino acid polymer) that is a polymer of D-isomers (e.g., selected from poly(D-arginine), poly(D-lysine), poly(D-histidine), poly(D-ornithine), and poly(D-citrulline)); and includes a second cationic polymer (e.g., amino acid polymer) that is a polymer of L-isomers (e.g., selected from poly(L-arginine), poly(L-lysine), poly (L-histidine), poly(L-ornithine), and poly(L-citrulline)). In some cases the ratio of the first cationic polymer (D-isomers) to the second cationic polymer (L-isomers) is in a range of from 10:1-1:10 (e.g., from 8:1-1:10, 6:1-1:10, 4:1-1:10, 3:1-1:10, 2:1-1:10, 1:1-1:10, 10:1-1:8, 8:1-1:8, 6:1-1:8, 4:1-1:8, 3:1-1:8, 2:1-1:8, 1:1-1:8, 10:1-1:6, 8:1-1:6, 6:1-1:6, 4:1-1:6, 3:1-1:6, 2:1-1:6, 1:1-1:6, 10:1-1:4, 8:1-1:4, 6:1-1:4, 4:1-1:4, 3:1-1:4, 2:1-1:4, 1:1-1:4, 10:1-1:3, 8:1-1:3, 6:1-1:3, 4:1-1:3, 3:1-1:3, 2:1-1:3, 1:1-1:3, 10:1-1:2, 8:1-1:2, 6:1-1:2, 4:1-1:2, 3:1-1:2, 2:1-1:2, 1:1-1:2, 10:1-1:1, 8:1-1:1, 6:1-1:1, 4:1-1:1, 3:1-1:1, or 2:1-1:1) In some embodiments, an cationic polymer includes (e.g., in addition to or in place of any of the foregoing examples of cationic polymers) poly(ethylenimine), poly(amidoamine) (PAMAM), poly(aspartamide), polypeptoids (e.g., for forming "spiderweb"-like branches for core condensation), a charge-functionalized polyester, a cationic polysaccharide, an acetylated amino sugar, chitosan, or a cationic polymer that comprises any combination thereof (e.g., in linear or branched forms).

In some embodiments, an cationic polymer can have a molecular weight in a range of from 1-200 kDa (e.g., from 1-150, 1-100, 1-50, 5-200, 5-150, 5-100, 5-50, 10-200, 10-150, 10-100, 10-50, 15-200, 15-150, 15-100, or 15-50 kDa). As an example, in some cases a cationic polymer includes poly(L-arginine), e.g., with a molecular weight of approximately 29 kDa. As another example, in some cases a cationic polymer includes linear poly(ethylenimine) with a molecular weight of approximately 25 kDa (PEI). As another example, in some cases a cationic polymer includes branched poly(ethylenimine) with a molecular weight of approximately 10 kDa. As another example, in some cases a cationic polymer includes branched poly(ethylenimine) with a molecular weight of approximately 70 kDa. In some cases a cationic polymer includes PAMAM.

In some cases, a cationic amino acid polymer includes a cysteine residue, which can facilitate conjugation, e.g., to a linker, an NLS, and/or a cationic polypeptide (e.g., a histone or HTP). For example, a cysteine residue can be used for crosslinking (conjugation) via sulfhydryl chemistry (e.g., a disulfide bond) and/or amine-reactive chemistry. Thus, in some embodiments a cationic amino acid polymer (e.g., poly(arginine)(PR), poly(lysine)(PK), poly(histidine)(PH), poly(ornithine), and poly(citrulline), poly(D-arginine) (PDR), poly(D-lysine)(PDK), poly(D-histidine)(PDH), poly (D-ornithine), and poly(D-citrulline), poly(L-arginine) (PLR), poly(L-lysine)(PLK), poly(L-histidine)(PLH), poly (L-ornithine), and poly(L-citrulline)) of a cationic polymer composition includes a cysteine residue. In some cases the cationic amino acid polymer includes cysteine residue on the N- and/or C-terminus. In some cases the cationic amino acid polymer includes an internal cysteine residue.

In some cases, a cationic amino acid polymer includes (and/or is conjugated to) a nuclear localization signal (NLS) (described in more detail below). Thus, in some embodiments a cationic amino acid polymer (e.g., poly(arginine) (PR), poly(lysine)(PK), poly(histidine)(PH), poly(ornithine), and poly(citrulline), poly(D-arginine)(PDR), poly(D-lysine)(PDK), poly(D-histidine)(PDH), poly(D-ornithine), and poly(D-citrulline), poly(L-arginine)(PLR), poly(L-lysine)(PLK), poly(L-histidine)(PLH), poly(L-ornithine), and poly(L-citrulline)) includes one or more (e.g., two or more, three or more, or four or more) NLSs. In some cases the cationic amino acid polymer includes an NLS on the N- and/or C-terminus. In some cases the cationic amino acid polymer includes an internal NLS.

Histone Tail Peptide (HTPs)

In some embodiments a charged polymer polypeptide domain includes a histone peptide or a fragment of a histone peptide, such as an N-terminal histone tail (e.g., a histone tail of an H1, H2 (e.g., H2A, H2AX, H2B), H3, or H4 histone protein). A tail fragment of a histone protein is referred to herein as a histone tail peptide (HTP). Because such a protein (a histone and/or HTP) can condense with a nucleic acid payload as part of a subject delivery molecule, a charged polymer polypeptide domain that includes one or more histones or HTPs is sometimes referred to herein as a nucleosome-mimetic domain. Histones and/or HTPs can be also be included as monomers, and in some cases form dimers, trimers, tetramers and/or octamers when condensing a nucleic acid payload. In some cases HTPs are not only capable of being deprotonated by various histone modifications, such as in the case of histone acetyltransferase-mediated acetylation, but may also mediate effective nuclear-specific unpackaging of components of the core (e.g., release of a payload).

In some embodiments a subject charged polymer polypeptide domain includes a protein having an amino acid sequence of an H2A, H2AX, H2B, H3, or H4 protein. In some cases a subject charged polymer polypeptide domain includes a protein having an amino acid sequence that corresponds to the N-terminal region of a histone protein. For example, the fragment (an HTP) can include the first 5, 10, 15, 20, 25, 30, 35, 40, 45, or 50 N-terminal amino acids of a histone protein. In some cases, a subject HTP includes from 5-50 amino acids (e.g., from 5-45, 5-40, 5-35, 5-30, 5-25, 5-20, 8-50, 8-45, 8-40, 8-35, 8-30, 10-50, 10-45, 10-40, 10-35, or 10-30 amino acids) from the N-terminal region of a histone protein. In some cases a subject a cationic polypeptide includes from 5-150 amino acids (e.g., from 5-100, 5-50, 5-35, 5-30, 5-25, 5-20, 8-150, 8-100, 8-50, 8-40, 8-35, 8-30, 10-150, 10-100, 10-50, 10-40, 10-35, or 10-30 amino acids).

In some cases a cationic polypeptide (e.g., a histone or HTP, e.g., H1, H2, H2A, H2AX, H2B, H3, or H4) of a charged polymer polypeptide domain includes a post-translational modification (e.g., in some cases on one or more histidine, lysine, arginine, or other complementary residues). For example, in some cases the cationic polypeptide is methylated (and/or susceptible to methylation/demethylation), acetylated (and/or susceptible to acetylation/deacetylation), crotonylated (and/or susceptible to crotonylation/decrotonylation), ubiquitinylated (and/or susceptible to ubiquitinylation/deubiquitinylation), phosphorylated (and/or susceptible to phosphorylation/dephosphorylation), SUMOylated (and/or susceptible to SUMOylation/deSUMOylation), farnesylated (and/or susceptible to farnesylation/defarnesylation), sulfated (and/or susceptible to sulfation/desulfation) or otherwise post-translationally modified. In some cases a cationic polypeptide (e.g., a histone or HTP, e.g., H1, H2, H2A, H2AX, H2B, H3, or H4) of a charged polymer polypeptide domain is p300/CBP substrate (e.g., see example HTPs below). In some cases a cationic polypeptide (e.g., a histone or HTP, e.g., H1, H2, H2A, H2AX, H2B, H3, or H4) of a charged polymer polypeptide domain includes one or more thiol residues (e.g., can include a cysteine and/or methionine residue) that is sulfated or susceptible to sulfation (e.g., as a thiosulfate sulfurtransferase substrate). In some cases a cationic polypeptide (e.g., a histone or HTP, e.g., H1, H2, H2A, H2AX, H2B, H3, or H4) of a cationic polypeptide is amidated on the C-terminus. Histones H2A, H2B, H3, and H4 (and/or HTPs) may be monomethylated, dimethylated, or trimethylated at any of their lysines to promote or suppress transcriptional activity and alter nuclear-specific release kinetics.

A cationic polypeptide can be synthesized with a desired modification or can be modified in an in vitro reaction. Alternatively, a cationic polypeptide (e.g., a histone or HTP) can be expressed in a cell population and the desired modified protein can be isolated/purified. In some cases the charged polymer polypeptide domain of a subject nanoparticle includes a methylated HTP, e.g., includes the HTP sequence of H3K4(Me3)—includes the amino acid sequence set forth as SEQ ID NO: 75 or 88). In some cases a cationic polypeptide (e.g., a histone or HTP, e.g., H1, H2, H2A, H2AX, H2B, H3, or H4) of a charged polymer polypeptide domain includes a C-terminal amide.

Examples of Histones and HTPs

Examples include but are not limited to the following sequences:

H2A (SEQ ID NO: 62)
SGRGKQGGKARAKAKTRSSR [1-20]

(SEQ ID NO: 63)
SGRGKQGGKARAKAKTRSSRAGLQFPVGRVHRLLRKGGG [1-39]

(SEQ ID NO: 64)
MSGRGKQGGKARAKAKTRSSRAGLQFPVGRVHRLLRKGNYAERVGAGAPVYLAAVLEYL
TAEILELAGNAARDNKKTRIIPRHLQLAIRNDEELNKLLGKVTIAQGGVLPNIQAVLLPKKTES
HHKAKGK [1-130]

H2AX (SEQ ID NO: 65)
CKATQASQEY [134-143]

(SEQ ID NO: 66)
KKTSATVGPKAPSGGKKATQASQEY [KK 120-129]

(SEQ ID NO: 67)
MSGRGKTGGKARAKAKSRSSRAGLQFPVGRVHRLLRKGHYAERVGAGAPVYLAAVLEYL
TAEILELAGNAARDNKKTRIIPRHLQLAIRNDEELNKLLGGVTIAQGGVLPNIQAVLLPKKTSA
TVGPKAPSGGKKATQASQEY [1-143]

H2B (SEQ ID NO: 68)
PEPA-K(cr)-SAPAPK [1-11 H2BK5(cr)]
[Cr: crotonylated (crotonylation)]

(SEQ ID NO: 69)
PEPAKSAPAPK [1-11]

(SEQ ID NO: 70)
AQKKDGKKRKRSRKE [21-35]

(SEQ ID NO: 71)
MPEPAKSAPAPKKGSKKAVTKAQKKDGKKRKRSRKESYSIYVYKVLKQVHPDTGISSKAM
GIMNSFVNDIFERIAGEASRLAHYNKRSTITSREIQTAVRLLLPGELAKHAVSEGTKAVTKYT
SSK [1-126]

H3

(SEQ ID NO: 72)
ARTKQTAR [1-8]

(SEQ ID NO: 73)
ART-K(Me1)-QTARKS [1-8 H3K4(Me1)]

(SEQ ID NO: 74)
ART-K(Me2)-QTARKS [1-8 H3K4(Me2)]

(SEQ ID NO: 75)
ART-K(Me3)-QTARKS [1-8 H3K4(Me3)]

(SEQ ID NO: 76)
ARTKQTARK-pS-TGGKA [1-15 H3pS10]

(SEQ ID NO: 77)
ARTKQTARKSTGGKAPRKWC-NH2 [1-18 WC, amide]

(SEQ ID NO: 78)
ARTKQTARKSTGG-K(Ac)-APRKQ [1-19 H3K14(Ac)]

(SEQ ID NO: 79)
ARTKQTARKSTGGKAPRKQL [1-20]

(SEQ ID NO: 80)
ARTKQTAR-K(Ac)-STGGKAPRKQL [1-20 H3K9(Ac)]

(SEQ ID NO: 81)
ARTKQTARKSTGGKAPRKQLA [1-21]

(SEQ ID NO: 82)
ARTKQTAR-K(Ac)-STGGKAPRKQLA [1-21 H3K9(Ac)]

(SEQ ID NO: 83)
ARTKQTAR-K(Me2)-STGGKAPRKQLA [1-21 H3K9(Me1)]

-continued

ARTKQTAR-K(Me2)-STGGKAPRKQLA [1-21 H3K9(Me2)] (SEQ ID NO: 84)

ARTKQTAR-K(Me2)-STGGKAPRKQLA [1-21 H3K9(Me3)] (SEQ ID NO: 85)

ART-K(Me1)-QTARKSTGGKAPRKQLA [1-21 H3K4(Me1)] (SEQ ID NO: 86)

ART-K(Me2)-QTARKSTGGKAPRKQLA [1-21 H3K4(Me2)] (SEQ ID NO: 87)

ART-K(Me3)-QTARKSTGGKAPRKQLA [1-21 H3K4(Me3)] (SEQ ID NO: 88)

ARTKQTAR-K(Ac)-pS-TGGKAPRKQLA [1-21 H3K9(Ac), pS10] (SEQ ID NO: 89)

ART-K(Me3)-QTAR-K(Ac)-pS-TGGKAPRKQLA [1-21 H3K4(Me3), K9(Ac), pS10] (SEQ ID NO: 90)

ARTKQTARKSTGGKAPRKQLAC [1-21 Cys] (SEQ ID NO: 91)

ARTKQTAR-K(Ac)-STGGKAPRKQLATKA [1-24 H3K9(Ac)] (SEQ ID NO: 92)

ARTKQTAR-K(Me3)-STGGKAPRKQLATKA [1-24 H3K9(Me3)] (SEQ ID NO: 93)

ARTKQTARKSTGGKAPRKQLATKAA [1-25] (SEQ ID NO: 94)

ART-K(Me3)-QTARKSTGGKAPRKQLATKAA [1-25 H3K4(Me3)] (SEQ ID NO: 95)

TKQTAR-K(Me1)-STGGKAPR [3-17 H3K9(Me1)] (SEQ ID NO: 96)

TKQTAR-K(Me2)-STGGKAPR [3-17 H3K9(Me2)] (SEQ ID NO: 97)

TKQTAR-K(Me3)-STGGKAPR [3-17 H3K9(Me3)] (SEQ ID NO: 98)

KSTGG-K(Ac)-APRKQ [9-19 H3K14(Ac)] (SEQ ID NO: 99)

QTARKSTGGKAPRKQLASK [5-23] (SEQ ID NO: 100)

APRKQLATKAARKSAPATGGVKKPH [15-39] (SEQ ID NO: 101)

ATKAARKSAPATGGVKKPHRYRPG [21-44] (SEQ ID NO: 102)

KAARKSAPA [23-31] (SEQ ID NO: 103)

KAARKSAPATGG [23-34] (SEQ ID NO: 104)

KAARKSAPATGGC [23-34 Cys] (SEQ ID NO: 105)

KAAR-K(Ac)-SAPATGG [H3K27(Ac)] (SEQ ID NO: 106)

KAAR-K(Me1)-SAPATGG [H3K27(Me1)] (SEQ ID NO: 107)

KAAR-K(Me2)-SAPATGG [H3K27(Me2)] (SEQ ID NO: 108)

KAAR-K(Me3)-SAPATGG [H3K27(Me3)] (SEQ ID NO: 109)

AT-K(Ac)-AARKSAPSTGGVKKPHRYRPG [21-44 H3K23(Ac)] (SEQ ID NO: 110)

-continued

ATKAARK-pS-APATGGVKKPHRYRPG [21-44 pS28]  (SEQ ID NO: 111)

ARTKQTARKSTGGKAPRKQLATKAARKSAPATGGV [1-35]  (SEQ ID NO: 112)

STGGV-K(Me1)-KPHRY [31-41 H3K36(Me1)]  (SEQ ID NO: 113)

STGGV-K(Me2)-KPHRY [31-41 H3K36(Me2)]  (SEQ ID NO: 114)

STGGV-K(Me3)-KPHRY [31-41 H3K36(Me3)]  (SEQ ID NO: 115)

GTVALREIRRYQ-K(Ac)-STELLIR [44-63 H3K56(Ac)]  (SEQ ID NO: 116)

ARTKQTARKSTGGKAPRKQLATKAARKSAPATGGVKKPHRYRPGTVALRE [1-50]  (SEQ ID NO: 117)

TELLIRKLPFQRLVREIAQDF-K(Me1)-TDLRFQSAAI [H3K79(Me1)]  (SEQ ID NO: 118)

EIAQDFKTDLR [73-83]  (SEQ ID NO: 119)

EIAQDF-K(Ac)-TDLR [73-83 H3K79(Ac)]  (SEQ ID NO: 120)

EIAQDF-K(Me3)-TDLR [73-83 H3K79(Me3)]  (SEQ ID NO: 121)

RLVREIAQDFKTDLRFQSSAV [69-89]  (SEQ ID NO: 122)

RLVREIAQDFK-(Me1)-TDLRFQSSAV [69-89 H3K79 (Me1), amide]  (SEQ ID NO: 123)

RLVREIAQDFK-(Me2)-TDLRFQSSAV [69-89 H3K79 (Me2), amide]  (SEQ ID NO: 124)

RLVREIAQDFK-(Me3)-TDLRFQSSAV [69-89 H3K79 (Me3), amide]  (SEQ ID NO: 125)

KRVTIMPKDIQLARRIRGERA [116-136]  (SEQ ID NO: 126)

MARTKQTARKSTGGKAPRKQLATKVARKSAPATGGVKKPHRYRPGTVALREIRRYQKST
ELLIRKLPFQRLMREIAQDFKTDLRFQSSAVMALQEACESYLVGLFEDTNLCVIHAKRVTIM
PKDIQLARRIRGERA [1-136]  (SEQ ID NO: 127)

H4

SGRGKGG [1-7]  (SEQ ID NO: 128)

RGKGGKGLGKGA [4-12]  (SEQ ID NO: 129)

SGRGKGGKGLGKGGAKRHRKV [1-21]  (SEQ ID NO: 130)

KGLGKGGAKRHRKVLRDNWC-NH2 [8-25 WC, amide]  (SEQ ID NO: 131)

SGRG-K(Ac)-GG-K(Ac)-GLG-K(Ac)-GGA-K(Ac)-RHRKVLRDNGSGSK [1-25 H4K5, 8, 12, 16(Ac)]  (SEQ ID NO: 132)

SGRGKGGKGLGKGGAKRHRK-NH2 [1-20 H4 PRMT7 (protein arginine methyltransferase 7) Substrate, M1]  (SEQ ID NO: 133)

SGRG-K(Ac)-GGKGLGKGGAKRHRK [1-20 H4K5 (Ac)]  (SEQ ID NO: 134)

SGRGKGG-K(Ac)-GLGKGGAKRHRK [1-20 H4K8 (Ac)]  (SEQ ID NO: 135)

```
                                                            (SEQ ID NO: 136)
SGRGKGGKGLG-K(Ac)-GGAKRHRK [1-20 H4K12 (Ac)]

(SEQ ID NO: 137)
SGRGKGGKGLGKGGA-K(Ac)-RHRK [1-20 H4K16 (Ac)]

(SEQ ID NO: 138)
KGLGKGGAKRHRKVLRDNWC-NH2 [1-25 WC, amide]

(SEQ ID NO: 139)
MSGRGKGGKGLGKGGAKRHRKVLRDNIQGITKPAIRRLARRGGVKRISGLIYEETRGVLKV
FLENVIRDAVTYTEHAKRKTVTAMDVVYALKRQGRTLYGFGG [1-103]
```

As such, a cationic polypeptide of a subject charged polymer polypeptide domain can include an amino acid sequence having the amino acid sequence set forth in any of SEQ ID NOs: 62-139. In some cases a cationic polypeptide of subject a charged polymer polypeptide domain includes an amino acid sequence having 80% or more sequence identity (e.g., 85% or more, 90% or more, 95% or more, 98% or more, 99% or more, or 100% sequence identity) with the amino acid sequence set forth in any of SEQ ID NOs: 62-139. In some cases a cationic polypeptide of subject a charged polymer polypeptide domain includes an amino acid sequence having 90% or more sequence identity (e.g., 95% or more, 98% or more, 99% or more, or 100% sequence identity) with the amino acid sequence set forth in any of SEQ ID NOs: 62-139. The cationic polypeptide can include any convenient modification, and a number of such contemplated modifications are discussed above, e.g., methylated, acetylated, crotonylated, ubiquitinylated, phosphorylated, SUMOylated, farnesylated, sulfated, and the like.

In some cases a cationic polypeptide of a charged polymer polypeptide domain includes an amino acid sequence having 80% or more sequence identity (e.g., 85% or more, 90% or more, 95% or more, 98% or more, 99% or more, or 100% sequence identity) with the amino acid sequence set forth in SEQ ID NO: 94. In some cases a cationic polypeptide of a charged polymer polypeptide domain includes an amino acid sequence having 95% or more sequence identity (e.g., 98% or more, 99% or more, or 100% sequence identity) with the amino acid sequence set forth in SEQ ID NO: 94. In some cases a cationic polypeptide of a charged polymer polypeptide domain includes the amino acid sequence set forth in SEQ ID NO: 94. In some cases a cationic polypeptide of a charged polymer polypeptide domain includes the sequence represented by H3K4(Me3) (SEQ ID NO: 95), which comprises the first 25 amino acids of the human histone 3 protein, and tri-methylated on the lysine 4 (e.g., in some cases amidated on the C-terminus).

In some embodiments a cationic polypeptide (e.g., a histone or HTP, e.g., H1, H2, H2A, H2AX, H2B, H3, or H4) of a charged polymer polypeptide domain includes a cysteine residue, which can facilitate conjugation to: a cationic (or in some cases anionic) amino acid polymer, a linker, an NLS, and/or other cationic polypeptides (e.g., in some cases to form a branched histone structure). For example, a cysteine residue can be used for crosslinking (conjugation) via sulfhydryl chemistry (e.g., a disulfide bond) and/or amine-reactive chemistry. In some cases the cysteine residue is internal. In some cases the cysteine residue is positioned at the N-terminus and/or C-terminus. In some cases, a cationic polypeptide (e.g., a histone or HTP, e.g., H1, H2, H2A, H2AX, H2B, H3, or H4) of a charged polymer polypeptide domain includes a mutation (e.g., insertion or substitution) that adds a cysteine residue. Examples of HTPs that include a cysteine include but are not limited to:

```
                                                            (SEQ ID NO: 140)
CKATQASQEY-from H2AX (SEQ ID NO: 141)
ARTKQTARKSTGGKAPRKQLAC-from H3

(SEQ ID NO: 142)
ARTKQTARKSTGGKAPRKWC (SEQ ID NO: 143)
KAARKSAPATGGC-from H3

(SEQ ID NO: 144)
KGLGKGGAKRHRKVLRDNWC-from H4

(SEQ ID NO: 145)
MARTKQTARKSTGGKAPRKQLATKVARKSAPATGGVKKPHRYRPGTVAL
REIRRYQKSTELLIRKLPFQRLMREIAQDFKTDLRFQSSAVMALQEACE
SYLVGLFEDTNLCVIHAKRVTIMPKDIQLARRIRGERA-from H3
```

In some embodiments a cationic polypeptide (e.g., a histone or HTP, e.g., H1, H2, H2A, H2AX, H2B, H3, or H4) of a charged polymer polypeptide domain is conjugated to a cationic (and/or anionic) amino acid polymer. As an example, a histone or HTP can be conjugated to a cationic amino acid polymer (e.g., one that includes poly(lysine)), via a cysteine residue, e.g., where the pyridyl disulfide group(s) of lysine(s) of the polymer are substituted with a disulfide bond to the cysteine of a histone or HTP.

Modified/Branching Structure

In some embodiments a charged polymer polypeptide domain has a linear structure. In some embodiments a charged polymer polypeptide domain has a branched structure.

For example, in some cases, a cationic polypeptide (e.g., HTPs, e.g., HTPs with a cysteine residue) is conjugated (e.g., at its C-terminus) to the end of a cationic polymer (e.g., poly(L-arginine), poly(D-lysine), poly(L-lysine), poly(D-lysine)), thus forming an extended linear polypeptide. In some cases, one or more (two or more, three or more, etc.) cationic polypeptides (e.g., HTPs, e.g., HTPs with a cysteine residue) are conjugated (e.g., at their C-termini) to the end(s) of a cationic polymer (e.g., poly(L-arginine), poly(D-lysine), poly(L-lysine), poly(D-lysine)), thus forming an extended linear polypeptide. In some cases the cationic polymer has a molecular weight in a range of from 4,500-150,000 Da).

As another example, in some cases, one or more (two or more, three or more, etc.) cationic polypeptides (e.g., HTPs, e.g., HTPs with a cysteine residue) are conjugated (e.g., at their C-termini) to the side-chains of a cationic polymer (e.g., poly(L-arginine), poly(D-lysine), poly(L-lysine), poly(D-lysine)), thus forming a branched structure (branched polypeptide). Formation of a branched structure can in some cases increase the amount of condensation (e.g., of a nucleic acid payload) that can be achieved. Thus, in some cases it is desirable to use components that form a branched structure.

Various types of branches structures are of interest, and examples of branches structures that can be generated (e.g., using subject cationic polypeptides such as HTPs, e.g., HTPs with a cysteine residue; peptoids, polyamides, and the like) include but are not limited to: brush polymers, webs (e.g., spider webs), graft polymers, star-shaped polymers, comb polymers, polymer networks, dendrimers, and the like.

As an example, FIG. 123 depicts a brush type of branched structure. In some cases, a branched structure includes from 2-30 cationic polypeptides (e.g., HTPs) (e.g., from 2-25, 2-20, 2-15, 2-10, 2-5, 4-30, 4-25, 4-20, 4-15, or 4-10 cationic polypeptides), where each can be the same or different than the other cationic polypeptides of the branched structure (see, e.g., FIG. 123). In some cases the cationic polymer has a molecular weight in a range of from 4,500-150,000 Da). In some cases, 5% or more (e.g., 10% or more, 20% or more, 25% or more, 30% or more, 40% or more, or 50% or more) of the side-chains of a cationic polymer (e.g., poly(L-arginine), poly(D-lysine), poly(L-lysine), poly(D-lysine)) are conjugated to a subject cationic polypeptide (e.g., HTP, e.g., HTP with a cysteine residue). In some cases, up to 50% (e.g., up to 40%, up to 30%, up to 25%, up to 20%, up to 15%, up to 10%, or up to 5%) of the side-chains of a cationic polymer (e.g., poly(L-arginine), poly(D-lysine), poly(L-lysine), poly(D-lysine)) are conjugated to a subject cationic polypeptide (e.g., HTP, e.g., HTP with a cysteine residue). Thus, an HTP can be branched off of the backbone of a polymer such as a cationic amino acid polymer.

In some cases formation of branched structures can be facilitated using components such as peptoids (polypeptoids), polyamides, dendrimers, and the like. For example, in some cases peptoids (e.g., polypeptoids) are used as part of a composition with a subject delivery molecule, e.g., in order to generate a web (e.g., spider web) structure, which can in some cases facilitate condensation.

One or more of the natural or modified polypeptide sequences herein may be modified with terminal or intermittent arginine, lysine, or histidine sequences. In one embodiment, each polypeptide is included in equal amine molarities within a nanoparticle core. In this embodiment, each polypeptide's C-terminus can be modified with 5R (5 arginines). In some embodiments, each polypeptide's C-terminus can be modified with 9R (9 arginines). In some embodiments, each polypeptide's N-terminus can be modified with 5R (5 arginines). In some embodiments, each polypeptide's N-terminus can be modified with 9R (9 arginines). In some cases, an H2A, H2B, H3 and/or H4 histone fragment (e.g., HTP) are each bridged in series with a FKFL Cathepsin B proteolytic cleavage domain or RGFFP Cathepsin D proteolytic cleavage domain. In some cases, an H2A, H2B, H3 and/or H4 histone fragment (e.g., HTP) can be bridged in series by a 5R (5 arginines), 9R (9 arginines), 5K (5 lysines), 9K (9 lysines), 5H (5 histidines), or 9H (9 histidines) cationic spacer domain. In some cases, one or more H2A, H2B, H3 and/or H4 histone fragments (e.g., HTPs) are disulfide-bonded at their N-terminus to protamine.

To illustrate how to generate a branched histone structure, example methods of preparation are provided. One example of such a method includes the following: covalent modification of equimolar ratios of Histone H2AX [134-143], Histone H3 [1-21 Cys], Histone H3 [23-34 Cys], Histone H4 [8-25 WC] and SV40 T-Ag-derived NLS can be performed in a reaction with 10% pyridyl disulfide modified poly(L-Lysine) [MW=5400, 18000, or 45000 Da; n=30, 100, or 250]. In a typical reaction, a 29 µL aqueous solution of 700 µM Cys-modified histone/NLS (20 nmol) can be added to 57 µL of 0.2 M phosphate buffer (pH 8.0). Second, 14 µL of 100 µM pyridyl disulfide protected poly(lysine) solution can then be added to the histone solution bringing the final volume to 100 µL with a 1:2 ratio of pyridyl disulfide groups to Cysteine residues. This reaction can be carried out at room temperature for 3 h. The reaction can be repeated four times and degree of conjugation can be determined via absorbance of pyridine-2-thione at 343 nm.

As another example, covalent modification of a 0:1, 1:4, 1:3, 1:2, 1:1, 1:2, 1:3, 1:4, or 1:0 molar ratio of Histone H3 [1-21 Cys] peptide and Histone H3 [23-34 Cys] peptide can be performed in a reaction with 10% pyridyl disulfide modified poly(L-Lysine) or poly(L-Arginine) [MW=5400, 18000, or 45000 Da; n=30, 100, or 250]. In a typical reaction, a 29 µL aqueous solution of 700 µM Cys-modified histone (20 nmol) can be added to 57 µL of 0.2 M phosphate buffer (pH 8.0). Second, 14 µL of 100 µM pyridyl disulfide protected poly(lysine) solution can then be added to the histone solution bringing the final volume to 100 µL with a 1:2 ratio of pyridyl disulfide groups to Cysteine residues. This reaction can be carried out at room temperature for 3 h. The reaction can be repeated four times and degree of conjugation can be determined via absorbance of pyridine-2-thione at 343 nm.

In some cases, the charged polymer polypeptide domain is condensed with a nucleic acid payload (see e.g., FIG. 1, panels E-F). In some cases, the charged polymer polypeptide domain is condensed with a protein payload. In some cases, the charged polymer polypeptide domain is co-condensed with silica, salts, and/or anionic polymers to provide added endosomal buffering capacity, stability, and, e.g., optional timed release. As noted above, in some cases, a charged polymer polypeptide domain of a subject delivery molecule is a stretch of repeating cationic residues (such as arginine, lysine, and/or histidine), e.g., in some 4-25 amino acids in length or 4-15 amino acids in length. Such a domain can allow the delivery molecule to interact electrostatically with an anionic sheddable matrix (e.g., a co-condensed anionic polymer). Thus, in some cases, a subject charged polymer polypeptide domain of a subject delivery molecule is a stretch of repeating cationic residues that interacts (e.g., electrostatically) with an anionic sheddable matrix and with a nucleic acid and/or protein payload. Thus, in some cases a subject delivery molecule interacts with a payload (e.g., nucleic acid and/or protein) and is present as part of a composition with an anionic polymer (e.g., co-condenses with the payload and with an anionic polymer).

The anionic polymer of an anionic sheddable matrix (i.e., the anionic polymer that interacts with the charged polymer polypeptide domain of a subject delivery molecule) can be any convenient anionic polymer/polymer composition. Examples include, but are not limited to: poly(glutamic acid) (e.g., poly(D-glutamic acid) [PDE], poly(L-glutamic acid) [PLE], both PDE and PLE in various desired ratios, etc.) In some cases, PDE is used as an anionic sheddable matrix. In some cases, PLE is used as an anionic sheddable matrix (anionic polymer). In some cases, PDE is used as an anionic sheddable matrix (anionic polymer). In some cases, PLE and PDE are both used as an anionic sheddable matrix (anionic polymer), e.g., in a 1:1 ratio (50% PDE, 50% PLE).

Anionic Polymer

An anionic polymer composition can include one or more anionic amino acid polymers. For example, in some cases a subject anionic polymer composition includes a polymer selected from: poly(glutamic acid)(PEA), poly(aspartic acid)(PDA), and a combination thereof. In some cases a given anionic amino acid polymer can include a mix of aspartic and glutamic acid residues. Each polymer can be present in the composition as a polymer of L-isomers or D-isomers, where D-isomers are more stable in a target cell because they take longer to degrade. Thus, inclusion of D-isomer poly(amino acids) can delay degradation and subsequent payload release. The payload release rate can therefore be controlled and is proportional to the ratio of polymers of D-isomers to polymers of L-isomers, where a higher ratio of D-isomer to L-isomer increases duration of payload release (i.e., decreases release rate). In other words, the relative amounts of D- and L-isomers can modulate the nanoparticle core's timed release kinetics and enzymatic susceptibility to degradation and payload release.

In some cases an anionic polymer composition includes polymers of D-isomers and polymers of L-isomers of an anionic amino acid polymer (e.g., poly(glutamic acid)(PEA) and poly(aspartic acid)(PDA)). In some cases the D- to L-isomer ratio is in a range of from 10:1-1:10 (e.g., from 8:1-1:10, 6:1-1:10, 4:1-1:10, 3:1-1:10, 2:1-1:10, 1:1-1:10, 10:1-1:8, 8:1-1:8, 6:1-1:8, 4:1-1:8, 3:1-1:8, 2:1-1:8, 1:1-1:8, 10:1-1:6, 8:1-1:6, 6:1-1:6, 4:1-1:6, 3:1-1:6, 2:1-1:6, 1:1-1:6, 10:1-1:4, 8:1-1:4, 6:1-1:4, 4:1-1:4, 3:1-1:4, 2:1-1:4, 1:1-1:4, 10:1-1:3, 8:1-1:3, 6:1-1:3, 4:1-1:3, 3:1-1:3, 2:1-1:3, 1:1-1:3, 10:1-1:2, 8:1-1:2, 6:1-1:2, 4:1-1:2, 3:1-1:2, 2:1-1:2, 1:1-1:2, 10:1-1:1, 8:1-1:1, 6:1-1:1, 4:1-1:1, 3:1-1:1, or 2:1-1:1).

Thus, in some cases an anionic polymer composition includes a first anionic polymer (e.g., amino acid polymer) that is a polymer of D-isomers (e.g., selected from poly(D-glutamic acid) (PDEA) and poly(D-aspartic acid) (PDDA)); and includes a second anionic polymer (e.g., amino acid polymer) that is a polymer of L-isomers (e.g., selected from poly(L-glutamic acid) (PLEA) and poly(L-aspartic acid) (PLDA)). In some cases the ratio of the first anionic polymer (D-isomers) to the second anionic polymer (L-isomers) is in a range of from 10:1-1:10 (e.g., from 8:1-1:10, 6:1-1:10, 4:1-1:10, 3:1-1:10, 2:1-1:10, 1:1-1:10, 10:1-1:8, 8:1-1:8, 6:1-1:8, 4:1-1:8, 3:1-1:8, 2:1-1:8, 1:1-1:8, 10:1-1:6, 8:1-1:6, 6:1-1:6, 4:1-1:6, 3:1-1:6, 2:1-1:6, 1:1-1:6, 10:1-1:4, 8:1-1:4, 6:1-1:4, 4:1-1:4, 3:1-1:4, 2:1-1:4, 1:1-1:4, 10:1-1:3, 8:1-1:3, 6:1-1:3, 4:1-1:3, 3:1-1:3, 2:1-1:3, 1:1-1:3, 10:1-1:2, 8:1-1:2, 6:1-1:2, 4:1-1:2, 3:1-1:2, 2:1-1:2, 1:1-1:2, 10:1-1:1, 8:1-1:1, 6:1-1:1, 4:1-1:1, 3:1-1:1, or 2:1-1:1) In some embodiments, an anionic polymer composition includes (e.g., in addition to or in place of any of the foregoing examples of anionic polymers) a glycosaminoglycan, a glycoprotein, a polysaccharide, poly(mannuronic acid), poly(guluronic acid), heparin, heparin sulfate, chondroitin, chondroitin sulfate, keratan, keratan sulfate, aggrecan, poly(glucosamine), or an anionic polymer that comprises any combination thereof.

In some embodiments, an anionic polymer can have a molecular weight in a range of from 1-200 kDa (e.g., from 1-150, 1-100, 1-50, 5-200, 5-150, 5-100, 5-50, 10-200, 10-150, 10-100, 10-50, 15-200, 15-150, 15-100, or 15-50 kDa). As an example, in some cases an anionic polymer includes poly(glutamic acid) with a molecular weight of approximately 15 kDa.

In some cases, an anionic amino acid polymer includes a cysteine residue, which can facilitate conjugation, e.g., to a linker, an NLS, and/or a cationic polypeptide (e.g., a histone or HTP). For example, a cysteine residue can be used for crosslinking (conjugation) via sulfhydryl chemistry (e.g., a disulfide bond) and/or amine-reactive chemistry. Thus, in some embodiments an anionic amino acid polymer (e.g., poly(glutamic acid) (PEA), poly(aspartic acid) (PDA), poly (D-glutamic acid) (PDEA), poly(D-aspartic acid) (PDDA), poly(L-glutamic acid) (PLEA), poly(L-aspartic acid) (PLDA)) of an anionic polymer composition includes a cysteine residue. In some cases the anionic amino acid polymer includes cysteine residue on the N- and/or C-terminus. In some cases the anionic amino acid polymer includes an internal cysteine residue.

In some cases, an anionic amino acid polymer includes (and/or is conjugated to) a nuclear localization signal (NLS) (described in more detail below). Thus, in some embodiments an anionic amino acid polymer (e.g., poly(glutamic acid) (PEA), poly(aspartic acid) (PDA), poly(D-glutamic acid) (PDEA), poly(D-aspartic acid) (PDDA), poly(L-glutamic acid) (PLEA), poly(L-aspartic acid) (PLDA)) of an anionic polymer composition includes (and/or is conjugated to) one or more (e.g., two or more, three or more, or four or more) NLSs. In some cases the anionic amino acid polymer includes an NLS on the N- and/or C-terminus. In some cases the anionic amino acid polymer includes an internal NLS.

In some cases, an anionic polymer is conjugated to a targeting ligand.

Linker

In some embodiments a targeting ligand according to the present disclosure is conjugated to a payload (e.g., a protein payload or a nucleic acid payload such as an siRNA) via an intervening linker (e.g., see FIG. 1 and FIG. 2). The linker can be a protein linker or non-protein linker.

Conjugation of a targeting ligand to a linker, a linker to a payload (e.g., a nucleic acid or protein payload), or a linker to a charged polymer polypeptide domain can be accomplished in a number of different ways. In some cases the conjugation is via sulfhydryl chemistry (e.g., a disulfide bond, e.g., between two cysteine residues, e.g., see FIG. 2). In some cases the conjugation is accomplished using amine-reactive chemistry. In some cases, a targeting ligand includes a cysteine residue and is conjugated to the linker via the cysteine residue. In some cases, the linker is a peptide linker and includes a cysteine residue. In some cases, the targeting ligand and a peptide linker are conjugated by virtue of being part of the same polypeptide.

In some cases, a subject linker is a polypeptide and can be referred to as a polypeptide linker. It is to be understood that while polypeptide linkers are contemplated, non-polypeptide linkers (chemical linkers) are used in some cases. For example, in some embodiments the linker is a polyethylene glycol (PEG) linker. Suitable protein linkers include polypeptides of between 4 amino acids and 40 amino acids in length (e.g., 4-30, 4-25, 4-20, 4-15, 4-10, 6-40, 6-30, 6-25, 6-20, 6-15, 6-10, 8-30, 8-25, 8-20, or 8-15 amino acids in length).

In some embodiments, a subject linker is rigid (e.g., a linker that include one or more proline residues). One non-limiting example of a rigid linker is GAPGAPGAP (SEQ ID NO: 17). In some cases, a polypeptide linker includes a C residue at the N- or C-terminal end. Thus, in some case a rigid linker is selected from: GAPGAPGAPC (SEQ ID NO: 18) and CGAPGAPGAP (SEQ ID NO: 19).

Peptide linkers with a degree of flexibility can be used. Thus, in some cases, a subject linker is flexible. The linking peptides may have virtually any amino acid sequence, bearing in mind that flexible linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use. Example linker polypeptides include glycine polymers $(G)_n$, glycine-serine polymers (including, for example, $(GS)_n$, $GSGGS_n$ (SEQ ID NO: 20), $GGSGGS_n$ (SEQ ID NO: 21), and $GGGS_n$ (SEQ ID NO: 22), where n is an integer of at least one), glycine-alanine polymers, alanine-serine polymers. Example linkers can comprise amino acid sequences including, but not limited to, GGSG (SEQ ID NO: 23), GGSGG (SEQ ID NO: 24), GSGSG (SEQ ID NO: 25), GSGGG (SEQ ID NO: 26), GGGSG (SEQ ID NO: 27), GSSSG (SEQ ID NO: 28), and the like. The ordinarily skilled artisan will recognize that design of a peptide conjugated to any elements described above can include linkers that are all or partially flexible, such that the linker can include a flexible linker as well as one or more portions that confer less flexible structure. Additional examples of flexible linkers include, but are not limited to: GGGGGSGGGGG (SEQ ID NO: 29) and GGGGGSGGGGS (SEQ ID NO: 30). As noted above, in some cases, a polypeptide linker includes a C residue at the N- or C-terminal end. Thus, in some cases a flexible linker includes an amino acid sequence selected from: GGGGGSGGGGGC (SEQ ID NO: 31), CGGGGGSGGGGG (SEQ ID NO: 32), GGGGGSGGGGSC (SEQ ID NO: 33), and CGGGGGSGGGGS (SEQ ID NO: 34).

In some cases, a subject polypeptide linker is endosomolytic. Endosomolytic polypeptide linkers include but are not limited to: KALA (SEQ ID NO: 35) and GALA (SEQ ID NO: 36). As noted above, in some cases, a polypeptide linker includes a C residue at the N- or C-terminal end. Thus, in some cases a subject linker includes an amino acid sequence selected from: CKALA (SEQ ID NO: 37), KALAC (SEQ ID NO: 38), CGALA (SEQ ID NO: 39), and GALAC (SEQ ID NO: 40).

Illustrative Examples of Sulfhydryl Coupling Reactions (e.g., for conjugation via sulfhydryl chemistry, e.g., using a cysteine residue)

(e.g., for conjugating a targeting ligand to a payload, conjugating a targeting ligand to a charged polymer polypeptide domain, conjugating a targeting ligand to a linker, conjugating a linker to a payload, conjugating a linker to a charged polymer polypeptide domain, and the like)

Disulfide Bond

Cysteine residues in the reduced state, containing free sulfhydryl groups, readily form disulfide bonds with protected thiols in a typical disulfide exchange reaction.

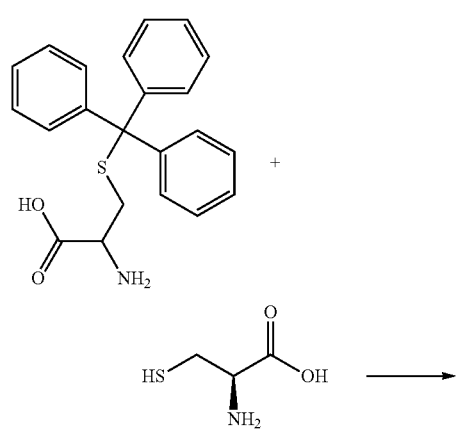

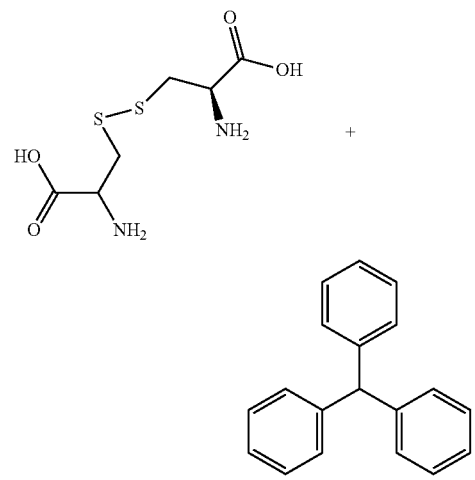

Thioether/Thioester Bond

Sulfhydryl groups of cysteine react with maleimide and acyl halide groups, forming stable thioether and thioester bonds respectively.

Maleimide

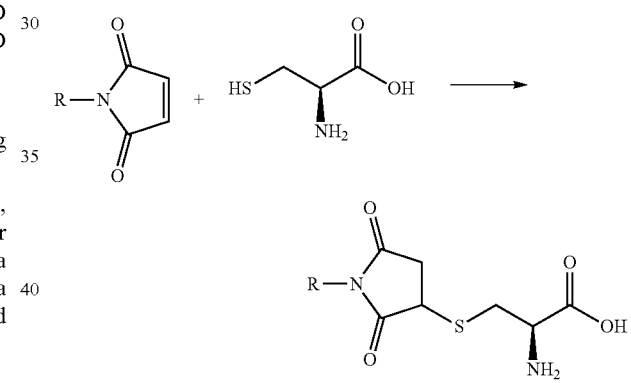

Acyl Halide

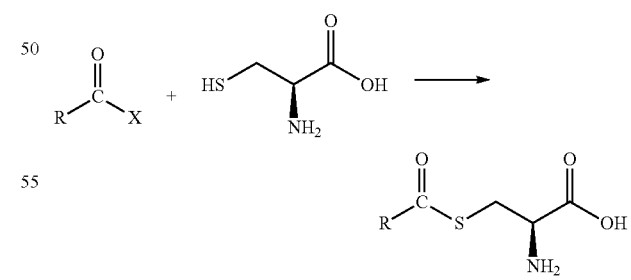

Azide—Alkyne Cycloaddition

This conjugation is facilitated by chemical modification of the cysteine residue to contain an alkyne bond, or by the use of L-propargyl cysteine (pictured below) in synthetic peptide preparation. Coupling is then achieved by means of Cu promoted click chemistry.

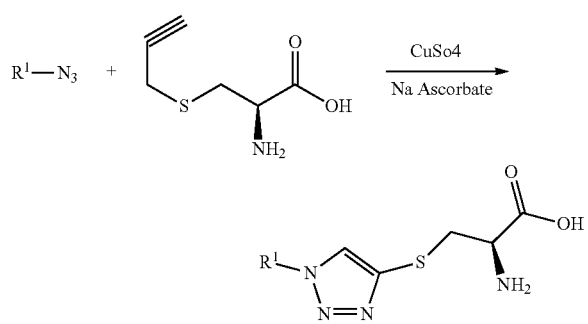

Illustrative Examples of Delivery Molecules and Components (0a) Cysteine Conjugation Anchor 1 (CCA1)
[Charged Polymer Polypeptide Domain-Linker (GAPGAPGAP)-Cysteine]

```
                                    (SEQ ID NO: 41)
RRRRRRRR GAPGAPGAP C
```

(0b) Cysteine Conjugation Anchor 2 (CCA2)
[Cysteine-Linker (GAPGAPGAP)-Charged Polymer Polypeptide Domain]

```
                                    (SEQ ID NO: 42)
C GAPGAPGAP RRRRRRRR
```

(1a) α5β1 Ligand
[Charged Polymer Polypeptide Domain-Linker (GAPGAPGAP)-Targeting Ligand]

```
                                    (SEQ ID NO: 45)
RRRRRRRR GAPGAPGAP RRETAWA
```

(1b) α5β1 Ligand
[Targeting Ligand-Linker (GAPGAPGAP)-Charged Polymer Polypeptide Domain]

```
                                    (SEQ ID NO: 46)
RRETAWA GAPGAPGAP RRRRRRRR
```

(1c) α5β1 Ligand-Cys Left

```
                                    (SEQ ID NO: 19)
CGAPGAPGAP
```

Note: This can be conjugated to CCA1 (see above) or conjugated to a nucleic acid payload (e.g., siRNA) either via sulfhydryl chemistry (e.g., a disulfide bond) or amine-reactive chemistry.

(1d) α5β1 Ligand-Cys Right

```
                                    (SEQ ID NO: 18)
GAPGAPGAPC
```

Note: This can be conjugated to CCA2 (see above) or conjugated to a nucleic acid payload (e.g., siRNA) either via sulfhydryl chemistry (e.g., a disulfide bond) or amine-reactive chemistry.

(2a) RGD α5β1 Ligand
[Charged Polymer Polypeptide Domain-Linker (GAPGAPGAP)-Targeting Ligand]

```
                                    (SEQ ID NO: 47)
RRRRRRRR GAPGAPGAP RGD
```

(2b) RGD a5b1 Ligand
[Targeting Ligand-Linker (GAPGAPGAP)-Charged Polymer Polypeptide Domain]

```
                                    (SEQ ID NO: 48)
RGD GAPGAPGAP RRRRRRRR
```

(2c) RGD Ligand-Cys Left

```
                                    (SEQ ID NO: 49)
CRGD
```

Note: This can be conjugated to CCA1 (see above) or conjugated to a nucleic acid payload (e.g., siRNA) either via sulfhydryl chemistry (e.g., a disulfide bond) or amine-reactive chemistry.

(2d) RGD Ligand-Cys Right

```
                                    (SEQ ID NO: 50)
RGDC
```

Note: This can be conjugated to CCA2 (see above) or conjugated to a nucleic acid payload (e.g., siRNA) either via sulfhydryl chemistry (e.g., a disulfide bond) or amine-reactive chemistry.

(3a) Transferrin Ligand
[Charged Polymer Polypeptide Domain-Linker (GAPGAPGAP)-Targeting Ligand]

```
                                    (SEQ ID NO: 51)
RRRRRRRR GAPGAPGAP THRPPMWSPVWP
```

(3b) Transferrin Ligand
[Targeting Ligand-Linker (GAPGAPGAP)-Charged Polymer Polypeptide Domain]

```
                                    (SEQ ID NO: 52)
THRPPMWSPVWP GAPGAPGAP RRRRRRRR
```

(3c) Transferrin Ligand-Cys Left

```
                                    (SEQ ID NO: 53)
CTHRPPMWSPVWP (SEQ ID NO: 54)
CPTHRPPMWSPVWP
```

Note: This can be conjugated to CCA1 (see above) or conjugated to a nucleic acid payload (e.g., siRNA) either via sulfhydryl chemistry (e.g., a disulfide bond) or amine-reactive chemistry.

(3d) Transferrin Ligand-Cys Right

```
                                    (SEQ ID NO: 55)
THRPPMWSPVWPC
```

Note: This can be conjugated to CCA2 (see above) or conjugated to a nucleic acid payload (e.g., siRNA) either via sulfhydryl chemistry (e.g., a disulfide bond) or amine-reactive chemistry.

(4a) E-Selectin Ligand [1-21]
[Charged Polymer Polypeptide Domain-Linker (GAPGAPGAP)-Targeting Ligand]

(SEQ ID NO: 56)
RRRRRRRR GAPGAPGAP MIASQFLSALTLVLLIKESGA (4b) E-Selectin Ligand [1-21]
[Targeting Ligand-Linker (GAPGAPGAP)-Charged Polymer Polypeptide Domain]

(SEQ ID NO: 57)
MIASQFLSALTLVLLIKESGA GAPGAPGAP RRRRRRRR (4c) E-Selectin Ligand [1-21]-Cys Left (SEQ ID NO: 58)
CMIASQFLSALTLVLLIKESGA Note: This can be conjugated to CCA1 (see above) or conjugated to a nucleic acid payload (e.g., siRNA) either via sulfhydryl chemistry (e.g., a disulfide bond) or amine-reactive chemistry.

(4d) E-selectin Ligand [1-21]-Cys Right (SEQ ID NO: 59)
MIASQFLSALTLVLLIKESGAC

Note: This can be conjugated to CCA2 (see above) or conjugated to a nucleic acid payload (e.g., siRNA) either via sulfhydryl chemistry (e.g., a disulfide bond) or amine-reactive chemistry.

(5a) FGF Fragment [26-47]
[Charged Polymer Polypeptide Domain-Linker (GAPGAPGAP)-Targeting Ligand]

(SEQ ID NO: 60)
RRRRRRRR GAPGAPGAP KNGGFFLRIHPDGRVDGVREKS

Note: This can be conjugated to CCA1 (see above) or conjugated to a nucleic acid payload (e.g., siRNA) either via sulfhydryl chemistry (e.g., a disulfide bond) or amine-reactive chemistry.

(5b) FGF Fragment [26-47]
[Targeting Ligand-Linker (GAPGAPGAP)-Charged Polymer Polypeptide Domain]

(SEQ ID NO: 61)
KNGGFFLRIHPDGRVDGVREKS GAPGAPGAP RRRRRRRR

Note: This can be conjugated to CCA1 (see above) or conjugated to a nucleic acid payload (e.g., siRNA) either via sulfhydryl chemistry (e.g., a disulfide bond) or amine-reactive chemistry.

(5c) FGF Fragment [25-47]-Cys on Left is Native (SEQ ID NO: 43)
CKNGGFFLRIHPDGRVDGVREKS Note: This can be conjugated to CCA1 (see above) or conjugated to a nucleic acid payload (e.g., siRNA) either via sulfhydryl chemistry (e.g., a disulfide bond) or amine-reactive chemistry.

(5d) FGF Fragment [26-47]-Cys Right (SEQ ID NO: 44)
KNGGFFLRIHPDGRVDGVREKSC

Note: This can be conjugated to CCA2 (see above) or conjugated to a nucleic acid payload (e.g., siRNA) either via sulfhydryl chemistry (e.g., a disulfide bond) or amine-reactive chemistry.

(6a) Exendin (S11C) [1-39]

(SEQ ID NO: 2)
HGEGTFTSDLCKQMEEEAVRLFIEWLKNGGPSSGAPPPS

Note: This can be conjugated to CCA1 (see above) or conjugated to a nucleic acid payload (e.g., siRNA) either via sulfhydryl chemistry (e.g., a disulfide bond) or amine-reactive chemistry.

Multivalent Compositions

In some cases a subject composition includes a population of delivery molecules such that the composition is multivalent (i.e., had more than one target, e.g., due to having multiple targeting ligands). In some cases, such a composition includes a combination of targeting ligands that provides for targeted binding to CD34 and heparin sulfate proteoglycans. For example, poly(L-arginine) can be used as part of such a composition to provide for targeted binding to heparin sulfate proteoglycans. Multivalence and also be achieved by includes more than one targeting ligand as part of the same delivery molecule. The descriptions below are intended to apply to both situations (where a composition includes more than one delivery molecule, and where a delivery molecule has more than one targeting ligand).

In some embodiments, a subject composition comprises a population of (two or more) targeting ligands, where the first and second ligands have different targets, and thus the subject composition is multivalent. A multivalent subject composition is one that includes two or more targeting ligands (e.g., two or more delivery molecules that include different ligands). An example of a multimeric (in this case trimeric) subject composition is one that includes the targeting ligands stem cell factor (SCF) (which targets c-Kit receptor, also known as CD117), CD70 (which targets CD27), and SH2 domain-containing protein 1A (SH2D1A) (which targets CD150). For example, in some cases, to target hematopoietic stem cells (HSCs) [KLS (c-Kit$^+$ Lin$^-$ Sca-1$^+$) and CD27$^+$/IL-7Ra$^-$/CD150$^+$/CD34$^-$], a subject composition includes a surface coat that includes a combination of the targeting ligands SCF, CD70, and SH2 domain-containing protein 1A (SH2D1A), which target c-Kit, CD27, and CD150, respectively (see, e.g., Table 1). In some cases, such a composition can selectively target HSPCs and long-term HSCs (c-Kit+/Lin−/Sca-1+/CD27+/IL-7Ra−/CD150+/CD34−) over other lymphoid and myeloid progenitors.

In some example embodiments, all three targeting ligands (SCF, CD70, and SH2D1A) are part of a subject composition. For example, (1) the targeting polypeptide SCF (which targets c-Kit receptor) can include XMEGICRNRVTNNVKDVTKLVANLPKDYM-ITLKYVPGMDVLPSHCWISEMVVQLSDSLTDLL-DKFS NISEGLSNYSIIDKLVNIVD-DLVECVKENSSKDLKKSFKSPEPRLFTPEEFFRIFNR-SIDAFKDFVVAS ETSDCVVSSTLS-PEKDSRVSVTKPFMLPPVAX (SEQ ID NO: xx), where the X is a charged polymer polypeptide domain (e.g., a poly-histidine such as 6H, a poly-arginine such as 9R, and the like), e.g., which can in some cases be present at the N- and/or C-terminal end, or can be embedded within the polypeptide sequence; (2) the targeting polypeptide CD70 (which targets CD27) can include XPEEGSGCSVRRRPYGCVLRAALVPLVAGLVICLVV-CIQRFAQAQQQLPLESLGWDVAELQLNHT GPQQDPRLYWQGGPALGRSFLHGPELDKGQL-RIHRDGIYMVHIQVTLAICSSTTASRHHPTTLAV GICSPASRSISLLRLSFHQGCTIASQRLT-PLARGDTLCTNLTGTLLPSRNTDETFFGVQWVRPX (SEQ ID NO: xx), where the X is a charged polymer polypeptide domain (e.g., a poly-histidine such as 6H, a poly-arginine such as 9R, and the like), e.g., which can in some cases be present at the N- and/or C-terminal end, or can be embedded within the polypeptide sequence; and (3) the targeting polypeptide SH2D1A (which targets CD150) can include XSSGLVPRGSHMDAVAVYHGKISRET-GEKLLLATGLDGSYLLRDSESVPGVY-CLCVLYHGYIYTYR VSQTETGSWSAETAPGVHKRY-FRKIKNLISAFQKPDQGIVIPLQYPVEKKSSARSTQGTT-GIREDP DVCLKAP (SEQ ID NO: xx), where the X is a charged polymer polypeptide domain (e.g., a poly-histidine such as 6H, a poly-arginine such as 9R, and the like), e.g., which can in some cases be present at the N- and/or C-terminal end, or can be embedded within the polypeptide sequence (e.g., such as MGSSXSSGL VPRGSHMDAVA-VYHGKISRETGEKLLLATGLDGSYLLRDSESVPGVY-CLCVLYHGY IYTYRVSQTETGSWSAETAPGVHKRY-FRKIKNLISAFQKPDQGIVIPLQYPVEKKSSARSTQGTT-GI REDPDVCLKAP (SEQ ID NO: xx)).

As noted above, compositions of the disclosure can include multiple targeting ligands in order to target a desired cell type, or in order to target a desired combination of cell types. Examples of various combinations of targeting ligands (of the mouse and human hematopoietic cell lineage) of interest include, but are not limited to: [Mouse] (i) CD150; (ii) Sca1, cKit, CD150; (iii) CD150 and CD49b; (iv) Sca1, cKit, CD150, and CD49b; (v) CD150 and Flt3; (vi) Sca1, cKit, CD150, and Flt3; (vii) Flt3 and CD34; (viii) Flt3, CD34, Sca1, and cKit; (ix) Flt3 and CD127; (x) Sca1, cKit, Flt3, and CD127; (xi) CD34; (xii) cKit and CD34; (xiii) CD16/32 and CD34; (xiv) cKit, CD16/32, and CD34; and (xv) cKit; and [Human] (i) CD90 and CD49f; (ii) CD34, CD90, and CD49f; (iii) CD34; (iv) CD45RA and CD10; (v) CD34, CD45RA, and CD10; (vi) CD45RA and CD135; (vii) CD34, CD38, CD45RA, and CD135; (viii) CD135; (ix) CD34, CD38, and CD135; and (x) CD34 and CD38. Thus, in some cases a subject composition includes one or more targeting ligands that provide targeted binding to a surface protein or combination of surface proteins selected from: [Mouse] (i) CD150; (ii) Sca1, cKit, CD150; (iii) CD150 and CD49b; (iv) Sca1, cKit, CD150, and CD49b; (v) CD150 and Flt3; (vi) Sca1, cKit, CD150, and Flt3; (vii) Flt3 and CD34; (viii) Flt3, CD34, Sca1, and cKit; (ix) Flt3 and CD127; (x) Sca1, cKit, Flt3, and CD127; (xi) CD34; (xii) cKit and CD34; (xiii) CD16/32 and CD34; (xiv) cKit, CD16/32, and CD34; and (xv) cKit; and [Human] (i) CD90 and CD49f; (ii) CD34, CD90, and CD49f; (iii) CD34; (iv) CD45RA and CD10; (v) CD34, CD45RA, and CD10; (vi) CD45RA and CD135; (vii) CD34, CD38, CD45RA, and CD135; (viii) CD135; (ix) CD34, CD38, and CD135; and (x) CD34 and CD38. Because a subject composition can include more than one targeting ligand, and because some cells include overlapping markers, multiple different cell types can be targeted using combinations of delivery molecules and/or targeting ligands, e.g., in some cases a composition may target one specific cell type while in other cases a composition may target more than one specific cell type (e.g., 2 or more, 3 or more, 4 or more cell types). For example, any combination of cells within the hematopoietic lineage can be targeted. As an illustrative example, targeting CD34 (using a targeting ligand that provides for targeted binding to CD34) can lead to delivery of a payload to several different cells within the hematopoietic lineage.

Payload

Delivery molecules of the disclosure can be conjugated a payload, or can in some cases interact electrostatically (e.g., are condensed) with a payload. A payload can be made of nucleic acid and/or protein. For example, in some cases a subject delivery molecule is used to deliver a nucleic acid payload (e.g., a DNA and/or RNA). The nucleic acid payload can be any nucleic acid of interest, e.g., the nucleic acid payload can be linear or circular, and can be a plasmid, a viral genome, an RNA (e.g., a coding RNA such as an mRNA or a non-coding RNA such as a guide RNA, a short interfering RNA (siRNA), a short hairpin RNA (shRNA), a microRNA (miRNA), and the like), a DNA, etc. In some cases, the nucleic payload is an RNAi agent (e.g., an shRNA, an siRNA, a miRNA, etc.) or a DNA template encoding an RNAi agent. In some cases, the nucleic acid payload is an siRNA molecule (e.g., one that targets an mRNA, one that targets a miRNA). In some cases, the nucleic acid payload is an LNA molecule (e.g., one that targets a miRNA). In some cases, the nucleic acid payload is a miRNA. In some cases the nucleic acid payload includes an mRNA that encodes a protein of interest (e.g., one or more reprograming and/or transdifferentiation factors such as Oct4, Sox2, Klf4, c-Myc, Nanog, and Lin28, e.g., alone or in any desired combination such as (i) Oct4, Sox2, Klf4, and c-Myc; (ii) Oct4, Sox2, Nanog, and Lin28; and the like; a gene editing endonuclease; a therapeutic protein; and the like). In some cases the nucleic acid payload includes a non-coding RNA (e.g., an RNAi agent, a CRISPR/Cas guide RNA, etc.) and/or a DNA molecule encoding the non-coding RNA. In some embodiments a nucleic acid payload includes a nucleic acid (DNA and/or mRNA) that encodes IL2Rα and IL12Rγ (e.g., to modulate the behavior or survival of a target cell). In some embodiments a nucleic acid payload includes a nucleic acid (DNA and/or mRNA) that encodes BCL-XL (e.g., to prevent apoptosis of a target cell due to engagement of Fas or TNFα receptors). In some embodiments a nucleic acid payload includes a nucleic acid (DNA and/or mRNA) that encodes Foxp3 (e.g., to promote an immune effector phenotype in targeted T-cells). In some embodiments a nucleic acid payload includes a nucleic acid (DNA and/or mRNA) that encodes SCF. In some embodiments a nucleic acid payload includes a nucleic acid (DNA and/or mRNA) that encodes HoxB4. In some embodiments a nucleic acid payload includes a nucleic acid (DNA and/or mRNA) that encodes SIRT6. In some embodiments a nucleic acid payload includes a nucleic acid molecule (e.g., an siRNA, an LNA, etc.) that targets (reduces expression of) a microRNA such as miR-155 (see, e.g., MiR Base accession: M10000681 and M10000177). In some embodiments a nucleic acid payload includes an siRNA that targets ku70 and/or an siRNA that targets ku80.

The term "nucleic acid payload" encompasses modified nucleic acids. Likewise, the terms "RNAi agent" and "siRNA" encompass modified nucleic acids. For example, the nucleic acid molecule can be a mimetic, can include a modified sugar backbone, one or more modified internucleoside linkages (e.g., one or more phosphorothioate and/or heteroatom internucleoside linkages), one or more modified bases, and the like. In some embodiments, a subject payload includes triplex-forming peptide nucleic acids (PNAs) (see, e.g., McNeer et al., Gene Ther. 2013 June; 20(6):658-69). Thus, in some cases a subject core includes PNAs. In some cases a subject core includes PNAs and DNAs.

A subject nucleic acid payload (e.g., an siRNA) can have a morpholino backbone structure. In some case, a subject nucleic acid payload (e.g., an siRNA) can have one or more locked nucleic acids (LNAs). Suitable sugar substituent groups include methoxy (—O—$CH_3$), aminopropoxy (—$OCH_2CH_2CH_2NH_2$), allyl (—$CH_2$—CH=$CH_2$), —O-allyl (—O— $CH_2$—CH=$CH_2$) and fluoro (F). 2'-sugar substituent groups may be in the arabino (up) position or ribo (down) position. Suitable base modifications include synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2 (3H)-one), carbazole cytidine (2H-pyrimido(4,5-b)indol-2-one), pyridoindole cytidine (H-pyrido(3',2':4,5)pyrrolo(2,3-d)pyrimidin-2-one).

In some cases, a nucleic acid payload can include a conjugate moiety (e.g., one that enhances the activity, stability, cellular distribution or cellular uptake of the nucleic acid payload). These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject nucleic acid.

Any convenient polynucleotide can be used as a subject nucleic acid payload. Examples include but are not limited to: species of RNA and DNA including mRNA, m1A modified mRNA (monomethylation at position 1 of Adenosine), siRNA, miRNA, aptamers, shRNA, AAV-derived nucleic acids and scaffolds, morpholino RNA, peptoid and peptide nucleic acids, cDNA, DNA origami, DNA and RNA with synthetic nucleotides, DNA and RNA with predefined secondary structures, multimers and oligomers of the aforementioned, and payloads whose sequence may encode other products such as any protein or polypeptide whose expression is desired.

In some cases a payload of a subject delivery molecule includes a protein. Examples of protein payloads include, but are not limited to: programmable gene editing proteins (e.g., transcription activator-like (TAL) effectors (TALEs), TALE nucleases (TALENs), zinc-finger proteins (ZFPs), zinc-finger nucleases (ZFNs), DNA-guided polypeptides such as *Natronobacterium gregoryi* Argonaute (NgAgo), CRISPR/Cas RNA-guided polypeptides such as Cas9, CasX, CasY, Cpf1, and the like); transposons (e.g., a Class I or Class II transposon—e.g., piggybac, sleeping beauty, Tc1/mariner, Tol2, PIF/harbinger, hAT, mutator, merlin, transib, helitron, maverick, frog prince, minos, Himar1 and the like); meganucleases (e.g., I-SceI, I-CeuI, I-CreI, I-DmoI, I-ChuI, I-DirI, I-FlmuI, I-FlmuII, I-AniI, I-SceIV, 1-CsmI, I-PanI, I-PanII, I-PanMI, I-SceII, I-PpoI, I-SceIII, I-LtrI, I-GpiI, I-GZeI, I-OnuI, I-HjeMI, I-MsoI, I-TevI, I-TevII, I-TevIII, PI-MleI, PI-MtuI, PI-PspI, PI-Tli I, PI-Tli II, PI-SceV, and the like); megaTALs (see, e.g., Boissel et al., Nucleic Acids Res. 2014 February; 42(4): 2591-2601); SCF; BCL-XL; Foxp3; HoxB4; and SiRT6. For any of the above proteins, a payload of a subject delivery molecule can include a nucleic acid (DNA and/or mRNA) encoding the protein, and/or can include the actual protein.

Gene Editing Tools

In some cases, a nucleic acid payload includes or encodes a gene editing tool (i.e., a component of a gene editing system, e.g., a site specific gene editing system such as a programmable gene editing system). For example, a nucleic acid payload can include one or more of: (i) a CRISPR/Cas guide RNA, (ii) a DNA encoding a CRISPR/Cas guide RNA, (iii) a DNA and/or RNA encoding a programmable gene editing protein such as a zinc finger protein (ZFP) (e.g., a zinc finger nuclease—ZFN), a transcription activator-like effector (TALE) protein (e.g., fused to a nuclease—TALEN), a DNA-guided polypeptide such as *Natronobacterium gregoryi* Argonaute (NgAgo), and/or a CRISPR/Cas RNA-guided polypeptide (e.g., Cas9, CasX, CasY, Cpf1, and the like); (iv) a DNA donor template; (v) a nucleic acid molecule (DNA, RNA) encoding a site-specific recombinase (e.g., Cre recombinase, Dre recombinase, Flp recombinase, KD recombinase, B2 recombinase, B3 recombinase, R recombinase, Hin recombinase, Tre recombinase, PhiC31 integrase, Bxb1 integrase, R4 integrase, lambda integrase, HK022 integrase, HP1 integrase, and the like); (vi) a DNA encoding a resolvase and/or invertase (e.g., Gin, Hin, γδ3, Tn3, Sin, Beta, and the like); and (vii) a transposon and/or a DNA derived from a transposon (e.g., bacterial transposons such as Tn3, Tn5, Tn7, Tn9, Tn10, Tn903, Tn1681, and the like; eukaryotic transposons such as Tc1/mariner super family transposons, PiggyBac superfamily transposons, hAT superfamily transposons, PiggyBac, Sleeping Beauty, Frog Prince, Minos, Himar1, and the like). In some cases a subject delivery molecule is used to deliver a protein payload, e.g., a gene editing protein such as a ZFP (e.g., ZFN), a TALE (e.g., TALEN), a DNA-guided polypeptide such as *Natronobacterium gregoryi* Argonaute (NgAgo), a CRISPR/Cas RNA-guided polypeptide (e.g., Cas9, CasX, CasY, Cpf1, and the like), a site-specific recombinase (e.g., Cre recombinase, Dre recombinase, Flp recombinase, KD recombinase, B2 recombinase, B3 recombinase, R recombinase, Hin recombinase, Tre recombinase, PhiC31 integrase, Bxb1 integrase, R4 integrase, lambda integrase, HK022 integrase, HP1 integrase, and the like), a resolvase/invertase (e.g., Gin, Hin, γδ3, Tn3, Sin, Beta, and the like); and/or a transposase (e.g., a transposase related to transposons such as bacterial transposons such as Tn3, Tn5, Tn7, Tn9, Tn10, Tn903, Tn1681, and the like; or eukaryotic transposons such as Tc1/mariner super family transposons, PiggyBac superfamily transposons, hAT superfamily transposons, PiggyBac, Sleeping Beauty, Frog Prince, Minos, Himar1, and the like). In some cases, the delivery molecule is used to deliver a nucleic acid payload and a protein payload, and in some such cases the payload includes a ribonucleoprotein complex (RNP).

Depending on the nature of the system and the desired outcome, a gene editing system (e.g. a site specific gene editing system such as a a programmable gene editing system) can include a single component (e.g., a ZFP, a ZFN, a TALE, a TALEN, a site-specific recombinase, a resolvase/integrase, a transpose, a transposon, and the like) or can include multiple components. In some cases a gene editing system includes at least two components. For example, in some cases a gene editing system (e.g. a programmable gene editing system) includes (i) a donor template nucleic acid; and (ii) a gene editing protein (e.g., a programmable gene editing protein such as a ZFP, a ZFN, a TALE, a TALEN, a DNA-guided polypeptide such as *Natronobacterium gregoryi* Argonaute (NgAgo), a CRISPR/Cas RNA-guided polypeptide such as Cas9, CasX, CasY, or Cpf1, and the like), or a nucleic acid molecule encoding the gene editing protein (e.g., DNA or RNA such as a plasmid or mRNA). As another example, in some cases a gene editing system (e.g. a programmable gene editing system) includes (i) a CRISPR/Cas guide RNA, or a DNA encoding the CRISPR/Cas guide RNA; and (ii) a CRISPR/CAS RNA-guided polypeptide (e.g., Cas9, CasX, CasY, Cpf1, and the like), or a nucleic acid molecule encoding the RNA-guided polypeptide (e.g., DNA or RNA such as a plasmid or mRNA). As another example, in some cases a gene editing system (e.g. a programmable gene editing system) includes (i) an NgAgo-like guide DNA; and (ii) a DNA-guided polypeptide (e.g., NgAgo), or a nucleic acid molecule encoding the DNA-guided polypeptide (e.g., DNA or RNA such as a plasmid or mRNA). In some cases a gene editing system (e.g. a programmable gene editing system) includes at least three components: (i) a donor DNA template; (ii) a CRISPR/Cas guide RNA, or a DNA encoding the CRISPR/Cas guide RNA; and (iii) a CRISPR/Cas RNA-guided polypeptide (e.g., Cas9, CasX, CasY, or Cpf1), or a nucleic acid molecule encoding the RNA-guided polypeptide (e.g., DNA or RNA such as a plasmid or mRNA). In some cases a gene editing system (e.g. a programmable gene editing system) includes at least three components: (i) a donor DNA template; (ii) an NgAgo-like guide DNA, or a DNA encoding the NgAgo-like guide DNA; and (iii) a DNA-guided polypeptide (e.g., NgAgo), or a nucleic acid molecule encoding the DNA-guided polypeptide (e.g., DNA or RNA such as a plasmid or mRNA).

In some embodiments, a subject delivery molecule is used to deliver a gene editing tool. In other words in some cases the payload includes one or more gene editing tools. The term "gene editing tool" is used herein to refer to one or more components of a gene editing system. Thus, in some cases the payload includes a gene editing system and in some cases the payload includes one or more components of a gene editing system (i.e., one or more gene editing tools). For example, a target cell might already include one of the components of a gene editing system and the user need only add the remaining components. In such a case the payload of a subject delivery molecule does not necessarily include all of the components of a given gene editing system. As such, in some cases a payload includes one or more gene editing tools.

As an illustrative example, a target cell might already include a gene editing protein (e.g., a ZFP, a TALE, a DNA-guided polypeptide (e.g., NgAgo), a CRISPR/Cas RNA-guided polypeptide such Cas9, CasX, CasY, Cpf1, and the like, a site-specific recombinase such as Cre recombinase, Dre recombinase, Flp recombinase, KD recombinase, B2 recombinase, B3 recombinase, R recombinase, Hin recombinase, Tre recombinase, PhiC31 integrase, Bxb1 integrase, R4 integrase, lambda integrase, HK022 integrase, HP1 integrase, and the like, a resolvase/invertase such as Gin, Hin, γδ3, Tn3, Sin, Beta, and the like, a transposase, etc.) and/or a DNA or RNA encoding the protein, and therefore the payload can include one or more of: (i) a donor template; and (ii) a CRISPR/Cas guide RNA, or a DNA encoding the CRISPR/Cas guide RNA; or an NgAgo-like guide DNA. Likewise, the target cell may already include a CRISPR/Cas guide RNA and/or a DNA encoding the guide RNA or an NgAgo-like guide DNA, and the payload can include one or more of: (i) a donor template; and (ii) a CRISPR/Cas RNA-guided polypeptide (e.g., Cas9, CasX, CasY, Cpf1, and the like), or a nucleic acid molecule encoding the RNA-guided polypeptide (e.g., DNA or RNA such as a plasmid or mRNA); or a DNA-guided polypeptide (e.g., NgAgo), or a nucleic acid molecule encoding the DNA-guided polypeptide.

As would be understood by one of ordinary skill in the art, a gene editing system need not be a system that 'edits' a nucleic acid. For example, it is well recognized that a gene editing system can be used to modify target nucleic acids (e.g., DNA and/or RNA) in a variety of ways without creating a double strand break (DSB) in the target DNA. For example, in some cases a double stranded target DNA is nicked (one strand is cleaved), and in some cases (e.g., in some cases where the gene editing protein is devoid of nuclease activity, e.g., a CRISPR/Cas RNA-guided polypeptide may harbor mutations in the catalytic nuclease domains), the target nucleic acid is not cleaved at all. For example, in some cases a CRISPR/Cas protein (e.g., Cas9, CasX, CasY, Cpf1) with or without nuclease activity, is fused to a heterologous protein domain. The heterologous protein domain can provide an activity to the fusion protein such as (i) a DNA-modifying activity (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity), (ii) a transcription modulation activity (e.g., fusion to a transcriptional repressor or activator), or (iii) an activity that modifies a protein (e.g., a histone) that is associated with target DNA (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity). As such, a gene editing system can be used in applications that modify a target nucleic acid in way that do not cleave the target nucleic acid, and can also be used in applications that modulate transcription from a target DNA.

For additional information related to programmable gene editing tools (e.g., CRISPR/Cas RNA-guided proteins such as Cas9, CasX, CasY, and Cpf1, Zinc finger proteins such as Zinc finger nucleases, TALE proteins such as TALENs, CRISPR/Cas guide RNAs, and the like) refer to, for example, Dreier, et al., (2001) J Biol Chem 276:29466-78; Dreier, et al., (2000) J Mol Biol 303:489-502; Liu, et al., (2002) J Biol Chem 277:3850-6); Dreier, et al., (2005) J Biol Chem 280:35588-97; Jamieson, et al., (2003) Nature Rev Drug Discov 2:361-8; Durai, et al., (2005) Nucleic Acids Res 33:5978-90; Segal, (2002) Methods 26:76-83; Porteus and Carroll, (2005) Nat Biotechnol 23:967-73; Pabo, et al., (2001) Ann Rev Biochem 70:313-40; Wolfe, et al., (2000) Ann Rev Biophys Biomol Struct 29:183-212; Segal and Barbas, (2001) Curr Opin Biotechnol 12:632-7; Segal, et al., (2003) Biochemistry 42:2137-48; Beerli and Barbas, (2002) Nat Biotechnol 20:135-41; Carroll, et al., (2006) Nature Protocols 1:1329; Ordiz, et al., (2002) Proc Natl Acad Sci USA 99:13290-5; Guan, et al., (2002) Proc Natl Acad Sci USA 99:13296-301; Sanjana et al., Nature Protocols, 7:171-192 (2012); Zetsche et al, Cell. 2015 Oct. 22; 163(3):759-71; Makarova et al, Nat Rev Microbiol. 2015 November; 13(11):722-36; Shmakov et al., Mol Cell. 2015 Nov. 5; 60(3):385-97; Jinek et al., Science. 2012 Aug. 17; 337 (6096):816-21; Chylinski et al., RNA Biol. 2013 May; 10(5):726-37; Ma et al., Biomed Res Int. 2013; 2013: 270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et. al., Genome Res. 2013 Oct. 31; Chen et. al., Nucleic Acids Res. 2013 Nov. 1; 41(20):e19; Cheng et. al., Cell Res. 2013 October; 23(10): 1163-71; Cho et. al., Genetics. 2013 November; 195(3): 1177-80; DiCarlo et al., Nucleic Acids Res. 2013 April; 41(7):4336-43; Dickinson et. al., Nat Methods. 2013 October; 10(10):1028-34; Ebina et. al., Sci Rep. 2013; 3:2510; Fujii et. al, Nucleic Acids Res. 2013 Nov. 1; 41(20):e187; Hu et. al., Cell Res. 2013 November; 23(11):1322-5; Jiang et. al., Nucleic Acids Res. 2013 Nov. 1; 41(20):e188; Larson et. al., Nat Protoc. 2013 November; 8(11):2180-96; Mali et. at., Nat Methods. 2013 October; 10(10):957-63; Nakayama et. al., Genesis. 2013 December; 51(12):835-43; Ran et. al., Nat Protoc. 2013 November; 8(11):2281-308; Ran et. al., Cell. 2013 Sep. 12; 154(6):1380-9; Upadhyay et. al., G3 (Bethesda). 2013 Dec. 9; 3(12):2233-8; Walsh et. al., Proc Natl Acad Sci USA. 2013 Sep. 24; 110(39):15514-5; Xie et. al., Mol Plant. 2013 Oct. 9; Yang et. al., Cell. 2013 Sep. 12; 154(6):1370-9; Briner et al., Mol Cell. 2014 Oct. 23; 56(2): 333-9; Burstein et al., Nature. 2016 Dec. 22—Epub ahead of print; Gao et al., Nat Biotechnol. 2016 July 34(7):768-73; as well as international patent application publication Nos. WO2002099084; WO00/42219; WO02/42459; WO2003062455; WO03/080809; WO05/014791; WO05/084190; WO08/021207; WO09/042186; WO09/054985; and WO10/065123; U.S. patent application publication Nos. 20030059767, 20030108880, 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; 20140377868; 20150166983; and 20160208243; and U.S. Pat. Nos. 6,140,466; 6,511,808; 6,453,242 8,685,737; 8,906,616; 8,895,308; 8,889,418; 8,889,356; 8,871,445; 8,865,406; 8,795,965; 8,771,945; and 8,697,359; all of which are hereby incorporated by reference in their entirety.

Delivery

Provided are methods of delivering a nucleic acid, protein, or ribonucleoprotein payload to a cell. Such methods include a step of contacting a cell with a subject delivery molecule. The cell can be any cell that includes a cell surface protein targeted by a targeting ligand of a delivery molecule of the disclosure. In some cases, the cell is a mammalian cell (e.g., a rodent cell, a rat cell, a mouse cell, a pig cell, a cow cell, a horse cell, a sheep cell, a rabbit cell, a guinea pig cell, a canine cell, a feline cell, a primate cell, a non-human primate cell, a human cell, and the like).

Such methods can include a step of contacting a cell with a subject delivery molecule. A subject delivery molecule can be used to deliver a payload to any desired eukaryotic target cell. In some cases, the target cell is a mammalian cell (e.g., a cell of a rodent, a mouse, a rat, an ungulate, a cow, a sheep, a pig, a horse, a camel, a rabbit, a canine (dog), a feline (cat), a primate, a non-human primate, or a human). Any cell type can be targeted, and in some cases specific targeting of particular cells depends on the presence of targeting ligands, e.g., as part of the delivery molecule, where the targeting ligands provide for targeting binding to a particular cell type. For example, cells that can be targeted include but are not limited to bone marrow cells, hematopoietic stem cells (HSCs), long-term HSCs, short-term HSCs, hematopoietic stem and progenitor cells (HSPCs), peripheral blood mononuclear cells (PBMCs), myeloid progenitor cells, lymphoid progenitor cells, T-cells, B-cells, NKT cells, NK cells, dendritic cells, monocytes, granulocytes, erythrocytes, megakaryocytes, mast cells, basophils, eosinophils, neutrophils, macrophages, erythroid progenitor cells (e.g., HUDEP cells), megakaryocyte-erythroid progenitor cells (MEPs), common myeloid progenitor cells (CMPs), multipotent progenitor cells (MPPs), hematopoietic stem cells (HSCs), short term HSCs (ST-HSCs), IT-HSCs, long term HSCs (LT-HSCs), endothelial cells, neurons, astrocytes, pancreatic cells, pancreatic β-islet cells, muscle cells, skeletal muscle cells, cardiac muscle cells, hepatic cells, fat cells, intestinal cells, cells of the colon, and cells of the stomach.

Examples of various applications (e.g., for targeting neurons, cells of the pancreas, hematopoietic stem cells and multipotent progenitors, etc.) are numerous. For example, Hematopoietic stem cells and multipotent progenitors can be targeted for gene editing (e.g., insertion) in vivo. Even editing 1% of bone marrow cells in vivo (approximately 15 billion cells) would target more cells than an ex vivo therapy (approximately 10 billion cells). As another example, pancreatic cells (e.g., p islet cells) can be targeted, e.g., to treat pancreatic cancer, to treat diabetes, etc. As another example, somatic cells in the brain such as neurons can be targeted (e.g., to treat indications such as Huntington's disease, Parkinson's (e.g., LRRK2 mutations), and ALS (e.g., SOD1 mutations)). In some cases this can be achieved through direct intracranial injections.

As another example, endothelial cells and cells of the hematopoietic system (e.g., megakaryocytes and/or any progenitor cell upstream of a megakaryocyte such as a megakaryocyte-erythroid progenitor cell (MEP), a common myeloid progenitor cell (CMP), a multipotent progenitor cell (MPP), a hematopoietic stem cells (HSC), a short term HSC (ST-HSC), an IT-HSC, a long term HSC (LT-HSC) can be targeted with a subject delivery molecule to treat Von Willebrand's disease. For example, a cell (e.g., an endothelial cell, a megakaryocyte and/or any progenitor cell upstream of a megakaryocyte such as an MEP, a CMP, an MPP, an HSC such as an ST-HSC, an IT-HSC, and/or an LT-HSC) harboring a mutation in the gene encoding von Willebrand factor (VWF) can be targeted (in vitro, ex vivo, in vivo) in order to introduce an active protein (e.g., via delivery of a functional VWF protein and/or a nucleic acid encoding a functional VWF protein) and/or in order to edit the mutated gene, e.g., by introducing a replacement sequence (e.g., via delivery of a gene editing tool and delivery of a DNA donor template). In some of the above cases (e.g., in cases related to treating Von Willebrand's disease, in cases related to targeting a cell harboring a mutation in the gene encoding VWF), a subject targeting ligand provides for targeted binding to E-selectin.

As another example, a cell of a stem cell lineage (e.g., a stem and/or progenitor cell of the hematopoietic lineage, e.g., a GMP, MEP, CMP, MLP, MPP, and/or an HSC) can be targeted with a subject delivery molecule (or subject viral or non-viral delivery vehicle) in order to increase expression of stem cell factor (SCF) in the cell, which can therefore drive proliferation of the targeted cell. For example, a subject delivery molecule can be used to deliver SCF and/or a nucleic acid (DNA or mRNA) encoding SCF to the targeted cell.

Methods and compositions of this disclosure can be used to treat any number of diseases, including any disease that is linked to a known causative mutation, e.g., a mutation in the genome. For example, methods and compositions of this disclosure can be used to treat sickle cell disease, B thalassemia, HIV, myelodysplastic syndromes, JAK2-mediated polycythemia vera, JAK2-mediated primary myelofibrosis, JAK2-mediated leukemia, and various hematological disorders. As additional non-limiting examples, the methods and compositions of this disclosure can also be used for B-cell antibody generation, immunotherapies (e.g., delivery of a checkpoint blocking reagent), and stem cell differentiation applications.

As noted above, in some embodiments, a targeting ligand provides for targeted binding to KLS CD27+/IL-7Ra−/CD150+/CD34− hematopoietic stem and progenitor cells (HSPCs). For example, a gene editing tool(s) (described elsewhere herein) can be introduced in order to disrupt expression of a BCL11a transcription factor and consequently generate fetal hemoglobin. As another example, the beta-globin (HBB) gene may be targeted directly to correct the altered E7V substitution with a corresponding homology-directed repair donor template. As one illustrative example, a CRISPR/Cas RNA-guided polypeptide (e.g., Cas9, CasX, CasY, Cpf1) can be delivered with an appropriate guide RNA such that it will bind to loci in the HBB gene and create double-stranded or single-stranded breaks in the genome, initiating genomic repair. In some cases, a DNA donor template (single stranded or double stranded) is introduced (as part of a payload). In some cases, a payload can include an siRNA for ku70 or ku80, e.g., which can be used to promote homologous directed repair (HDR) and limit indel formation. In some cases, an mRNA for SIRT6 is released over 14-30d to promote HDR-driven insertion of a donor strand following nuclease-mediated site-specific cleavage.

In some embodiments, a targeting ligand provides for targeted binding to CD4+ or CD8+ T-cells, hematopoietic stem and progenitor cells (HSPCs), or peripheral blood mononuclear cells (PBMCs), in order to modify the T-cell receptor. For example, a gene editing tool(s) (described elsewhere herein) can be introduced in order to modify the T-cell receptor. The T-cell receptor may be targeted directly and substituted with a corresponding homology-directed repair donor template for a novel T-cell receptor. As one example, a CRISPR/Cas RNA-guided polypeptide (e.g., Cas9, CasX, CasY, Cpf1) can be delivered with an appropriate guide RNA such that it will bind to loci in the TCR gene and create double-stranded or single-stranded breaks in the genome, initiating genomic repair. In some cases, a DNA donor template (single stranded or double stranded) is introduced (as part of a payload) for HDR. It would be evident to skilled artisans that other CRISPR guide RNA and HDR donor sequences, targeting beta-globin, CCR5, the T-cell receptor, or any other gene of interest, and/or other expression vectors may be employed in accordance with the present disclosure.

In some cases, the contacting is in vitro (e.g., the cell is in culture), e.g., the cell can be a cell of an established tissue culture cell line. In some cases, the contacting is ex vivo (e.g., the cell is a primary cell (or a recent descendant) isolated from an individual, e.g. a patient). In some cases, the cell is in vivo and is therefore inside of (part of) an organism. As an example of in vivo contact, in some cases the contacting step includes administration of a delivery molecule (e.g., a targeting ligand conjugated to a nucleic acid or protein payload, nanoparticle coated with a subject targeting ligand, a targeting ligand conjugated to a charged polymer polypeptide domain that is condensed with a nucleic acid payload, and the like) to an individual.

A subject delivery molecule may be introduced to the subject (i.e., administered to an individual) via any of the following routes: systemic, local, parenteral, subcutaneous (s.c.), intravenous (i.v.), intracranial (i.c.), intraspinal, intraocular, intradermal (i.d.), intramuscular (i.m.), intralymphatic (i.l.), or into spinal fluid. A subject delivery molecule may be introduced by injection (e.g., systemic injection, direct local injection, local injection into or near a tumor and/or a site of tumor resection, etc.), catheter, or the like. Examples of methods for local delivery (e.g., delivery to a tumor and/or cancer site) include, e.g., by bolus injection, e.g. by a syringe, e.g. into a joint, tumor, or organ, or near a joint, tumor, or organ; e.g., by continuous infusion, e.g. by cannulation, e.g. with convection (see e.g. US Application No. 20070254842, incorporated here by reference).

The number of administrations of treatment to a subject may vary. Introducing a subject delivery molecule into an individual may be a one-time event; but in certain situations, such treatment may elicit improvement for a limited period of time and require an on-going series of repeated treatments. In other situations, multiple administrations of a subject delivery molecule may be required before an effect is observed. As will be readily understood by one of ordinary skill in the art, the exact protocols depend upon the disease or condition, the stage of the disease and parameters of the individual being treated.

A "therapeutically effective dose" or "therapeutic dose" is an amount sufficient to effect desired clinical results (i.e., achieve therapeutic efficacy). A therapeutically effective dose can be administered in one or more administrations. For purposes of this disclosure, a therapeutically effective dose of a subject delivery molecule is an amount that is sufficient, when administered to the individual, to palliate, ameliorate, stabilize, reverse, prevent, slow or delay the progression of a disease state/ailment.

An example therapeutic intervention is one that creates resistance to HIV infection in addition to ablating any retroviral DNA that has been integrated into the host genome. T-cells are directly affected by HIV and thus a hybrid blood targeting strategy for CD34+ and CD45+ cells may be explored for delivering dual guided nucleases. By simultaneously targeting HSCs and T-cells and delivering an ablation to the CCR5-A32 and gag/rev/pol genes through multiple guided nucleases (e.g., within a single particle), a universal HIV cure can be created with persistence through the patient's life.

A subject delivery molecule can be modified, e.g., joined to a wide variety of other oligopeptides or proteins for a variety of purposes. For example, post-translationally modified, for example by prenylation, acetylation, amidation, carboxylation, glycosylation, PEGylation (covalent attachment of polyethylene glycol (PEG) polymer chains), etc. Such modifications can also include modifications of glycosylation, e.g. those made by modifying the glycosylation patterns of a polypeptide during its synthesis and processing or in further processing steps; e.g. by exposing the delivery molecule to enzymes which affect glycosylation, such as mammalian glycosylating or deglycosylating enzymes. In some embodiments, a subject delivery molecule has one or more phosphorylated amino acid residues, e.g. phosphotyrosine, phosphoserine, or phosphothreonine.

In some other embodiments, a delivery molecule of the disclosure can be modified to improve resistance to proteolytic degradation or to optimize solubility properties or to render it more suitable as a therapeutic agent. For example, delivery molecules of the present disclosure can include analogs containing residues other than naturally occurring L-amino acids, e.g. D-amino acids or non-naturally occurring synthetic amino acids. D-amino acids may be substituted for some or all of the amino acid residues.

In some cases, a subject delivery molecule can be embedded on a surface (e.g., in a dish/plate format), e.g., instead of antibodies, for biosensing applications. In some cases a subject delivery molecule can be added to nanodiamonds (e.g., can be used to coat nanodiamonds).

Also within the scope of the disclosure are kits. For example, in some cases a subject kit can include one or more of (in any combination): (i) a targeting ligand, (ii) a linker, (iii) a targeting ligand conjugated to a linker, (iv) a targeting ligand conjugated to a charged polymer polypeptide domain (e.g., with or without a linker), (v) an siRNA or a transcription template for an siRNA or shRNA; and (iv) an agent for use as an anionic nanoparticle stabilization coat. In some cases, a subject kit can include instructions for use. Kits typically include a label indicating the intended use of the contents of the kit. The term label includes any writing, or recorded material supplied on or with the kit, or which otherwise accompanies the kit.

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-50 (SET A) and 1-59 (SET B) are provided below. As will be apparent to those of ordinary skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Set A

1. A delivery molecule, comprising a peptide targeting ligand conjugated to a protein or nucleic acid payload, or conjugated to a charged polymer polypeptide domain, wherein the targeting ligand provides for (i) targeted binding to a cell surface protein, and (ii) engagement of long endosomal recycling pathways.
2. The delivery molecule of 1, wherein the targeting ligand comprises an internal cysteine residue.
3. The delivery molecule of 1 or 2, wherein the targeting ligand comprises a cysteine substitution or insertion, at one or more internal amino acid positions, relative to a corresponding wild type amino acid sequence.
4. The delivery molecule of any one of 1-3, wherein the targeting ligand comprises a cysteine residue at an N- and/or C-terminus.
5. The delivery molecule of 4, wherein the cysteine residue at the N- and/or C-terminus is a substitution or an insertion relative to a corresponding wild type amino acid sequence
6. The delivery molecule of any one of 1-6, wherein the targeting ligand has a length of from 5-50 amino acids.
7. The delivery molecule of any one of 1-6, wherein the targeting ligand is a fragment of a wild type protein.
8. The delivery molecule of any one of 1-7, wherein the targeting ligand provides for targeted binding to a cell surface protein selected from a family B G-protein coupled receptor (GPCR), a receptor tyrosine kinase (RTK), a cell surface glycoprotein, and a cell-cell adhesion molecule.
9. The delivery molecule of 8, wherein the targeting ligand provides for binding to both an allosteric-affinity domain and an orthosteric domain of a family B GPCR to provide for the targeted binding and the engagement of long endosomal recycling pathways, respectively.
10. The delivery molecule of 9, wherein targeting ligand comprises an amino acid sequence having 85% or more identity (e.g., 100% identity) to the exendin-4 amino acid sequence:

(SEQ ID NO. 1)
HGEGTFTSDLSKQMEEEAVRLFIEWLKNGGPSSGAPPPS.

11. The delivery molecule of 10, wherein the targeting ligand comprises a cysteine substitution at one or more of positions corresponding to L10, S11, and K12 of the amino acid sequence set forth in SEQ ID NO: 1).
12. The delivery molecule of 9, wherein the targeting ligand comprises the amino acid sequence:

(SEQ ID NO. 2)
HGEGTFTSDLCKQMEEEAVRLFIEWLKNGGPSSGAPPPS.

13. The delivery molecule of 8, wherein the targeting ligand provides for targeted binding to an RTK.
14. The delivery molecule of 13, wherein the RTK is a fibroblast growth factor (FGF) receptor.
15. The delivery molecule of 14, wherein the targeting ligand is a fragment of an FGF.
16. The delivery molecule of 14 or 15, wherein the targeting ligand binds to a segment of the RTK that is occupied during orthosteric binding.
17. The delivery molecule of any one of 13-16, wherein the targeting ligand binds to a heparin-affinity domain of the RTK.
18. The delivery molecule of any one of 13-17, the targeting ligand provides for targeted binding to an FGF receptor, and wherein the targeting ligand comprises an amino acid sequence having 85% or more identity (e.g., 100% identity) to the amino acid sequence KNGGFFL-RIHPDGRVDGVREKS (SEQ ID NO: 4).

19. The delivery molecule of any one of 13-17, the targeting ligand provides for targeted binding to an FGF receptor, and wherein the targeting ligand comprises the amino acid sequence HFKDPK (SEQ ID NO: 5).

20. The delivery molecule of any one of 13-17, the targeting ligand provides for targeted binding to an FGF receptor, and wherein the targeting ligand comprises the amino acid sequence LESNNYNT (SEQ ID NO: 6).

21. The delivery molecule of 8, wherein the targeting ligand provides for targeted binding to a cell surface glycoprotein and/or a cell-cell adhesion factor.

22. The delivery molecule of 21, wherein the targeting ligand is a fragment of E-selectin, L-selectin, or P-selectin.

23. The delivery molecule of 21, wherein the targeting ligand comprises an amino acid sequence having 85% or more identity (e.g., 100% identity) to the amino acid sequence MIASQFLSALTLVLLIKESGA (SEQ ID NO: 7).

24. The delivery molecule of 21, wherein the targeting ligand comprises an amino acid sequence having 85% or more identity (e.g., 100% identity) to the amino acid sequence MVFPWRCEGTYWGSR-NILKLWVWTLLCCDFLIHHGTHC (SEQ ID NO: 8), MIFPWKCQSTQRDLWNIFKLWGWTMLCCD-FLAHHGTDC (SEQ ID NO: 9), and/or MIFPWKCQSTQRDLWNIFKLWGWTMLCC (SEQ ID NO: 10)

25. The delivery molecule of 8, wherein the targeting ligand provides for targeted binding to a cell-to-cell adhesion molecule.

26. The delivery molecule of any one of 1-7, wherein the targeting ligand provides for targeted binding to a transferrin receptor, and wherein the targeting ligand comprises an amino acid sequence having 85% or more identity (e.g., 100% identity) to the amino acid sequence THRPPMWSPVWP (SEQ ID NO: 11).

27. The delivery molecule of any one of 1-7, wherein the targeting ligand provides for targeted binding to α5β1 integrin.

28. The delivery molecule of 27, wherein the targeting ligand comprises the amino acid sequence RRETAWA (SEQ ID NO: 12).

29. The delivery molecule of 27, wherein the targeting ligand comprises the amino acid sequence RGD.

30. The delivery molecule of any one of 1-29, wherein the targeting ligand provides engagement of β-arrestin upon binding to the cell surface protein (e.g., to provide for signaling bias and to promote internalization via endocytosis following orthosteric binding).

31. The delivery molecule of any one of 1-30, wherein the targeting ligand is conjugated to a nucleic acid payload.

32. The delivery molecule of 31, wherein the nucleic acid payload is an RNAi agent.

33. The delivery molecule of 32, wherein the RNAi agent is an siRNA molecule.

34. The delivery molecule of any one of 1-30, wherein the targeting ligand is conjugated to a protein payload.

35. The delivery molecule of any one of 1-30, wherein the payload is a ribonucleoprotein complex and the targeting ligand is conjugated to a nucleic acid or protein component of said complex.

36. The delivery molecule of any one of 1-30, wherein the targeting ligand is conjugated to a charged polymer polypeptide domain.

37. The delivery molecule of 36, wherein the charged polymer polypeptide domain is condensed with a nucleic acid payload.

38. The delivery molecule of 36, wherein the charged polymer polypeptide domain of the delivery molecule is interacting electrostatically with a charged stabilization layer of a nanoparticle.

39. The delivery molecule of any one of 36-38, wherein the charged polymer polypeptide domain is a cationic domain selected from RRRRRRRRR (9R) (SEQ ID NO: 15) and HHHHHH (6H) (SEQ ID NO: 16).

40. The delivery molecule of any one of 1-39, wherein the targeting ligand comprises a cysteine residue and is conjugated to the payload via the cysteine residue.

41. The delivery molecule of any one of 1-40, wherein the targeting ligand is conjugated to the payload via sulfhydryl or amine-reactive chemistry.

42. The delivery molecule of any one of 1-41, wherein the targeting ligand is conjugated to the payload via an intervening linker.

43. The delivery molecule of 42, wherein targeting ligand comprises a cysteine residue and is conjugated to the linker via the cysteine residue.

44. The delivery molecule of 42 or 43, wherein the linker is conjugated to the targeting ligand and/or the payload via sulfhydryl or amine-reactive chemistry.

45. The delivery molecule of any one of 42-44, wherein the linker is rigid.

46. The delivery molecule of any one of 42-44, wherein the linker is flexible.

47. The delivery molecule of any one of 42-44, wherein the linker is endosomolytic.

48. The delivery molecule of any one of 42-47, wherein the linker is a polypeptide.

49. The delivery molecule any one of 42-47, wherein the linker is not a polypeptide.

50. A method of delivering a nucleic acid, protein, or ribonucleoprotein payload to a cell, comprising: contacting a cell with the delivery molecule of any one of 1-49.

51. The method of 50, wherein the cell is a mammalian cell.

52. The method of 50 or 51, wherein the cell is in vitro or ex vivo.

53. The method of 50 or 51, wherein the cell is in vivo.

Set B

1. A delivery molecule, comprising a peptide targeting ligand conjugated to a protein or nucleic acid payload, or conjugated to a charged polymer polypeptide domain, wherein the targeting ligand provides for targeted binding to a cell surface protein.

2. The delivery molecule of 1, wherein the targeting ligand comprises an internal cysteine residue.

3. The delivery molecule of 1 or 2, wherein the targeting ligand comprises a cysteine substitution or insertion, at one or more internal amino acid positions, relative to a corresponding wild type amino acid sequence.

4. The delivery molecule of any one of 1-3, wherein the targeting ligand comprises a cysteine residue at an N- and/or C-terminus.

5. The delivery molecule of 4, wherein the cysteine residue at the N- and/or C-terminus is a substitution or an insertion relative to a corresponding wild type amino acid sequence 6. The delivery molecule of any one of 1-5, wherein the targeting ligand has a length of from 5-50 amino acids.

7. The delivery molecule of any one of 1-6, wherein the targeting ligand is a fragment of a wild type protein.

8. The delivery molecule of any one of 1-7, wherein the targeting ligand provides for targeted binding to a cell surface protein selected from a family B G-protein coupled receptor (GPCR), a receptor tyrosine kinase (RTK), a cell surface glycoprotein, and a cell-cell adhesion molecule.

9. The delivery molecule of 8, wherein the targeting ligand provides for binding to both an allosteric-affinity domain and an orthosteric domain of a family B GPCR to provide for the targeted binding and the engagement of long endosomal recycling pathways, respectively.

10. The delivery molecule of 9, wherein targeting ligand comprises an amino acid sequence having 85% or more identity to the exendin-4 amino acid sequence:

```
                                           (SEQ ID NO. 1)
HGEGTFTSDLSKQMEEEAVRLFIEWLKNGGPSSGAPPPS.
```

11. The delivery molecule of 10, wherein the targeting ligand comprises a cysteine substitution at one or more of positions corresponding to L10, S11, and K12 of the amino acid sequence set forth in SEQ ID NO: 1).

12. The delivery molecule of 9, wherein the targeting ligand comprises the amino acid sequence:

```
                                           (SEQ ID NO. 2)
HGEGTFTSDLCKQMEEEAVRLFIEWLKNGGPSSGAPPPS.
```

13. The delivery molecule of 8, wherein the targeting ligand provides for targeted binding to an RTK.

14. The delivery molecule of 13, wherein the RTK is a fibroblast growth factor (FGF) receptor.

15. The delivery molecule of 14, wherein the targeting ligand is a fragment of an FGF.

16. The delivery molecule of 14 or 15, wherein the targeting ligand binds to a segment of the RTK that is occupied during orthosteric binding.

17. The delivery molecule of any one of 13-16, wherein the targeting ligand binds to a heparin-affinity domain of the RTK.

18. The delivery molecule of any one of 13-17, the targeting ligand provides for targeted binding to an FGF receptor, and wherein the targeting ligand comprises an amino acid sequence having 85% or more identity to the amino acid sequence KNGGFFLRIHPDGRVDGVREKS (SEQ ID NO: 4).

19. The delivery molecule of any one of 13-17, the targeting ligand provides for targeted binding to an FGF receptor, and wherein the targeting ligand comprises the amino acid sequence HFKDPK (SEQ ID NO: 5).

20. The delivery molecule of any one of 13-17, the targeting ligand provides for targeted binding to an FGF receptor, and wherein the targeting ligand comprises the amino acid sequence LESNNYNT (SEQ ID NO: 6).

21. The delivery molecule of 8, wherein the targeting ligand provides for targeted binding to a cell surface glycoprotein and/or a cell-cell adhesion factor.

22. The delivery molecule of 21, wherein the targeting ligand is a fragment of E-selectin, L-selectin, or P-selectin.

23. The delivery molecule of 21, wherein the targeting ligand comprises an amino acid sequence having 85% or more identity to the amino acid sequence MIASQFLSAL-TLVLLIKESGA (SEQ ID NO: 7).

24. The delivery molecule of 21, wherein the targeting ligand comprises an amino acid sequence having 85% or more identity to the amino acid sequence MVFPWRCEGTYWGSRNILKLWVWTLLCCDF-LIHHGTHC (SEQ ID NO: 8), MIFPWKCQSTQRDLWNIFKLWGWTMLCCD-FLAHHGTDC (SEQ ID NO: 9), and/or MIFPWKCQSTQRDLWNIFKLWGWTMLCC (SEQ ID NO: 10)

25. The delivery molecule of 8, wherein the targeting ligand provides for targeted binding to a cell-to-cell adhesion molecule.

26. The delivery molecule of any one of 1-7, wherein the targeting ligand provides for targeted binding to a transferrin receptor, and wherein the targeting ligand comprises an amino acid sequence having 85% or more identity to the amino acid sequence THRPPMWSPVWP (SEQ ID NO: 11).

27. The delivery molecule of any one of 1-7, wherein the targeting ligand provides for targeted binding to α5β1 integrin.

28. The delivery molecule of 27, wherein the targeting ligand comprises the amino acid sequence RRETAWA (SEQ ID NO: 12).

29. The delivery molecule of 27, wherein the targeting ligand comprises the amino acid sequence RGD.

30. The delivery molecule of any one of 1-29, wherein the targeting ligand provides engagement of β-arrestin upon binding to the cell surface protein.

31. The delivery molecule of any one of 1-30, wherein the targeting ligand is conjugated to a nucleic acid payload.

32. The delivery molecule of 31, wherein the nucleic acid payload is an RNAi agent.

33. The delivery molecule of 32, wherein the RNAi agent is an siRNA molecule.

34. The delivery molecule of any one of 1-30, wherein the targeting ligand is conjugated to a protein payload.

35. The delivery molecule of any one of 1-30, wherein the payload is a ribonucleoprotein complex and the targeting ligand is conjugated to a nucleic acid or protein component of said complex.

36. The delivery molecule of any one of 1-30, wherein the targeting ligand is conjugated to a charged polymer polypeptide domain.

37. The delivery molecule of 36, wherein the charged polymer polypeptide domain is condensed with a nucleic acid payload.

38. The delivery molecule of 36 or 37, wherein the charged polymer polypeptide domain is interacting electrostatically with a protein payload.

39. The delivery molecule of any one of 36-38, wherein the delivery molecule is present in a composition that comprises an anionic polymer.

40. The delivery molecule of 39, wherein said composition comprises at least one anionic polymer selected from: poly (glutamic acid) and poly(aspartic acid).

41. The delivery molecule of 36, wherein the charged polymer polypeptide domain of the delivery molecule is interacting electrostatically with a charged stabilization layer of a nanoparticle.

42. The delivery molecule of any one of 36-41, wherein the charged polymer polypeptide domain is a cationic domain selected from RRRRRRRRR (9R) (SEQ ID NO: 15) and HHHHHH (6H) (SEQ ID NO: 16).

43. The delivery molecule of any one of 36-42, wherein the charged polymer polypeptide domain comprises a histone tail peptide (HTP).

44. The delivery molecule of any one of 1-43, wherein the targeting ligand comprises a cysteine residue and is conjugated to the payload via the cysteine residue.

45. The delivery molecule of any one of 1-44, wherein the targeting ligand is conjugated to the payload via sulfhydryl or amine-reactive chemistry.

46. The delivery molecule of any one of 1-45, wherein the targeting ligand is conjugated to the payload via an intervening linker.

47. The delivery molecule of 46, wherein targeting ligand comprises a cysteine residue and is conjugated to the linker via the cysteine residue.

48. The delivery molecule of 46 or 47, wherein the linker is conjugated to the targeting ligand and/or the payload via sulfhydryl or amine-reactive chemistry.

49. The delivery molecule of any one of 46-48, wherein the linker is rigid.

50. The delivery molecule of any one of 46-48, wherein the linker is flexible.

51. The delivery molecule of any one of 46-48, wherein the linker is endosomolytic.

52. The delivery molecule of any one of 46-51, wherein the linker is a polypeptide.

53. The delivery molecule any one of 46-51, wherein the linker is not a polypeptide.

54. The delivery molecule any one of 1-53, wherein the targeting ligand provides for engagement of long endosomal recycling pathways.

55. A method of delivering a nucleic acid, protein, or ribonucleoprotein payload to a cell, comprising:
contacting a cell with the delivery molecule of any one of 1-54.

56. The method of 55, wherein the cell is a mammalian cell.

57. The method of 55 or 56, wherein the cell is in vitro or ex vivo.

58. The method of 55 or 56, wherein the cell is in vivo.

59. The method of any one of 55-58, wherein the cell is a cell selected from: a T cell, a hematopoietic stem cell (HSC), a bone marrow cell, and a blood cell.

It will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of the invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Figure 3:
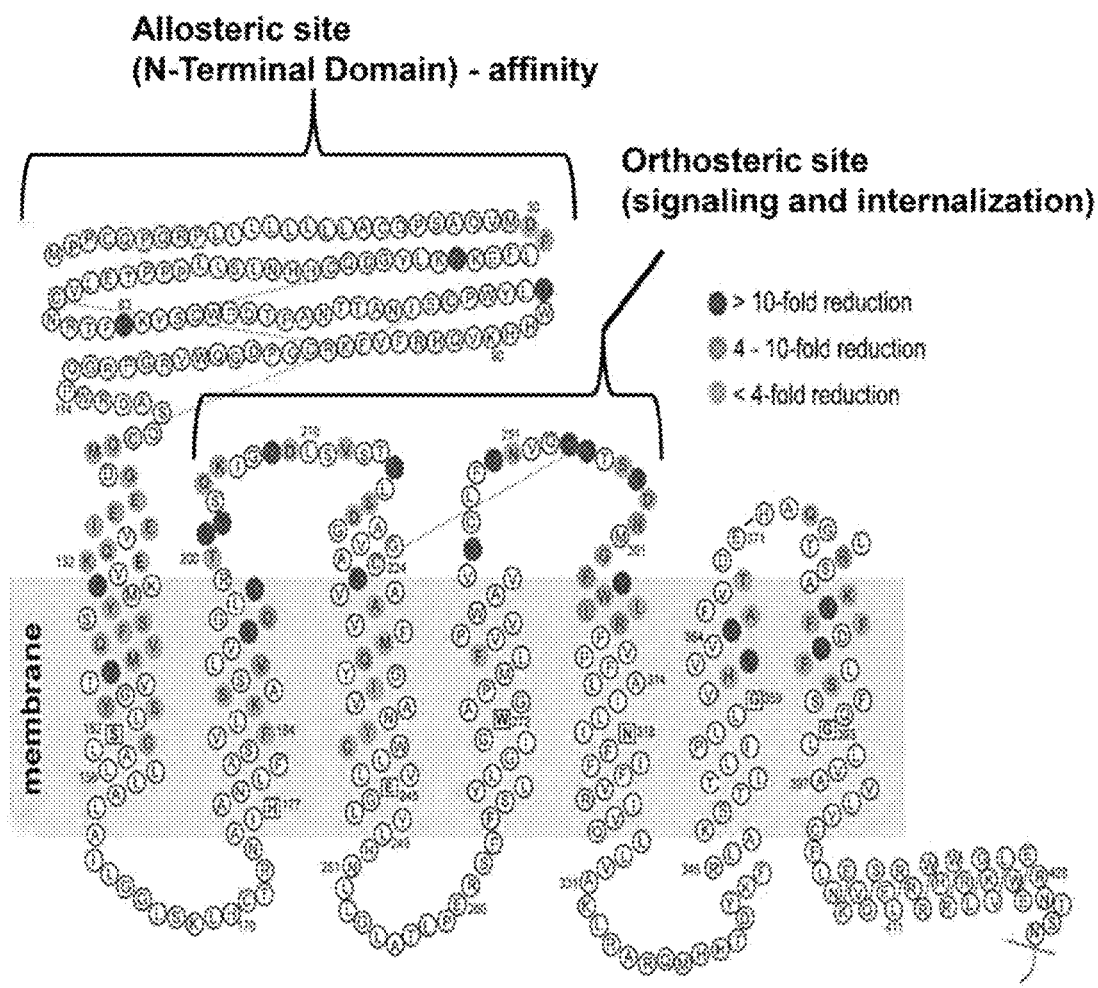
FIG. 3 provides a schematic diagram of a family B GPCR, highlighting separate domains to be considered when evaluating a targeting ligand, e.g., for binding to allosteric/affinity N-terminal domains and orthosteric endosomal-sorting/signaling domains. (Figure is adapted from Siu, Fai Yiu, et al., Nature 499.7459 (2013): 444-449).

Example 1: Targeting Ligand that Provides for Targeted Binding to a Family B GPCR FIG. 3 provides a schematic diagram of a family B GPCR, highlighting separate domains to consider when evaluating a targeting ligand, e.g., for binding to allosteric/affinity N-terminal domains and orthosteric endosomal-sorting/signaling domains. (Figure is adapted from Siu, Fai Yiu, et al., Nature 499.7459 (2013): 444-449). Such domains were considered when selecting a site within the targeting ligand exendin-4 for cysteine substitution.

Figure 4:
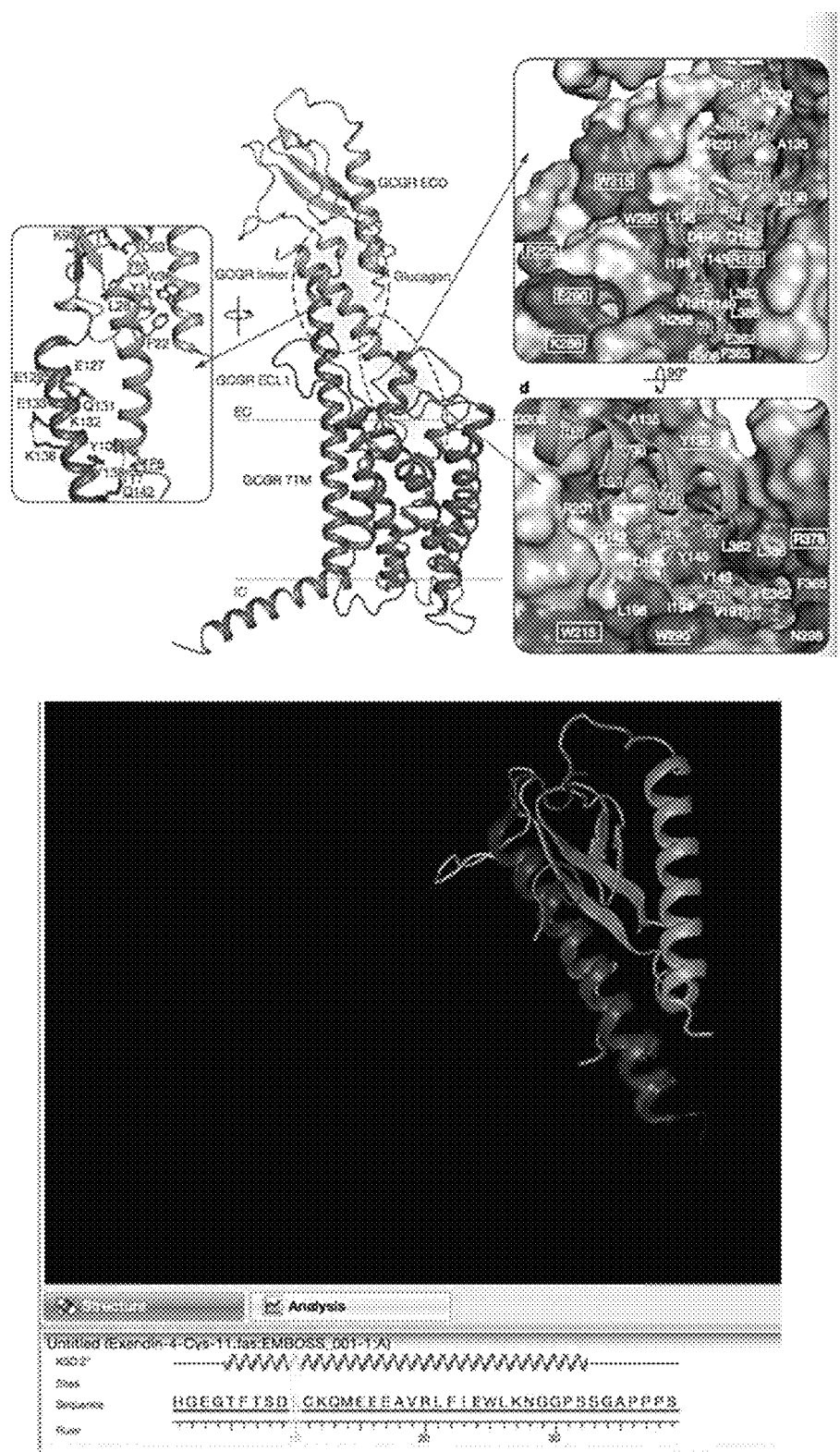
FIG. 4 provides an example of identifying an internal amino acid position for insertion and/or substitution (e.g., with a cysteine residue) for a targeting ligand such that affinity is maintained and the targeting ligand engages long endosomal recycling pathways that promote nucleic acid release and limit nucleic acid degradation. In this case, the targeting ligand is exendin-4 and amino acid positions 10, 11, and 12 were identified as sites for possible insertion and/or substitution (e.g., with a cysteine residue, e.g., an S11C mutation). The figure shows an alignment of simulated Exendin-4 (SEQ ID NO: 1) to known crystal structures of glucagon-GCGR (4ERS) and GLP1-GLP1R-ECD complex (PDB: 3IOL), and PDB renderings that were rotated in 3-dimensional space.

In FIG. 4, a cysteine 11 substitution (S11C) was identified as one possible amino acid modification for conjugating exendin-4 to an siRNA, protein, or a charged polymer polypeptide domain in such a way that maintains affinity and also engages long endosomal recycling pathways that promote nucleic acid release and limit nucleic acid degradation. Following alignment of simulated Exendin-4 (SEQ ID NO: 1) to known crystal structures of glucagon-GCGR (4ERS) and GLP1-GLP1R-ECD complex (PDB: 3IOL), the PDB renderings were rotated in 3-dimensional space in order to anticipate the direction that a cross-linked complex must face in order not to disrupt the two binding clefts. When the cross-linking site of a secretin-family ligand was sufficiently orthogonal to the two binding clefts of the corresponding secretin-family receptor, then it was determined that high-affinity binding may occur as well as concomitant long endosomal recycling pathway sequestration for optimal payload release. Using this technique, Amino acid positions 10, 11, and 12 of Exendin-4 were identified as positions for insertion of or substitution with a cysteine residue.

Example 2: Targeting Ligand that Provides for Targeted Binding to an RTK

Figure 5:
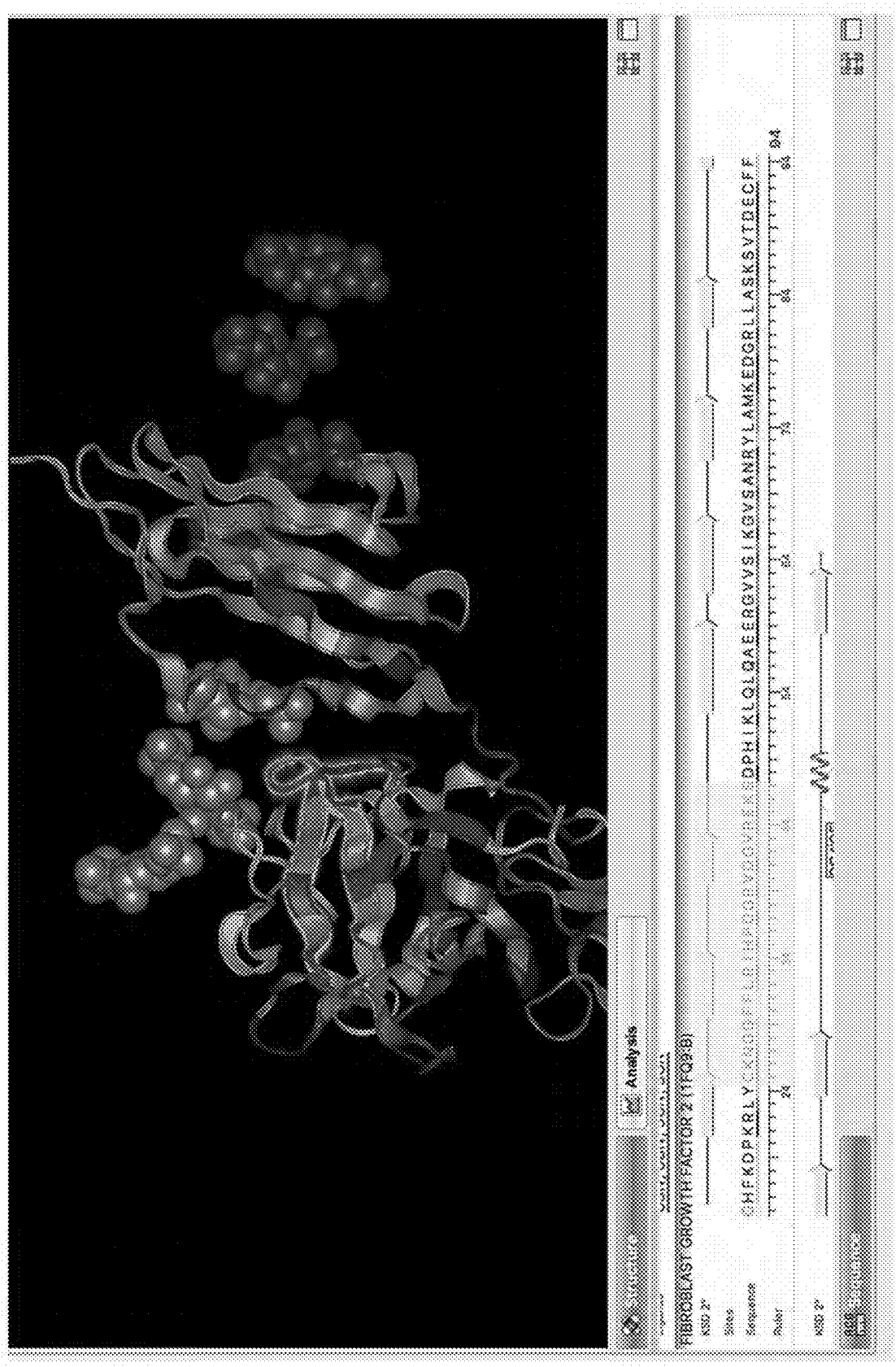
FIG. 5 shows a tbFGF fragment as part of a ternary FGF2-FGFR1-HEPARIN complex (1fq9 on PDB). CKNGGFFLRIHPDGRVDGVREKS (highlighted) (SEQ ID NO: 43) was determined to be important for affinity to FGFR1.
Figure 6:
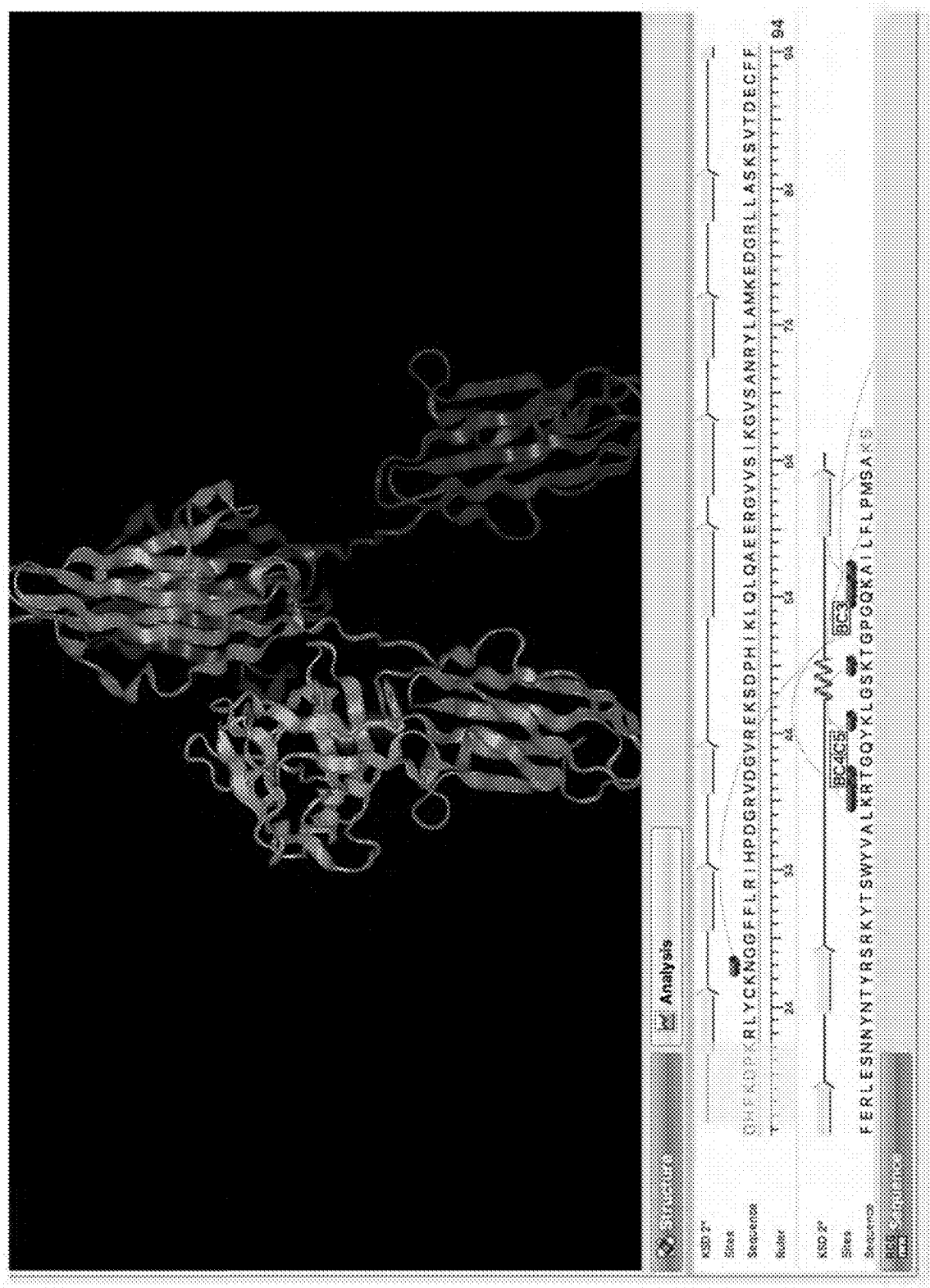
FIG. 6 provides an alignment and PDB 3D rendering used to determine that HFKDPK (SEQ ID NO: 5) is a peptide that can be used for ligand-receptor orthosteric activity and affinity.
Figure 7:
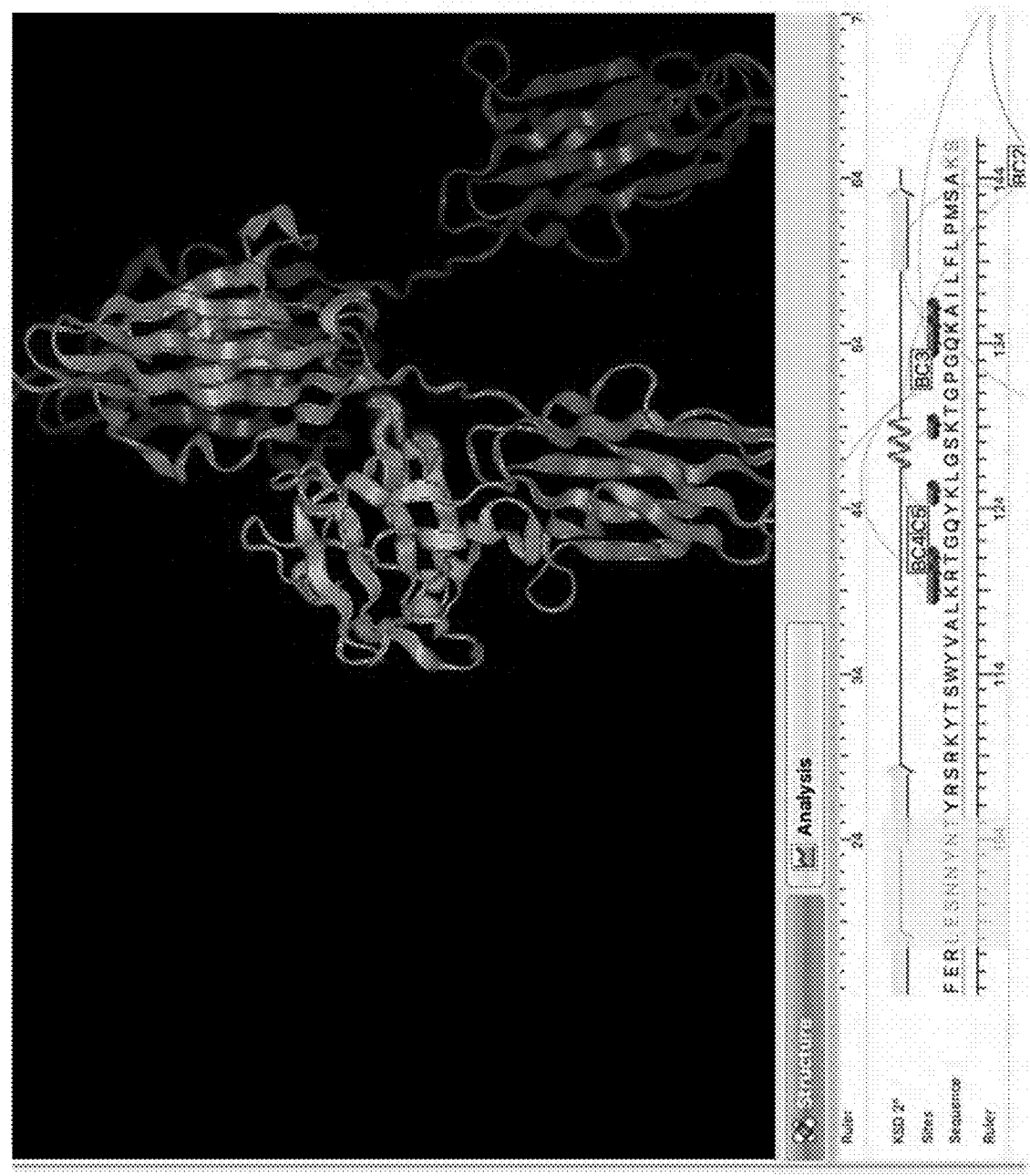
FIG. 7 provides an alignment and PDB 3D rendering used to determine that LESNNYNT (SEQ ID NO: 6) is a peptide that can be used for ligand-receptor orthosteric activity and affinity.

FIG. 5 shows a tbFGF fragment as part of a ternary FGF2-FGFR1-HEPARIN complex (1fq9 on PDB). CKNGGFFLRIHPDGRVDGVREKS (highlighted) (SEQ ID NO: 14) was determined to be important for affinity to FGFR1. FIG. 6 shows that HFKDPK (SEQ ID NO: 5) was determined as a peptide to use for ligand-receptor orthosteric activity and affinity. FIG. 7 shows that LESNNYNT (SEQ ID NO: 6) was also determined as a peptide to use for ligand-receptor orthosteric activity and affinity.

Example 3

Table 2-Table 4 provide a guide for the components used in the experiments that follow (e.g., condensation data; physiochemical data; and flow cytometry and imaging data).

TABLE 2

Features of delivery molecules used in the experiments below. Targeting Ligand Name/nomenclature Format: A_B_C_D_E_F where A = Receptor Name: Name of receptor ligand is targeting; B = Targeting Ligand Source: Name of ligand targeting the receptor (Prefix "m" or "rm" for modified if Ligand is NOT wild type); C = Linker Name; D = Charged Polypeptide Name; E = Linker Terminus based on B; and F = Version Number (To distinguish between two modified targeting ligands that come from the same WT but differ in AA sequence);

| Targeting Ligand (TL)/ Peptide Catalogue Name | Sequence | SEQ ID NO: | Anchor Charge | Anchor Mers/ Total Mers | Linker Mers/ Total Mers | Ligand Mers/ Total Mers |
|---|---|---|---|---|---|---|
| PLR10 | RRRRRRRRRR | 147 | 10 | 100.00% | 0.00% | 0.00% |
| CD45_mSiglec_(4GS)2_9R_C | SNRVVLDVKGGGGGSGGGGSRRRRRRRRR | 148 | 9 | 32.14% | 35.71% | 32.14% |
| CD28_mCD80_(4GS)2_9R_N | RRRRRRRRRGGGGSGGGGSVVLKYEKDAFKR | 149 | 9 | 26.47% | 29.41% | 44.12% |
| CD28_mCD80_(4GS)2_9R_C | VVLKYEKDAFKRGGGGSGGGGSRRRRRRRRR | 150 | 9 | 26.47% | 29.41% | 44.12% |
| CD28_mCD86_(4GS)2_9R_N_1 | RRRRRRRRRGGGGSGGGGSENLVLNE | 151 | 9 | 34.62% | 38.46% | 26.92% |
| CD28_mCD86_(4GS)2_9R_C | ENLVLNEGGGGSGGGGSRRRRRRRRR | 152 | 9 | 34.62% | 38.46% | 26.92% |
| CD28_mCD86_(4GS)2_9R_N_2 | RRRRRRRRRGGGGSGGGGSPTGMIRIHQM | 153 | 9 | 31.03% | 34.48% | 34.48% |
| CD137_m41BB_(4GS)2_9R_N | RRRRRRRRRGGGGSGGGGSAAQEE | 154 | 9 | 36.00% | 40.00% | 24.00% |
| CD3_mCD3Ab_(4GS)2_9R_N | RRRRRRRRRGGGGSGGGGSTSVGKYPNTGYYGD | 155 | 9 | 27.27% | 30.30% | 42.42% |
| CD3_mCD3Ab_(4GS)2_9R_C | TSVGKYPNTGYYGDGGGGSGGGGSRRRRRRRRR | 156 | 9 | 27.27% | 30.30% | 42.42% |
| IL2R_mIL2_(4GS)2_9R_N | RRRRRRRRRGGGGSGGGGSNPKLTRMLTFKFY | 157 | 9 | 28.13% | 31.25% | 40.63% |
| IL2R_mIL2_(4GS)2_9R_C | NPKLTRMLTFKFYGGGGSGGGGSRRRRRRRRR | 158 | 9 | 28.13% | 31.25% | 40.63% |
| PLK10_PEG22 | KKKKKKKKKK-PEG22 | 159 | 10 | 31.25% | 68.75% | 0.00% |
| ALL_LIGANDS_EQUIMOLAR | N/A | | 9 | 30.25% | 33.61% | 36.13% |
| ESELLg_mESEL_(4GS)2_9R_N | RRRRRRRRRGGGGSGGGGSMIASQFLSALTLVLLIKESGA | 160 | 9 | 22.50% | 25.00% | 52.50% |
| ESELLg_mESEL_(4GS)2_9R_C | MIASQFLSALTLVLLIKESGAGGGGSGGGGSRRRRRRRRR | 161 | 9 | 22.50% | 25.00% | 52.50% |

TABLE 2-continued

Features of delivery molecules used in the experiments below. Targeting Ligand Name/nomenclature Format: A_B_C_D_E_F where A = Receptor Name: Name of receptor ligand is targeting; B = Targeting Ligand Source: Name of ligand targeting the receptor (Prefix "m" or "rm" for modified if Ligand is NOT wild type); C = Linker Name; D = Charged Polypeptide Name; E = Linker Terminus based on B; and F = Version Number (To distinguish between two modified targeting ligands that come from the same WT but differ in AA sequence);

| Targeting Ligand (TL)/ Peptide Catalogue Name | Sequence | SEQ ID NO: | Anchor Mers/ Charge | Anchor Mers/ Total Mers | Linker Mers/ Total Mers | Ligand Mers/ Total Mers |
|---|---|---|---|---|---|---|
| cKit_mSCF_(4GS)2_9R_N | RRRRRRRRRGG GGSGGGGSEKFIL KVRPAFKAV | 162 | 10 | 31.25% | 68.75% | 0.00% |
| EPOR_mEPO_6R_N | RRRRRRTYSCHF GPLTVWCKPQGG | 163 | 6 | 25.00% | 0.00% | |
| EPOR_mEPO_6R_C | TYSCHFGPLTVW CKPQGGRRRRRR | 164 | 6 | 25.00% | 0.00% | |
| TfR_TfTP_6R_N | RRRRRRTHRPPM WSPVWP | 165 | 6 | 33.33% | 0.00% | |
| TfR_TfTP_6R_C | THRPPMWSPVWP RRRRRR | 166 | 6 | 33.33% | 0.00% | |
| mH3_K4Me3_1 | ART-K(Me3)- QTARKSTGGKAP RKQLA | 167 | 6 | 100.00% | 0.00% | 0.00% |
| mH4_K16Ac_1 | SGRGKGGKGLGK GGA-K(Ac)-RHRK | 168 | 8 | 100.00% | 0.00% | 0.00% |
| mH2A_1 | SGRGKQGGKARA KAKTRSSR | 169 | 8 | 100.00% | 0.00% | 0.00% |
| SCF_rmAc-cKit_(4GS) 2_9R_C | Ac- SNYSAibADKAibA NAibADDAibAEAib AKENSGGGGSGG GGSRRRRRRRRR | 170 | 9 | 19.15% | 21.28% | 59.57% |
| cKit_rmSCF_(4GS)2_9R_N | RRRRRRRRRGG GGSGGGGSEKFIL KVRPAFKAV | 171 | 10 | | | |

TABLE 3

Payloads used in the experiments below.

| Payloads | Nucleotide | Single or Double Stranded? | Protein Mol. Wt. |
|---|---|---|---|
| BLOCK-iT Alexa Fluor 555 siRNA | 20 | 2 | N/A |
| NLS-Cas9-EGFP + gRNA | 98 | 1 | 186229.4531 |
| Cy5 EGFP mRNA | 998 | 1 | N/A |
| VWF-GFP pDNA + Cy5 PNA | 13000 | 2 | N/A |

TABLE 4

Guide Key for the components used in the experiments below.
KEY: N = "nanoparticle"; cat. = "cationic";
an. = "anionic"; spec. = "species"; c:p = "Carboxyl:Phospate";

| Project Code | N | Payload (Pl) | Targeting Ligand (TL) |
|---|---|---|---|
| TCell.001 | 1 | NLS_Cas9_gRNA_EGFP_RNP | N/A |
| TCell.001 | 2 | NLS_Cas9_gRNA_EGFP_RNP | N/A |
| TCell.001 | 3 | NLS_Cas9_gRNA_EGFP_RNP | CD45_mSiglec_(4GS)2_9R_C |
| TCell.001 | 4 | NLS_Cas9_gRNA_EGFP_RNP | CD28_mCD80_(4GS)2_9R_N |
| TCell.001 | 5 | NLS_Cas9_gRNA_EGFP_RNP | CD28_mCD80_(4GS)2_9R_C |
| TCell.001 | 6 | NLS_Cas9_gRNA_EGFP_RNP | CD28_mCD86_(4GS)2_9R_N_1 |
| TCell.001 | 7 | NLS_Cas9_gRNA_EGFP_RNP | CD28_mCD86_(4GS)2_9R_C |
| TCell.001 | 8 | NLS_Cas9_gRNA_EGFP_RNP | CD28_mCD86_(4GS)2_9R_N_2 |
| TCell.001 | 9 | NLS_Cas9_gRNA_EGFP_RNP | CD137_m41BB_(4GS)2_9R_N |
| TCell.001 | 10 | NLS_Cas9_gRNA_EGFP_RNP | CD137_m41BB_(4GS)2_9R_C |
| TCell.001 | 11 | NLS_Cas9_gRNA_EGFP_RNP | CD3_mCD3Ab_(4GS)2_9R_N |
| TCell.001 | 12 | NLS_Cas9_gRNA_EGFP_RNP | CD3_mCD3Ab_(4GS)2_9R_C |
| TCell.001 | 13 | NLS_Cas9_gRNA_EGFP_RNP | IL2R_mIL2_(4GS)2_9R_N |
| TCell.001 | 14 | NLS_Cas9_gRNA_EGFP_RNP | IL2R_mIL2_(4GS)2_9R_C |
| TCell.001 | 15 | NLS_Cas9_gRNA_EGFP_RNP | ALL_LIGANDS_EQUIMOLAR (C7-C18) |
| TCell.001 | 16 | Cy5_EGFP_mRNA | N/A |
| TCell.001 | 17 | Cy5_EGFP_mRNA | N/A |
| TCell.001 | 18 | Cy5_EGFP_mRNA | CD45_mSiglec_(4GS)2_9R_C |
| TCell.001 | 19 | Cy5_EGFP_mRNA | CD28_mCD80_(4GS)2_9R_N |
| TCell.001 | 20 | Cy5_EGFP_mRNA | CD28_mCD80_(4GS)2_9R_C |
| TCell.001 | 21 | Cy5_EGFP_mRNA | CD28_mCD86_(4GS)2_9R_N_1 |
| TCell.001 | 22 | Cy5_EGFP_mRNA | CD28_mCD86_(4GS)2_9R_C |
| TCell.001 | 23 | Cy5_EGFP_mRNA | CD28_mCD86_(4GS)2_9R_N_2 |
| TCell.001 | 24 | Cy5_EGFP_mRNA | CD137_m41BB_(4GS)2_9R_N |
| TCell.001 | 25 | Cy5_EGFP_mRNA | CD137_m41BB_(4GS)2_9R_C |
| TCell.001 | 26 | Cy5_EGFP_mRNA | CD3_mCD3Ab_(4GS)2_9R_N |
| TCell.001 | 27 | Cy5_EGFP_mRNA | CD3_mCD3Ab_(4GS)2_9R_C |
| TCell.001 | 28 | Cy5_EGFP_mRNA | IL2R_mIL2_(4GS)2_9R_N |
| TCell.001 | 29 | Cy5_EGFP_mRNA | IL2R_mIL2_(4GS)2_9R_C |
| TCell.001 | 30 | Cy5_EGFP_mRNA | ALL_LIGANDS_EQUIMOLAR (C7-C18) |
| TCell.001 | 31 | VWF_GFP_Cy5_pDNA | N/A |
| TCell.001 | 32 | VWF_GFP_Cy5_pDNA | N/A |
| TCell.001 | 33 | VWF_GFP_Cy5_pDNA | CD45_mSiglec_(4GS)2_9R_C |
| TCell.001 | 34 | VWF_GFP_Cy5_pDNA | CD28_mCD80_(4GS)2_9R_N |
| TCell.001 | 35 | VWF_GFP_Cy5_pDNA | CD28_mCD80_(4GS)2_9R_C |
| TCell.001 | 36 | VWF_GFP_Cy5_pDNA | CD28_mCD86_(4GS)2_9R_N_1 |
| TCell.001 | 37 | VWF_GFP_Cy5_pDNA | CD28_mCD86_(4GS)2_9R_C |
| TCell.001 | 38 | VWF_GFP_Cy5_pDNA | CD28_mCD86_(4GS)2_9R_N_2 |
| TCell.001 | 39 | VWF_GFP_Cy5_pDNA | CD137_m41BB_(4GS)2_9R_N |
| TCell.001 | 40 | VWF_GFP_Cy5_pDNA | CD137_m41BB_(4GS)2_9R_C |
| TCell.001 | 41 | VWF_GFP_Cy5_pDNA | CD3_mCD3Ab_(4GS)2_9R_N |
| TCell.001 | 42 | VWF_GFP_Cy5_pDNA | CD3_mCD3Ab_(4GS)2_9R_C |
| TCell.001 | 43 | VWF_GFP_Cy5_pDNA | IL2R_mIL2_(4GS)2_9R_N |
| TCell.001 | 44 | VWF_GFP_Cy5_pDNA | IL2R_mIL2_(4GS)2_9R_C |
| TCell.001 | 45 | VWF_GFP_Cy5_pDNA | ALL_LIGANDS_EQUIMOLAR (C7-C18) |
| TCell.001 | 46 | BLOCK_iT_Alexa_Fluor_555_siRNA | N/A |
| TCell.001 | 47 | BLOCK_iT_Alexa_Fluor_555_siRNA | N/A |
| TCell.001 | 48 | BLOCK_iT_Alexa_Fluor_555_siRNA | CD45_mSiglec_(4GS)2_9R_C |
| TCell.001 | 49 | BLOCK_iT_Alexa_Fluor_555_siRNA | CD28_mCD80_(4GS)2_9R_N |
| TCell.001 | 50 | BLOCK_iT_Alexa_Fluor_555_siRNA | CD28_mCD80_(4GS)2_9R_C |
| TCell.001 | 51 | BLOCK_iT_Alexa_Fluor_555_siRNA | CD28_mCD86_(4GS)2_9R_N_1 |
| TCell.001 | 52 | BLOCK_iT_Alexa_Fluor_555_siRNA | CD28_mCD86_(4GS)2_9R_C |
| TCell.001 | 53 | BLOCK_iT_Alexa_Fluor_555_siRNA | CD28_mCD86_(4GS)2_9R_N_2 |
| TCell.001 | 54 | BLOCK_iT_Alexa_Fluor_555_siRNA | CD137_m41BB_(4GS)2_9R_N |
| TCell.001 | 55 | BLOCK_iT_Alexa_Fluor_555_siRNA | CD137_m41BB_(4GS)2_9R_C |
| TCell.001 | 56 | BLOCK_iT_Alexa_Fluor_555_siRNA | CD3_mCD3Ab_(4GS)2_9R_N |
| TCell.001 | 57 | BLOCK_iT_Alexa_Fluor_555_siRNA | CD3_mCD3Ab_(4GS)2_9R_C |
| TCell.001 | 58 | BLOCK_iT_Alexa_Fluor_555_siRNA | IL2R_mIL2_(4GS)2_9R_N |
| TCell.001 | 59 | BLOCK_iT_Alexa_Fluor_555_siRNA | IL2R_mIL2_(4GS)2_9R_C |
| TCell.001 | 60 | BLOCK_iT_Alexa_Fluor_555_siRNA | ALL_LIGANDS_EQUIMOLAR (C7-C18) |
| TCell.002 | 61 | NLS_Cas9_gRNA_RNP | N/A |
| TCell.002 | 62 | NLS_Cas9_gRNA_RNP | IL2R_mIL2_(4GS)2_9R_N |
| TCell.002 | 63 | NLS_Cas9_gRNA_RNP | CD3_mCD3Ab_(4GS)2_9R_N |
| TCell.002 | 64 | NLS_Cas9_gRNA_RNP | CD45_mSiglec_(4GS)2_9R_C |
| TCell.002 | 65 | NLS_Cas9_gRNA_RNP | CD28_mCD86_(4GS)2_9R_N_2 |
| TCell.002 | 66 | NLS_Cas9_gRNA_RNP | CD3_mCD3Ab_(4GS)2_9R_N + CD28_mCD86_(4GS)2_9R_N_2 |
| TCell.002 | 67 | NLS_Cas9_gRNA_RNP | CD3_mCD3Ab_(4GS)2_9R_N + CD28_mCD86_(4GS)2_9R_N_3 + CD45_mSiglec_(4GS)2_9R_C |

TABLE 4-continued

Guide Key for the components used in the experiments below.
KEY: N = "nanoparticle"; cat. = "cationic";
an. = "anionic"; spec. = "species"; c:p = "Carboxyl:Phospate";

| | | | |
|---|---|---|---|
| TCell.002 | 68 | NLS_Cas9_gRNA_RNP | CD3_mCD3Ab_(4GS)2_9R_N + CD28_mCD86_(4GS)2_9R_N_3 + CD45_mSiglec_(4GS)2_9R_C + IL2R_mIL2_(4GS)2_9R_N |
| HSC.004 | 69 | Cy5_EGFP_mRNA | N/A |
| HSC.004 | 70 | Cy5_EGFP_mRNA | N/A |
| HSC.004 | 71 | Cy5_EGFP_mRNA | N/A |
| HSC.004 | 72 | Cy5_EGFP_mRNA | ESELLg_mESEL_(4GS)2_9R_N |
| HSC.004 | 73 | Cy5_EGFP_mRNA | ESELLg_mESEL_(4GS)2_9R_N + cKit_rmSCF_(4GS)2_9R_N |
| HSC.004 | 74 | Cy5_EGFP_mRNA | cKit_rmSCF_(4GS)2_9R_N |
| CynoBM.002 | 75 | NLS_Cas9_gRNA_EGFP_RNP | N/A |
| CynoBM.002 | 76 | NLS_Cas9_gRNA_EGFP_RNP | N/A |
| CynoBM.002 | 77 | NLS_Cas9_gRNA_EGFP_RNP | IL2R_mIL2_(4GS)2_9R_N |
| CynoBM.002 | 78 | NLS_Cas9_gRNA_EGFP_RNP | ESELLg_mESEL_(4GS)2_9R_N |
| CynoBM.002 | 79 | NLS_Cas9_gRNA_EGFP_RNP | SCF_mcKit_(4GS)2_9R_N |
| CynoBM.002 | 80 | NLS_Cas9_gRNA_EGFP_RNP | d |
| CynoBM.002 | 81 | NLS_Cas9_gRNA_EGFP_RNP | IL2R_mIL2_(4GS)2_9R_N + ESELLg_mESEL_(4GS)2_9R_N + cKit_mSCF_(4GS)2_9R_N |
| CynoBM.002 | 82 | NLS_Cas9_gRNA_EGFP_RNP + Cy5_EGFP_mRNA | N/A |
| CynoBM.002 | 83 | NLS_Cas9_gRNA_EGFP_RNP + Cy5_EGFP_mRNA | IL2R_mIL2_(4GS)2_9R_N |
| CynoBM.002 | 84 | NLS_Cas9_gRNA_EGFP_RNP + Cy5_EGFP_mRNA | ESELLg_mESEL_(4GS)2_9R_N |
| CynoBM.002 | 85 | NLS_Cas9_gRNA_EGFP_RNP + Cy5_EGFP_mRNA | cKit_mSCF_(4GS)2_9R_N |
| CynoBM.002 | 86 | NLS_Cas9_gRNA_EGFP_RNP + Cy5_EGFP_mRNA | IL2R_mIL2_(4GS)2_9R_N + ESELLg_mESEL_(4GS)2_9R_N + cKit_mSCF_(4GS)2_9R_N |
| Blood.001 | 87 | Cy5_EGFP_mRNA | CD45_mSiglec_(4GS)2_9R_C |
| Blood.002 | 88 | Cy5_EGFP_mRNA | CD45_mSiglec_(4GS)2_9R_C |
| Blood.002 | 89 | Cy5_EGFP_mRNA | CD45_mSiglec_(4GS)2_9R_C |
| Blood.002 | 90 | Cy5_EGFP_mRNA | N/A |
| Blood.002 | 91 | Cy5_EGFP_mRNA | N/A |
| Blood.002 | 92 | Vehicle | CD45_mSiglec_(4GS)2_9R_C |

| Project Code | Cat. Spec. | An. Spec. | C:P Ratio | +/− Ratio |
|---|---|---|---|---|
| TCell.001 | PLR10 | pLE100:pDE100 | 2:1 | 2:1 |
| TCell.001 | PLK10_PEG22 | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | PLR10 | pLE100:pDE100 | 1.35:1 | 0.82:1 |
| TCell.001 | PLK10_PEG22 | pLE100:pDE100 | 1.35:1 | 0.82:1 |
| TCell.001 | TL | pLE100:pDE100 | 1.35:1 | 0.82:1 |
| TCell.001 | TL | pLE100:pDE100 | 1.35:1 | 0.82:1 |
| TCell.001 | TL | pLE100:pDE100 | 1.35:1 | 0.82:1 |
| TCell.001 | TL | pLE100:pDE100 | 1.35:1 | 0.82:1 |
| TCell.001 | TL | pLE100:pDE100 | 1.35:1 | 0.82:1 |
| TCell.001 | TL | pLE100:pDE100 | 1.35:1 | 0.82:1 |
| TCell.001 | TL | pLE100:pDE100 | 1.35:1 | 0.82:1 |
| TCell.001 | TL | pLE100:pDE100 | 1.35:1 | 0.82:1 |
| TCell.001 | TL | pLE100:pDE100 | 1.35:1 | 0.82:1 |
| TCell.001 | TL | pLE100:pDE100 | 1.35:1 | 0.82:1 |
| TCell.001 | TL | pLE100:pDE100 | 1.35:1 | 0.82:1 |
| TCell.001 | TL | pLE100:pDE100 | 1.35:1 | 0.82:1 |
| TCell.001 | PLR10 | pLE100:pDE100 | 2:1 | 2:1 |
| TCell.001 | PLK10_PEG22 | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |

TABLE 4-continued

Guide Key for the components used in the experiments below.
KEY: N = "nanoparticle"; cat. = "cationic";
an. = "anionic"; spec. = "species"; c:p =
"Carboxyl:Phospate";

| | | | | |
|---|---|---|---|---|
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | PLR10 | pLE100:pDE100 | 2:1 | 2:1 |
| TCell.001 | PLK10_PEG22 | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.001 | TL | pLE100:pDE100 | 2:1 | 2:1 |
| TCell.002 | PLR10 | pLE100:pDE100 | 2:1 | 2:1 |
| TCell.002 | TL | pLE100:pDE100 | 2:1 | 2:1 |
| TCell.002 | TL | pLE100:pDE100 | 2:1 | 2:1 |
| TCell.002 | TL | pLE100:pDE100 | 2:1 | 2:1 |
| TCell.002 | TL | pLE100:pDE100 | 2:1 | 2:1 |
| TCell.002 | TL | pLE100:pDE100 | 2:1 | 2:1 |
| TCell.002 | TL | pLE100:pDE100 | 2:1 | 2:1 |
| HSC.004 | PLR10 | pLE20 | 2:1 | 2:1 |
| HSC.004 | PLR50 | pLE20 | 2:1 | 2:1 |
| HSC.004 | PLK10_PEG22 | pLE20 | 2:1 | 2:1 |
| HSC.004 | TL | pLE20 | 2:1 | 2:1 |
| HSC.004 | TL | pLE20 | 2:1 | 2:1 |
| HSC.004 | TL | pLE20 | 2:1 | 2:1 |
| CynoBM.002 | PLR10 | pLE100:pDE100 | 2:1 | 2:1 |
| CynoBM.002 | mH4_K16Ac_1:mH2A_1 | pLE100:pDE100 | 2:1 | 2:1 |
| CynoBM.002 | TL | pLE100:pDE100 | 2:1 | 2:1 |
| CynoBM.002 | TL | pLE100:pDE100 | 2:1 | 2:1 |
| CynoBM.002 | TL | pLE100:pDE100 | 2:1 | 2:1 |
| CynoBM.002 | TL | pLE100:pDE100 | 2:1 | 2:1 |
| CynoBM.002 | TL | pLE100:pDE100 | 2:1 | 2:1 |
| CynoBM.002 | PLR50 | pLE100:pDE100 | 2:1 | 2:1 |
| CynoBM.002 | TL | pLE100:pDE100 | 2:1 | 2:1 |
| CynoBM.002 | TL | pLE100:pDE100 | 2:1 | 2:1 |
| CynoBM.002 | TL | pLE100:pDE100 | 2:1 | 2:1 |
| Blood.001 | TL | pLE100 | 1.35:1 | 0.82:1 |
| Blood.002 | TL | pLE100 | 1.35:1 | 0.82:1 |
| Blood.002 | TL | pLE100 | 1.35:1 | 0.82:1 |
| Blood.002 | PLK30_PEG113 | pLE100 | | |
| Blood.002 | PLR50 | pLE100 | | |
| Blood.002 | TL | pLE100 | N/A | 1.93:1 |

*Subcellular trafficking peptides used in the nanoparticle formulations were nuclear localization signal peptides conjugated to certain payloads (e.g., "NLS_Cas9 . . . ")
*Cationic species used in the nanoparticle formulations were conjugated to the targeting ligands (TL) as a poly(arginine) chain with amino acid length 9 (9R). Nanoparticles without targeting ligands contained the non-conjugated cationic species poly(arginine) AA chain with length 10 (PLR10) or PEGylated poly(lysine) with AA chain length of 10. All cationic species in the table have L:D isomer ratios of 1:0.
*HSC = hematopoietic stem cells; BM = bone marrow cells; Tcell = T cells; blood = whole blood; cynoBM = cynomolgus bone marrow Materials and Methods Ligand Synthesis Most targeting ligand sequences were designed in-house and custom manufactured by 3rd party commercial providers. Peptide ligands were derived from native polypeptide sequences and in some cases, mutated to improve binding affinity. Computational analysis of binding kinetics and the determination of optimal mutations was achieved through the use of Rosetta software. In the case where targeting ligands were manufactured in-house, the method and materials were as follows:

Peptides were synthesized using standard Fmoc-based solid-phase peptide synthesis (SPPS). Peptides were synthesized on Rink-amide AM resin. Amino acid couplings were performed with O-(1H-6-Chlorobenzotriazole-1-yl)-1,1,3,3-tetramethyluronium hexafluorophosphate (HCTU) coupling reagent and N-methylmorpholine (NMM) in dimethyl formamide (DMF). Deprotection and cleavage of peptides were performed with trifluoroacetic acid (TFA), triisopropyl silane (TIPS), and water. Crude peptide mixtures were purified by reverse-phase HPLC (RP-HPLC). Pure peptide fractions were frozen and lyophilized to yield purified peptides.

Nanoparticle Synthesis

Nanoparticles were synthesized at room temperature, 37 C or a differential of 37 C and room temperature between cationic and anionic components. Solutions were prepared in aqueous buffers utilizing natural electrostatic interactions during mixing of cationic and anionic components. At the start, anionic components were dissolved in Tris buffer (30 mM-60 mM; pH=7.4-9) or HEPES buffer (30 mM, pH=5.5) while cationic components were dissolved in HEPES buffer (30 mM-60 mM, pH=5-6.5).

Specifically, payloads (e.g., genetic material (RNA or DNA), genetic material-protein-nuclear localization signal polypeptide complex (ribonucleoprotein), or polypeptide) were reconstituted in a basic, neutral or acidic buffer. For analytical purposes, the payload was manufactured to be covalently tagged with or genetically encode a fluorophore. With pDNA payloads, a Cy5-tagged peptide nucleic acid (PNA) specific to TATATA tandem repeats was used to fluorescently tag fluorescent reporter vectors and fluorescent reporter-therapeutic gene vectors. A timed-release component that may also serve as a negatively charged condensing species (e.g. poly(glutamic acid)) was also reconstituted in a basic, neutral or acidic buffer. Targeting ligands with a wild-type derived or wild-type mutated targeting peptide conjugated to a linker-anchor sequence were reconstituted in acidic buffer. In the case where additional condensing species or nuclear localization signal peptides were included in the nanoparticle, these were also reconstituted in buffer as 0.03% w/v working solutions for cationic species, and 0.015% w/v for anionic species. Experiments were also conducted with 0.1% w/v working solutions for cationic species and 0.1% w/v for anionic species. All polypeptides, except those complexing with genetic material, were sonicated for ten minutes to improve solubilization.

Each separately reconstituted component of the nanoparticle was then mixed in the order of addition that was being investigated. Different orders of additions investigated include:

1) payload<cationic species
2) payload<cationic species (anchor)<cationic species (anchor-linker-ligand)
3) payload<anionic species<cationic species
4) payload<cationic species<anionic species
5) payload<cationic species (anchor)<cationic species (anchor-linker-ligand)<anionic species
6) payload<anionic species<cationic species (anchor)+cationic species (anchor-linker-ligand)
7) payload+anionic species<cationic species (anchor)+cationic species (anchor-linker-ligand)
8) payload 1 (ribonucleoprotein or other genetic/protein material)<cationic species (histone fragment, NLS or charged polypeptide anchor without linker-ligand)<anionic species
9) payload 1 (ribonucleoprotein or other genetic/protein material)<cationic species (histone fragment, NLS or charged polypeptide anchor without linker-ligand)<anionic species<cationic species (histone fragment, NLS, or charged polypeptide anchor with or without linker-ligand)
10) payload 1 (ribonucleoprotein or other genetic/protein material)<cationic species (histone fragment, NLS or charged polypeptide anchor without linker-ligand) <payload 2/3/4 (one or more payloads)<cationic species (histone fragment, NLS, or charged polypeptide anchor with or without linker-ligand)
11) payload 1 (ribonucleoprotein or other genetic/protein material)<cationic species (histone fragment, NLS or charged polypeptide anchor without linker-ligand) <payload 2/3/4 (one or more payloads)+anionic species<cationic species (histone fragment, NLS, or charged polypeptide anchor with or without linker-ligand)
12) payload 1/2/3/4 (one or more ribonucleoprotein, protein or nucleic acid payloads)+anionic species<cationic species (histone fragment, NLS, or charged polypeptide anchor with or without linker-ligand)
13) payload 1/2/3/4 (one or more ribonucleoprotein, protein or nucleic acid payloads)<cationic species (histone fragment, NLS, or charged polypeptide anchor with or without linker-ligand)

Cell Culture

T Cells 24 hours prior to transfection, a cryovial containing 20M human primary Pan-T cells (Stemcell #70024) was thawed and seeded in 4×66 wells of 4 96-well plates at 200 µl and 75,000 cells/well (1.5E6 cells/ml). Cells were cultured in antibiotic free RPMI 1640 media (Thermofisher #11875119) supplemented with 10% FBS and L-glutamine, and maintained by exchanging the media every 2 days.

Hematopoietic Stem Cells (HSC)

24 hours prior to transfection a cryovial containing 500 k human primary CD34+ cells (Stemcell #70002) was thawed and seeded in 48 wells of a 96-well plate, at 200 µl and 10-12 k cells per well. The culture media consisted of Stemspan SFEM II (Stemcell #09605) supplemented with 10% FBS, 25 ng/ml TPO, 50 ng/ml Flt-3 ligand, and 50 ng/ml SCF and the cells were maintained by exchanging the media every 2 days.

Cynomolgus Bone Marrow (HSC)

48 hours prior to transfection, a cryovial containing 1.25M Cynomolgus monkey bone marrow cells (IQ Biosciences #IQB-MnBM1) was thawed and 48 wells of a round bottom 96-well plate, were seeded at 200 µl and ~30 k cells/well. The cells are cultured in antibiotic free RPMI 1640 media supplemented with 12% FBS, and maintained by exchanging the media every 2 days.

Human Whole Blood 5 mL of whole blood was drawn through venous puncture. 1 mL was mixed with 14 mL of PBS. Nanoparticles were either directly transfected into 15 mL tubes, or 100 µl of blood was titrated into each well of a 96-well plate prior to nanoparticle transfection.

Transfection

After forming stock solutions of nanoparticles, 10 µl of nanoparticles were added per well of 96-well plates and incubated without changes to cell culture conditions or supplementation of media (See Table 5). 96-well plates were maintained during live cell imaging via a BioTek Cytation 5 under a CO2 and temperature controlled environment.

TABLE 5

| Payload | Dosage per well (96 well plate) | Volume of Nanoparticle Suspension |
| --- | --- | --- |
| mRNA | 100 ng mRNA | 10 ul |
| CRISPR RNP | 100 ng sgRNA, | 10 ul |
| pDNA | 200 ng pDNA | 10 ul |
| siRNA | 50 ng | 10 ul |

Analysis
Condensation and Inclusion Curves

Condensation curves were generated by mixing 50 µl solutions containing 0.0044 ug/µl of hemoglobin subunit beta (HBB) gRNA or von Willebrand factor (VWF)-EGFP-pDNA with pDNA binding site or mRNA or siRNA with 1 µl of SYBR 0.4× suspended in 30 mM Tris buffer (pH=7.4-8.5). HBB gRNA was present as complexed in RNP. The fluorescence emission from intercalated SYBR Gold was monitored before and after a single addition of PLE20, PLE35, PLE100, or PLE100:PDE100 (1:1 D:L ratio) where the carboxylate-to-phosphate (C:P) ratio ranged between 1 and 150. Afterwards, cationic species were added in order to reach the desired amine to phosphate (N:P) or amine to phosphate+carboxylate [N:(P+C)] ratios. Representative cationic species included PLR10, PLR50, PLR150, anchor-linker peptides, various mutated targeting ligands conjugated to GGGGSGGGGS (SEQ ID NO: 146) linker conjugated to a charged poly(arginine) chain (i.e. internal name: SCF_mcKit (4GS)2_9R_C), Histone_H3K4(Me3) peptide [1-22] (mH3_K4Me3_1), Histone_H4K16(Ac) peptide [1-20] (mH4_K16Ac_1), Histone_H2A peptide [1-20] (mH2A_1), corresponding to different positive to negative charge ratios (CR). In some experiments, cationic species were added prior to anionic species according to the above instructions.

Inclusion curves were obtained after performing multiple additions of SYBR GOLD 0.2× diluted in Tris buffer 30 mM (pH=7.4) to nanoparticles suspended in 60 mM HEPES (pH=5.5) solutions containing known amounts (100 to 600 ng) of VWF-EGFP-pDNA, gRNA HBB, Alexa555 Block-IT-siRNA encapsulated in different nanoparticle formulations.

Fluorescence emissions from intercalated SYBR Gold in the GFP channel were recorded in a flat bottom, half area, 96 well-plate using a Synergy Neo2 Hybrid Multi-mode reader (Biotek, USA) or a CLARIOstar Microplate reader (BMG, Germany).

Nanoparticle Tracking Analysis (Zeta)

The hydrodynamic diameter and zeta potential of the nanoparticle formulations were investigated by nanoparticle tracking analysis using a ZetaView instrument (Particle Metrix, Germany). Samples are diluted 1:100 in PBS (1:12) before injection into the instrument. To obtain the measurement, the camera settings are adjusted to the optimal sensitivity and particles/frame (~100-150) before analysis.

Fluorescence Microscopy—BioTek Cytation 5

A Cytation 5 high-content screening live-cell imaging microscope (BioTek, USA) was utilized to image transfection efficiency prior to evaluation by flow cytometry. Briefly, cells were imaged prior to transfection, in 15 m increments post-transfection for 4 h, and then in 2 h increments for the following 12 hours utilizing the GFP and/or Cy5 channels as well as bright field under a 10× objective. Images were subsequently gathered as representative of continuous kinetics or discrete 1-18, 24, 36, or 48-hour time-points.

Flow-Cytometry

Cell labeling experiments were conducted performing a washing step to remove cell media followed by incubation of the cells with Zombie NIR viability kit stain and/or CellEvent™ Caspase-3/7 Green (Invitrogen, U.S.A.) dissolved in PBS at room temperature for 30 minutes. The total volume of the viability labeling mixture was 25 µl per well. A panel of fluorescent primary antibodies was then added to the mixture (0.25 µl of each antibody per well) and left incubating for 15 minutes. Positive controls and negative single-channel controls were generated utilizing UltraComp eBeads Compensation Beads and Negative Beads or Cy5 nuclear stains of live cells. All incubation steps were performed on a rotary shaker and in the dark. Attune multi-parametric flow cytometry measurements were conducted on live cells using an Attune NxT Flow Cytometer (ThermoFisher, USA) after appropriate compensations among different channels have been applied. Representative populations of cells were chosen by selection of appropriate gates of forward and side scattering intensities. The detection of cell fluorescence was continued until at least 10000 events had been collected.

Results/Data

FIG. 8-FIG. 33: Condensation Data

FIG. 8. (a) SYBR Gold exclusion assay showing fluorescence intensity variations as a function of positive to negative charge ratio (CR) in nanoparticles containing VWF-EGFP pDNA with PNA payload initially intercalated with SYBR Gold. The carboxylate to phosphate (C:P) ratios shown in the legend are based on the nanoparticle's ratio of carboxylate groups on anionic polypeptides species (PLE100) to phosphate groups on the genetic material of the payload. CR was increased via stepwise addition of cationic PLR150. The fluorescence decrease observed show that increasing the CR through addition of PLR150 causes SYBR to be displaced from the payload as the particle condenses. Additionally, condensation remains consistent across various c:p ratios. Blank solutions contain SYBR Gold in absence of the payload. (b) Fluorescence intensity variations as a function of the positive to negative charge ratio (CR) in nanoparticles without PLE100.

Figure 9:
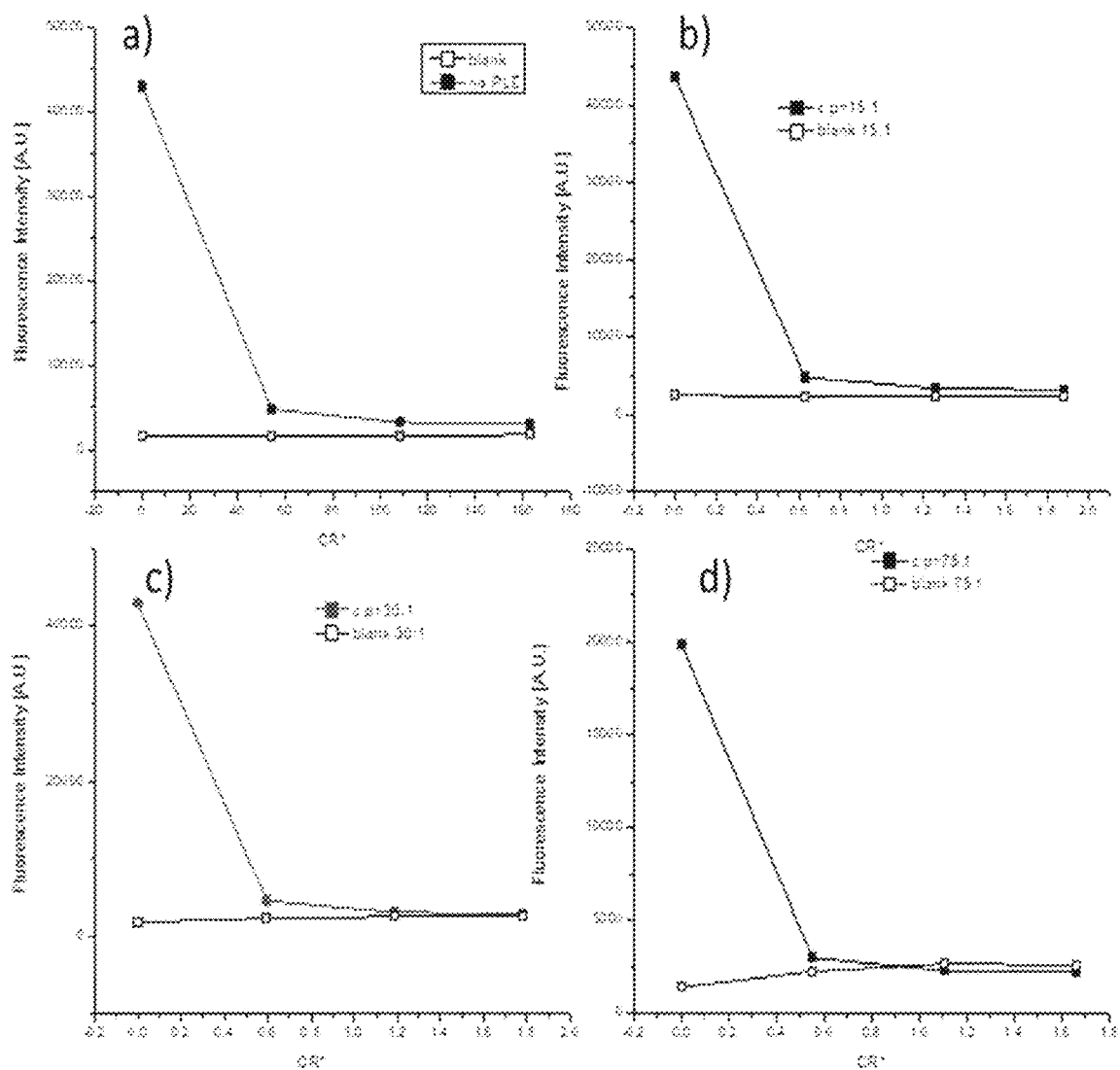
FIG. 9 provides condensation curves on nanoparticles with payload: NLS-CAS9-NLS RNP complexed to HBB gRNA.

FIG. 9. SYBR Gold exclusion assay showing fluorescence intensity variations as a function of positive to negative charge ratio (CR*) in nanoparticles containing NLS-CAS9-NLS RNP complexed w/HBB gRNA payload initially intercalated with SYBR Gold. Additionally, determination of CR* does not include the negatively charged portion of the gRNA shielded by complexation with cas9. The carboxylate to phosphate (C:P) ratios shown in the legend are based on the nanoparticle's ratio of carboxylate groups on anionic polypeptides species (PLE100) to phosphate groups on the genetic material of the payload.

CR was increased via stepwise addition of cationic PLR150. Blank solutions contain SYBR Gold in absence of the payload. The fluorescence decrease observed show that increasing the CR through addition of PLR150 causes SYBR to be displaced from the payload as the particle condenses. Additionally, condensation remains consistent across various c:p ratios.

Figure 10:
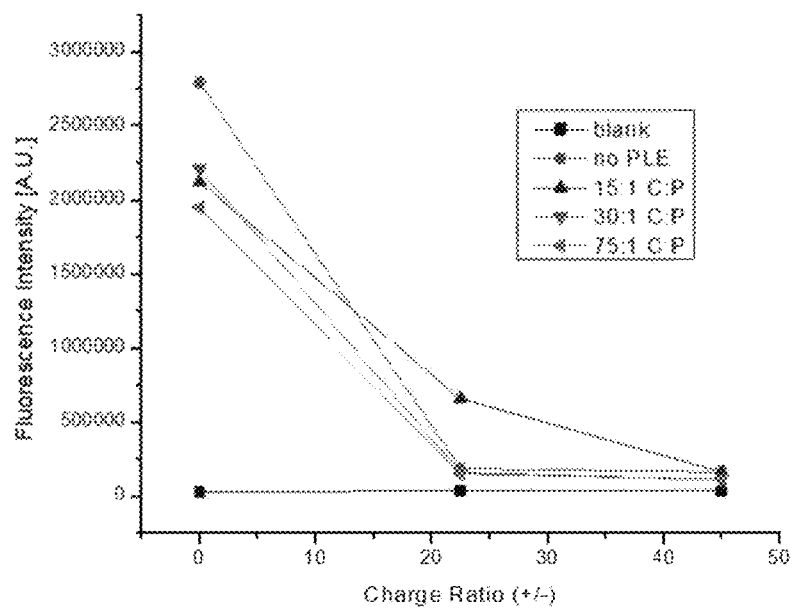
FIG. 10 provides condensation curves on nanoparticles with payload: HBB gRNA.

FIG. 10. SYBR Gold exclusion assay showing fluorescence intensity variations as a function of positive to negative charge ratio (CR) in nanoparticles containing gRNA HBB payloads initially intercalated with SYBR Gold. The carboxylate to phosphate (C:P) ratios shown in the legend are based on the nanoparticle's ratio of carboxylate groups on anionic polypeptides species (PLE100) to phosphate groups on the genetic material of the payload.

CR was increased via stepwise addition of PLR150. Blank solutions contain SYBR Gold in absence of the payload. The fluorescence decrease observed show that increasing the CR through addition of PLR150 causes SYBR to be displaced from the payload as the particle condenses. Additionally, condensation with respect to CR remains consistent across various C:P ratios.

TABLE 6

Hydrodynamic diameter and zeta potential for some formulations were measured at the condensation end-points and are reported in the following table.

| Payload | C:P | Hydrodynamic diameter [nm] | Zeta Potential [mV] |
| --- | --- | --- | --- |
| pDNA | 0 | 120 ± 49 | — |
| HBB gRNA | 0 | 99 ± 32 | 6.7 ± 0.6 |
| RNP (NLS-Cas9-NLS and HBB gRNA) | 0 | 90 ± 36 | −0.6 ± 0.9 |
| RNP (NLS-Cas9-NLS and HBB gRNA | 15 | 110 ± 49 | 26.7 ± 1 |
| pDNA | 15 | 88 ± 49 | 11.7 ± 0.6 |

Figure 11:
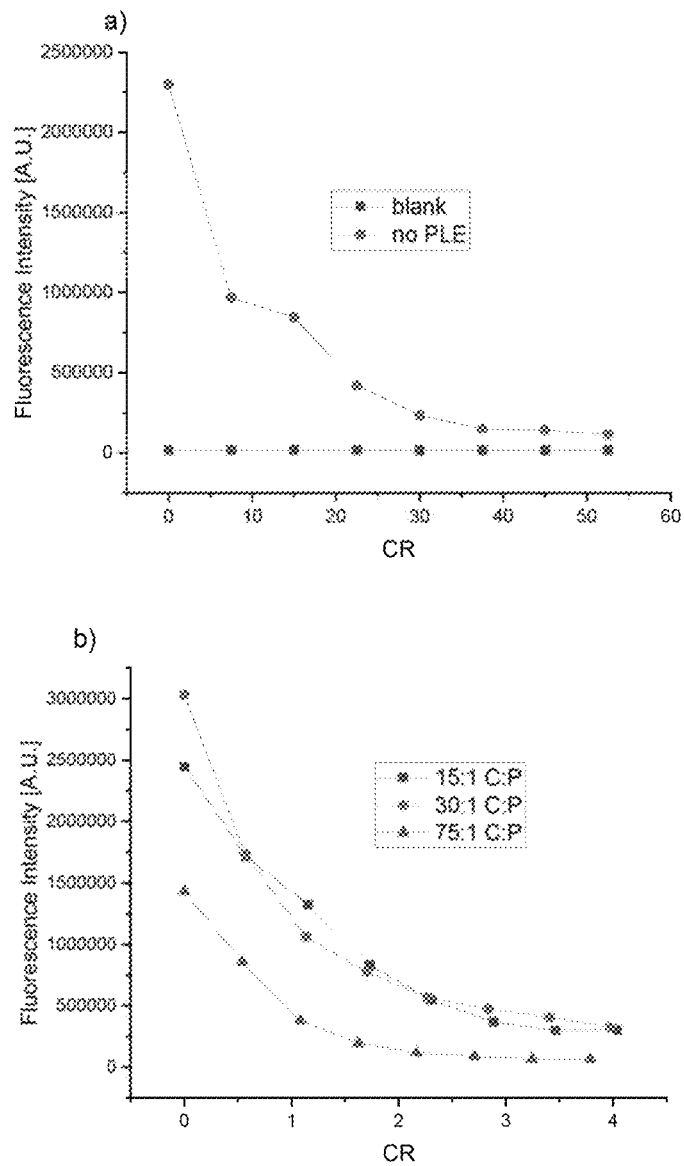
FIG. 11 provides condensation curves on nanoparticles with payload: HBB gRNA.
Figure 12:
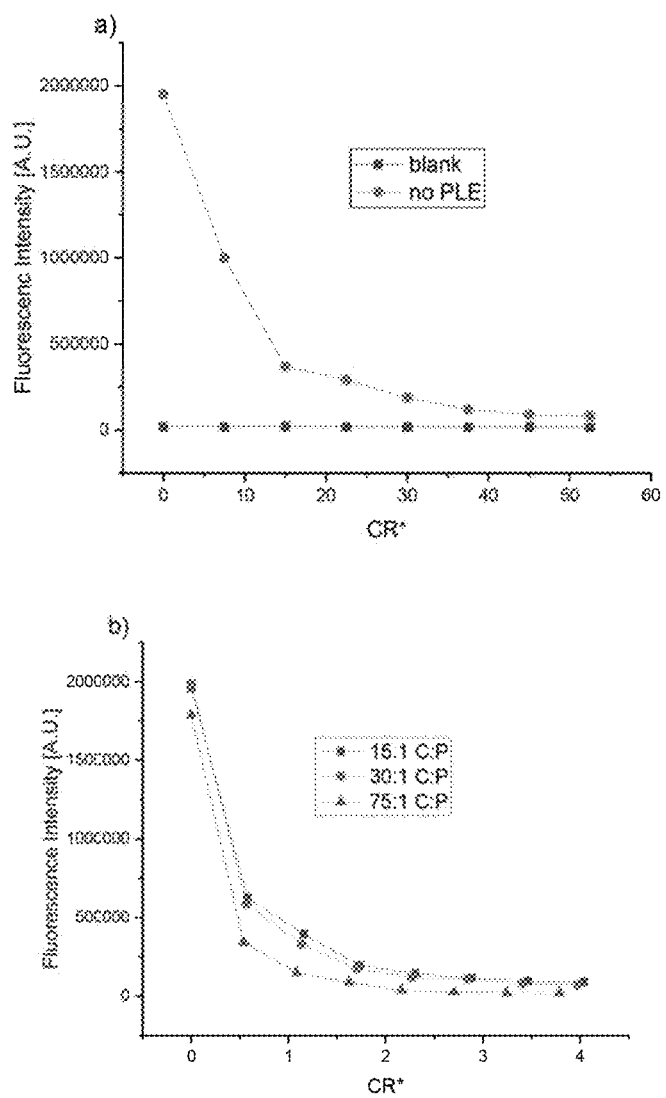
FIG. 12 provides condensation curves on nanoparticles with payload: NLS-CAS9-NLS RNP complexed to HBB gRNA.
Figure 13:
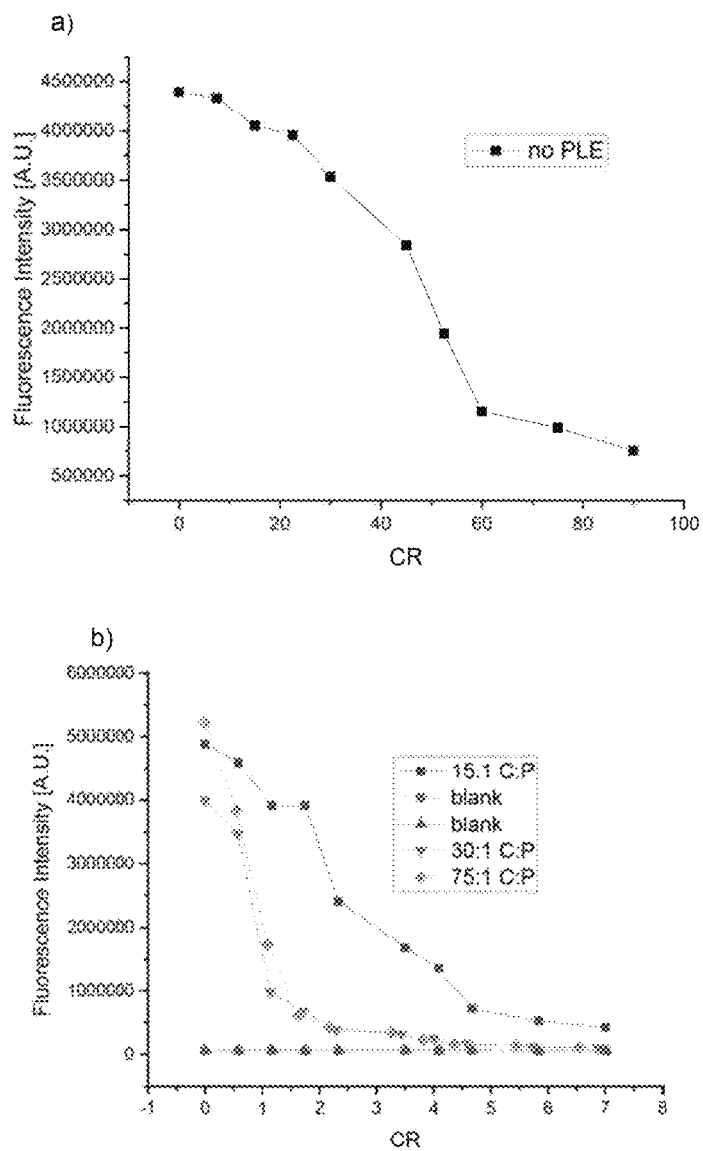
FIG. 13 provides condensation curves on nanoparticles with payload: VWF-EGFP pDNA with peptide nucleic acid (PNA) Binding Site.

FIG. 11-FIG. 13: Condensation Curves with Peptide SCF_rmAc-cKit (4GS)2_9R_C as Cationic Material FIG. 11. (a)(b) SYBR Gold exclusion assay showing fluorescence intensity variations as a function of positive to negative charge ratio (CR) in nanoparticles containing HBB gRNA payload initially intercalated with SYBR Gold. The carboxylate to phosphate (C:P) ratios shown in the legend are based on the nanoparticle's ratio of carboxylate groups on anionic polypeptides species (PLE100) to phosphate groups on the genetic material of the payload. CR was increased via stepwise addition of cationic mutated cKit targeting ligand conjugated to a (GGGS)2 linker conjugated to positively charged poly(arginine) (internal ligand name: SCF_rmAc-cKit_(4GS)2_9R_C). The fluorescence decrease observed show that increasing the CR through addition of SCF_rmAc-cKit (4GS)2_9R_C causes SYBR to be displaced from the payload as the particle condenses. Additionally, condensation remains consistent across various c:p ratios. Blank solutions contain SYBR Gold in absence of the payload.

FIG. 12. (a)(b) SYBR Gold exclusion assay showing fluorescence intensity variations as a function of positive to negative charge ratio (CR) in nanoparticles containing NLS-CAS9-NLS RNP complexed w/HBB gRNA payload initially intercalated with SYBR Gold. The carboxylate to phosphate (C:P) ratios shown in the legend are based on the nanoparticle's ratio of carboxylate groups on anionic polypeptides species (PLE100) to phosphate groups on the genetic material of the payload.

CR was increased via stepwise addition of cationic mutated cKit targeting ligand conjugated to a (GGGS)2 linker conjugated to positively charged poly(arginine) (internal ligand name: SCF_rmAc-cKit_(4GS)2_9R_C). The fluorescence decrease observed show that increasing the CR through addition of SCF_rmAc-cKit_(4GS)2_9R_C causes SYBR to be displaced from the payload as the particle condenses. Additionally, condensation remains consistent across various c:p ratios. Blank solutions contain SYBR Gold in absence of the payload.

FIG. 13. (a)(b) SYBR Gold exclusion assay showing fluorescence intensity variations as a function of positive to negative charge ratio (CR) in nanoparticles containing VWF-EGFP pDNA with PNA payload initially intercalated with SYBR Gold. The carboxylate to phosphate (C:P) ratios shown in the legend are based on the nanoparticle's ratio of carboxylate groups on anionic polypeptides species (PLE100) to phosphate groups on the genetic material of the payload.

CR was increased via stepwise addition of cationic mutated cKit targeting ligand conjugated to a (GGGS)2 linker conjugated to positively charged poly(arginine) (internal ligand name: SCF_rmAc-cKit_(4GS)2_9R_C). The fluorescence decrease observed show that increasing the CR through addition of SCF_rmAc-cKit_(4GS)2_9R_C causes SYBR to be displaced from the payload as the particle condenses. Additionally, condensation remains consistent across various c:p ratios. Blank solutions contain SYBR Gold in absence of the payload.

Figure 14:
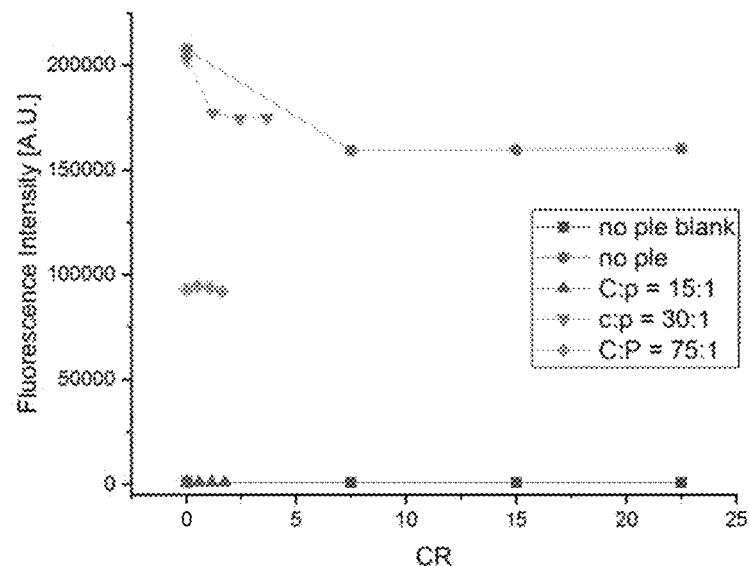
FIG. 14 provides condensation curves on nanoparticles with payload: VWF-EGFP pDNA with peptide nucleic acid (PNA) Binding Site.
Figure 15:
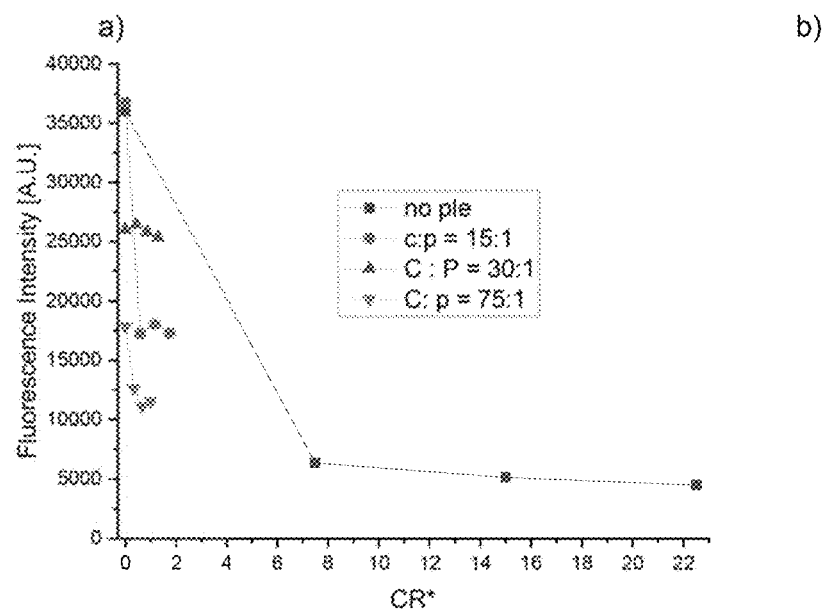
FIG. 15 provides condensation curves on nanoparticles with payload: RNP of NLS-CAS9-NLS with HBB gRNA.
Figure 16:
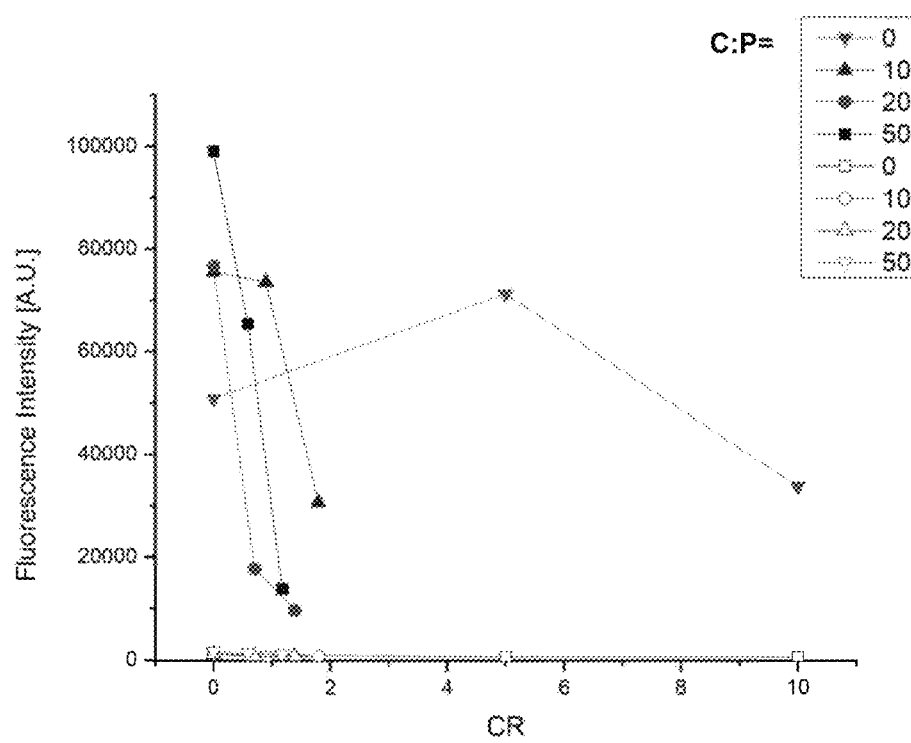
FIG. 16 provides condensation curves on nanoparticles with payload: VWF-EGFP pDNA with peptide nucleic acid (PNA) Binding Site.

FIG. 14-FIG. 15: Condensation Curves with Histone H3K4Me as Cationic Material

FIG. 14. SYBR Gold exclusion assay showing fluorescence intensity variations as a function of positive to negative charge ratio (CR) in nanoparticles containing VWF-EGFP pDNA with PNA payload initially intercalated with SYBR Gold. The carboxylate to phosphate (C:P) ratios shown in the legend are based on the nanoparticle's ratio of carboxylate groups on anionic polypeptides species (PLE100) to phosphate groups on the genetic material of the payload. CR was increased via stepwise addition of cationic mutated Histone_H3K4(Me3) peptide [1-22](internal peptide name mH3_K4Me3_1). The fluorescence changes observed show that increasing the CR through addition of mH3_K4Me3_1, in the presence of PLE100, fail to sufficiently cause SYBR to be displaced from the payload. Blank solutions contain SYBR Gold in absence of the payload.

FIG. 15. (a) SYBR Gold exclusion assay showing fluorescence intensity variations as a function of positive to negative charge ratio (CR) in nanoparticles containing NLS-CAS9-NLS RNP complexed w/HBB gRNA payload initially intercalated with SYBR Gold. The carboxylate to phosphate (C:P) ratios shown in the legend are based on the nanoparticle's ratio of carboxylate groups on anionic polypeptides species (PLE100) to phosphate groups on the genetic material of the payload. CR was increased via stepwise addition of cationic mutated Histone_H3K4(Me3) peptide [1-22] (internal peptide name mH3_K4Me3_1). The fluorescence changes observed show that increasing the CR through addition of mH3_K4Me3_1, in the presence of PLE100, fails to consistently cause SYBR to be displaced from the payload. However, Histone_H3K4(Me3) is shown to be an effective condensing agent at CR≤8:1 in the absence of anionic polypeptide.

FIG. 16-FIG. 19: Condensation Curves with Peptide CD45_aSiglec_(4GS)2_9R_C as Cationic Material FIG. 16. SYBR Gold exclusion assay showing fluorescence intensity variations as a function of positive to negative charge ratio (CR) in nanoparticles containing VWF-EGFP pDNA with PNA payload initially intercalated with SYBR Gold. The carboxylate to phosphate (C:P) ratios shown in the legend are based on the nanoparticle's ratio of carboxylate groups on anionic polypeptides species (PLE100) to phosphate groups on the genetic material of the payload. CR was increased via stepwise addition of cationic mutated CD45 receptor targeting ligand conjugated to a (GGGS)2 linker conjugated to positively charged poly(arginine) (internal ligand name: CD45_mSiglec_(4GS)2_9R_C). Empty symbols represent blank solutions containing SYBR Gold in absence of the payload.

The fluorescence decrease observed show that increasing the CR through addition of CD45_mSiglec_(4GS)2_9R_C causes SYBR to be displaced from the payload as the particle condenses. Additionally, condensation remains consistent across various C:P ratios.

Figure 17:
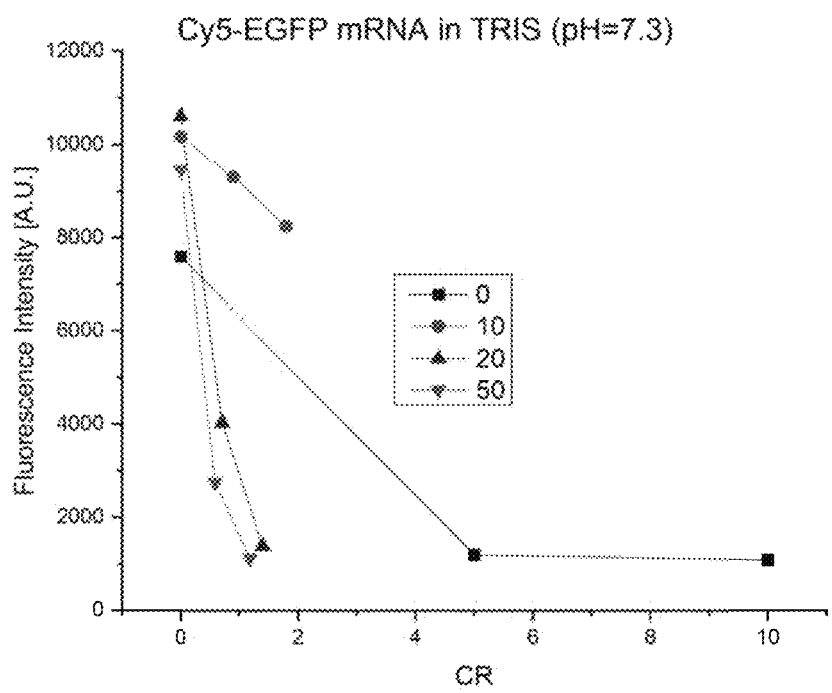
FIG. 17 provides condensation curves on nanoparticles with payload: Cy5_EGFP mRNA.
Figure 18:
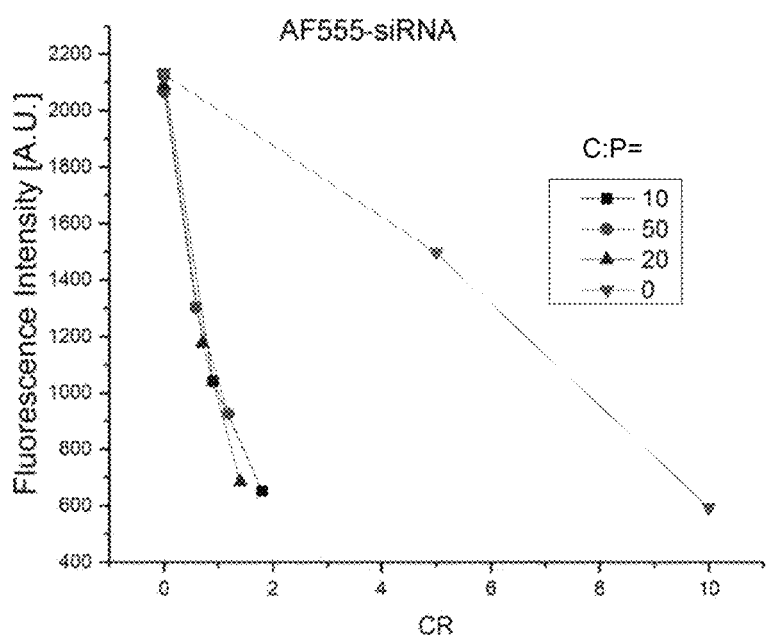
FIG. 18 provides condensation curves on nanoparticles with payload: BLOCK-iT Alexa Fluor 555 siRNA.
Figure 20:
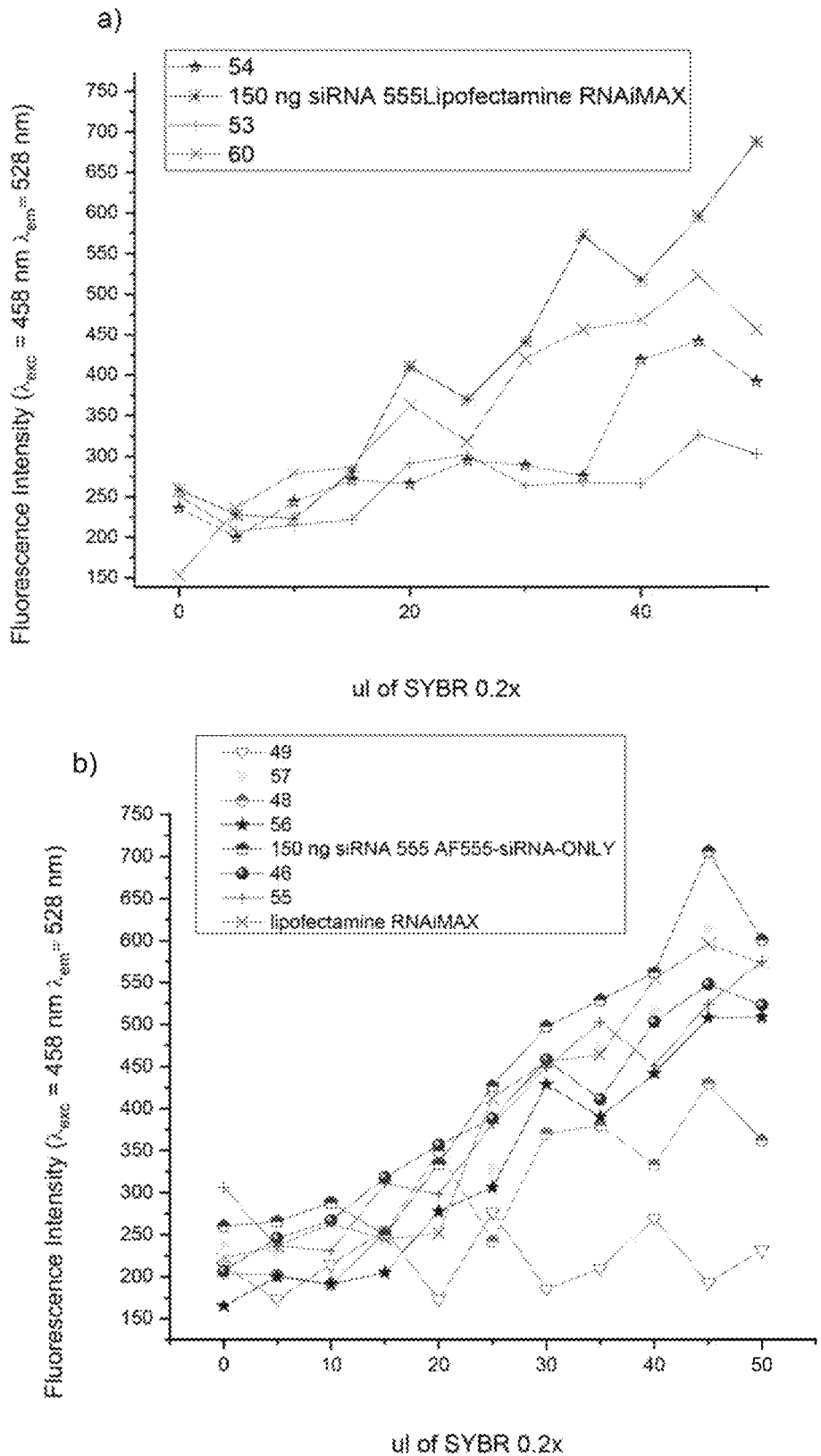
FIG. 20 provides data collected when using nanoparticles with Alexa 555 Block-IT siRNA as payload.
Figure 20:
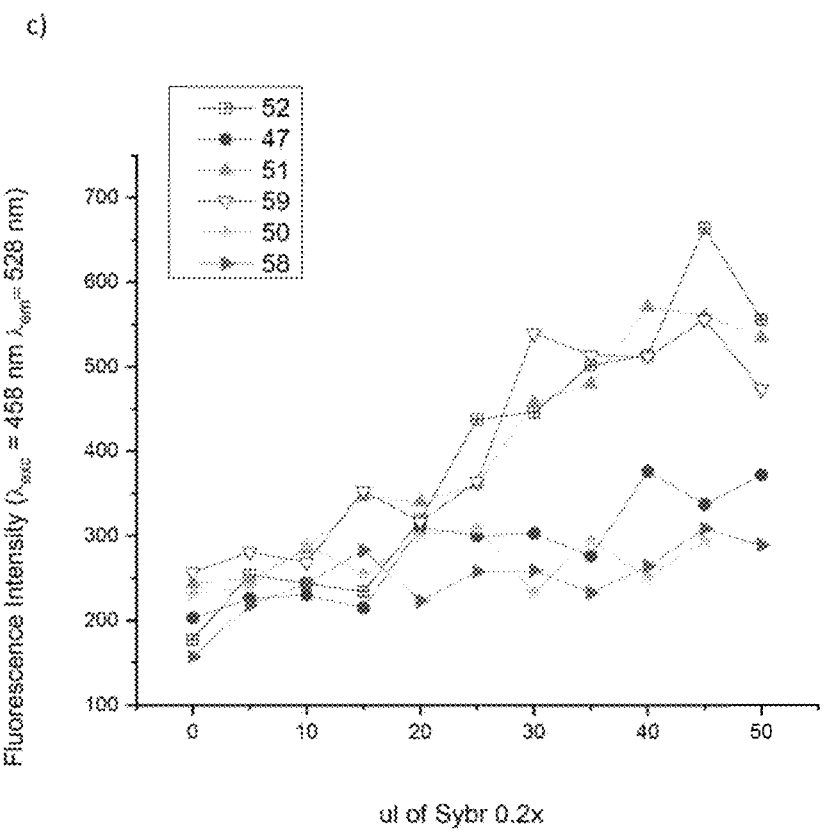
Figure 21:
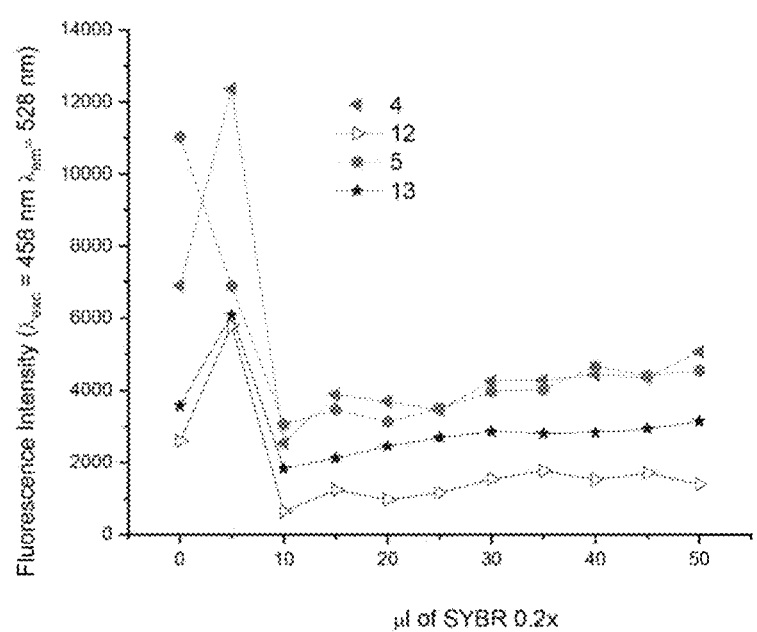
FIG. 21 provides data collected when using nanoparticles with ribonuclear protein (RNP) formed by NLS-Cas9-GFP and HBB guide RNA as payload.
Figure 23:
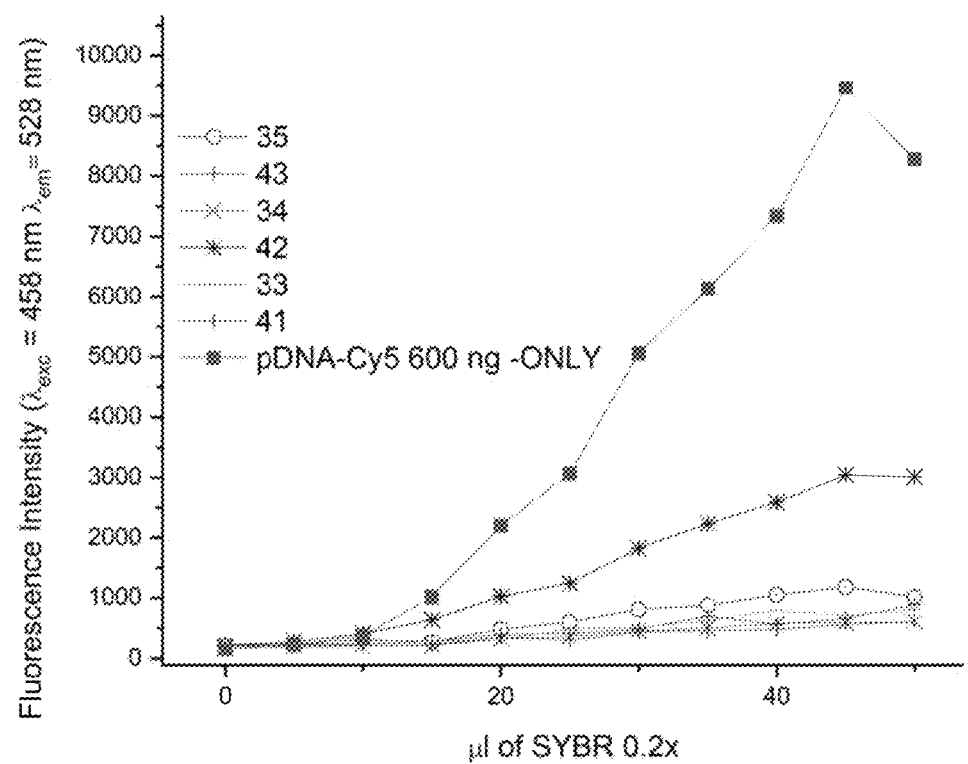
FIG. 23 provides data collected when using nanoparticles with payload: VWF-EGFP pDNA with Cy5 tagged peptide nucleic acid (PNA) Binding Site.

FIG. 17. SYBR Gold exclusion assay showing fluorescence intensity variations as a function of positive to negative charge ratio (CR) in nanoparticles containing Cy5-EGFP mRNA payload initially intercalated with SYBR Gold. The carboxylate to phosphate (C:P) ratios shown in the legend are based on the nanoparticle's ratio of carboxylate groups on anionic polypeptides species (PLE100) to phosphate groups on the genetic material of the payload. CR was increased via stepwise addition of cationic mutated CD45 receptor targeting ligand conjugated to a (GGGS)2 linker conjugated to positively charged poly(arginine) (internal ligand name: CD45_mSiglec_(4GS)2_9R_C). Filled symbols represent blank solutions containing SYBR Gold in absence of the payload.

The fluorescence decrease observed show that increasing the CR through addition of CD45_mSiglec_(4GS)2_9R_C causes SYBR to be displaced from the payload as the particle condenses. Additionally, condensation remains consistent across various c:p ratios.

(b) Representative image of hydrodynamic diameter distribution for nanoparticles without PLE and having a charge ratio=22. The mean diameter is <d>=134 nm±65.

TABLE 7

Hydrodynamic diameter and zeta potential for some formulations were measured at the condensation end-points and are reported in the following table.

| Payload | C:P | Cationic Peptide | Hydrodynamic diameter [nm] | Zeta Potential [mV] |
|---|---|---|---|---|
| RNP (NLS-Cas9-EGFP and gRNA) | 0 | CD45_mSiglec_(4GS)2_9R_C | 134 ± 65 | 13 ± 1 |
| RNP (NLS-Cas9-EGFP and gRNA | 10 | CD45_mSiglec_(4GS)2_9R_C | 166 ± 75 | 19.2 ± 1 |
| RNP (NLS-Cas9-EGFP and gRNA | 20 | CD45_mSiglec_(4GS)2_9R_C | 179 ± 92 | 21 ± 1 |

FIG. 20-FIG. 23: Inclusion Curves

FIG. 20. SYBR Gold inclusion assay showing fluorescence intensity variations as a function of stepwise SYBR addition to different nanoparticles formulations all containing 150 ng of BLOCK-iT Alexa Fluor 555 siRNA payload. The delta change in fluorescence from Opl to 50 μl of SYBR indicates the stability of the nanoparticle formulations. The less stably condensed a formulation, the more likely SYBR Gold is to intercalate with the genetic payload. Lipofectamine RNAiMAX is used here as a positive control. Tables 2-4.

FIG. 21. SYBR Gold inclusion assay showing fluorescence intensity variations as a function of stepwise SYBR addition to different nanoparticles formulations all containing 300 ng the HBB gRNA payload. The delta change in fluorescence from 0 μl to 50 μl of SYBR indicates the stability of the nanoparticle formulations. The less stably condensed a formulation, the more likely SYBR Gold is to intercalate with the genetic payload. Lipofectamine CRISPRMAX is used here as a positive control. Tables 2-4.

FIG. 22. SYBR Gold inclusion assay showing fluorescence intensity variations as a function of stepwise SYBR addition to different nanoparticles formulations all containing the Cy5 EGFP mRNA payload. The delta change in fluorescence from 0 μl to 50 μl of SYBR indicates the stability of the nanoparticle formulations. The less stably condensed a formulation, the more likely SYBR Gold is to intercalate with the genetic payload. Lipofectamine MessengerMAX is used here as a positive control. Tables 2-4.

FIG. 23. SYBR Gold inclusion assay showing fluorescence intensity variations as a function of stepwise SYBR addition to different nanoparticles formulations all containing 600 ng of VWF-EGFP pDNA with Cy5 tagged peptide nucleic acid (PNA) Binding Site payload. The delta change in fluorescence from 0 μl to 50 μl of SYBR indicates the stability of the nanoparticle formulations. The less stably condensed a formulation, the more likely SYBR Gold is to intercalate with the genetic payload. Lipofectamine 3000 is used here as a positive control. Tables 2-4.

FIG. 24-FIG. 33: SYBR Exclusion/Condensation Assays on TC.001 (See Tables 2-4)

These data show that formulations used in experiment TC.001 are stable, moreover they show that H2A and H4 histone tail peptides, unlike H3, are effective condensing agents on their own for all listed payloads. It also shows that H2A and H4 can be further combined with anchor-linker-ligands. Finally, evidence is presented that the subsequent addition of anionic polymers (in this embodiment, PLE100) does not affect particle stability, or enhances stability as demonstrated through size and zeta potential measurements on various anchor-linker-ligand peptides conjugated to nucleic acid or ribonucleoprotein payloads prior to addition to anionic polymers.

Figure 24:
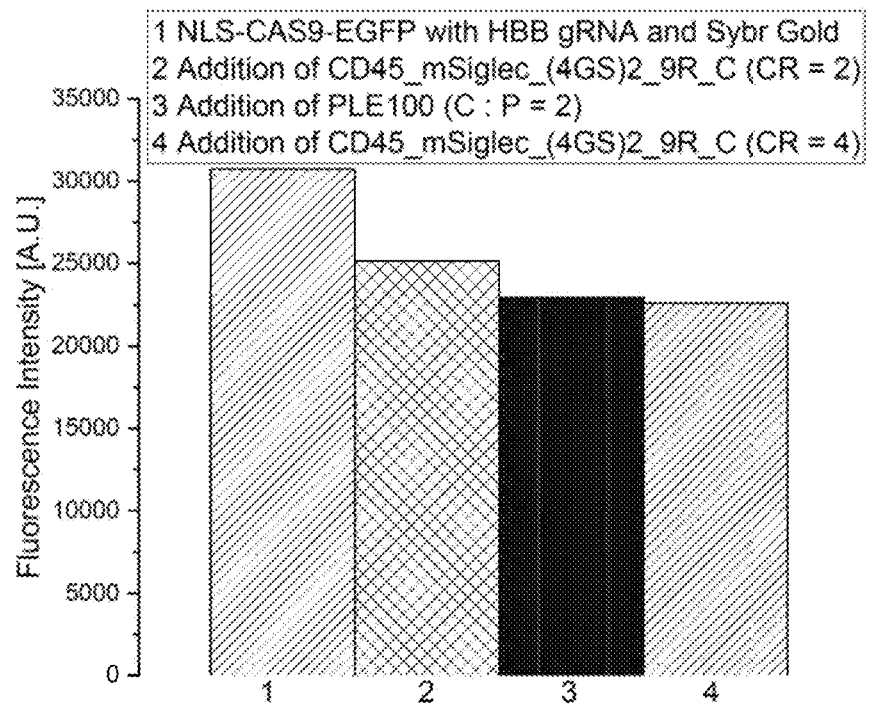
FIG. 24 provides data from a SYBR Gold exclusion assay showing fluorescence intensity decrease by addition of cationic polypeptide CD45_mSiglec_(4GS)2_9R_C followed by PLE100 and by further addition of the cationic polypeptide to RNP.

FIG. 24. SYBR Gold exclusion assay showing fluorescence intensity decrease by addition of cationic polypeptide CD45_mSiglec_(4GS)2_9R_C followed by PLE100 and by further addition of the cationic polypeptide to RNP. The fluorescence background signal id due to GFP fluorescence from the RNP.

Figure 25:
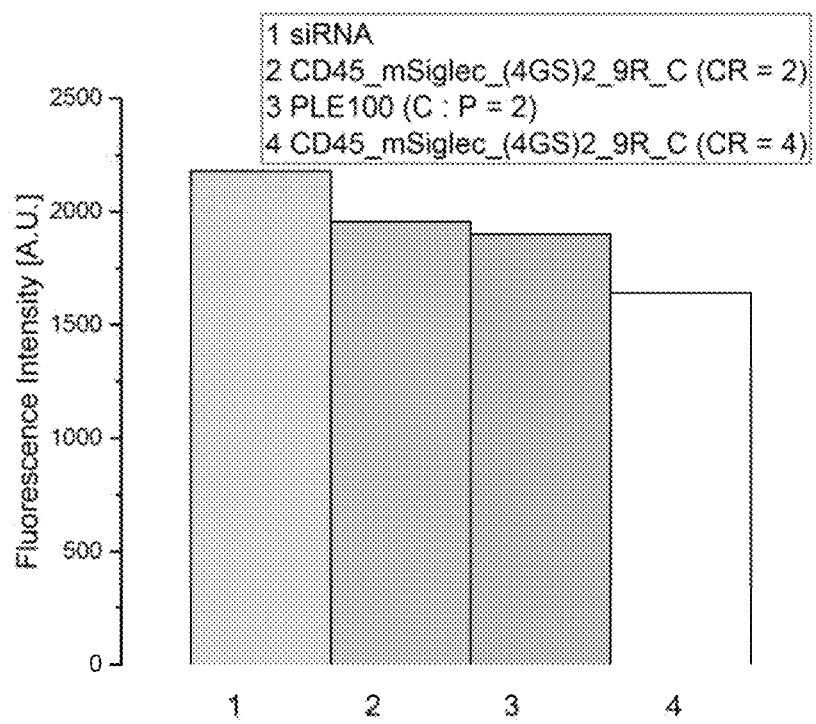
FIG. 25 provides data from a SYBR Gold exclusion assay showing fluorescence intensity variations by addition of cationic polypeptide CD45_mSiglec_(4GS)2_9R_C followed by PLE100 and by further addition of the cationic polypeptide to siRNA and SYBR Gold.

FIG. 25. SYBR Gold exclusion assay showing fluorescence intensity variations by addition of cationic polypeptide CD45_mSiglec_(4GS)2_9R_C followed by PLE100 and by further addition of the cationic polypeptide to siRNA and SYBR Gold.

Figure 26:
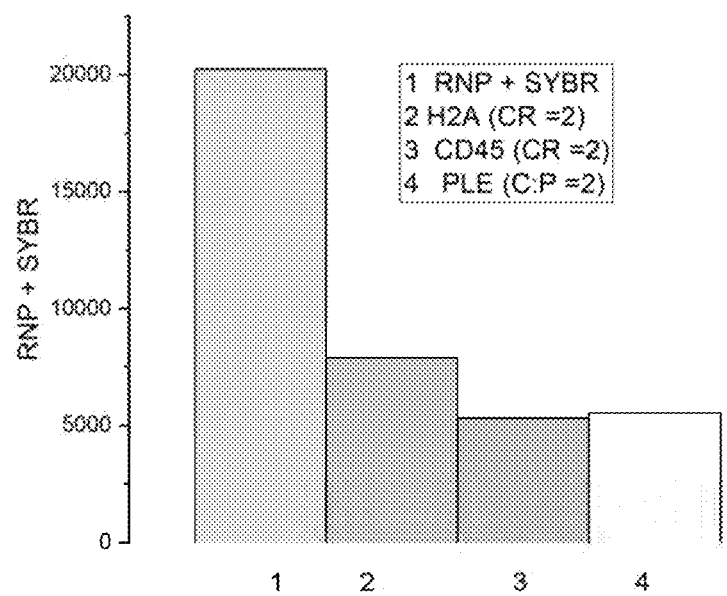
FIG. 26 provides data from a SYBR Gold exclusion assay showing fluorescence intensity variations by addition of cationic polypeptide histone peptide H2A followed by CD45_mSiglec_(4GS)2_9R_C and by further addition of PLE100 to RNP of NLS-Cas9-EGFP with HBB gRNA and SYBR Gold.

FIG. 26. SYBR Gold exclusion assay showing fluorescence intensity variations by addition of cationic polypeptide histone peptide H2A followed by CD45_mSiglec_(4GS)2_9R_C and by further addition of PLE100 to RNP of NLS-Cas9-EGFP with HBB gRNA and SYBR Gold.

Figure 27:
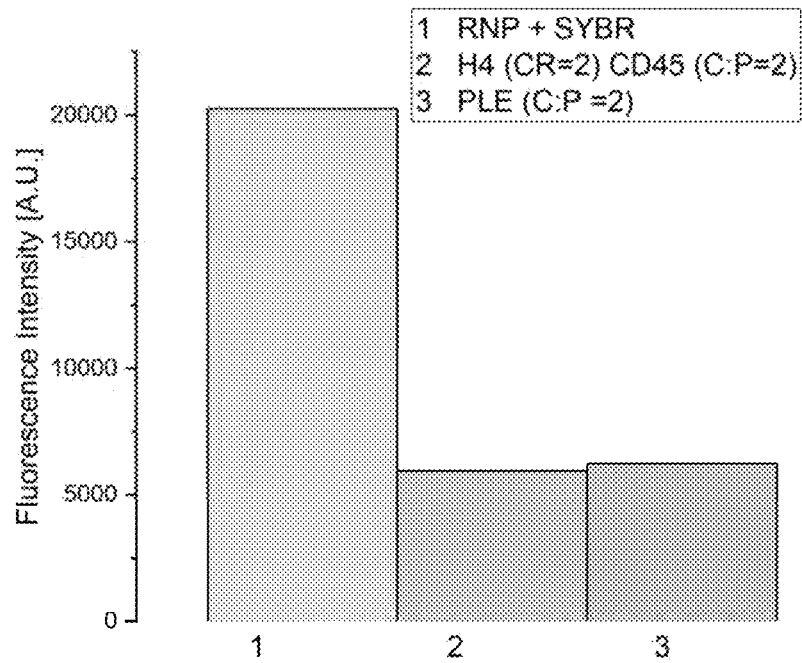
FIG. 27 provides data from a SYBR Gold exclusion assay showing fluorescence intensity variations by addition of cationic polypeptide histone peptide H4 together with CD45_mSiglec_(4GS)2_9R_C and by further addition of PLE100 to RNP of NLS-Cas9-EGFP with HBB gRNA and SYBR Gold.

FIG. 27. SYBR Gold exclusion assay showing fluorescence intensity variations by addition of cationic polypeptide histone peptide H4 together with CD45_mSiglec_(4GS)2_9R_C and by further addition of PLE100 to RNP of NLS-Cas9-EGFP with HBB gRNA and SYBR Gold.

Figure 28:
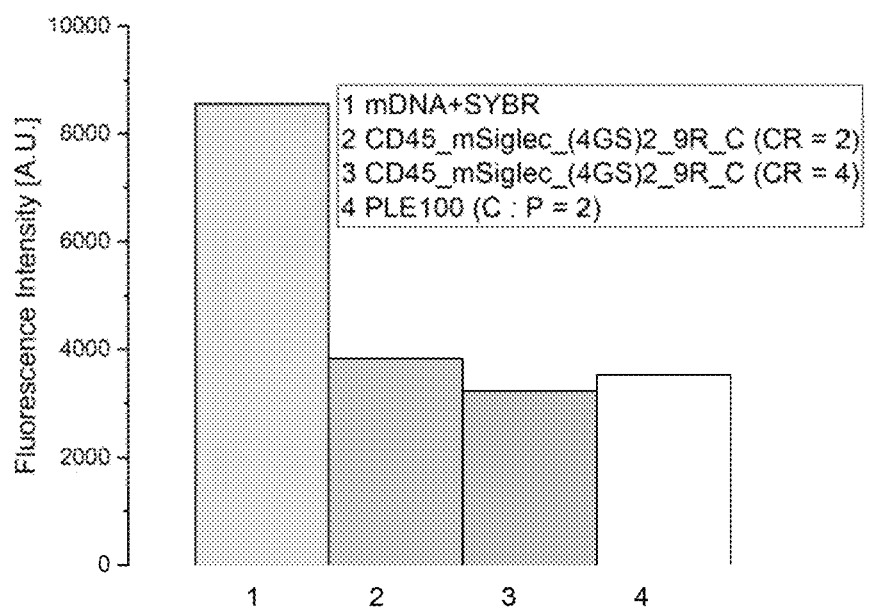
FIG. 28 provides data from a SYBR Gold exclusion assay showing fluorescence intensity variations by addition of cationic polypeptide CD45_mSiglec_(4GS)2_9R_C fand by further addition of PLE100 to mRNA.

FIG. 28. SYBR Gold exclusion assay showing fluorescence intensity variations by addition of cationic polypeptide CD45_mSiglec_(4GS)2_9R_C and by further addition of PLE100 to mRNA.

Figure 29:
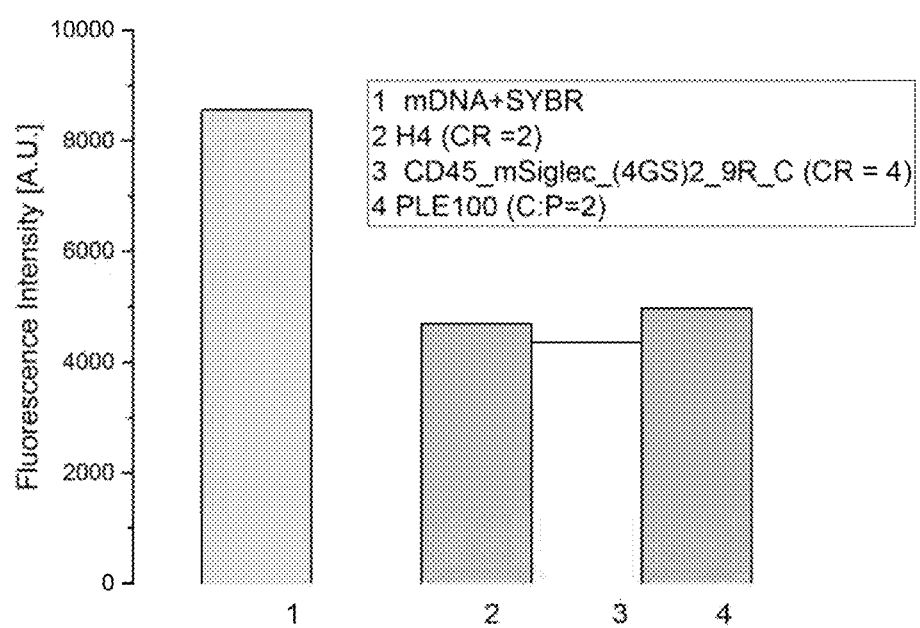
FIG. 29 provides data from a SYBR Gold exclusion assay showing fluorescence intensity variations by addition histone H4 and by further addition of CD45-mSiglec-(4GS)2_9R_c and PLE100 to mRNA.

FIG. 29. SYBR Gold exclusion assay showing fluorescence intensity variations by addition histone H4 and by further addition of CD45-mSiglec-(4GS)2_9R_c and PLE100 to mRNA.

Figure 30:
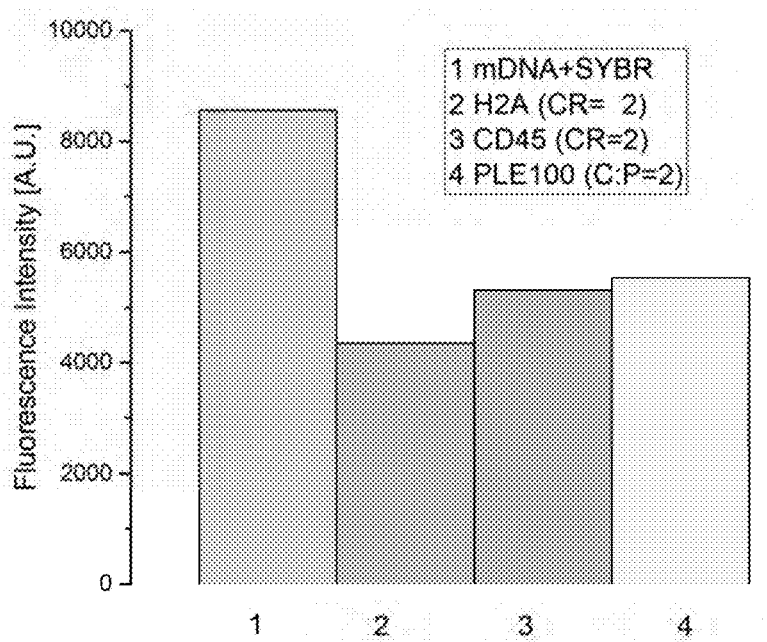
FIG. 30 provides data from a SYBR Gold exclusion assay showing fluorescence intensity variations by addition histone H2A and by further addition of CD45-mSiglec-(4GS)2_9R_c and PLE100 to mRNA.

FIG. 30. SYBR Gold exclusion assay showing fluorescence intensity variations by addition histone H2A and by further addition of CD45-mSiglec-(4GS)2_9R_c and PLE100 to mRNA.

Figure 31:
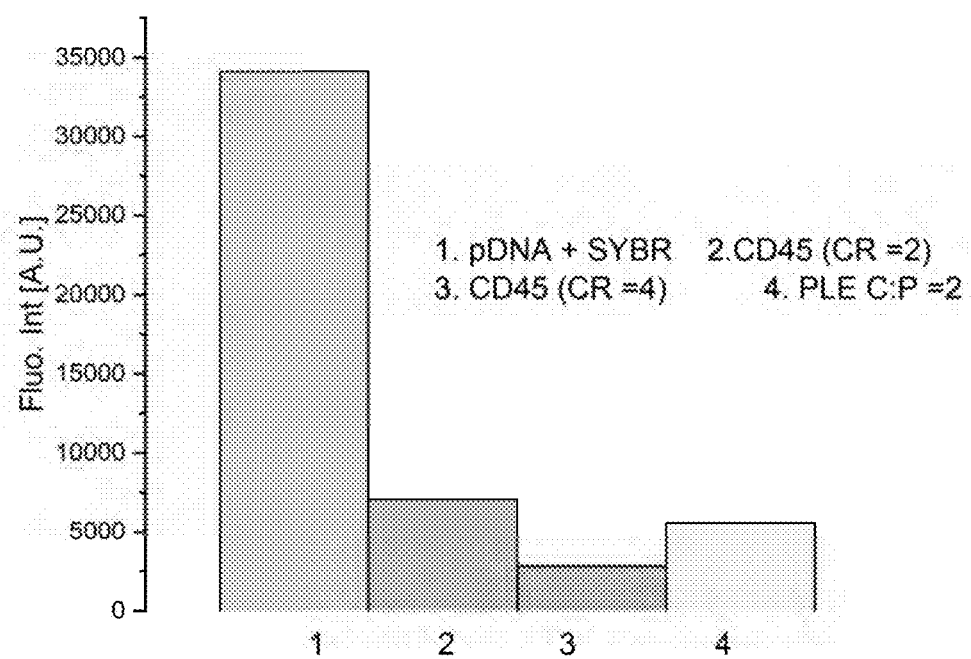
FIG. 31 provides data from a SYBR Gold exclusion assay from intercalation with VWF_EGFP pDNA showing fluorescence intensity variations by addition of cationic polypeptide CD45_mSiglec_(4GS)2_9R_C followed by PLE100.

FIG. 31. SYBR Gold exclusion assay from intercalation with VWF_EGFP pDNA showing fluorescence intensity variations by addition of cationic polypeptide CD45_mSiglec_(4GS)2_9R_C followed by PLE100.

Figure 32:
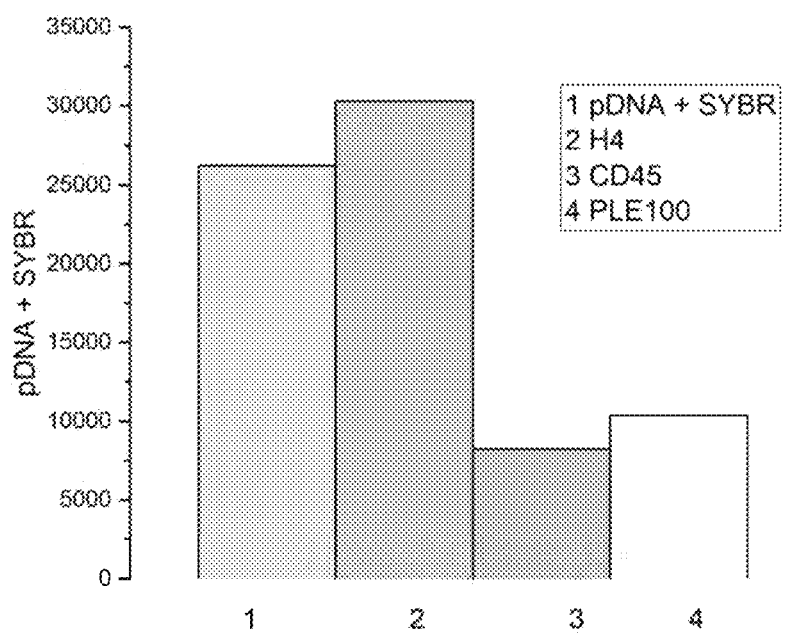
FIG. 32 provides data from a SYBR Gold exclusion assay from intercalation with VWF_EGFP pDNA showing fluorescence intensity variations by addition of histone H4, followed by cationic polypeptide CD45_mSiglec_(4GS)2_9R_C followed by PLE100.

FIG. 32. SYBR Gold exclusion assay from intercalation with VWF_EGFP pDNA showing fluorescence intensity variations by addition of histone H4, followed by cationic polypeptide CD45_mSiglec_(4GS)2_9R_C followed by PLE100.

Figure 33:
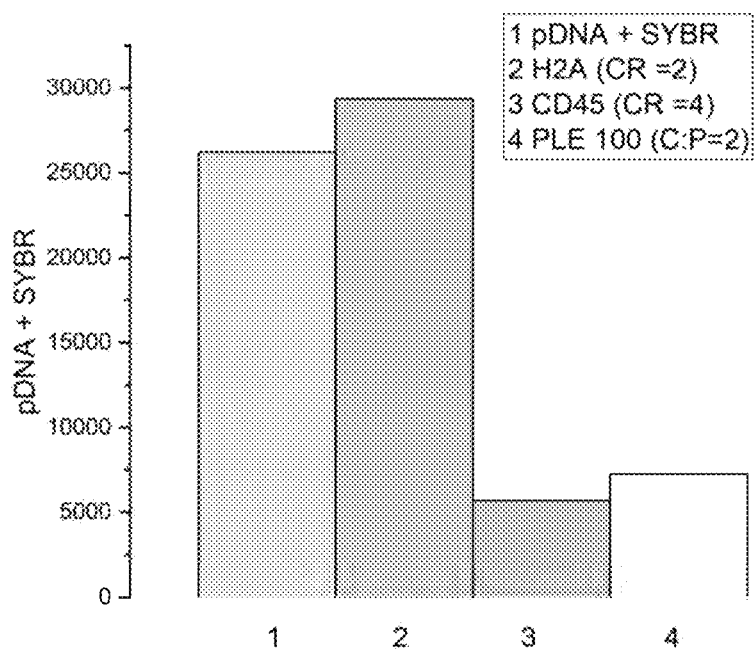
FIG. 33 provides data from a SYBR Gold exclusion assay from intercalation with VWF_EGFP pDNA showing fluorescence intensity variations by addition of histone H4, followed by cationic polypeptide CD45_mSiglec_(4GS)2_9R_C followed by PLE100.
Figure 34:
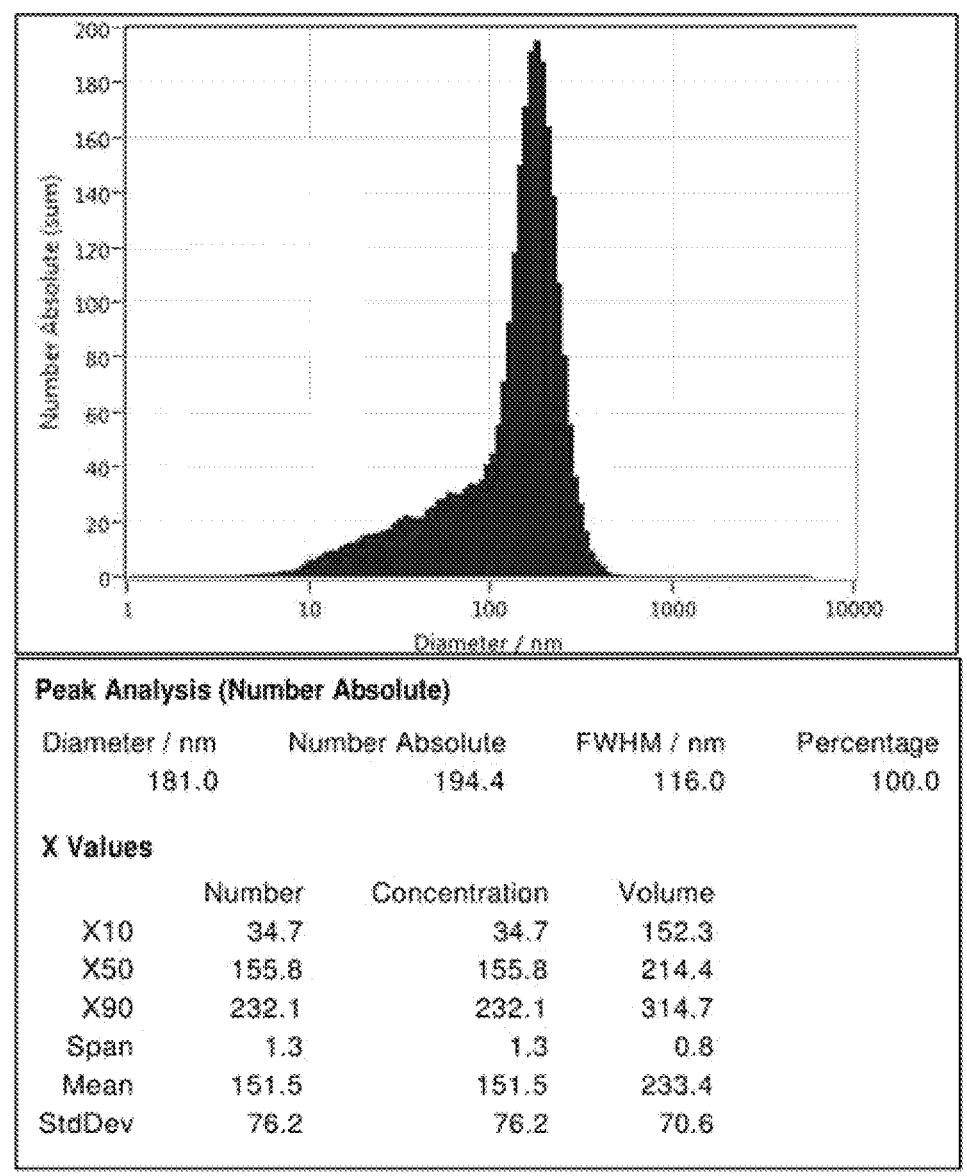
FIG. 34 (panels A-C) provide data related to polyplex size distribution, silica coated size and zeta potential distribution, and ligand coated/functionalized particle size and zeta potential distribution.
Figure 35:
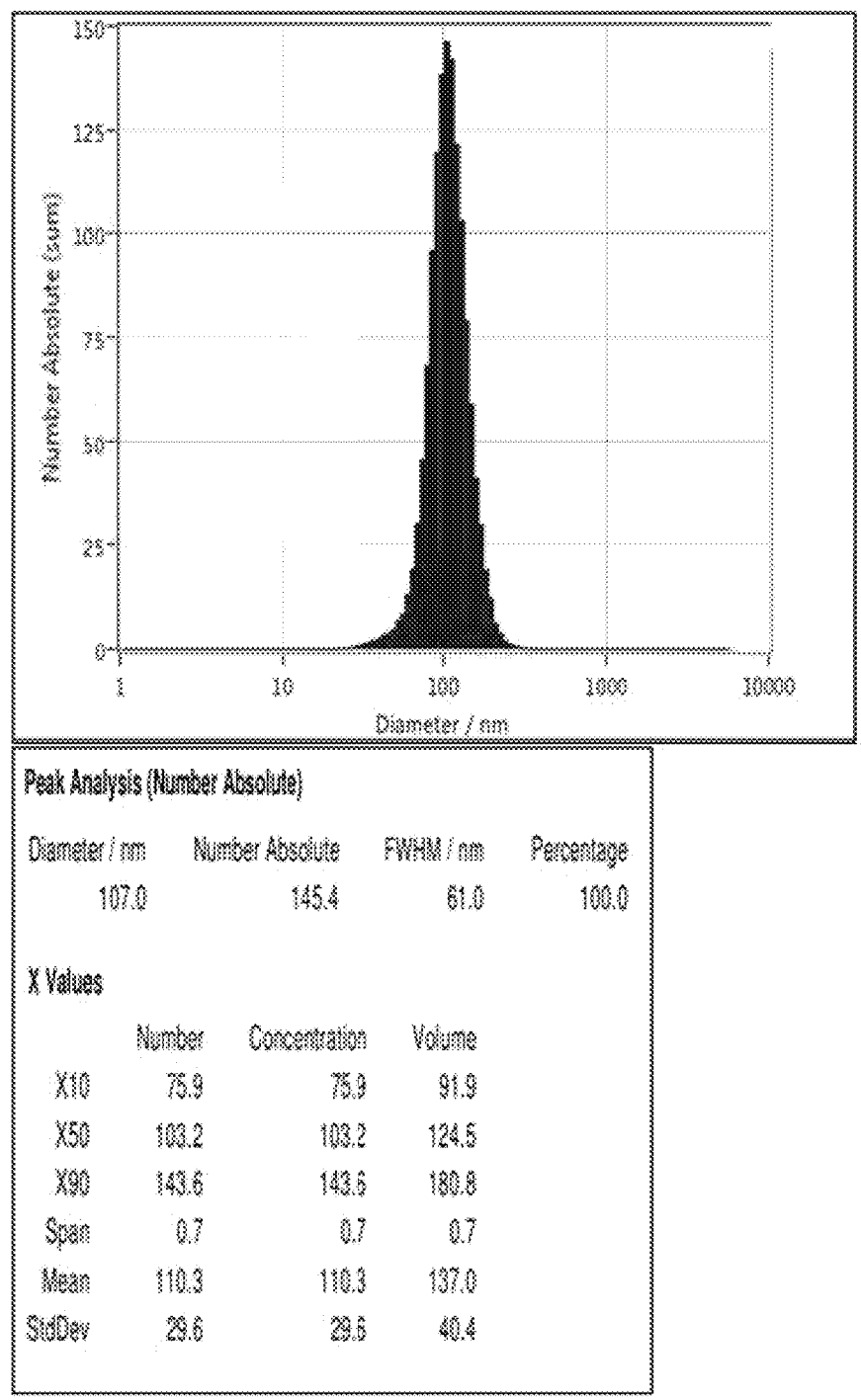
FIG. 35 provides data related to branched histone peptide conjugate pilot particles.

FIG. 33. SYBR Gold exclusion assay from intercalation with VWF_EGFP pDNA showing fluorescence intensity variations by addition of histone H4, followed by cationic polypeptide CD45_mSiglec_(4GS)2_9R_C followed by PLE100.

FIG. 34-FIG. 72: Physicochemical Data

Particle size and zeta potential are routine measurements used in the characterization of colloidal nanomaterials. These measurements are primarily acquired through light scattering techniques such as DLS (dynamic light scattering). Nanoparticle tracking analysis (NTA) utilizes laser scattering microscopy and image analysis to obtain measurements of particle size and zeta potential with high resolution.

Analysis

Dispersity is a measure of sample heterogeneity and is determined by the distribution, where a low standard of deviation and single peak indicates particle uniformity.

Targeting ligands consisting of polypeptides with a ligand, (GGGGS)2 linker, and electrostatic anchor domain were synthesized by solid phase peptide synthesis and used to functionalize the silica surface (sheddable layer) of particles carrying pEGFP-N1 plasmid DNA payload. The resulting particle size and zeta potential distributions were obtained by nanoparticle tracking analysis using a ZetaVIEW instrument (Particle Metrix, Germany).

FIG. 34. (A) Core Polyplex Size distribution, consisting of pEGFP-N1 plasmid complexed with H3K4(Me3) and poly(L-Arginine) (29 kD, n=150). (B) Polyplex of FIG. 34A with silica sheddable layer exhibiting characteristic negative zeta potential and mean particle size of 124 nm. (C) E Selectin ligand with N terminal anchor and glycine-serine linker ((GGGGS)2) coated upon the particles shown in FIG. 34B.

FIG. 35. Branched Histone Peptide Conjugate Pilot Particle. Histone H3 peptide with a C-terminal Cysteine was conjugated to 48 kD poly(L-Lysine) with 10% side-chain thiol substitutions. The final product, purified by centrifugal filtration and molecular weight exclusion, was used to complex plasmid DNA (pEGFP-N1). The resulting measurements, portrayed in FIG. 35, show a narrow size distribution. Size Distribution of H3-Poly(L-Lysine) conjugate in complex with plasmid DNA (pEGFP-N1) For FIGS. 36-72, the data are indexed by experiment number (project code). In many cases, this can be cross-referenced to the project code of Table 4 (HSC=hematopoietic stem cells; BM=bone marrow cells; Tcell=T cells; blood=whole blood; cynoBM=cynomolgus bone marrow).

FIG. 36 provides data related to project HSC.001.001.

FIG. 37 provides data related to project HSC.001.002, which used H3-poly(L-Lysine) conjugate complexed to PNA-tagged pDNA and an E-Selectin targeting peptide (ESELLg_mESEL_(4GS)2_9R_N).

FIG. 38-FIG. 41 provide data for experiments in which various targeting ligands or stealth molecules were coated upon silica-coated particles and silica-coated nanodiamonds (for diagnostic enhanced fluorescent applications). Size and Zeta Potential distributions are presented with associated statistics. Targeting ligands were ESELLg_mESEL_(4GS)2_9R_N, ESELLg_mESEL_(4GS)2_9R_C, CD45_mSiglec_(4GS)2_9R_C, and Cy5mRNA-SiO2-PEG, respectively.

Performance of nanoformulations and targeting ligands was significantly improved in all data that follows-elimination of silica layer and replacement with a charged anionic sheddable polypeptide matrix significantly enhanced transfection efficiencies of nanoparticles across all formulations, with a variety of payloads and ligand-targeting approaches. However, the multilayering techniques used in the data above, as well as enhanced condensation with branched histone complexes and subsequent peptide matrix engineering (working examples are presented in Tcell.001, HSC.004, CYNOBM.002, and Blood.002) demonstrate the flexibility of the techniques (e.g., multilayering) and core biomaterials (e.g., see entirety of disclosure and subsequent experiments). All techniques described herein may be applied to any particle core, whether diagnostic or therapeutic, as well as to self-assembled materials. For example, branched histones may be conjugated to linker-ligand domains or co-condensed with a plurality of embodiments and uses thereof.

FIG. 42-FIG. 46 depict particles carrying Cy5-EGFP mRNA payload, complexed with a sheddable poly(glutamic acid) surface matrix and CD45 ligand. Nanoparticles produced using this formulation were highly uniform in particle size and zeta potential. Particles with poly(glutamic acid) added after SIGLEC-derived peptide association with mRNA (BLOOD.002.88) were more stable and monodisperse than particles with poly(glutamic acid) added before SIGLEC-derived association with mRNA and poly(glutamic acid), indicating that a particular order of addition can be helpful in forming more stable particles. Additionally, particles formed from poly(glutamic acid) complexed with SIGLEC-derived peptides without a phosphate-containing nucleic acid were highly anionic monodispersed (BLOOD.002.92). Particles formed from PLR50 with PLE100 added after PLR association with mRNA were highly stable, monodispersed and cationic (BLOOD.002.91). In contrast, PLK-PEG association with mRNA prior to PLE100 addition resulted in very small particles with heterogenous charge distributions. The efficacy of these order of addition and SIGLEC-derivative peptaides was demonstrated by flow cytometry data wherein ligand-targeted SIGLEC-derivative particles resulted in nearly two orders of magnitude more Cy5 intensity in whole blood cells despite similar transfection efficiencies to PEGylated controls.

FIG. 42 provides data from BLOOD.002.88. Nanoparticles had zeta potential of −3.32+/−0.29 mV with 90% having diameters less than 180 nm. These nanoparticles resulted in 58.6% efficient Cy5_EGFP_mRNA uptake in whole blood according to flow cytometry data. The narrow and uniform peak is exemplary of excellent charge distributions and was reproducible in forming net anionic particles in TCELL.001.18. This demonstrates broad applicability of SIGLEC-derived targeting peptides for systemic delivery (e.g., see flow cytometry and imaging data below).

FIG. 43 provides data from BLOOD.002.89. Nanoparticles hadzeta potential of −0.25+/−0.12 mV with 90% having diameters less than 176 nm. These nanoparticles resulted in 58.6% efficient Cy5_EGFP_mRNA uptake in whole blood respectively according to flow cytometry data. This demonstrates broad applicability of Siglec derived targeting peptide for systemic delivery (e.g., see flow cytometry and imaging data below).

FIG. 44 provides data from BLOOD.002.90. Nanoparticles had zeta potential of 2.54+/−0.03 mV with 90% having diameters less than 99 nm. These nanoparticles resulted in 79.9% efficient Cy5_EGFP_mRNA uptake in whole blood respectively according to flow cytometry data (e.g., see flow cytometry and imaging data below).

FIG. 45 provides data from BLOOD.002.91. Nanoparticles had zeta potential of 27.10 FWHM 18.40 mV with 90% having diameters less than 130 nm. These nanoparticles resulted in 96.7% efficient Cy5_EGFP_mRNA uptake in whole blood respectively according to flow cytometry data (e.g., see flow cytometry and imaging data below). Strongly positively charged zeta potentials led to high efficiencies and intensities of Cy5+ signal on whole blood cells. Briefly, in this embodiment, a larger dose of PLR50 (15 µl of PLR50 0.1% w/v solution) was added to 100 µl pH 5.5 30 mM HEPES with 2.5 ug Cy5 mRNA (TriLink). After 5 minutes at 37° C., 1.5 µl of PLE100 0.1% was added to the solution. In contrast, other experiments involved adding larger relative volumes (5-20% of total solution volume) of PLE100 to a preformed cationic polymer+anionic material core.

FIG. 46 provides data from BLOOD.002.92. Nanoparticles had zeta potential of −22.16 FWHM 18.40 mV with 90% having diameters less than 130 nm. These nanoparticles did not result in detectable Cy5_EGFP_mRNA uptake in whole blood according to flow cytometry data, as they were not labeled with a fluorophore (e.g., see flow cytometry and imaging data below). The effective condensation of these nanoparticles without a payload (vehicle) also has implications in non-genetic material payload delivery, such as conjugation of the charged polymer to a small molecule or chemotherapeutic agent.

FIG. 47-FIG. 62 depict results from experiments performed to characterize representative particles containing CRISPR ribonucleoprotein (RNP) (TCELL.001.01-TCELL.001.15), mRNA (TCELL.001.16-TCELL.001.30), plasmid DNA (TCELL.001.31-TCELL.001.45) and siRNA (TCELL.001.46-TCELL.001.60) and patterned with identical ligands in corresponding groups.

FIG. 47 provides data from TCELL.001.1. Nanoparticles had zeta potential of −3.24+/−0.32 mV with 90% having diameters less than 77 nm. These nanoparticles resulted in 99.16% and 98.47% efficient CRISPR-GFP-RNP uptake in viable CD4+ and CD8a+ pan T cells respectively according to flow cytometry data (e.g., see flow cytometry and imaging data below). These formulations were also reflective of physicochemical properties of all CYNOBM.002.75, as well as the cores serving as substrates for subsequent layering in CYNOBM.002.82-CYNOBM.002.85, wherein the PLR10-coated particle was complexed with a sheddable anionic coat of one or more anionic polypeptides, nucleic acids and/or charged macromolecules of a range of D:L ratios, molecular weights, and compositions. TCELL.001.1 was subsequently coated in PLE100+mRNA prior to addition of charged polymers or charged anchor-linker-ligands in CYNOBM.002.82-CYNOBM.002.85.

FIG. 48 provides data from TCELL.001.3. Nanoparticles had zeta potential of −0.98+/−0.08 mV with 90% having diameters less than 65 nm. Despite ideal size ranges, these nanoparticles resulted in 11.6% and 13.2% efficient CRISPR-GFP-RNP uptake in viable CD4+ and CD8a+ pan T cells, respectively, according to flow cytometry data in contrast to the strongly anionic similarly-sized particles in TCELL.001.1 that achieved ~99% efficiency in the same cell populations. The relationship of particle size and stable negative zeta potential and methods and uses thereof are shown to be predicable constraints through the experiments described herein. An ideal nanoparticle has a majority of particles <70 nm with zeta potentials of <−5 mV, and the sheddable anionic coating methods described herein as well as multistage-layering sheddable matrices for codelivery described in CYNOBM.002 achieve stable and extremely efficient transfection of sensitive primary cells from human and cynomolgus blood, bone marrow, and specific cells within the aforementioned. The reduced efficiency of TCELL.001.3 is a marked contrast to the results of TCELL.01.27, where the same ligands achieved stable condensation of mRNA at an altered amine-to-phosphate-to-carboxylate ratio than the one used for this particular CRISPR formulation (e.g., see flow cytometry and imaging data below).

FIG. 49 provides data from TCELL.001.13. Nanoparticles have zeta potential of 2.19+/−0.08 mV with 90% having diameters less than 101 nm. See flow cytometry/imaging data below for the efficiency of CRISPR-GFP-RNP uptake in viable CD4+ and CD8a+ pan T cells.

FIG. 50 provides data from TCELL.001.14. Nanoparticles have zeta potential of −9.37+/−0.16 mV with 90% having diameters less than 111 nm. These nanoparticles resulted in 25.7% and 28.6% efficient CRISPR-GFP-RNP uptake in viable CD4+ and CD8a+ pan T cells respectively according to flow cytometry data. (e.g., see flow cytometry and imaging data below).

FIG. 51 provides data from TCELL.001.16.

FIG. 52 provides data from TCELL.001.18. The size and zeta potential of these particles demonstrate average particle sizes of 80.9 nm with zeta potentials of −20.26+/−0.15 mV and 90% of particles with 39.2-129.8 nm diameters, indicating strong particle stability at a 1.35 carboxylate-to-phosphate (C:P) and 0.85 amine-to-phosphate ratio wherein poly(glutamic acid) was added following inclusion of the cationic anchor-linker-ligand. Please reference all zeta potential, size, flow cytometry and microscopy data of TCELL.001.2, TCELL.001.18, and CYNOBM.002 for additional general patterns, engineering constraints, observations and empirical measurements as relate to attaining high-efficiency primary cell transfections (e.g., see Table 4 and flow cytometry and imaging data below).

FIG. 53 provides data from TCELL.001.28. FIG. 54 provides data from TCELL.001.29. FIG. 55 provides data from TCELL.001.31. FIG. 56 provides data from TCELL.001.33. FIG. 57 provides data from TCELL.001.43. FIG. 58 provides data from TCELL.001.44. FIG. 59 provides data from TCELL.001.46. FIG. 60 provides data from TCELL.001.48. FIG. 61 provides data from TCELL.001.58. FIG. 62 provides data from TCELL.001.59.

FIG. 63-FIG. 72 depict results characterizing the formulations used in cynomolgus bone marrow cells.

FIG. 63 provides data from CYNOBM.002.82. Particles successfully deleted the BCL11a erythroid enhancer in whole bone marrow erythroid progenitor cells as evidenced by fetal hemoglobin protein expression in 3% of live cells. CYNOBM.002.82 nanoparticles had zeta potential of 2.96+/−0.14 mV with 90% having diameters less than 132 nm and 50% of particles with diameters less than 30 nm. These nanoparticles resulted in ~48%, ~53%, and ~97% efficient CRISPR-GFP-RNP+Cy5_EGFP_mRNA colocalized uptake of CRISPR RNP and Cy5 mRNA in viable CD3+, CD45+, and CD34+ bone marrow subpopulations, respectively, despite only 11.4% overall bone marrow viable subpopulation targeting according to flow cytometry data.

In contrast, CYNOBM.002.75, with an identical core template consisting of PLR10, PLE100, PDE100 and Cas9 RNP but without an mRNA co-delivery component or additional layer of PLR50, exhibited ~20%, ~14%, and ~100% efficient CRISPR-GFP-RNP uptake in viable CD3+, CD45+, and CD34+ bone marrow subpopulations, respectively, and 18.0% overall bone marrow viable subpopulation targeting according to flow cytometry data.

With these data, it can be inferred that larger particles may be less amenable to selective targeting even when minor enhancements were seen in overall transfection efficiency within a mixed bone marrow primary population. The effects of bimodal distributions of particles on primary cell culture transfections remains to be determined. In prior work, osteoblasts were found to endocytose 150-200 nm particles with high efficiency. Strikingly, the majority of population of particles with CYNOBM.002.82 was below the 85 nm peak, similarly to TCELL.001.1 but with a positively charged positive matrix of PLR50 surrounding the underlying polypeptide-ribonucleoprotein-mRNA-protein matrix of PLE, PDE, mRNA and Cas9 RNP.

Additionally, 3.0% of overall viable cells were positive for fetal hemoglobin, with none of these cells being CD34+, suggesting successful clonal expansion of BCL11a erythroid progenitor knockout populations within CD34− erythroid progenitor cells. (e.g., see flow cytometry and imaging data below). The results may also implicate successful targeting in endothelial cells, osteoblasts, osteoclasts, and other cells of the bone marrow.

FIG. 64 provides data from CYNOBM.002.83. Particles successfully deleted the BCL11a erythroid enhancer in whole bone marrow erythroid progenitor cells as evidenced by fetal hemoglobin protein expression in 1.9% of live cells, with none of these cells being CD34+. The nanoparticles had a zeta potential of −2.47+/−0.33 mV with 90% having diameters less than 206 nm, leading to improved transfection efficiency vs. CYNOBM.002.03 with the same IL2-mimetic peptide coating. The large charge distribution with tails at approximately −50 mV and +25 mV were indicative of a polydisperse particle population with a variance of particle stabilities, similarly to CYNOBM.002.83, and in contrast to CYNOBM.002.84 which has a stable anionic single-peak zeta potential of −18 mV and corresponding increase in cellular viability compared to other CRISPR+ mRNA co-delivery particle groups (CYNOBM.002.82-CYNOBM.002.85). The next-best nanoparticle group in terms of overall cynomolgus bone marrow co-delivery was CYNOBM.002.86, which demonstrated similar highly net-negatively charged zeta potential of −20 mV and a corresponding high efficiency of transfection, CD34 clonal expansion, and fetal hemoglobin production from BCL11a erythroid enhancer knockout. These nanoparticles resulted in ~100% efficient CRISPR-GFP-RNP+Cy5_EGFP_mRNA uptake in viable CD34+ bone marrow cells, within mixed cell populations, as well as 8.1% of whole bone marrow viable subpopulations according to flow cytometry data. The flow cytometry data indicates induction of selective CD34+ proliferation in cynomolgus bone marrow cells. suggesting successful clonal expansion of BCL11a erythroid progenitor knockout populations within CD34− erythroid progenitor cells. (e.g., see flow cytometry and imaging data below). The results also implicate successful targeting in endothelial cells, osteoblasts, osteoclasts, and/or other cells of the bone marrow.

FIG. 65 provides data from CYNOBM.002.84. Particles successfully deleted the BCL11a erythroid enhancer in whole bone marrow erythroid progenitor cells as evidenced by fetal hemoglobin protein expression in 9.5% of live whole bone marrow cells and no positive fetal hemoglobin measurements in CD34+, CD45 or CD3+ subpopulations despite moderate transfection efficiencies, as measured by Cy5-mRNA+ and CRISPR-GFP-RNP+ gates in each selective subpopulation. CYNOBM.002.84 nanoparticles had zeta potential of −18.07+/−0.71 mV with 90% having diameters less than 205 nm. The high net-negative charge indicates stable particle formation. These nanoparticles resulted in 76.5%, 71%, and ~100% efficient CRISPR-GFP-RNP+ Cy5_EGFP_mRNA uptake in viable CD3+, CD45+, and CD34+ bone marrow cells, respectively, as well as 25.5% of whole bone marrow viable subpopulations according to flow cytometry data. Additionally, 9.5% of overall viable cells were positive for fetal hemoglobin, with none of these cells being CD34+, suggesting successful clonal expansion of BCL11a erythroid progenitor knockout populations within CD34− erythroid progenitor cells. (e.g., see flow cytometry and imaging data below). The results also implicate successful targeting in endothelial cells, osteoblasts, osteoclasts, and/or other cells of the bone marrow.

FIG. 66 provides data from CYNOBM.002.85. Nanoparticles had zeta potential of −12.54+/−0.25 mV with 90% having diameters less than 186 nm. These nanoparticles resulted in ~33%, ~23%, and ~100% efficient CRISPR-GFP-RNP+Cy5_EGFP_mRNA uptake in viable CD3+, CD45+, and CD34+ bone marrow cells, respectively, according to flow cytometry data. (e.g., see flow cytometry and imaging data below). The results may implicate successful targeting in endothelial, osteoblasts, osteoclasts, and other cells of the bone marrow. Particle sizes and charge distributions were consistent with subsequent CYNOBM.002 groups and their expected biological performance in cynomolgus bone marrow CRISPR and/or mRNA delivery.

FIG. 67 provides data from CYNOBM.002.86. Nanoparticles had zeta potential of −20.02+/−0.10 mV with 90% having diameters less than 120 nm. These nanoparticles resulted in 20.1% efficient codelivery of CRISPR-GFP-RNP+Cy5_EGFP_mRNA in viable cynomolgus bone marrow, with ~68%, 70%, and ~97% efficient CD3+, CD45+, and CD34+ respective targeting according to flow cytometry data. (e.g., see flow cytometry and imaging data below). The results may implicate successful targeting in endothelial, osteoblasts, osteoclasts, and other cells of the bone marrow. A highly negatively charged zeta potential and of 90% of particles counts <200 nm predicts high efficiency.

FIG. 68 provides data from CYNOBM.002.76. Nanoparticles had zeta potential of −12.02+/−0.59 mV with 90% having diameters less than 135 nm. These nanoparticles resulted in 18.4%, 10.3%, and ~100% efficient CRISPR-GFP-RNP uptake in viable CD3+, CD45+, and CD34+ bone marrow cells, respectively, according to flow cytometry data (e.g., see flow cytometry and imaging data below). Additionally, particles exhibit limited toxicity as expected from a histone-mimetic particle with highly negative zeta potential 10th-50th percentile particle sizes of 25.8-80.6 nm with no large aggregates as seen in CYNOBM.002.78, which exhibits similar zeta potential distributions and sizes with the addition of a large volume peak at ~500 nm.

FIG. 69 provides data from CYNOBM.002.77. Nanoparticles had 90% of their diameters below 254 nm with a large portion in the 171-254 nm range. (e.g., see flow cytometry and imaging data below). Additionally, the 10th-50th percentile particles by number were 70-172 nm, indicating a reasonable size distribution within this population. Consistent with other studies where a large number of particles >200 nm existed in solution and/or had a large, distributed zeta potential and/or a non-anionic zeta potential, these particles lead to significant cell death. These nanoparticles resulted in high uptake percentages overall, but a large number of cells (>90%) being dead. Ultimately, the particles resulted in negligible uptake at the limits of detection of CRISPR-GFP-RNP in viable CD3+, CD45+, and CD34+ bone marrow cells, and 3.8% CRISPR uptake within whole bone marrow viable subpopulations according to flow cytometry data. In contrast, 90% of CYNOBM.002.83 (a CRISPR & mRNA codelivery variant) particles with the same surface coating were below 200 nm with the number average being 121 nm. Other particles in CYNOBM.002.75-CYNOBM.002.81, which were produced via a different method than particles in TCELL.001.01-TCELL.001.15 with similar formulations, had more favorable size and zeta potential distributions and resulted in high transfection efficiencies (up to 99%) in viable human CD4+ and CD8a+ T-cells.

FIG. 70 provides data from CYNOBM.002.78. Nanoparticles had zeta potential of −11.72+/−0.79 mV with 90% having diameters less than 223 nm. (e.g., see flow cytometry and imaging data below). Similarly, 90% of CYNOBM.002.84 (a CRISPR & mRNA codelivery variant) particles with the same surface coating were below 200 nm with the number average being 125 nm, though the zeta potential of CYNOBM.002.84 is significantly more negative (−18.07 mV vs. −11.72 mV), indicating enhanced stability with an anionic sheddable interlayer step intermediate to initial Cas9 RNP charge homogenization with PLR10 and subsequent coating with ligands or additional, optionally molecular weight staggered polymers or polypeptides. The differential physicochemical properties of these monodelivery vs. co-delivery (or interlayer vs. direct conjugation of ligands to RNP) nanoparticles and their respective size ranges is strongly correlated to transfection efficiency and toxicity.

FIG. 71 provides data from CYNOBM.002.79. Nanoparticles had diameters less than 200 nm. These nanoparticles resulted in very low (3.7%) GFP-RNP uptake in bone marrow overall, but the cells retained exceptional viability (70.0% vs. 71.6% for negative controls) in the culture. Despite very low overall uptake, the particles demonstrated selective uptake for ~9.0% of viable CD3+ cells, 4.4% of viable CD45+ cells, and ~100% of viable CD34+ cells according to flow cytometry data, which is at the limits of detection for cell counts in the CD34+ subpopulation. (e.g., see flow cytometry and imaging data below). The results implicate specific targeting of CD34+ hematopoietic stem cells within mixed cell populations.

FIG. 72 provides data from CYNOBM.002.80. Nanoparticles had zeta potential of 1.36+/−1.69 mV. These nanoparticles resulted in 8% transfection efficiency and ~100% efficient CRISPR-GFP-RNP uptake in viable CD34+ bone marrow cells according to flow cytometry data, which is at the limits of detection for cell counts. (e.g., see flow cytometry and imaging data below). The results may implicate successful targeting in endothelial, osteoblasts, osteoclasts, and other cells of the bone marrow. The even peak at ~0 mV with wide surfaces is indicative of a zwitterionic particle surface. A high degree of cellular viability indicates that particles were well tolerated with this size and that a c-Kit-receptor-derived particle surface is likely to mimic presentation of native stem cell population surface markers within the bone marrow during cell-cell interactions.

FIG. 73-FIG. 109: Flow Cytometry and Imaging Data

Figure 73:
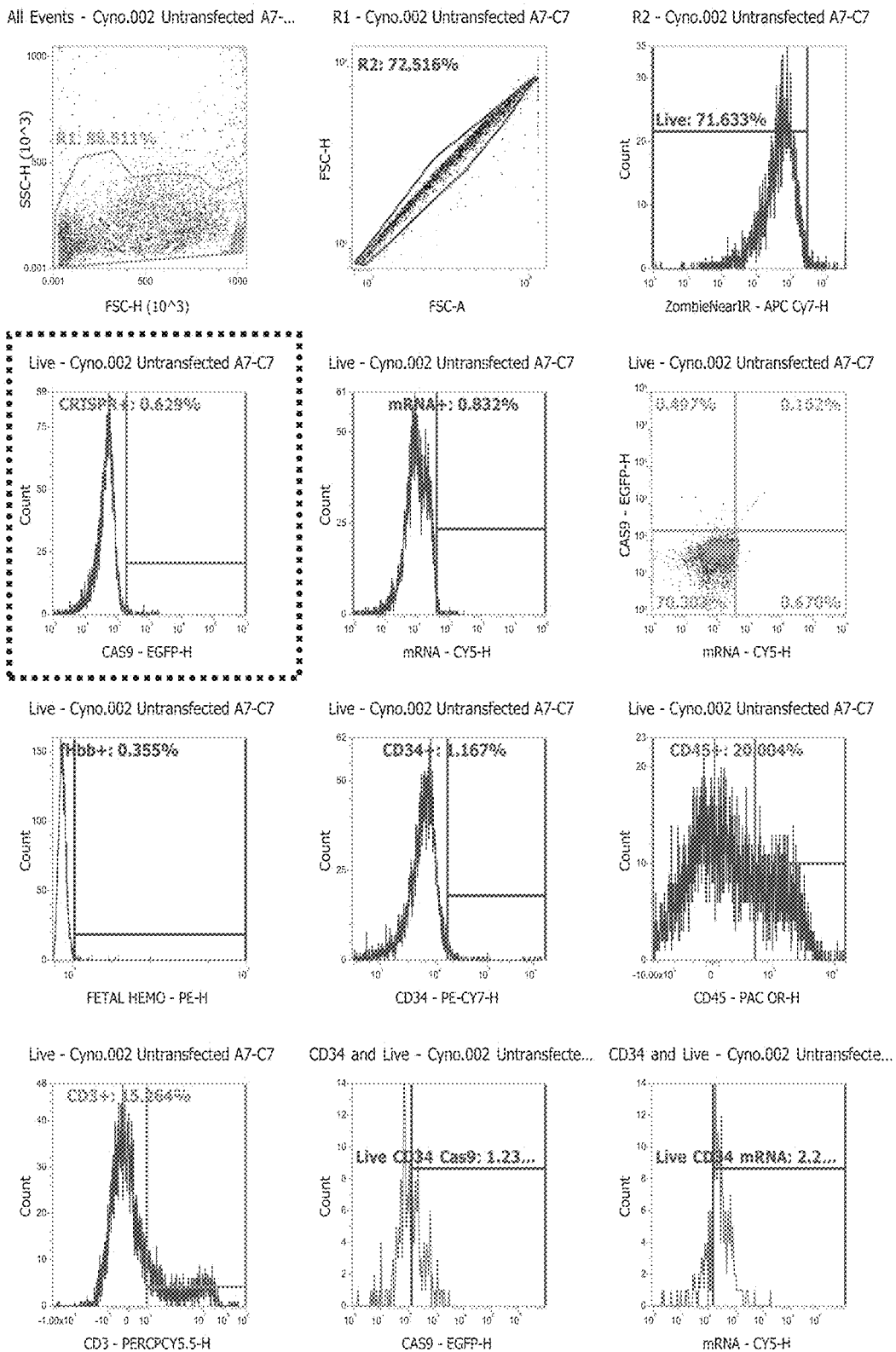
FIG. 73 provides data related to untransfected controls for CynoBM.002 samples.

FIG. 73. Untransfected controls for CynoBM.002 samples in cynomolgus bone marrow. Microscope images—Top: digital phase contrast; middle: GFP; bottom: merge. Flow cytometry data—with viability, CD34, CD3, and CD45 stains.

Figure 74:
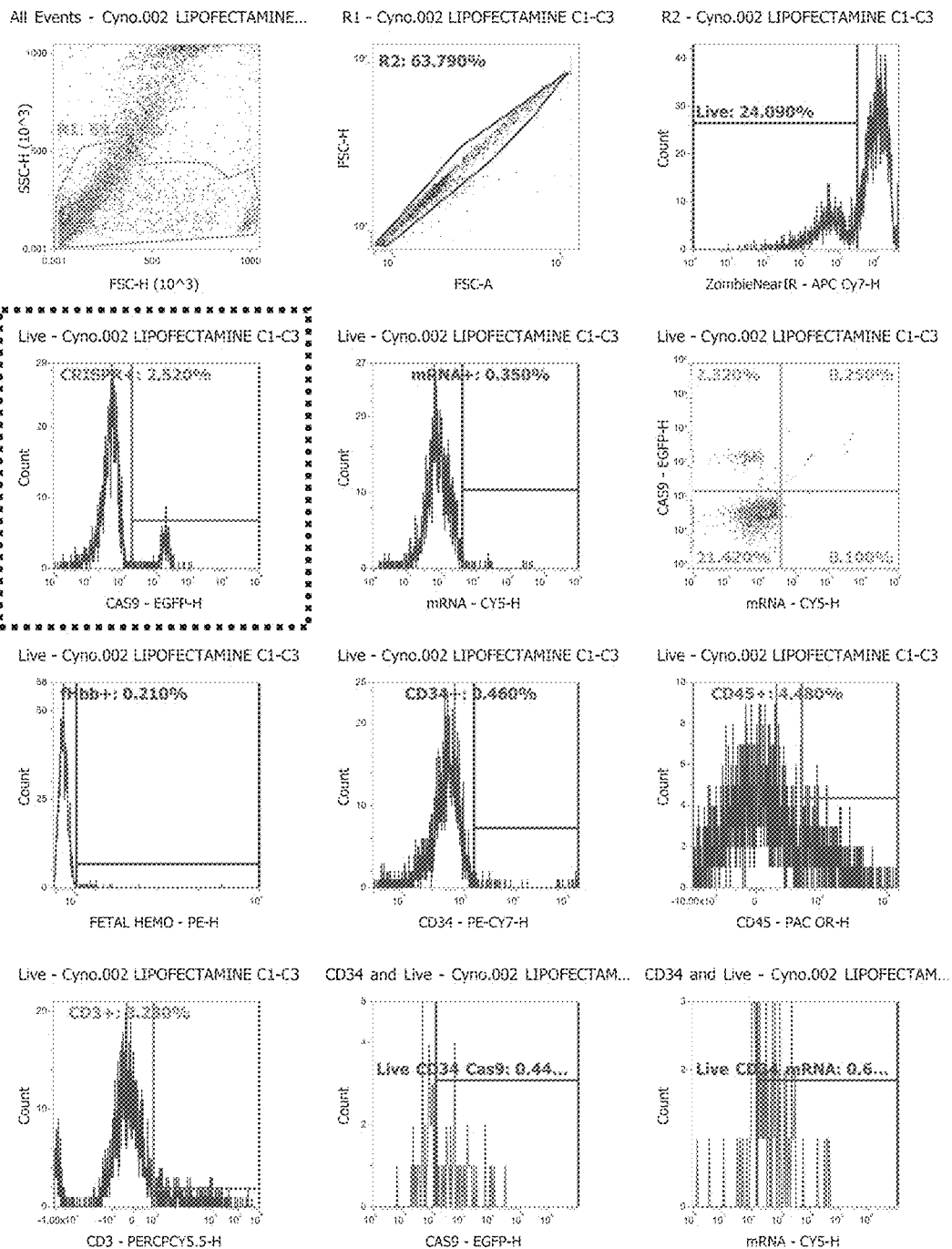
FIG. 74 provides data related to lipofectamine CRISPR-MAX delivery of NLS-Cas9-EGFP BCL11a gRNA RNPs.
Figure 81:
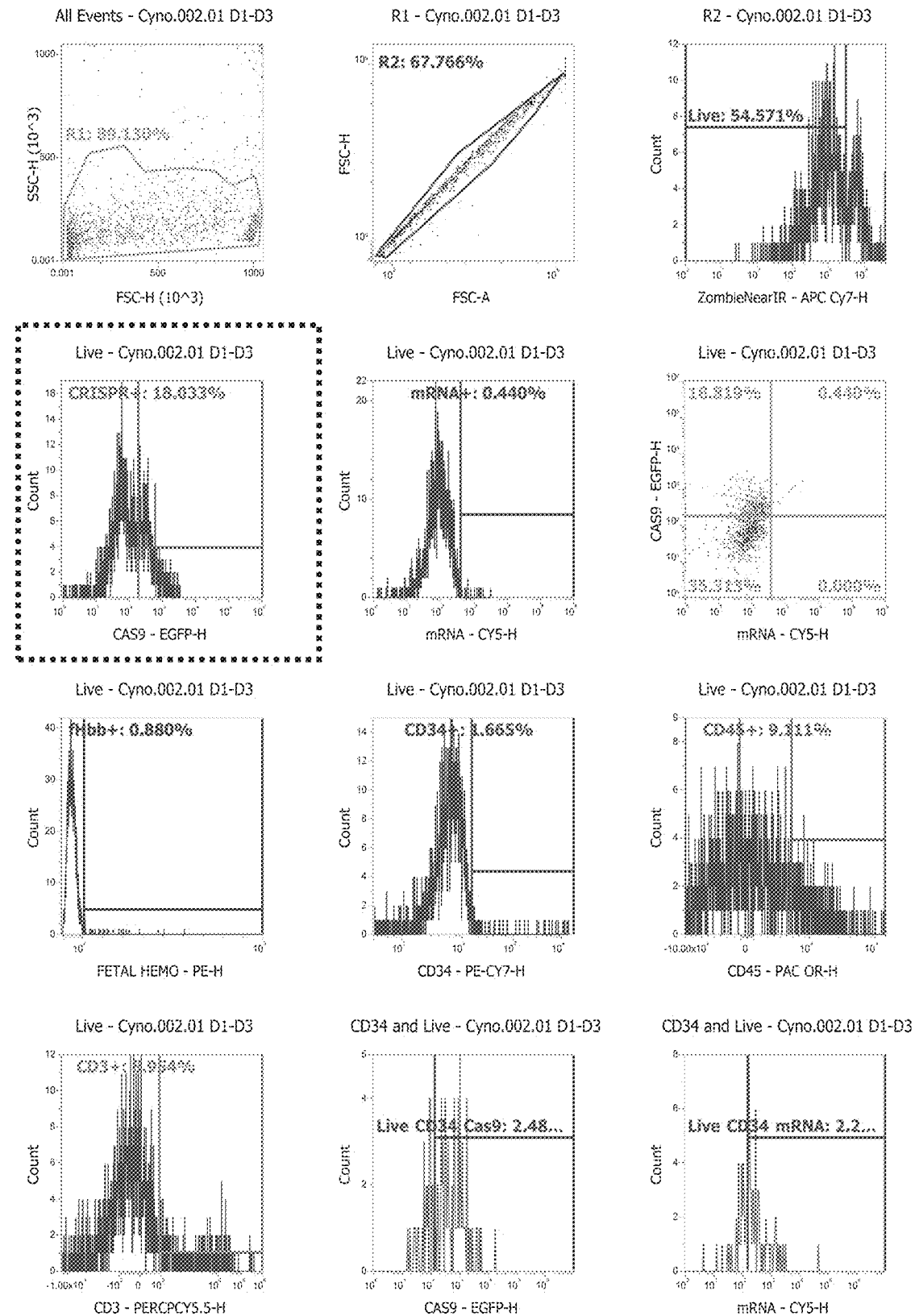
FIG. 81 provides data related to project CynoBM.002.75 (see Table 4).

FIG. 74. Lipofectamine CRISPRMAX delivery of NLS-Cas9-EGFP BCL11a gRNA RNPs attains 2.5% transfection efficiency in viable cells and causes significant toxicity, with percentage of CD45 and CD3 relative subpopulations significantly decreased compared to negative controls in cynomolgus bone marrow. Lipofectamine CRISPRMAX does not exhibit cell-selectivity as exemplified by 7.4% efficient targeting of remaining CD3+ cells and negligible remaining populations of CD45+ and CD34+ cells. Microscope images—Top: digital phase contrast; middle: GFP; bottom: merge.

FIG. 75. CynoBM.002 RNP-Only controls show NLS-Cas9-EGFP BCL11a gRNA RNPs attaining negligible transfection efficiencies in cynomolgus bone marrow without a delivery vector, but with both payloads pre-combined prior to transfection. A high degree of colocalization despite no delivery vector and minimal events is indicative of association of the ribonucleoprotein complex with mRNA, and exemplary of anionic functionalization of CRISPR RNPs. (In this instance, the mRNA acts as a loosely-associated sheddable coat for the RNP and could be further layered upon with cationic materials). Calculating colocalization coefficient. X: % CRISPR uptake in live cells:
Y: % mRNA uptake in live cells
C: % of cells with CRISPR AND mRNA
Z: value of X or Y, whichever is greater
Colocalization Coefficient=C/Z
Cas9-mRNA Colocalization Coefficient: 92.2%

FIG. 76. CynoBM.002.82 demonstrated that non-specifically-targeted NLS-Cas9-EGFP achieves 11.3% efficient mRNA delivery and 11.4% efficient CRISPR delivery to cynomolgus bone marrow with a 98.9% colocalization coefficient. Subcellular localization demonstrated that noonspecifically targeted NLS-Cas9-EGFP BCL11a gRNA RNPs co-localize with Cy5 mRNA and attain high transfection efficiencies. A high degree of colocalization determines that discrete particles were loaded with both payloads. Additionally, Cas9 can be seen neatly localized in a separate compartment from the mRNA, wherein the mRNA forms a ringed structure around the nuclear-associated Cas9. This indicates cytosolic (mRNA) vs. nuclear (CRISPR) localization of the two payloads. Microscope images—Top: digital phase contrast; middle: Cy5 mRNA; bottom: merge. and top: Cas9-GFP RNP; bottom: Cy5 mRNA colocalized with Cas9-GFP RNP.

See above data for physicochemical parameters and additional observations. CYNOBM.002.82 had zeta potential of 2.96+/−0.14 mV with 90% having diameters less than 132 nm and 50% of particles with diameters less than 30 nm. These nanoparticles resulted in 45.5%, 56.0%, and 97.3% efficient CRISPR-GFP-RNP+Cy5_EGFP_mRNA uptake in viable CD3+, CD45+, and CD34+ bone marrow subpopulations, respectively, despite only 11.4% overall bone marrow viable subpopulation targeting. Cas9-mRNA Colocalization Coefficient: 94.8%. Viable CD34+ and CRISPR+: 97.2% of Viable CD34+. Fetal Hemoglobin Positive: 3.022% of viable cells FIG. 77. CynoBM.002.83 achieves 8.1% efficient mRNA delivery and 8.1% efficient CRISPR delivery to cynomolgus bone marrow with a 93.0% colocalization coefficient. Subcellular localization demonstrated that homovalently-targeted IL2-derived peptides associated with NLS-Cas9-EGFP BCL11a gRNA RNPs co-localize with Cy5 mRNA and attain high transfection efficiencies. A high degree of colocalization determines that discrete particles were loaded with both payloads. Additionally, Cas9 can be seen neatly localized in a separate compartment from the mRNA, wherein the mRNA forms a ringed structure around the nuclear-associated Cas9. This indicates cytosolic (mRNA) vs. nuclear (CRISPR) localization of the two payloads. Microscope images—Top: digital phase contrast; middle: Cy5 mRNA; bottom: merge. and top: Cas9-GFP RNP; bottom: Cy5 mRNA colocalized with Cas9-GFP RNP.

See above data for physicochemical parameters and additional observations. These nanoparticles resulted in ~27%, 41%, and ~100% efficient CRISPR-GFP-RNP+Cy5_EGFP_mRNA uptake in viable CD3+, CD45+, and CD34+ bone marrow cells, respectively. Cas9-mRNA Colocalization Coefficient: 93.0%. Fetal Hemoglobin Positive: 1.9% of viable cells FIG. 78. CYNOBM.002.84 particles successfully delete the BCL11a erythroid enhancer in whole bone marrow erythroid progenitor cells as evidenced by fetal hemoglobin protein expression in 9.5% of live whole bone marrow cells and no positive fetal hemoglobin measurements in CD34+, CD45 or CD3+ subpopulations despite moderate transfection efficiencies, as measured by Cy5-mRNA+ and CRISPR-GFP-RNP+ gates in each selective subpopulation. Subcellular localization demonstrated that homovalently-targeted E-selectin-derived peptides associated with NLS-Cas9-EGFP BCL11a gRNA RNPs co-localize with Cy5 mRNA and attain high transfection efficiencies. A high degree of colocalization determines that discrete particles were loaded with both payloads. Additionally, Cas9 can be seen neatly localized in a separate compartment from the mRNA, wherein the mRNA forms a ringed structure around the nuclear-associated Cas9. This indicates cytosolic (mRNA) vs. nuclear (CRISPR) localization of the two payloads. Microscope images—Top: digital phase contrast; middle: Cy5 mRNA; bottom: merge. and top: Cas9-GFP RNP; bottom: Cy5 mRNA colocalized with Cas9-GFP RNP.

See above data for physicochemical parameters and additional observations. These nanoparticles resulted in 76.5%, 71%, and ~100% efficient CRISPR-GFP-RNP+Cy5_EGFP_mRNA colocalized uptake in viable CD3+, CD45+, and CD34+ bone marrow cells, respectively, as well as ~25.5% of whole bone marrow viable subpopulations according to flow cytometry data. Additionally, 9.5% of overall viable cells were positive for fetal hemoglobin, with none of these cells being CD34+, CD3+, or CD45+, suggesting successful clonal expansion of BCL11a erythroid progenitor knockout populations within CD34− erythroid progenitor cells. Cas9-mRNA Colocalization Coefficient: 97.1%. Fetal Hemoglobin (HbF) Positive: 9.5% of viable cells 14% CD34+ cells; 0% colocalization of CD34+ and HbF+

FIG. 79. CynoBM.002.85 achieved 5.2% efficient mRNA delivery and 5.3% efficient CRISPR delivery to cynomolgus bone marrow with a 87.2% colocalization coefficient. Despite 5.3% efficient CRISPR delivery to viable cells, CynoBM.002.85 did not lead to a concomitant increase in fetal hemoglobin positive cells as seen in other codelivery embodiments. Subcellular localization demonstrated that homovalently-targeted SCF-derived peptides associated with NLS-Cas9-EGFP BCL11a gRNA RNPs co-localize with Cy5 mRNA and attain high transfection efficiencies. A high degree of colocalization determined that discrete particles were loaded with both payloads. Additionally, Cas9 could be seen neatly localized in a separate compartment from the mRNA, wherein the mRNA forms a ringed structure around the nuclear-associated Cas9. This indicates cytosolic (mRNA) vs. nuclear (CRISPR) localization of the two payloads. Microscope images—Top: digital phase contrast; middle: Cy5 mRNA; bottom: merge. and top: Cas9-GFP RNP; bottom: Cy5 mRNA colocalized with Cas9-GFP RNP.

See above data for additional physicochemical characteristics. These nanoparticles resulted in ~33%, ~23%, and ~100% efficient CRISPR-GFP-RNP+Cy5_EGFP_mRNA uptake in viable CD3+, CD45+, and CD34+ bone marrow cells, respectively. Cas9-mRNA Colocalization Coefficient: 87.2%. Fetal Hemoglobin Positive: 0.9% of viable cells FIG. 80. CynoBM.002.86 achieved 20.1% efficient mRNA delivery and 21.8% efficient CRISPR delivery to cynomolgus bone marrow with a 98.6% colocalization coefficient. Subcellular localization demonstrated that heterotrivalently-targeted IL2-, E-selectin- and SCF-derived NLS-Cas9-EGFP BCL11a gRNA RNPs co-localized with Cy5 mRNA and attain high transfection efficiencies. A high degree of colocalization determined that discrete particles were loaded with both payloads. Additionally, Cas9 could be seen neatly localized in a separate compartment from the mRNA, wherein the mRNA forms a ringed structure around the nuclear-associated Cas9. This indicates cytosolic (mRNA) vs. nuclear (CRISPR) localization of the two payloads. Microscope images—Top: digital phase contrast; middle: Cy5 mRNA; bottom: merge. and top: Cas9-GFP RNP; bottom: Cy5 mRNA colocalized with Cas9-GFP RNP.

See above data for additional physicochemical characteristics.Cas9-mRNA Colocalization Coefficient: 91.3%. Fetal Hemoglobin Positive: 7.6% of viable cells FIG. 81. CynoBM.002.75 demonstrated that non-specifically-targeted NLS-Cas9-EGFP BCL11a gRNA RNPs with sheddable anionic polypeptide coats attain 18.0% transfection efficiency in viable cynomolgus bone marrow. Overall, 20% of viable CD3+ T-cells were CRISPR+ in the mixed population cynomolgus bone marrow culture model herein, in contrast to 97-99% of viable CD4 and CD8a T-cells in human primary Pan T-cells being CRISPR+ in TCELL.001. Particle sizes of an identical formulation were smaller and more uniform in TCELL1, which was synthesized via fluid-handling robotics as opposed to by hand. See above data for additional qualitative and quantitative commentary and data comparisons. Top: digital phase contrast; middle: GFP; bottom: merge.

Figure 82:
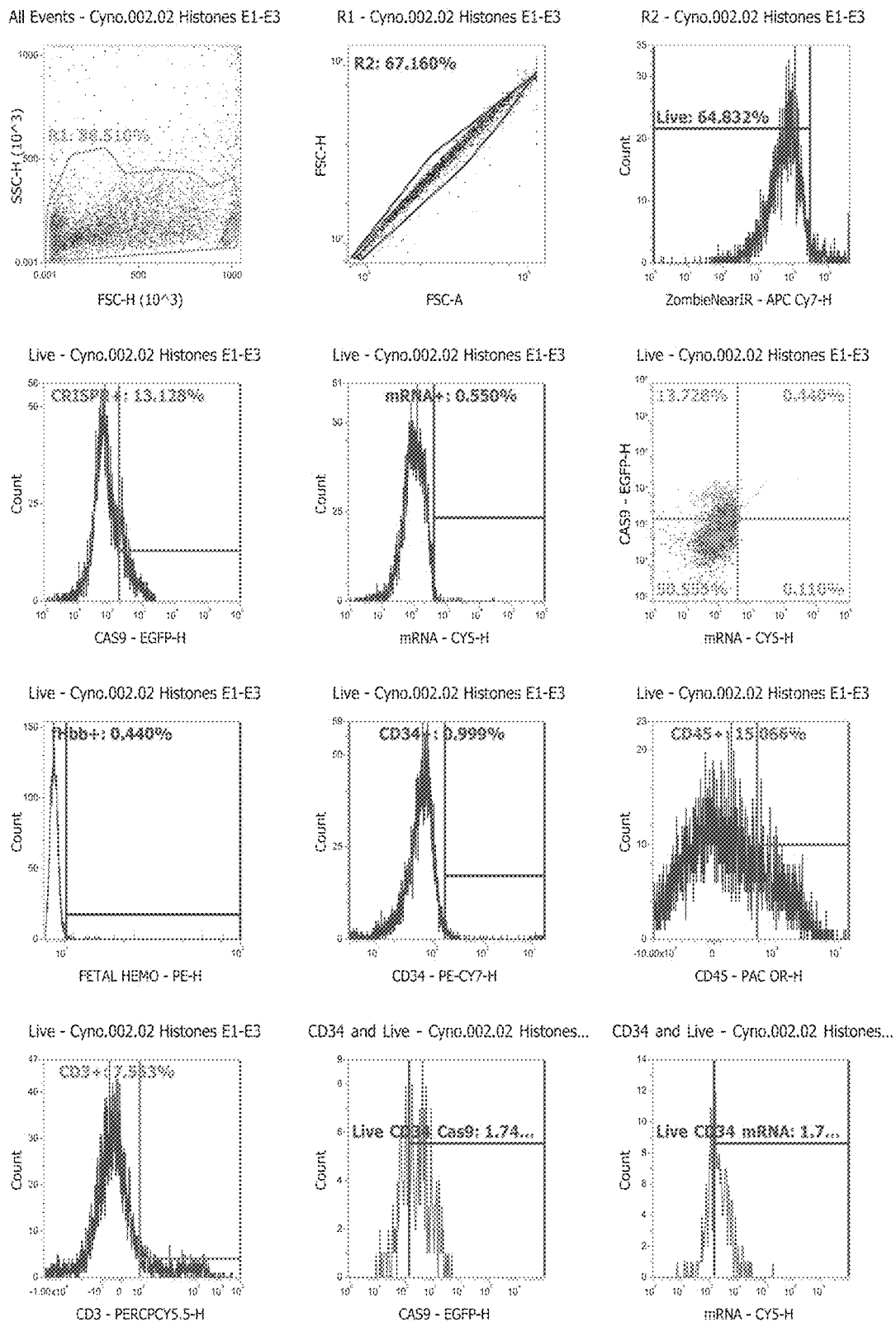
FIG. 82 provides data related to project CynoBM.002.76 (see Table 4).

FIG. 82. CynoBM.002.76 demonstrated that dual-histone-fragment-associated and non-specifically-targeted NLS-Cas9-EGFP BCL11a gRNA RNPs attain 13.1% transfection efficiency and limited toxicity versus negative controls in cynomolgus bone marrow. 18%, 10%, and 0% of CD3+, CD45+ and CD34+ viable subpopulations were CRISPR+. See above data for additional physicochemical characteristics and observations. Top: digital phase contrast; middle: GFP; bottom: merge.

Figure 83:
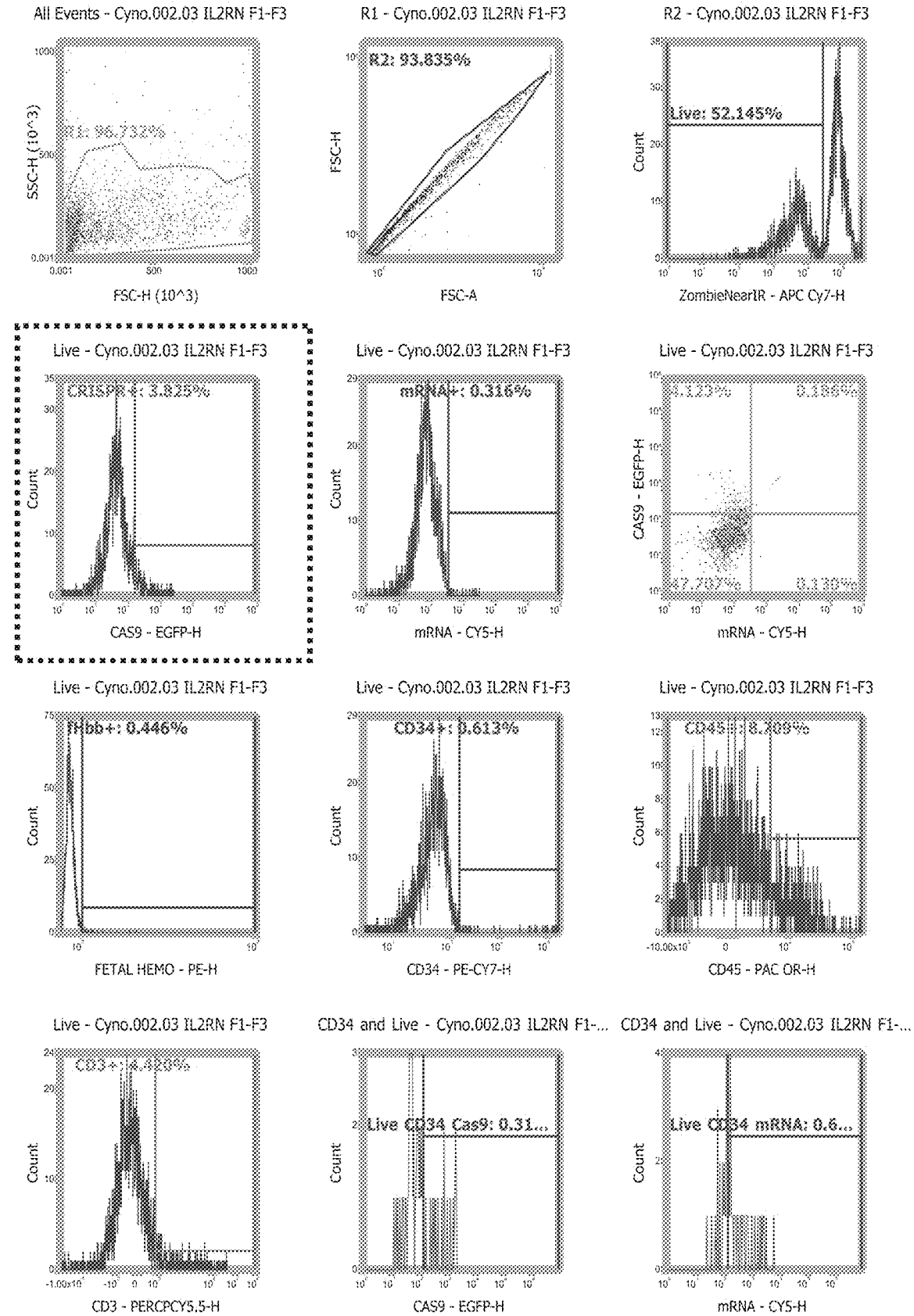
FIG. 83 provides data related to project CynoBM.002.77 (see Table 4).

FIG. 83. CynoBM.002.77 demonstrated that homovalently-targeted IL2-derived peptides associated with NLS-Cas9-EGFP BCL11a gRNA RNPs attain 3.8% transfection efficiency and enhanced viability over negative controls in cynomolgus bone marrow. ~90% of transfected cells were dead. Ultimately, the particles resulted in negligible uptake at the limits of detection of CRISPR-GFP-RNP in viable CD3+, CD45+, and CD34+ bone marrow cells, indicating that the remaining 3.8% of live CRISPR+ cells were not from those subpopulations. Size data supports a causative role for toxicity in large particle polydispersity and ~999 nm 90th volume percentile particle sizes. See above data for additional physicochemical properties. Top: digital phase contrast; middle: GFP; bottom: merge.

Figure 84:
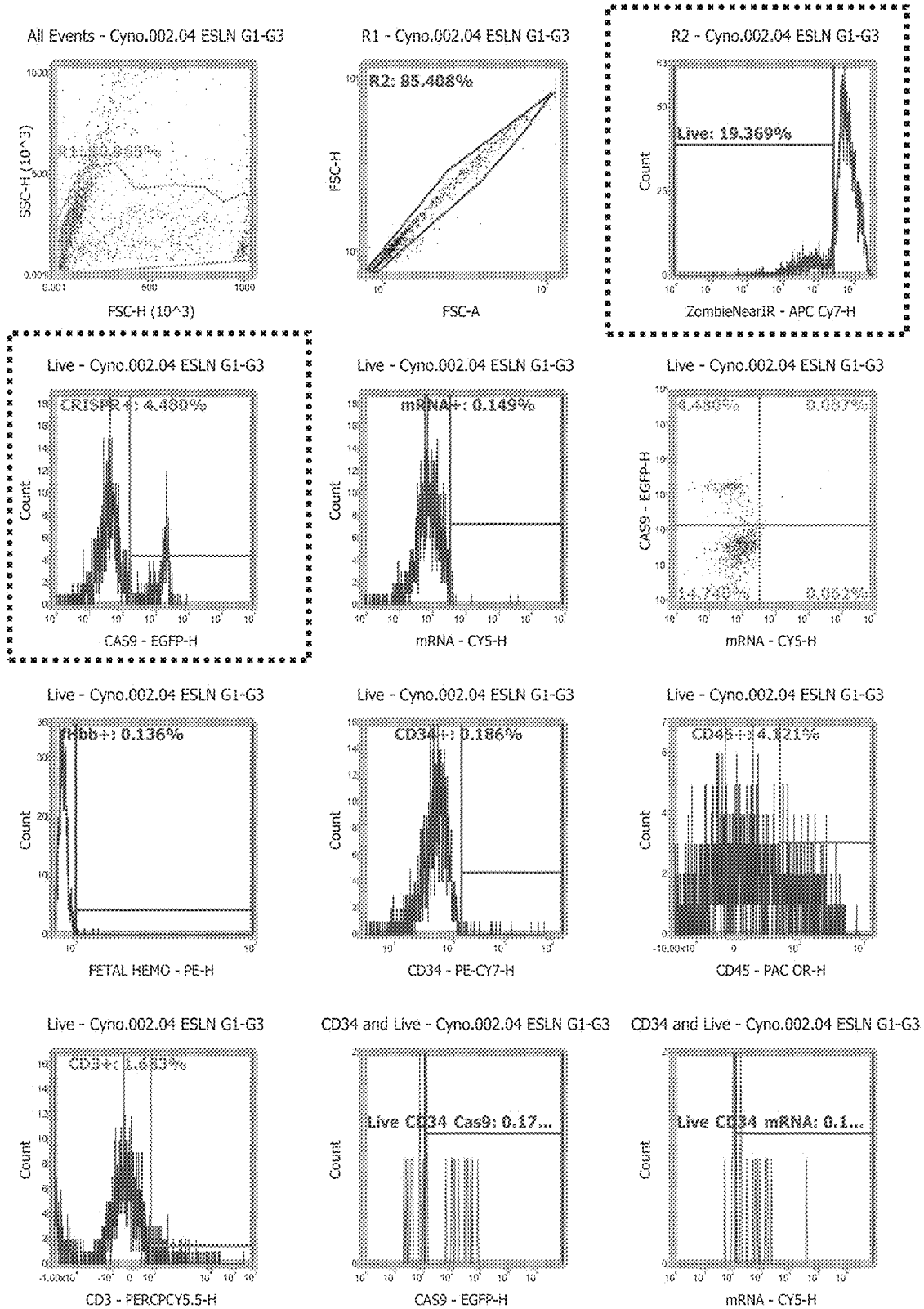
FIG. 84 provides data related to project CynoBM.002.78 (see Table 4).

FIG. 84. CynoBM.002.78 demonstrated that homovalently-targeted E-selectin-derived peptides associated with NLS-Cas9-EGFP BCL11a gRNA RNPs attain ~71% transfection efficiency overall (including dead cells), with only 4.5% of live cells remaining transfected in cynomolgus bone marrow. This is indicative of particle toxicity and may be correlated to a large size distribution, despite 50% of the particles by number being 33.1-113.1 nm. The >250 nm particles, comprising the majority of particle mass and volume in solution, likely led to the reduced viability of this experiment. CD45+ and CD3+ subpopulation densities were manifold reduced in this embodiment as well. See above data for more detailed physicochemical characteristics and qualitative observations comparing nanoparticle groups from the same transfection. Top: digital phase contrast; middle: GFP; bottom: merge.

Figure 85:
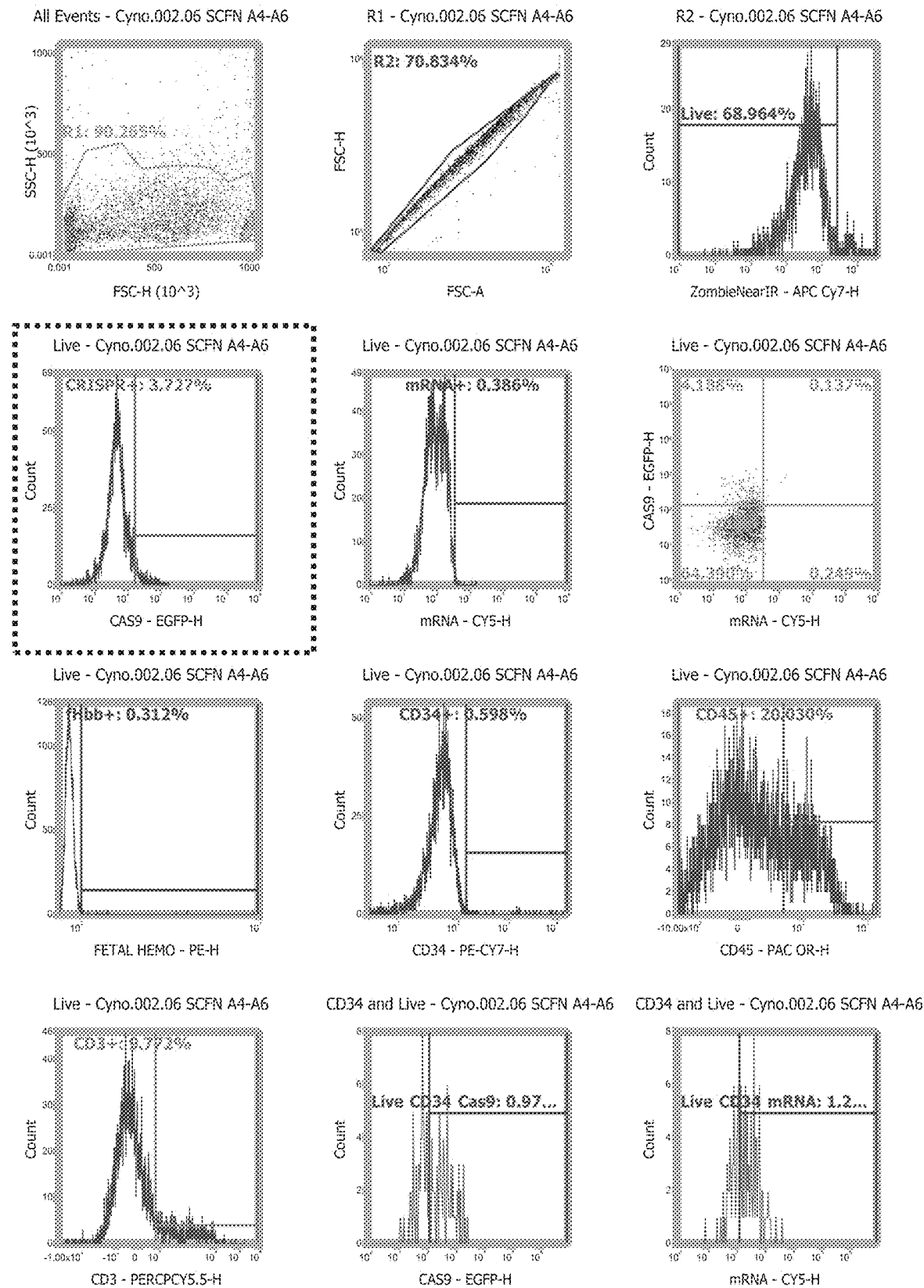
FIG. 85 provides data related to project CynoBM.002.79 (see Table 4).

FIG. 85. CynoBM.002.79 demonstrated that homovalently-targeted SCF-derived peptides associated with NLS-Cas9-EGFP BCL11a gRNA RNPs attain 3.7% transfection efficiencies and excellent viability over negative controls in cynomolgus bone marrow. These nanoparticles resulted in very low (3.7%) GFP-RNP uptake in bone marrow overall, but the cells retained exceptional viability (69.0% vs. 71.6% for negative controls) in the culture. Despite very low overall uptake, the particles demonstrated selective uptake for ~5% of viable CD3+ cells, ~4% of viable CD45+ cells, and ~100% of viable CD34+ cells (the latter which were at the limits of detection in number). The high degree of cellular viability coupled with a strongly negative zeta potential and significantly more CD45+ cells than other groups is implicative of a SCF-mimetic particle surface's multifactorial role in establishing stem cell niche targeting and proliferation and/or survival techniques. See above data for additional physicochemical parameters. Top: digital phase contrast; middle: GFP; bottom: merge.

Figure 86:
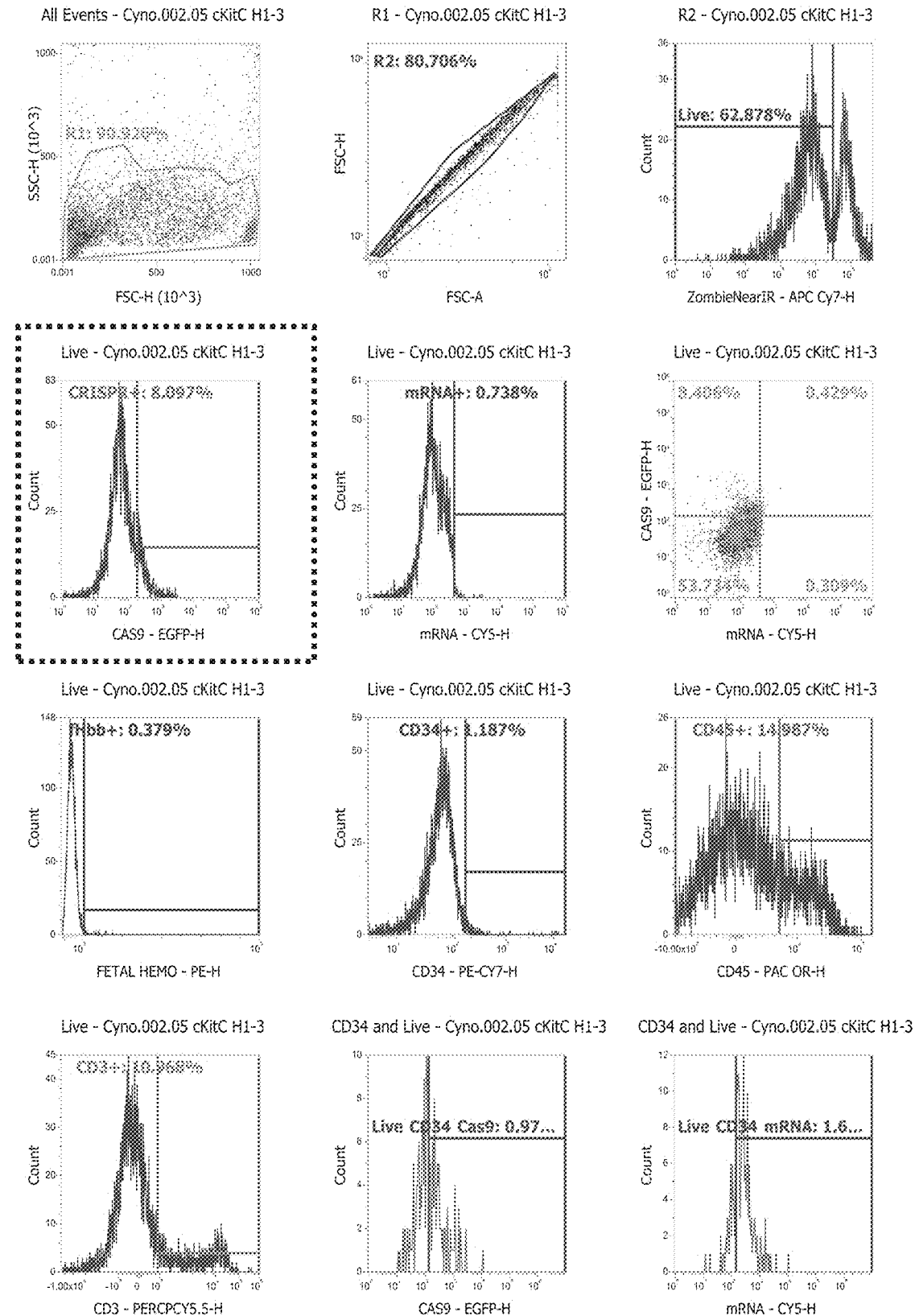
FIG. 86 provides data related to project CynoBM.002.80 (see Table 4).

FIG. 86. CynoBM.002.80 demonstrated that homovalently-targeted c-Kit-(CD117)-derived peptides associated with NLS-Cas9-EGFP BCL11a gRNA RNPs attain 8.097% transfection efficiencies. Transfection efficiencies were 3.3%, 2.4%, and at the limits of detection for CD3+, CD45+ and CD34+ viable subpopulations, respectively, indicating low selectivity for CD3+ and CD45+ cells. See above data for more quantitative and qualitative data. Top: digital phase contrast; middle: GFP; bottom: merge. (cont.): flow cytometry data.

Figure 87:
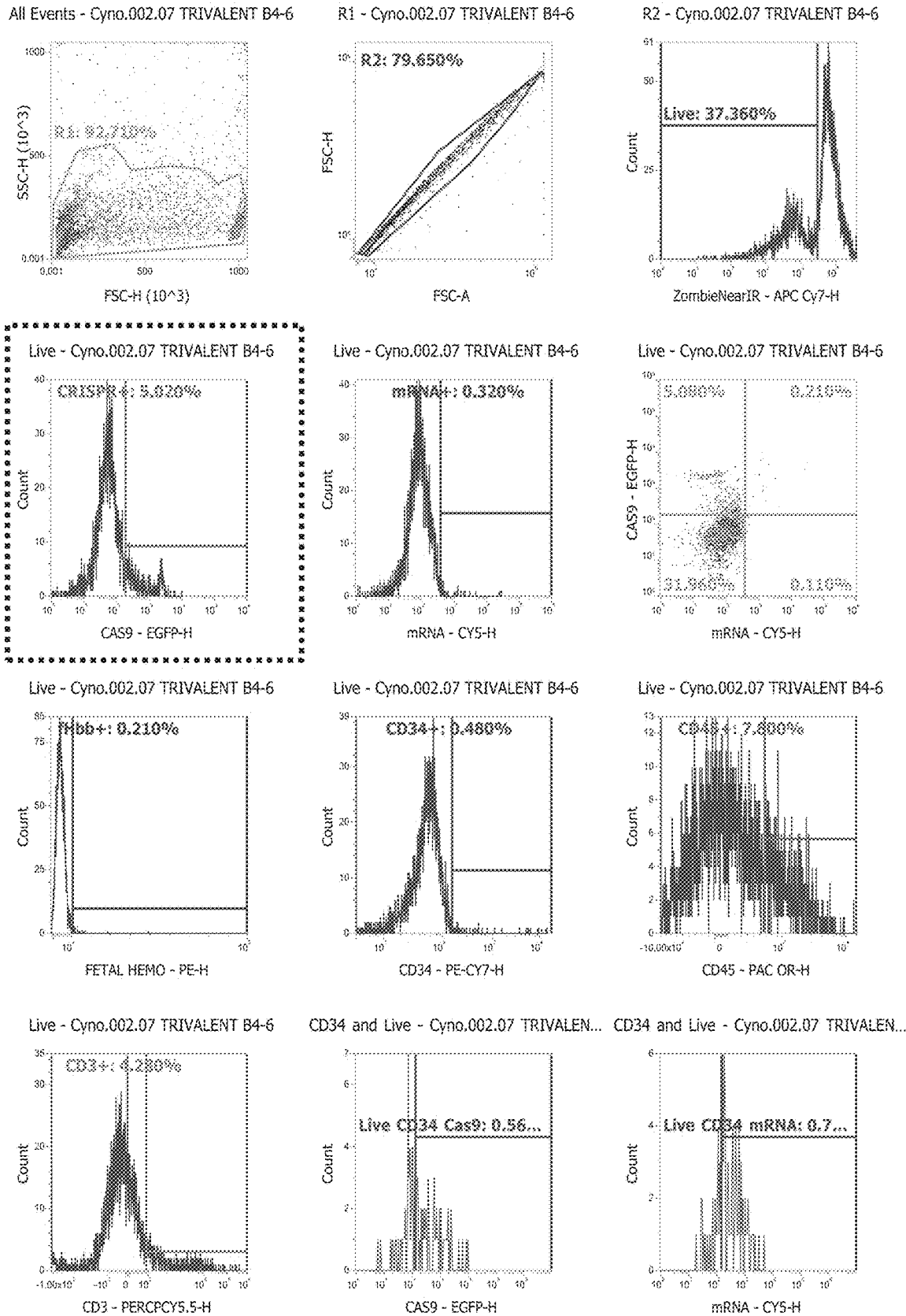
FIG. 87 provides data related to project CynoBM.002.81 (see Table 4).

FIG. 87. CynoBM.002.81 demonstrated that heterotrivalently-targeted IL2-, E-selectin- and SCF-derived NLS-Cas9-EGFP BCL11a gRNA RNPs attain 5% transfection efficiency in cynomolgus bone marrow with ~10% of transfected cells being live CD34+ cells despite only 0.48% of cells being CD34+. This indicates nearly 100% efficient selective transfection of CD34+ cells. Top: digital phase contrast; middle: GFP; bottom: merge.

FIG. 88. Qualitative images of CynoBM.002 RNP-Only control show NLS-Cas9-EGFP BCL11a gRNA RNPs attaining mild positive signal in cynomolgus bone marrow without a delivery vector. Top: digital phase contrast; middle: GFP; bottom: merge.

FIG. 89. HSC.004 (nanoparticles 69-74, see Table 4) High-Content Screening. Fluorescence microscopy images (Cy5 mRNA) of HSC.004 Cy5 mRNA delivery 12-15 h post-transfection in Primary Human CD34+ Hematopoietic Stem Cells. With this particular embodiment of mRNA formulation, heterobivalent targeting with SCF peptides and E-selectin, as well as homovalent targeting with E-selectin but not SCF peptides, achieves higher transfection efficiencies than Lipofectamine MessengerMAX. HSC.001.69: A1-A6; HSC.001.70: 1-B6; HSC.001.71: C1-C6; HSC.001.72: D1-D6; HSC.001.73: E1-E6; HSC.001.74: F1-F6; HSC.004 Lipofectamine MessengerMAX Dose 1: G1-G2 & G4-G5; TC.001 Lipofectamine MessengerMAX Dose 2: H1-H2 & H4-H5; TC.001 Negative: G3, G6, H3, H6

FIG. 90. TCELL.001 (nanoparticles 1-15, see Table 4) High-Content Screening. Robotic formulations were performed for TC.001.1-TC.001.60, representing 15 ligands across 4 payloads (CRISPR RNP, mRNA, siRNA and pDNA). Shown are embodiments of T-cell CRISPR delivery and qualitative transfection efficiencies—thumbnail images of 12-15 h post-transfection composite microscopy of TCELL.001 CRISPR-EGFP RNP delivery to Primary Human Pan T-cells. Plate layout: TC.001.1: A1-C1; TC.001.3: D1-F1; TC.001.4: A2-C2; TC.001.5: D2-F2; TC.001.6: A3-C3; TC.001.7: D3-F3; TC.001.8: A4-C4; TC.001.9: D4-F4; TC.001.10: A5-C5; TC.001.11: D5-F5; TC.001.12: A6-C6; TC.001.13: D6-F6; TC.001.14: A7-A9; TC.001.15: B7-B9; TC.001.2: A10-A12; TC.001 Lipofectamine CRISPRMAX Dose 1: B10-B12; TC.001 Lipofectamine CRISPRMAX Dose 2: C7-C9; TC.001 RNP Only: C10-C12; TC.001 Negative: D7-E12.

FIG. 91. TCELL.001 Lipofectamine CRISPRMAX. Lipofectamine CRISPRMAX attained 4.7% and 4.8% efficient delivery of NLS-Cas9-EGFP RNP in viable CD4+ and CD8a+ subpopulations, respectively, of human primary Pan T-cells at 24 h post-transfection. Overall, 12.5% of CRISPR+ cells and 65.9% of overall cells were viable.

FIG. 92: TCell.001.1 demonstrated 99.163% efficient and 98.447% efficient non-specifically-targeted CRISPR-GFP Ribonucleoprotein uptake in viable CD4+ and CD8a+ subpopulations, respectively, of human primary Pan T-cells at 24 h post-transfection. Overall, 60.2% of CRISPR+ cells and 57.2% of overall cells were viable.

FIG. 93. TCell.001.2, a non-specifically-targeted PEGylated control, demonstrated 5.5% efficient and 6.9% efficient CRISPR-GFP Ribonucleoprotein uptake in viable CD4+ and CD8a+ subpopulations, respectively, of human primary Pan T-cells at 24 h post-transfection. Overall, 5.6% of CRISPR+ cells and 40.5% of overall cells were viable.

FIG. 94. TCell.001.3 demonstrated that homovalently-targeted sialoadhesin-derived peptides associated with CRISPR-GFP Ribonucleoprotein generate 11.6% and 13.2% efficient uptake in viable CD4+ and CD8a+ subpopulations, respectively, of human primary Pan T-cells at 24 h post-transfection. Overall, 40.0% of CRISPR+ cells and 79.2% of overall cells were viable.

FIG. 95. TCell.001.4 demonstrated that homovalently-targeted CD80-derived peptides associated with CRISPR-GFP Ribonucleoprotein generate 6.8% and 8.8% efficient uptake in viable CD4+ and CD8a+ subpopulations, respectively, of human primary Pan T-cells at 24 h post-transfection. Overall, 12.9% of CRISPR+ cells and 60.2% of overall cells were viable.

FIG. 96. TCell.001.5 demonstrated that homovalently-targeted CD80-derived peptides associated with CRISPR-GFP Ribonucleoprotein generate 10.3% and 10.9% efficient CRISPR-GFP Ribonucleoprotein uptake in viable CD4+ and CD8a+ subpopulations, respectively, of human primary Pan T-cells at 24 h post-transfection. Overall, 48.3% of CRISPR+ cells and 85.1% of overall cells were viable. Note that across 9 wells of negative controls (n=3 negatives for TCELL.001 flow cytometry), viabilities were 81.4%, 84.7%, and 82.5%, which demonstrated that a C-terminally anchored, CD80-derived CD28-targeting peptide may have mild survival-promoting effects on non-transfected cells in culture solution. In contrast, TCell.001.4, an identical N-terminally anchored peptide, displayed marked toxicity, as did TC.001.6 and TC.001.7, which are also CD80-derived fragments with different allosterism for the CD28 transmembrane receptor.

FIG. 97. TCell.001.6 demonstrated that homovalently-targeted CD86-derived peptides associated with CRISPR-GFP Ribonucleoprotein generate 1.7% and 2.9% efficient uptake in viable CD4+ and CD8a+ subpopulations, respectively, of human primary Pan T-cells at 24 h post-transfection. Overall, 6.8% of CRISPR+ cells and 69.1% of overall cells were viable.

FIG. 98. TCell.001.7 demonstrated that homovalently-targeted CD86-derived peptides associated with CRISPR-GFP Ribonucleoprotein generate 1.6% and 2.1% efficient uptake in viable CD4+ and CD8a+ subpopulations, respectively, of human primary Pan T-cells at 24 h post-transfection. Overall, 10.3% of CRISPR+ cells and 76.4% of overall cells were viable.

FIG. 99. TCell.001.8 demonstrated that homovalently-targeted CD86-derived peptides associated with CRISPR-GFP Ribonucleoprotein generate 14.5% and 16.0% efficient uptake in viable CD4+ and CD8a+ subpopulations, respectively, of human primary Pan T-cells at 24 h post-transfection. Overall, 39.1% of CRISPR+ cells and 76.3% of overall cells were viable.

FIG. 100. TCell.001.9 demonstrated that homovalently-targeted 4-1BB-derived peptides associated with CRISPR-GFP Ribonucleoprotein generate 3.6% and 3.2% efficient uptake in viable CD4+ and CD8a+ subpopulations, respectively, of human primary Pan T-cells at 24 h post-transfection. Overall, 27.5% of CRISPR+ cells and 87.8% of overall cells were viable. Note that across 9 wells of negative controls (n=3 negatives for TCELL.001 flow cytometry), viabilities were 81.4%, 84.7%, and 82.5%, which demonstrated that a C-terminally anchored, 4-1 BB-derived CD137-targeting peptide, which has innate survival signaling with T-cells, has mild survival-promoting effects on non-transfected cells in culture solution.

FIG. 101. TCell.001.10 demonstrated that homovalently-targeted 4-1 BB-derived peptides associated with CRISPR-GFP Ribonucleoprotein generate 5.8% and 5.4% efficient uptake in viable CD4+ and CD8a+ subpopulations, respectively, of human primary Pan T-cells at 24 h post-transfection. Overall, 30.8% of CRISPR+ cells and 84.2% of overall cells were viable. Note that across 9 wells of negative controls (n=3 negatives for TCELL.001 flow cytometry), viabilities were 81.4%, 84.7%, and 82.5%, which demonstrated that a C-terminally anchored, 4-1 BB-derived CD137-targeting peptide, which has innate survival signaling with T-cells, demonstrates no overall toxicity in culture solution.

FIG. 102. TCell.001.11 demonstrated that homovalently-targeted CD3-Ab-derived peptides associated with CRISPR-GFP Ribonucleoprotein generate 12.9% and 12.4% efficient uptake in viable CD4+ and CD8a+ subpopulations, respectively, of human primary Pan T-cells at 24 h post-transfection. Overall, 50.0% of CRISPR+ cells and 77.6% of overall cells were viable.

FIG. 103. TCell.001.12 demonstrated that homovalently-targeted CD3-Ab-derived peptides associated with CRISPR-GFP Ribonucleoprotein generate 9.0% and 9.5% efficient uptake in viable CD4+ and CD8a+ subpopulations, respectively, of human primary Pan T-cells at 24 h post-transfection. Overall, 38.9% of CRISPR+ cells and 80.7% of overall cells were viable.

FIG. 104. TCell.001.13 demonstrated that homovalently-targeted IL2-derived peptides associated with CRISPR-GFP Ribonucleoprotein generate 25.7% and 28.6% efficient uptake in viable CD4+ and CD8a+ subpopulations, respectively, of human primary Pan T-cells at 24 h post-transfection. Overall, 40.3% of CRISPR+ cells and 68.1% of overall cells were viable.

FIG. 105. TCell.001.14 demonstrated that homovalently-targeted IL2-derived peptides associated with CRISPR-GFP Ribonucleoprotein generate 24.9% and 25.8% efficient uptake in viable CD4+ and CD8a+ subpopulations, respectively, of human primary Pan T-cells at 24 h post-transfection. Overall, 45.9% of CRISPR+ cells and 70.1% of overall cells were viable.

FIG. 106. TCell.001.15, a dodecavalently-targeted 12-ligand variant, does not lead to endocytic uptake or CRISPR delivery. Overall, 59.8% of overall cells were viable.

FIG. 107. TCELL.001 Negative Controls. Representative results from one of 9 wells of negative (non-transfected) control. Overall, 81.4%, 84.7%, and 82.5% of total cells were viable 52 h after cell seeding (24 h post-transfection).

FIG. 108. Blood.002 attains 60%-97% mRNA delivery efficiency in the lymphocyte gate of whole human blood through utilizing a SIGLEC derivative for glycosylated cell surface marker targeting; shown is Cy5-tagged EGFP mRNA assayed via an Attune NxT flow cytometer. Ligand targeting is a significant enhancer of cellular signal versus a PEGylated control. See above data for additional physicochemical properties predictive of nanoparticle behavior. Blood.002 Control: Untransfected. Blood.002.88: CD45- and Neu5Ac-targeting SIGLEC derivative (cationic anchor-linker-ligand peptide added before anionic polymer). Blood.002.89: CD45- and Neu5Ac-targeting SIGLEC derivative (cationic anchor-linker-ligand peptide added after anionic polymer). Blood.002.90: PEGylated control (cationic anchor-PEG added before anionic polymer). Blood.002.91: Non-specifically-targeted variant. Blood.002.92: CD45- and Neu5Ac-targeting SIGLEC derivative without payload (anchor-linker-ligand is directly conjugated to anionic polymer, negative fluorescent control).

FIG. 109. TCell.001.27 demonstrated that homovalently-targeted SIGLEC-derived peptides direct 45% efficient Cy5 mRNA uptake in viable CD8a+ and CD4+ subpopulations of human primary Pan T-cells at 5 h post-transfection, as measured via flow cytometry. The size and zeta potential of these particles demonstrated average particle sizes of 171 nm with zeta potentials of −25.5+/−0.15 mV, indicating strong particle stability at a 1.35 carboxylate-to-phosphate (C:P) and 0.85 amine-to-phosphate ratio wherein poly(glutamic acid) is added following inclusion of the cationic anchor-linker-ligand. See above data for zeta potential and size data, TCell.001.2 and TCell.001.18. See above data for additional quantitative details. Top-right: bright field; middle-right: Cy5 mRNA; bottom-right: merge Top: bright field of negative control; bottom: Cy5 channel of negative control.

Example 4

Figure 110:
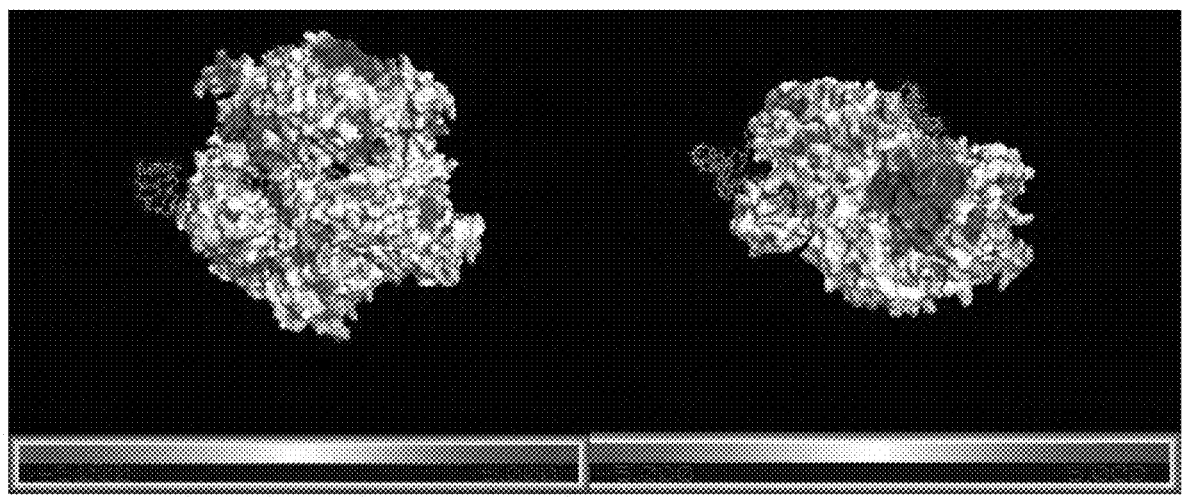
FIG. 110 depicts charge density plots of CRISPR RNP (a possible payload), which allows for determining whether an anionic or cationic peptide/material should be added to form a stable charged layer on the protein surface.

FIG. 110. Rationale for Ribonucleoprotein and Protein Delivery. Charge density plots of CRISPR RNP allow for determining whether an anionic or cationic peptide/material should be added to form a stable charged layer on the protein surface. In one embodiment, exposed nucleic acid (anionic) and anionic charge pockets serve as strong electrostatic anchoring sites for charged cations prior to addition of charged anions, or as their own ligand-linker anionic anchors. Scale bar: charge.

Figure 111:
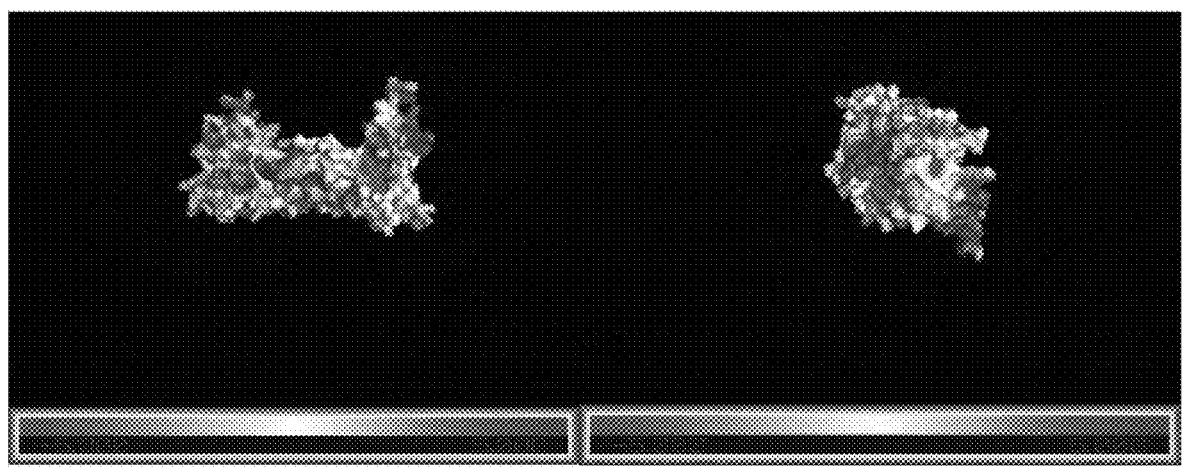
FIG. 111 depicts charge density plots of Sleeping Beauty Transposons (a possible payload), which allows for determining whether an anionic or cationic peptide/material should be added to form a stable charged layer on the protein surface.
Figure 111:
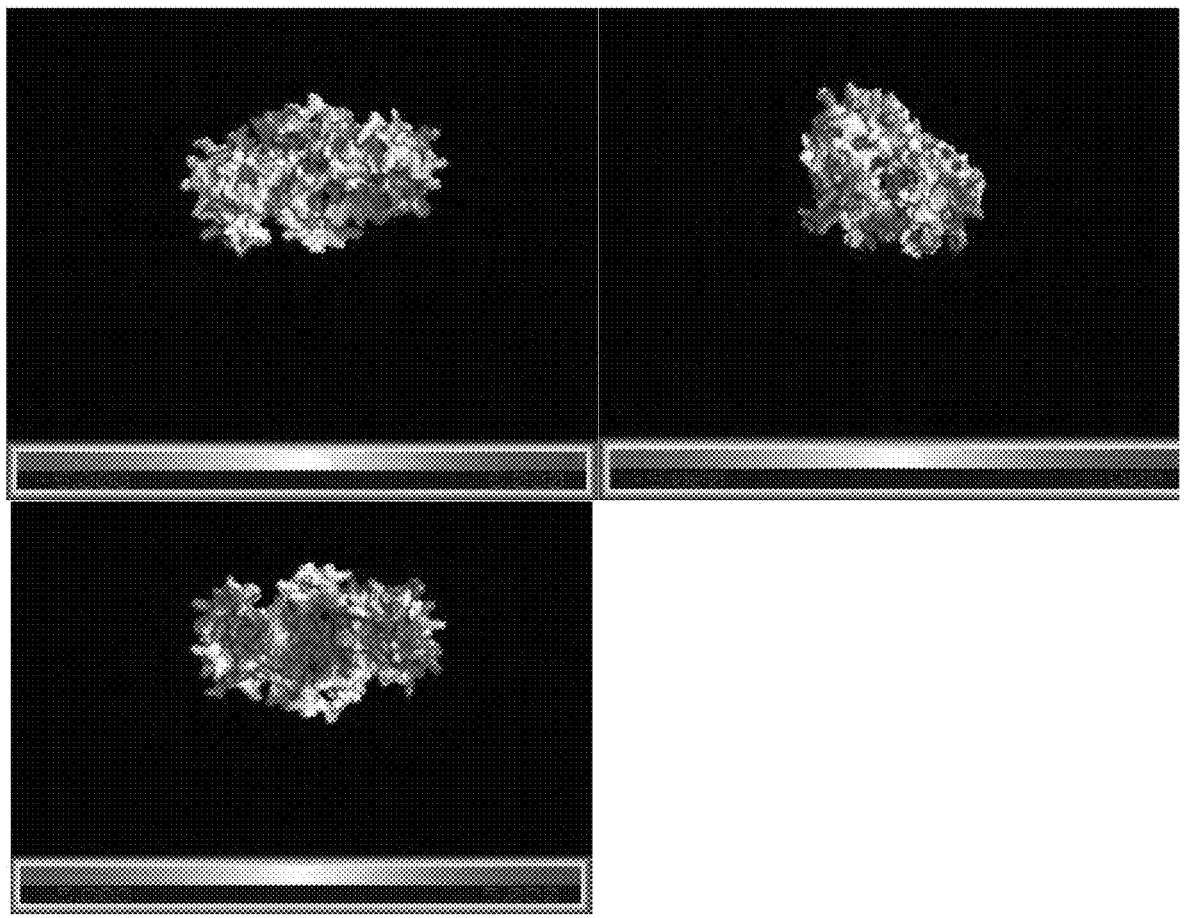

FIG. 111. Rationale for Ribonucleoprotein and Protein Delivery. Charge density plots of Sleeping Beauty Transposons allow for determining whether an anionic or cationic peptide/material should be added to form a stable charged layer on the protein surface. In another embodiment, cationic charge pockets serve as strong electrostatic anchoring sites for charged anions, either as their own ligand-linker-anionic anchor domains, or prior to addition of charged cations. Scale bar: charge.

Figure 112:
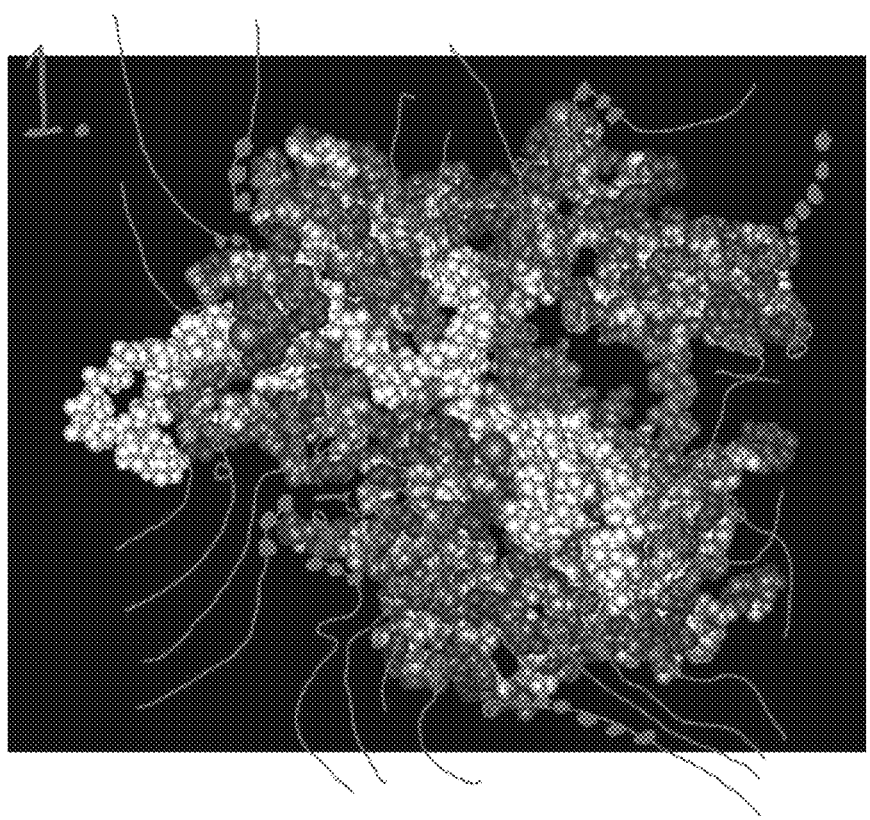
FIG. 112 depicts (1) Exemplary anionic peptides (9-10 amino acids long, approximately to scale to 10 nm diameter CRISPR RNP) anchoring to cationic sites on the CRISPR RNP surface prior to (2) addition of cationic anchors as (2a) anchor-linker-ligands or standalone cationic anchors, with or without addition of (2b) subsequent multilayering chemistries, co-delivery of multiple nucleic acid or charged therapeutic agents, or layer stabilization through cross-linking.
Figure 112:
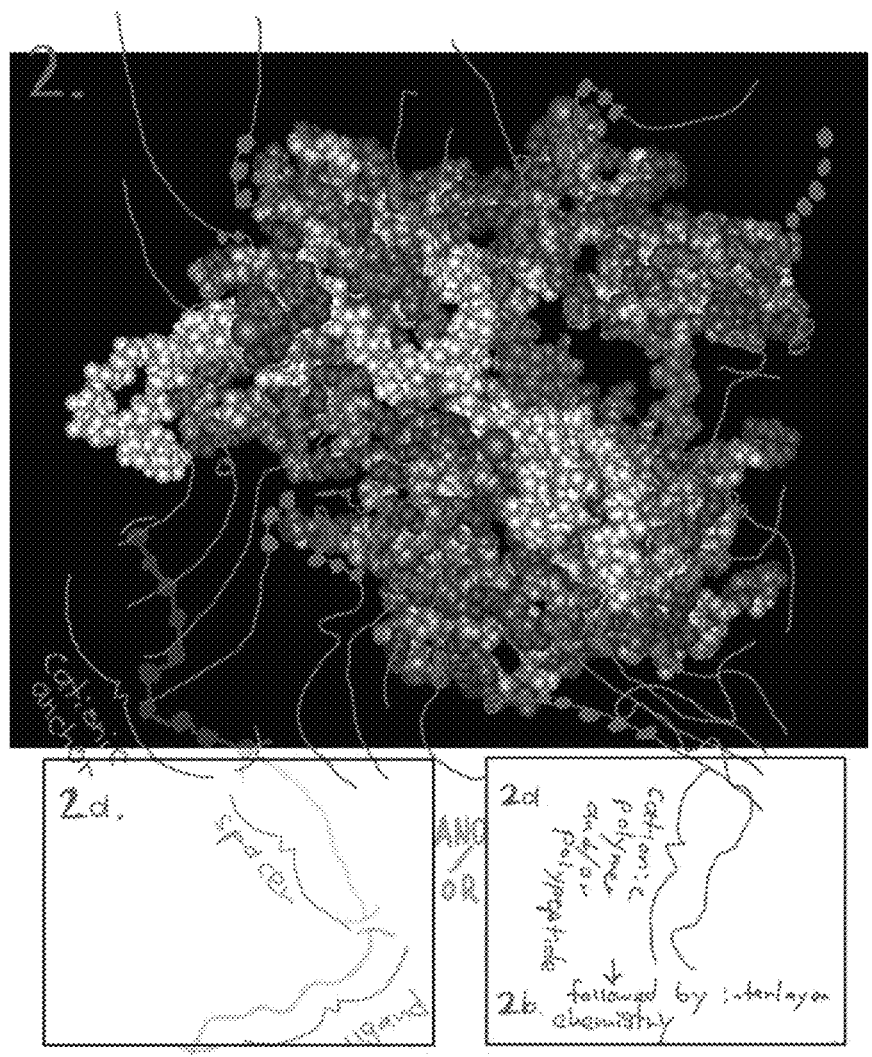

FIG. 112. (1) Exemplary anionic peptides (9-10 amino acids long, approximately to scale to 10 nm diameter CRISPR RNP) anchoring to cationic sites on the CRISPR RNP surface prior to (2) addition of cationic anchors as (2a) anchor-linker-ligands or standalone cationic anchors, with or without addition of (2b) subsequent multilayering chemistries, co-delivery of multiple nucleic acid or charged therapeutic agents, or layer stabilization through cross-linking.

Handwriting in drawing from left to right converted to text: 'cationic anchor'. 'spacer'. 'ligand'. 'And/Or'. '2d'. 'cationic polymer and/or polypeptide'. '2b. followed by interlayer chemistry'.

Figure 113:
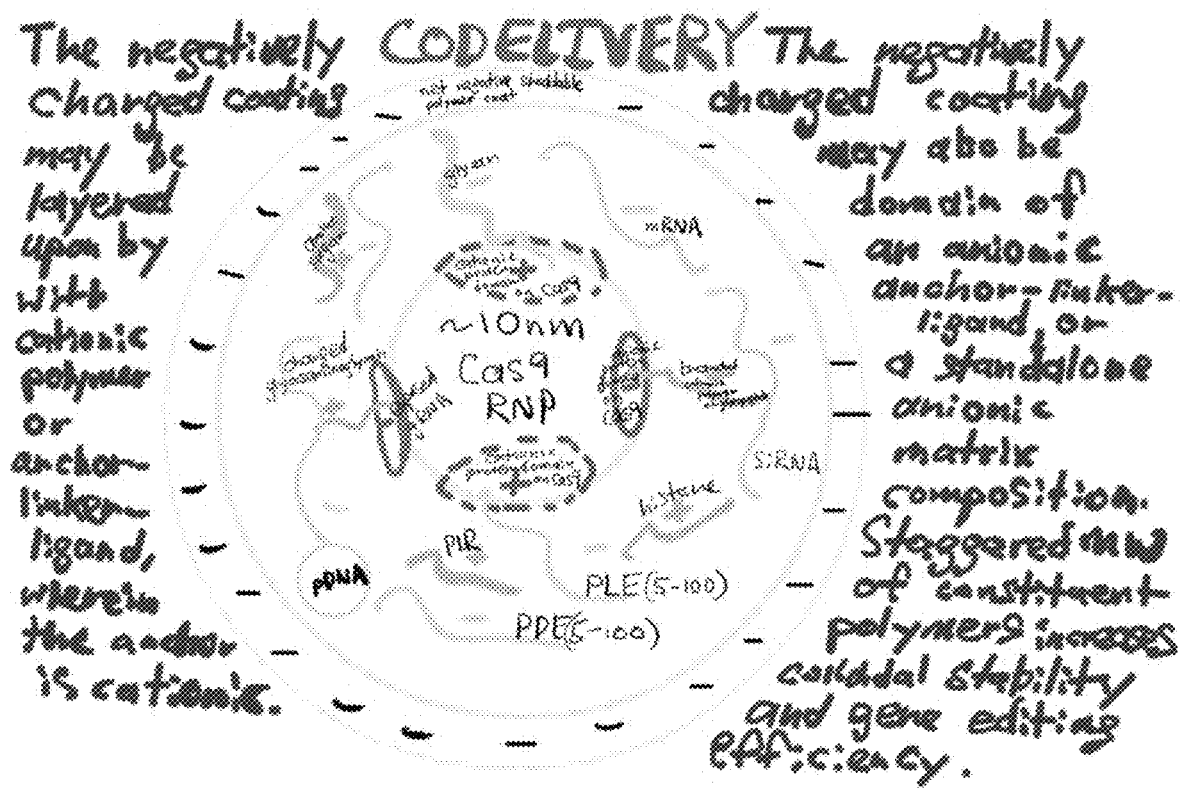
FIG. 113 depicts examples of orders of addition and electrostatic matrix compositions based on core templates, which may include Cas9 RNP or any homogenously or zwitterionically charged surface.

FIG. 113. Rationale for Payload Co-delivery with Charged Protein Core Templates. Examples of orders of addition and electrostatic matrix compositions based on core templates, which may include Cas9 RNP or any homogenously or zwitterionically charged surface. A method for homogenizing the charge of a zwitterionic surface utilizing a variety of polymers is shown. A ~10 nm core particle consisting of CRISPR-Cas9 RNP bound to gRNA is shown with zwitterionic domains. Briefly, a cationic polymer or anionic polymer may be added to homogenize the surface charge prior to addition of oppositely charged polymers. Staggd molecular weight of anionic constituents is demonstrated to increase the transfection efficiency and gene editing efficiency of particles with RNP cores and mRNA-PLE interlayers with a variety of surface coatings in CYN-OBM.002.82-CYNOBM.002-86 vs. single payload delivery variants in CYNOBM.002.75-CYNOBM.002.81. Charged core template embodiments encompass any charged surface including a charged dendrimer or oligosaccharide-dendrimer, recombinant or synthetic histone dimer/trimer/tetramer/octamer, nanodiamond, gold nanoparticle, quantum dot, MRI contrast agent, or combination thereof with the above.

Handwriting in drawing from left to right converted to text: 'The negatively charged coating may be layered upon by with cationic polymer or anchor-linker-ligand, wherein the anchor is cationic.' 'amino sugar'. 'charged glycosaminoglycan'. 'pDNA'. 'CODELIVERY'. 'exposed gRNA'. 'net negative sheddable polymer coat'. 'glycan'. 'cationic protein domain on cas9'. '-10 nm cas9 RNP'. 'cationic protein domain on cas9'. 'PLR'. 'PDE (5-100)'. 'PLE(5-100)'. 'anionic protein domain on cas9'. 'mRNA'. 'branched cationic polymer on glycopeptide'. 'histone'. 'siRNA'. 'The negatively charged coating may also be domain of an anionic anchor-linker-ligand or a standalone anionic matrix composition. Staggered mw of consistent polymers increases colloidal stability and gene editing efficiency.

Example 5

Figure 114:
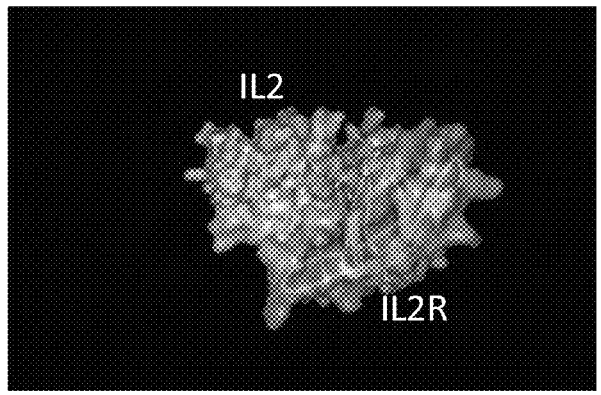
FIG. 114 provides a modeled structure of IL2 bound to IL2R.

FIG. 114. PEPTIDE ENGINEERING—Novel IL2-Mimetic Fragment for IL2R targeting. Interleukin-2 (left) bound to the Interleukin-2 Receptor (right) (PDB: 1Z92) The sequence ASN(33)-PRO(34)-LYS(35)-LEU(36)-THR(37)-ARG(38)-MET(39)-LEU(40)-THR(41)-PHE(42)-LYS(43)-PHE(44)-TYR(45) is selected from IL2 (PDB 1Z92), correlating to the areas of active binding to the IL2 receptor alpha chain. Engineering complementary binding through selecting the interacting motifs of IL2R with IL2: here, the sequence CYS(3)-ASP(4)-ASP(5)-ASP(6)-MET(25)-LEU(26)-ASN(27)-CYS(28)-GLU(29) is selected for two binding motifs from IL2 receptor.

Figure 115:
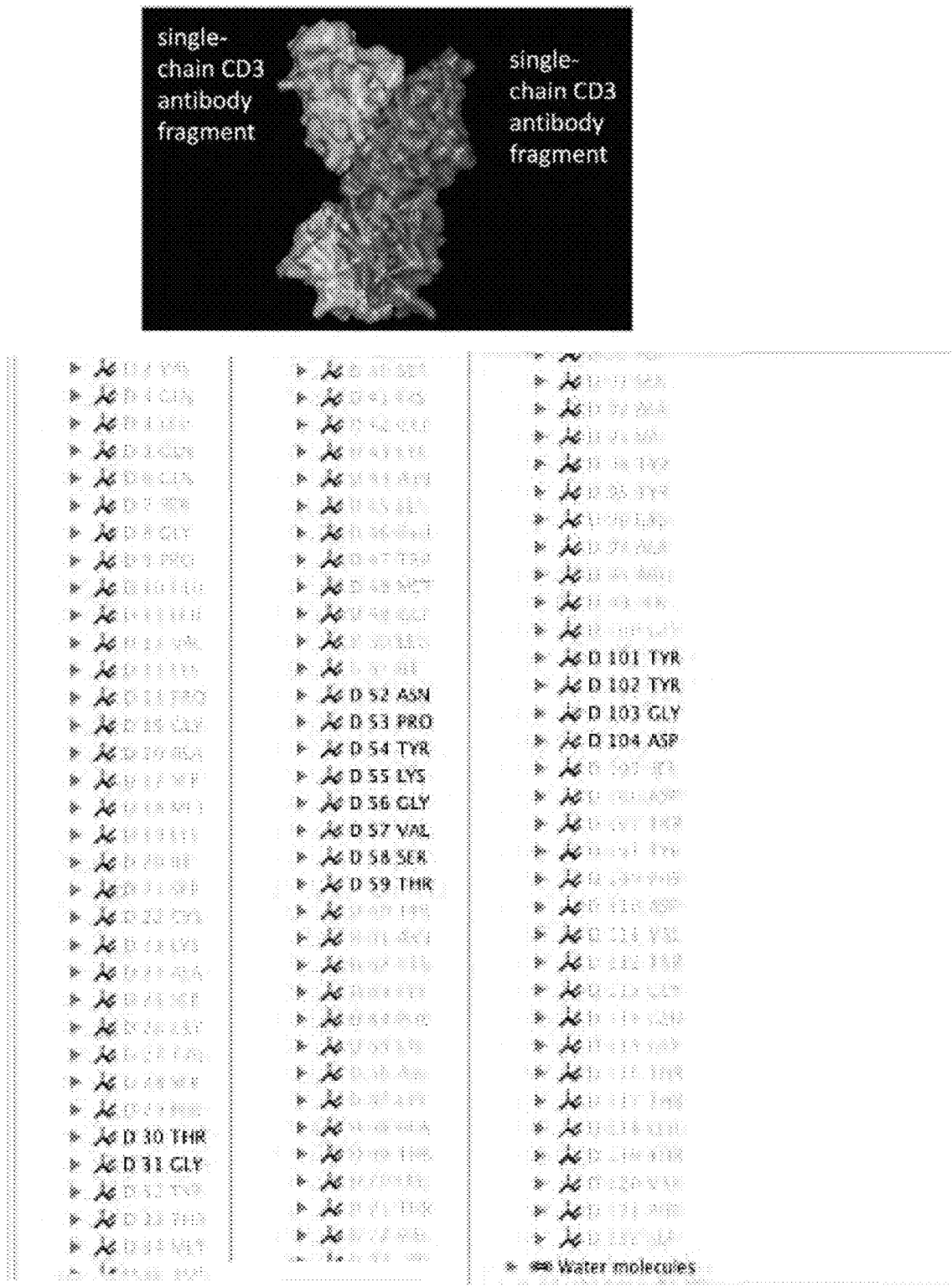
FIG. 115 provides a modeled structure of single chain CD3 antibody fragments.

FIG. 115: PEPTIDE ENGINEERING—A Novel Antibody-Derived "Active Binding Pocket" Engineering Proof of Concept with CD3. The sequence THR(30)-GLY(31)-ASN(52)-PRO(53)-TYR(54)-LYS(55)-GLY(56)-VAL(57)-SER(58)-THR(59)-TYR(101)-TYR(102)-GLY(103)-ASP(104) is selected from a CD3 antibody (PDB 1XIW), correlating to the areas of active binding to CD3 epsilon and delta chains. The order of the amino acids is rearranged in order to reflect binding kinetics of a 2-dimensional plane of peptides in the binding pocket which no longer have tertiary structure maintained by the larger protein. This dimensional reduction results in: THR(59)-SER(58)-VAL(57)-GLY(56)-LYS(55)-TYR(54)-PRO(53)-ASN(52)-THR(30)-GLY(31)-TYR(101)-TYR(102)-GLY(103)-ASP(104).

Figure 116:
FIG. 116 provides a modeled structure of sialoadhesin N-terminal in complex with N-Acetylneuraminic acid (Neu5Ac).
Figure 117:
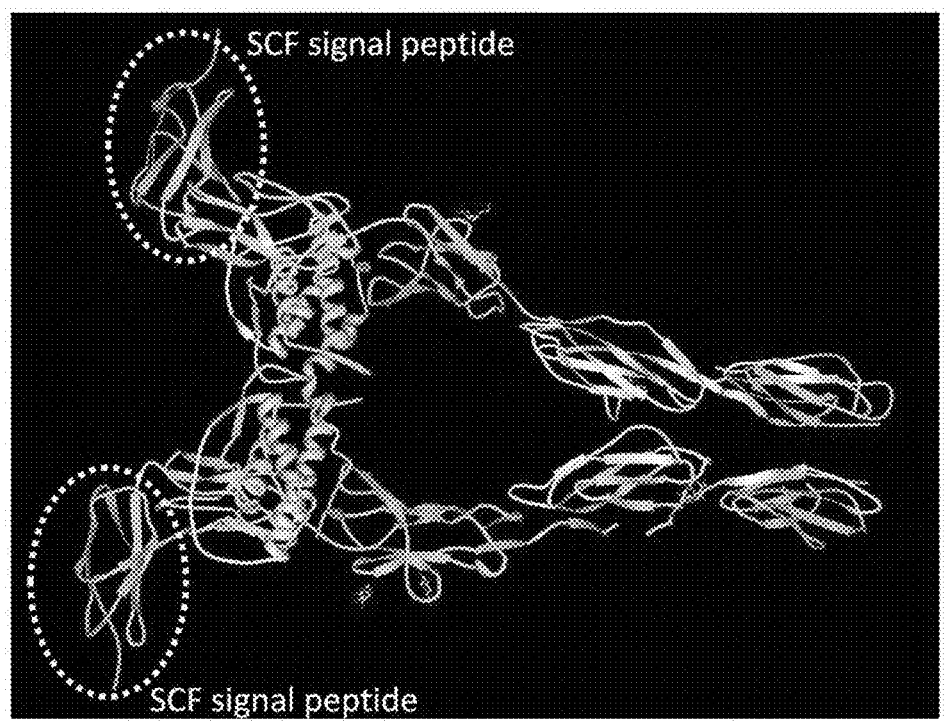
FIG. 117 provides a modeled structure of Stem Cell Factor (SCF).
Figure 118:
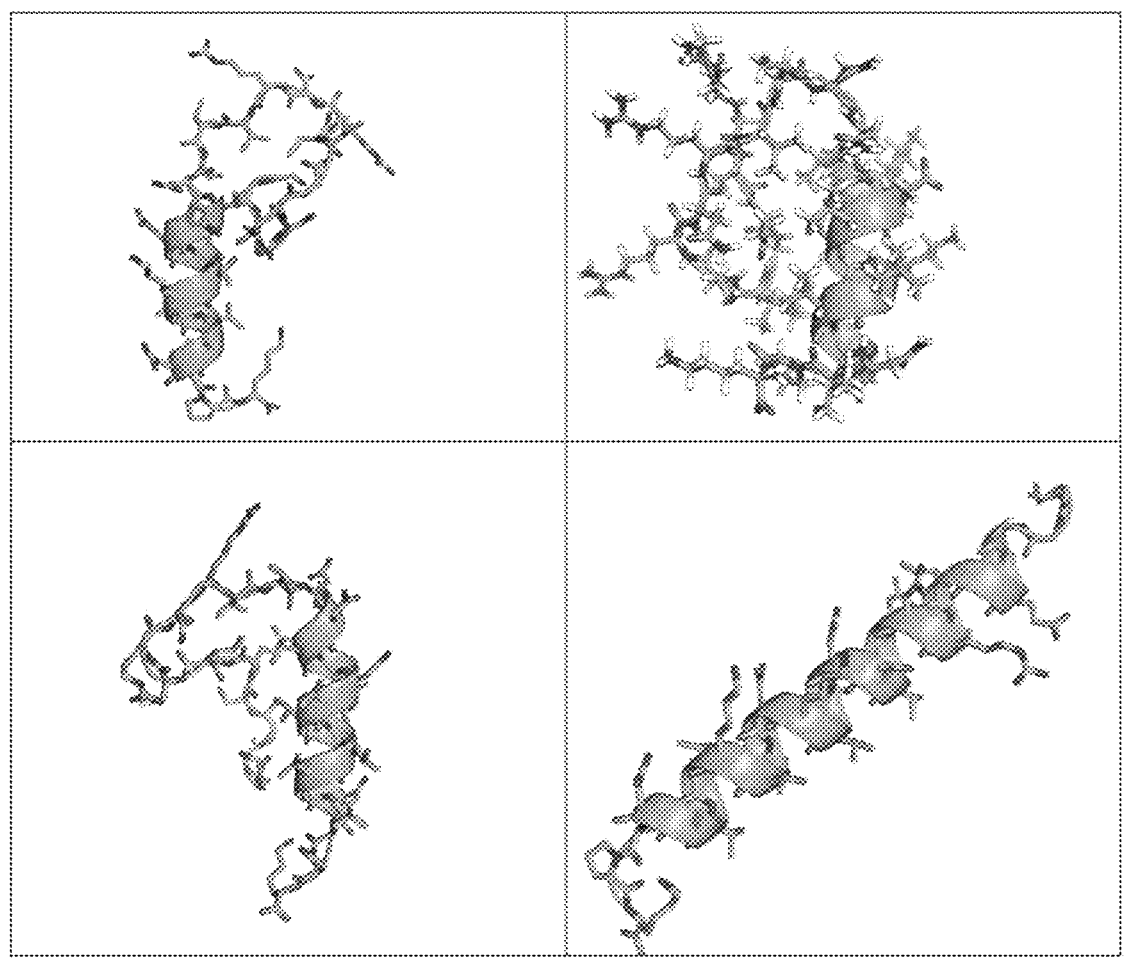
FIG. 118 provides example images generated during rational design of a cKit Receptor Fragment.

FIG. 116: PEPTIDE ENGINEERING—A Novel SIGLEC Derivative for CD45 Glycosylation Targeting. PDB r <223> OTHER INFORMATION: Synthetic sequence

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 2
<211> LENGTH: 39
<212> TYPE: PRT
<213> ORGANISM: Artificial sequence
<220> FEATURE:
<223> OTHER INFORMATION: Synthetic sequence

<400> SEQUENCE: 2

His Gly Glu Gly Thr Phe Thr Ser Asp Leu Cys Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 3
<211> LENGTH: 86
<212> TYPE: PRT
<213> ORGANISM: Artificial sequence
<220> FEATURE:
<223> OTHER INFORMATION: Synthetic sequence

<400> SEQUENCE: 3

Lys Arg Leu Tyr Cys Lys Asn Gly Gly Phe Phe Leu Arg Ile His Pro
1               5                   10                  15

Asp Gly Arg Val Asp Gly Val Arg Glu Lys Ser Asp Pro His Ile Lys
            20                  25                  30

Leu Gln Leu Gln Ala Glu Glu Arg Gly Val Val Ser Ile Lys Gly Val
        35                  40                  45

Cys Ala Asn Arg Tyr Leu Ala Met Lys Glu Asp Gly Arg Leu Leu Ala
    50                  55                  60

Ser Lys Cys Val Thr Asp Glu Cys Phe Phe Phe Glu Arg Leu Glu Ser
65                  70                  75                  80

Asn Asn Tyr Asn Thr Tyr
                85

<210> SEQ ID NO 4
<211> LENGTH: 22
<212> TYPE: PRT
<213> ORGANISM: Artificial sequence
<220> FEATURE:
<223> OTHER INFORMATION: Synthetic sequence

<400> SEQUENCE: 4

Lys Asn Gly Gly Phe Phe Leu Arg Ile His Pro Asp Gly Arg Val Asp
1               5                   10                  15

Gly Val Arg Glu Lys Ser
            20

<210> SEQ ID NO 5
<211> LENGTH: 6

```
<212> TYPE: PRT
<213> ORGANISM: Artificial sequence
<220> FEATURE:
<223> OTHER INFORMATION: Synthetic sequence

<400> SEQUENCE: 5

His Phe Lys Asp Pro Lys
1               5

<210> SEQ ID NO 6
<211> LENGTH: 8
<212> TYPE: PRT
<213> ORGANISM: Artificial sequence
<220> FEATURE:
<223> OTHER INFORMATION: Synthetic sequence

<400> SEQUENCE: 6

Leu Glu Ser Asn Asn Tyr Asn Thr
1               5

<210> SEQ ID NO 7
<211> LENGTH: 21
<212> TYPE: PRT
<213> ORGANISM: Artificial sequence
<220> FEATURE:
<223> OTHER INFORMATION: Synthetic sequence

<400> SEQUENCE: 7

Met Ile Ala Ser Gln Phe Leu Ser Ala Leu Thr Leu Val Leu Leu Ile
1               5                   10                  15

Lys Glu Ser Gly Ala
            20

<210> SEQ ID NO 8
<211> LENGTH: 38
<212> TYPE: PRT
<213> ORGANISM: Artificial sequence
<220> FEATURE:
<223> OTHER INFORMATION: Synthetic sequence

<400> SEQUENCE: 8

Met Val Phe Pro Trp Arg Cys Glu Gly Thr Tyr Trp Gly Ser Arg Asn
1               5                   10                  15

Ile Leu Lys Leu Trp Val Trp Thr Leu Leu Cys Cys Asp Phe Leu Ile
            20                  25                  30

His His Gly Thr His Cys
        35

<210> SEQ ID NO 9
<211> LENGTH: 38
<212> TYPE: PRT
<213> ORGANISM: Artificial sequence
<220> FEATURE:
<223> OTHER INFORMATION: Synthetic sequence

<400> SEQUENCE: 9

Met Ile Phe Pro Trp Lys Cys Gln Ser Thr Gln Arg Asp Leu Trp Asn
1               5                   10                  15

Ile Phe Lys Leu Trp Gly Trp Thr Met Leu Cys Cys Asp Phe Leu Ala
            20                  25                  30

His His Gly Thr Asp Cys
        35

<210> SEQ ID NO 10
```

```
<211> LENGTH: 28
<212> TYPE: PRT
<213> ORGANISM: Artificial sequence
<220> FEATURE:
<223> OTHER INFORMATION: Synthetic sequence

<400> SEQUENCE: 10

Met Ile Phe Pro Trp Lys Cys Gln Ser Thr Gln Arg Asp Leu Trp Asn
1               5                   10                  15

Ile Phe Lys Leu Trp Gly Trp Thr Met Leu Cys Cys
            20                  25

<210> SEQ ID NO 11
<211> LENGTH: 12
<212> TYPE: PRT
<213> ORGANISM: Artificial sequence
<220> FEATURE:
<223> OTHER INFORMATION: Synthetic sequence

<400> SEQUENCE: 11

Thr His Arg Pro Pro Met Trp Ser Pro Val Trp Pro
1               5                   10

<210> SEQ ID NO 12
<211> LENGTH: 7
<212> TYPE: PRT
<213> ORGANISM: Artificial sequence
<220> FEATURE:
<223> OTHER INFORMATION: Synthetic sequence

<400> SEQUENCE: 12

Arg Arg Glu Thr Ala Trp Ala
1               5

<210> SEQ ID NO 13
<211> LENGTH: 86
<212> TYPE: PRT
<213> ORGANISM: Artificial sequence
<220> FEATURE:
<223> OTHER INFORMATION: Synthetic sequence

<400> SEQUENCE: 13

Lys Arg Leu Tyr Cys Lys Asn Gly Gly Phe Phe Leu Arg Ile His Pro
1               5                   10                  15

Asp Gly Arg Val Asp Gly Val Arg Glu Lys Ser Asp Pro His Ile Lys
            20                  25                  30

Leu Gln Leu Gln Ala Glu Glu Arg Gly Val Val Ser Ile Lys Gly Val
        35                  40                  45

Cys Ala Asn Arg Tyr Leu Ala Met Lys Glu Asp Gly Arg Leu Leu Ala
    50                  55                  60

Ser Lys Cys Val Thr Asp Glu Cys Phe Phe Phe Glu Arg Leu Glu Ser
65                  70                  75                  80

Asn Asn Tyr Asn Thr Tyr
                85

<210> SEQ ID NO 14
<211> LENGTH: 23
<212> TYPE: PRT
<213> ORGANISM: Artificial sequence
<220> FEATURE:
<223> OTHER INFORMATION: Synthetic sequence

<400> SEQUENCE: 14

Cys Lys Asn Gly Gly Phe Phe Leu Arg Ile His Pro Asp Gly Arg Val
```

```
1               5                   10                  15

Asp Gly Val Arg Glu Lys Ser
            20

<210> SEQ ID NO 15
<211> LENGTH: 9
<212> TYPE: PRT
<213> ORGANISM: Artificial sequence
<220> FEATURE:
<223> OTHER INFORMATION: Synthetic sequence

<400> SEQUENCE: 15

Arg Arg Arg Arg Arg Arg Arg Arg
1               5

<210> SEQ ID NO 16
<211> LENGTH: 6
<212> TYPE: PRT
<213> ORGANISM: Artificial sequence
<220> FEATURE:
<223> OTHER INFORMATION: Synthetic sequence

<400> SEQUENCE: 16

His His His His His His
1               5

<210> SEQ ID NO 17
<211> LENGTH: 9
<212> TYPE: PRT
<213> ORGANISM: Artificial sequence
<220> FEATURE:
<223> OTHER INFORMATION: Synthetic sequence

<400> SEQUENCE: 17

Gly Ala Pro Gly Ala Pro Cys Ala Pro
1               5

<210> SEQ ID NO 18
<211> LENGTH: 10
<212> TYPE: PRT
<213> ORGANISM: Artificial sequence
<220> FEATURE:
<223> OTHER INFORMATION: Synthetic sequence

<400> SEQUENCE: 18

Gly Ala Pro Gly Ala Pro Cys Ala Pro Cys
1               5                   10

<210> SEQ ID NO 19
<211> LENGTH: 10
<212> TYPE: PRT
<213> ORGANISM: Artificial sequence
<220> FEATURE:
<223> OTHER INFORMATION: Synthetic sequence

<400> SEQUENCE: 19

Cys Gly Ala Pro Gly Ala Pro Gly Ala Pro
1               5                   10

<210> SEQ ID NO 20
<211> LENGTH: 5
<212> TYPE: PRT
<213> ORGANISM: Artificial sequence
<220> FEATURE:
<223> OTHER INFORMATION: Synthetic sequence

<400> SEQUENCE: 20
```

```
Gly Ser Gly Gly Ser
1               5

<210> SEQ ID NO 21
<211> LENGTH: 6
<212> TYPE: PRT
<213> ORGANISM: Artificial sequence
<220> FEATURE:
<223> OTHER INFORMATION: Synthetic sequence

<400> SEQUENCE: 21

Gly Gly Ser Gly Gly Ser
1               5

<210> SEQ ID NO 22
<211> LENGTH: 4
<212> TYPE: PRT
<213> ORGANISM: Artificial sequence
<220> FEATURE:
<223> OTHER INFORMATION: Synthetic sequence

<400> SEQUENCE: 22

Gly Gly Gly Ser
1

<210> SEQ ID NO 23
<211> LENGTH: 4
<212> TYPE: PRT
<213> ORGANISM: Artificial sequence
<220> FEATURE:
<223> OTHER INFORMATION: Synthetic sequence

<400> SEQUENCE: 23

Gly Gly Ser Gly
1

<210> SEQ ID NO 24
<211> LENGTH: 5
<212> TYPE: PRT
<213> ORGANISM: Artificial sequence
<220> FEATURE:
<223> OTHER INFORMATION: Synthetic sequence

<400> SEQUENCE: 24

Gly Gly Ser Gly Gly
1               5

<210> SEQ ID NO 25
<211> LENGTH: 5
<212> TYPE: PRT
<213> ORGANISM: Artificial sequence
<220> FEATURE:
<223> OTHER INFORMATION: Synthetic sequence

<400> SEQUENCE: 25

Gly Ser Gly Ser Gly
1               5

<210> SEQ ID NO 26
<211> LENGTH: 5
<212> TYPE: PRT
<213> ORGANISM: Artificial sequence
<220> FEATURE:
<223> OTHER INFORMATION: Synthetic sequence

<400> SEQUENCE: 26
```

```
Gly Ser Gly Gly Gly
1               5

<210> SEQ ID NO 27
<211> LENGTH: 5
<212> TYPE: PRT
<213> ORGANISM: Artificial sequence
<220> FEATURE:
<223> OTHER INFORMATION: Synthetic sequence

<400> SEQUENCE: 27

Gly Gly Gly Ser Gly
1               5

<210> SEQ ID NO 28
<211> LENGTH: 5
<212> TYPE: PRT
<213> ORGANISM: Artificial sequence
<220> FEATURE:
<223> OTHER INFORMATION: Synthetic sequence

<400> SEQUENCE: 28

Gly Ser Ser Ser Gly
1               5

<210> SEQ ID NO 29
<211> LENGTH: 11
<212> TYPE: PRT
<213> ORGANISM: Artificial sequence
<220> FEATURE:
<223> OTHER INFORMATION: Synthetic sequence

<400> SEQUENCE: 29

Gly Gly Gly Gly Gly Ser Gly Gly Gly Gly Gly
1               5                   10

<210> SEQ ID NO 30
<211> LENGTH: 11
<212> TYPE: PRT
<213> ORGANISM: Artificial sequence
<220> FEATURE:
<223> OTHER INFORMATION: Synthetic sequence

<400> SEQUENCE: 30

Gly Gly Gly Gly Gly Ser Gly Gly Gly Gly Ser
1               5                   10

<210> SEQ ID NO 31
<211> LENGTH: 12
<212> TYPE: PRT
<213> ORGANISM: Artificial sequence
<220> FEATURE:
<223> OTHER INFORMATION: Synthetic sequence

<400> SEQUENCE: 31

Gly Gly Gly Gly Gly Ser Gly Gly Gly Gly Gly Cys
1               5                   10

<210> SEQ ID NO 32
<211> LENGTH: 12
<212> TYPE: PRT
<213> ORGANISM: Artificial sequence
<220> FEATURE:
<223> OTHER INFORMATION: Synthetic sequence

<400> SEQUENCE: 32

Cys Gly Gly Gly Gly Gly Ser Gly Gly Gly Gly Gly
```

```
1               5              10
```

<210> SEQ ID NO 33
<211> LENGTH: 12
<212> TYPE: PRT
<213> ORGANISM: Artificial sequence
<220> FEATURE:
<223> OTHER INFORMATION: Synthetic sequence

<400> SEQUENCE: 33

```
Gly Gly Gly Gly Gly Ser Gly Gly Gly Gly Ser Cys
1               5                  10
```

<210> SEQ ID NO 34
<211> LENGTH: 12
<212> TYPE: PRT
<213> ORGANISM: Artificial sequence
<220> FEATURE:
<223> OTHER INFORMATION: Synthetic sequence

<400> SEQUENCE: 34

```
Cys Gly Gly Gly Gly Gly Ser Gly Gly Gly Gly Ser
1               5                  10
```

<210> SEQ ID NO 35
<211> LENGTH: 4
<212> TYPE: PRT
<213> ORGANISM: Artificial sequence
<220> FEATURE:
<223> OTHER INFORMATION: Synthetic sequence

<400> SEQUENCE: 35

```
Lys Ala Leu Ala
1
```

<210> SEQ ID NO 36
<211> LENGTH: 4
<212> TYPE: PRT
<213> ORGANISM: Artificial sequence
<220> FEATURE:
<223> OTHER INFORMATION: Synthetic sequence

<400> SEQUENCE: 36

```
Gly Ala Leu Ala
1
```

<210> SEQ ID NO 37
<211> LENGTH: 5
<212> TYPE: PRT
<213> ORGANISM: Artificial sequence
<220> FEATURE:
<223> OTHER INFORMATION: Synthetic sequence

<400> SEQUENCE: 37

```
Cys Lys Ala Leu Ala
1               5
```

<210> SEQ ID NO 38
<211> LENGTH: 5
<212> TYPE: PRT
<213> ORGANISM: Artificial sequence
<220> FEATURE:
<223> OTHER INFORMATION: Synthetic sequence

<400> SEQUENCE: 38

```
Lys Ala Leu Ala Cys
1               5
```

```
<210> SEQ ID NO 39
<211> LENGTH: 5
<212> TYPE: PRT
<213> ORGANISM: Artificial sequence
<220> FEATURE:
<223> OTHER INFORMATION: Synthetic sequence

<400> SEQUENCE: 39

Cys Gly Ala Leu Ala
1               5

<210> SEQ ID NO 40
<211> LENGTH: 5
<212> TYPE: PRT
<213> ORGANISM: Artificial sequence
<220> FEATURE:
<223> OTHER INFORMATION: Synthetic sequence

<400> SEQUENCE: 40

Gly Ala Leu Ala Cys
1               5

<210> SEQ ID NO 41
<211> LENGTH: 19
<212> TYPE: PRT
<213> ORGANISM: Artificial sequence
<220> FEATURE:
<223> OTHER INFORMATION: Synthetic sequence

<400> SEQUENCE: 41

Arg Arg Arg Arg Arg Arg Arg Arg Arg Gly Ala Pro Gly Ala Pro Gly
1               5                   10                  15

Ala Pro Cys

<210> SEQ ID NO 42
<211> LENGTH: 19
<212> TYPE: PRT
<213> ORGANISM: Artificial sequence
<220> FEATURE:
<223> OTHER INFORMATION: Synthetic sequence

<400> SEQUENCE: 42

Cys Gly Ala Pro Gly Ala Pro Gly Ala Pro Arg Arg Arg Arg Arg Arg
1               5                   10                  15

Arg Arg Arg

<210> SEQ ID NO 43
<211> LENGTH: 23
<212> TYPE: PRT
<213> ORGANISM: Artificial sequence
<220> FEATURE:
<223> OTHER INFORMATION: Synthetic sequence

<400> SEQUENCE: 43

Cys Lys Asn Gly Gly Phe Phe Leu Arg Ile His Pro Asp Gly Arg Val
1               5                   10                  15

Asp Gly Val Arg Glu Lys Ser
            20

<210> SEQ ID NO 44
<211> LENGTH: 23
<212> TYPE: PRT
<213> ORGANISM: Artificial sequence
<220> FEATURE:
```

<223> OTHER INFORMATION: Synthetic sequence

<400> SEQUENCE: 44

Lys Asn Gly Gly Phe Phe Leu Arg Ile His Pro Asp Gly Arg Val Asp
1               5                   10                  15

Gly Val Arg Glu Lys Ser Cys
            20

<210> SEQ ID NO 45
<211> LENGTH: 25
<212> TYPE: PRT
<213> ORGANISM: Artificial sequence
<220> FEATURE:
<223> OTHER INFORMATION: Synthetic sequence

<400> SEQUENCE: 45

Arg Arg Arg Arg Arg Arg Arg Arg Gly Ala Pro Gly Ala Pro Gly
1               5                   10                  15

Ala Pro Arg Arg Glu Thr Ala Trp Ala
            20                  25

<210> SEQ ID NO 46
<211> LENGTH: 25
<212> TYPE: PRT
<213> ORGANISM: Artificial sequence
<220> FEATURE:
<223> OTHER INFORMATION: Synthetic sequence

<400> SEQUENCE: 46

Arg Arg Glu Thr Ala Trp Ala Gly Ala Pro Gly Ala Pro Gly Ala Pro
1               5                   10                  15

Arg Arg Arg Arg Arg Arg Arg Arg Arg
            20                  25

<210> SEQ ID NO 47
<211> LENGTH: 21
<212> TYPE: PRT
<213> ORGANISM: Artificial sequence
<220> FEATURE:
<223> OTHER INFORMATION: Synthetic sequence

<400> SEQUENCE: 47

Arg Arg Arg Arg Arg Arg Arg Arg Arg Gly Ala Pro Gly Ala Pro Gly
1               5                   10                  15

Ala Pro Arg Gly Asp
            20

<210> SEQ ID NO 48
<211> LENGTH: 21
<212> TYPE: PRT
<213> ORGANISM: Artificial sequence
<220> FEATURE:
<223> OTHER INFORMATION: Synthetic sequence

<400> SEQUENCE: 48

Arg Gly Asp Gly Ala Pro Gly Ala Pro Gly Ala Pro Arg Arg Arg Arg
1               5                   10                  15

Arg Arg Arg Arg Arg
            20

<210> SEQ ID NO 49
<211> LENGTH: 4
<212> TYPE: PRT
<213> ORGANISM: Artificial sequence

```
<220> FEATURE:
<223> OTHER INFORMATION: Synthetic sequence

<400> SEQUENCE: 49

Cys Arg Gly Asp
1

<210> SEQ ID NO 50
<211> LENGTH: 4
<212> TYPE: PRT
<213> ORGANISM: Artificial sequence
<220> FEATURE:
<223> OTHER INFORMATION: Synthetic sequence

<400> SEQUENCE: 50

Arg Gly Asp Cys
1

<210> SEQ ID NO 51
<211> LENGTH: 30
<212> TYPE: PRT
<213> ORGANISM: Artificial sequence
<220> FEATURE:
<223> OTHER INFORMATION: Synthetic sequence

<400> SEQUENCE: 51

Arg Arg Arg Arg Arg Arg Arg Arg Arg Gly Ala Pro Gly Ala Pro Gly
1               5                   10                  15

Ala Pro Thr His Arg Pro Pro Met Trp Ser Pro Val Trp Pro
            20                  25                  30

<210> SEQ ID NO 52
<211> LENGTH: 30
<212> TYPE: PRT
<213> ORGANISM: Artificial sequence
<220> FEATURE:
<223> OTHER INFORMATION: Synthetic sequence

<400> SEQUENCE: 52

Thr His Arg Pro Pro Met Trp Ser Pro Val Trp Pro Gly Ala Pro Gly
1               5                   10                  15

Ala Pro Gly Ala Pro Arg Arg Arg Arg Arg Arg Arg Arg Arg
            20                  25                  30

<210> SEQ ID NO 53
<211> LENGTH: 13
<212> TYPE: PRT
<213> ORGANISM: Artificial sequence
<220> FEATURE:
<223> OTHER INFORMATION: Synthetic sequence

<400> SEQUENCE: 53

Cys Thr His Arg Pro Pro Met Trp Ser Pro Val Trp Pro
1               5                   10

<210> SEQ ID NO 54
<211> LENGTH: 14
<212> TYPE: PRT
<213> ORGANISM: Artificial sequence
<220> FEATURE:
<223> OTHER INFORMATION: Synthetic sequence

<400> SEQUENCE: 54

Cys Pro Thr His Arg Pro Pro Met Trp Ser Pro Val Trp Pro
1               5                   10
```

```
<210> SEQ ID NO 55
<211> LENGTH: 13
<212> TYPE: PRT
<213> ORGANISM: Artificial sequence
<220> FEATURE:
<223> OTHER INFORMATION: Synthetic sequence

<400> SEQUENCE: 55

Thr His Arg Pro Pro Met Trp Ser Pro Val Trp Pro Cys
1               5                   10

<210> SEQ ID NO 56
<211> LENGTH: 39
<212> TYPE: PRT
<213> ORGANISM: Artificial sequence
<220> FEATURE:
<223> OTHER INFORMATION: Synthetic sequence

<400> SEQUENCE: 56

Arg Arg Arg Arg Arg Arg Arg Arg Gly Ala Pro Gly Ala Pro Gly
1               5                   10                  15

Ala Pro Met Ile Ala Ser Gln Phe Leu Ser Ala Leu Thr Leu Val Leu
                20                  25                  30

Leu Ile Lys Glu Ser Gly Ala
            35

<210> SEQ ID NO 57
<211> LENGTH: 39
<212> TYPE: PRT
<213> ORGANISM: Artificial sequence
<220> FEATURE:
<223> OTHER INFORMATION: Synthetic sequence

<400> SEQUENCE: 57

Met Ile Ala Ser Gln Phe Leu Ser Ala Leu Thr Leu Val Leu Leu Ile
1               5                   10                  15

Lys Glu Ser Gly Ala Gly Ala Pro Gly Ala Pro Gly Ala Pro Arg Arg
                20                  25                  30

Arg Arg Arg Arg Arg Arg Arg
            35

<210> SEQ ID NO 58
<211> LENGTH: 22
<212> TYPE: PRT
<213> ORGANISM: Artificial sequence
<220> FEATURE:
<223> OTHER INFORMATION: Synthetic sequence

<400> SEQUENCE: 58

Cys Met Ile Ala Ser Gln Phe Leu Ser Ala Leu Thr Leu Val Leu Leu
1               5                   10                  15

Ile Lys Glu Ser Gly Ala
            20

<210> SEQ ID NO 59
<211> LENGTH: 22
<212> TYPE: PRT
<213> ORGANISM: Artificial sequence
<220> FEATURE:
<223> OTHER INFORMATION: Synthetic sequence

<400> SEQUENCE: 59

Met Ile Ala Ser Gln Phe Leu Ser Ala Leu Thr Leu Val Leu Leu Ile
1               5                   10                  15
```

Lys Glu Ser Gly Ala Cys
            20

<210> SEQ ID NO 60
<211> LENGTH: 40
<212> TYPE: PRT
<213> ORGANISM: Artificial sequence
<220> FEATURE:
<223> OTHER INFORMATION: Synthetic sequence

<400> SEQUENCE: 60

Arg Arg Arg Arg Arg Arg Arg Arg Gly Ala Pro Gly Ala Pro Gly
1               5                   10                  15

Ala Pro Lys Asn Gly Gly Phe Phe Leu Arg Ile His Pro Asp Gly Arg
            20                  25                  30

Val Asp Gly Val Arg Glu Lys Ser
        35                  40

<210> SEQ ID NO 61
<211> LENGTH: 40
<212> TYPE: PRT
<213> ORGANISM: Artificial sequence
<220> FEATURE:
<223> OTHER INFORMATION: Synthetic sequence

<400> SEQUENCE: 61

Lys Asn Gly Gly Phe Phe Leu Arg Ile His Pro Asp Gly Arg Val Asp
1               5                   10                  15

Gly Val Arg Glu Lys Ser Gly Ala Pro Gly Ala Pro Gly Ala Pro Arg
            20                  25                  30

Arg Arg Arg Arg Arg Arg Arg
        35                  40

<210> SEQ ID NO 62
<211> LENGTH: 20
<212> TYPE: PRT
<213> ORGANISM: Artificial sequence
<220> FEATURE:
<223> OTHER INFORMATION: Synthetic sequence

<400> SEQUENCE: 62

Ser Gly Arg Gly Lys Gln Gly Gly Lys Ala Arg Ala Lys Ala Lys Thr
1               5                   10                  15

Arg Ser Ser Arg
            20

<210> SEQ ID NO 63
<211> LENGTH: 39
<212> TYPE: PRT
<213> ORGANISM: Artificial sequence
<220> FEATURE:
<223> OTHER INFORMATION: Synthetic sequence

<400> SEQUENCE: 63

Ser Gly Arg Gly Lys Gln Gly Gly Lys Ala Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Gly Gly
        35

<210> SEQ ID NO 64

<211> LENGTH: 130
<212> TYPE: PRT
<213> ORGANISM: Artificial sequence
<220> FEATURE:
<223> OTHER INFORMATION: Synthetic sequence

<400> SEQUENCE: 64

Met Ser Gly Arg Gly Lys Gln Gly Gly Lys Ala Arg Ala Lys Ala Lys
1               5                   10                  15

Thr Arg Ser Ser Arg Ala Gly Leu Gln Phe Pro Val Gly Arg Val His
            20                  25                  30

Arg Leu Leu Arg Lys Gly Asn Tyr Ala Glu Arg Val Gly Ala Gly Ala
        35                  40                  45

Pro Val Tyr Leu Ala Ala Val Leu Glu Tyr Leu Thr Ala Glu Ile Leu
    50                  55                  60

Glu Leu Ala Gly Asn Ala Ala Arg Asp Asn Lys Lys Thr Arg Ile Ile
65                  70                  75                  80

Pro Arg His Leu Gln Leu Ala Ile Arg Asn Asp Glu Glu Leu Asn Lys
                85                  90                  95

Leu Leu Gly Lys Val Thr Ile Ala Gln Gly Gly Val Leu Pro Asn Ile
            100                 105                 110

Gln Ala Val Leu Leu Pro Lys Lys Thr Glu Ser His His Lys Ala Lys
        115                 120                 125

Gly Lys
    130

<210> SEQ ID NO 65
<211> LENGTH: 10
<212> TYPE: PRT
<213> ORGANISM: Artificial sequence
<220> FEATURE:
<223> OTHER INFORMATION: Synthetic sequence

<400> SEQUENCE: 65

Cys Lys Ala Thr Gln Ala Ser Gln Glu Tyr
1               5                   10

<210> SEQ ID NO 66
<211> LENGTH: 25
<212> TYPE: PRT
<213> ORGANISM: Artificial sequence
<220> FEATURE:
<223> OTHER INFORMATION: Synthetic sequence

<400> SEQUENCE: 66

Lys Lys Thr Ser Ala Thr Val Gly Pro Lys Ala Pro Ser Gly Gly Lys
1               5                   10                  15

Lys Ala Thr Gln Ala Ser Gln Glu Tyr
            20                  25

<210> SEQ ID NO 67
<211> LENGTH: 143
<212> TYPE: PRT
<213> ORGANISM: Artificial sequence
<220> FEATURE:
<223> OTHER INFORMATION: Synthetic sequence

<400> SEQUENCE: 67

Met Ser Gly Arg Gly Lys Thr Gly Gly Lys Ala Arg Ala Lys Ala Lys
1               5                   10                  15

Ser Arg Ser Ser Arg Ala Gly Leu Gln Phe Pro Val Gly Arg Val His
            20                  25                  30

```
Arg Leu Leu Arg Lys Gly His Tyr Ala Glu Arg Val Gly Ala Gly Ala
        35                  40                  45

Pro Val Tyr Leu Ala Ala Val Leu Glu Tyr Leu Thr Ala Glu Ile Leu
 50                  55                  60

Glu Leu Ala Gly Asn Ala Ala Arg Asp Asn Lys Lys Thr Arg Ile Ile
 65                  70                  75                  80

Pro Arg His Leu Gln Leu Ala Ile Arg Asn Asp Glu Glu Leu Asn Lys
                 85                  90                  95

Leu Leu Gly Gly Val Thr Ile Ala Gln Gly Gly Val Leu Pro Asn Ile
                100                 105                 110

Gln Ala Val Leu Leu Pro Lys Lys Thr Ser Ala Thr Val Gly Pro Lys
            115                 120                 125

Ala Pro Ser Gly Gly Lys Lys Ala Thr Gln Ala Ser Gln Glu Tyr
        130                 135                 140
```

<210> SEQ ID NO 68
<211> LENGTH: 11
<212> TYPE: PRT
<213> ORGANISM: Artificial sequence
<220> FEATURE:
<223> OTHER INFORMATION: Synthetic sequence

<400> SEQUENCE: 68

```
Pro Glu Pro Ala Lys Ser Ala Pro Ala Pro Lys
 1               5                  10
```

<210> SEQ ID NO 69
<211> LENGTH: 11
<212> TYPE: PRT
<213> ORGANISM: Artificial sequence
<220> FEATURE:
<223> OTHER INFORMATION: Synthetic sequence

<400> SEQUENCE: 69

```
Pro Glu Pro Ala Lys Ser Ala Pro Ala Pro Lys
 1               5                  10
```

<210> SEQ ID NO 70
<211> LENGTH: 15
<212> TYPE: PRT
<213> ORGANISM: Artificial sequence
<220> FEATURE:
<223> OTHER INFORMATION: Synthetic sequence

<400> SEQUENCE: 70

```
Ala Gln Lys Lys Asp Gly Lys Lys Arg Lys Arg Ser Arg Lys Glu
 1               5                  10                  15
```

<210> SEQ ID NO 71
<211> LENGTH: 126
<212> TYPE: PRT
<213> ORGANISM: Artificial sequence
<220> FEATURE:
<223> OTHER INFORMATION: Synthetic sequence

<400> SEQUENCE: 71

```
Met Pro Glu Pro Ala Lys Ser Ala Pro Ala Pro Lys Lys Gly Ser Lys
 1               5                  10                  15

Lys Ala Val Thr Lys Ala Gln Lys Lys Asp Gly Lys Lys Arg Lys Arg
                20                  25                  30

Ser Arg Lys Glu Ser Tyr Ser Ile Tyr Val Tyr Lys Val Leu Lys Gln
            35                  40                  45
```

```
Val His Pro Asp Thr Gly Ile Ser Ser Lys Ala Met Gly Ile Met Asn
    50                  55                  60

Ser Phe Val Asn Asp Ile Phe Glu Arg Ile Ala Gly Glu Ala Ser Arg
65                  70                  75                  80

Leu Ala His Tyr Asn Lys Arg Ser Thr Ile Thr Ser Arg Glu Ile Gln
                85                  90                  95

Thr Ala Val Arg Leu Leu Leu Pro Gly Glu Leu Ala Lys His Ala Val
            100                 105                 110

Ser Glu Gly Thr Lys Ala Val Thr Lys Tyr Thr Ser Ser Lys
        115                 120                 125
```

<210> SEQ ID NO 72
<211> LENGTH: 8
<212> TYPE: PRT
<213> ORGANISM: Artificial sequence
<220> FEATURE:
<223> OTHER INFORMATION: Synthetic sequence

<400> SEQUENCE: 72

```
Ala Arg Thr Lys Gln Thr Ala Arg
1               5
```

<210> SEQ ID NO 73
<211> LENGTH: 10
<212> TYPE: PRT
<213> ORGANISM: Artificial sequence
<220> FEATURE:
<223> OTHER INFORMATION: Synthetic sequence

<400> SEQUENCE: 73

```
Ala Arg Thr Lys Gln Thr Ala Arg Lys Ser
1               5                   10
```

<210> SEQ ID NO 74
<211> LENGTH: 10
<212> TYPE: PRT
<213> ORGANISM: Artificial sequence
<220> FEATURE:
<223> OTHER INFORMATION: Synthetic sequence

<400> SEQUENCE: 74

```
Ala Arg Thr Lys Gln Thr Ala Arg Lys Ser
1               5                   10
```

<210> SEQ ID NO 75
<211> LENGTH: 10
<212> TYPE: PRT
<213> ORGANISM: Artificial sequence
<220> FEATURE:
<223> OTHER INFORMATION: Synthetic sequence

<400> SEQUENCE: 75

```
Ala Arg Thr Lys Gln Thr Ala Arg Lys Ser
1               5                   10
```

<210> SEQ ID NO 76
<211> LENGTH: 15
<212> TYPE: PRT
<213> ORGANISM: Artificial sequence
<220> FEATURE:
<223> OTHER INFORMATION: Synthetic sequence

<400> SEQUENCE: 76

```
Ala Arg Thr Lys Gln Thr Ala Arg Lys Ser Thr Gly Gly Lys Ala
```

```
<210> SEQ ID NO 77
<211> LENGTH: 20
<212> TYPE: PRT
<213> ORGANISM: Artificial sequence
<220> FEATURE:
<223> OTHER INFORMATION: Synthetic sequence

<400> SEQUENCE: 77

Ala Arg Thr Lys Gln Thr Ala Arg Lys Ser Thr Gly Gly Lys Ala Pro
1               5                   10                  15

Arg Lys Trp Cys
            20

<210> SEQ ID NO 78
<211> LENGTH: 19
<212> TYPE: PRT
<213> ORGANISM: Artificial sequence
<220> FEATURE:
<223> OTHER INFORMATION: Synthetic sequence

<400> SEQUENCE: 78

Ala Arg Thr Lys Gln Thr Ala Arg Lys Ser Thr Gly Gly Lys Ala Pro
1               5                   10                  15

Arg Lys Gln

<210> SEQ ID NO 79
<211> LENGTH: 20
<212> TYPE: PRT
<213> ORGANISM: Artificial sequence
<220> FEATURE:
<223> OTHER INFORMATION: Synthetic sequence

<400> SEQUENCE: 79

Ala Arg Thr Lys Gln Thr Ala Arg Lys Ser Thr Gly Gly Lys Ala Pro
1               5                   10                  15

Arg Lys Gln Leu
            20

<210> SEQ ID NO 80
<211> LENGTH: 20
<212> TYPE: PRT
<213> ORGANISM: Artificial sequence
<220> FEATURE:
<223> OTHER INFORMATION: Synthetic sequence

<400> SEQUENCE: 80

Ala Arg Thr Lys Gln Thr Ala Arg Lys Ser Thr Gly Gly Lys Ala Pro
1               5                   10                  15

Arg Lys Gln Leu
            20

<210> SEQ ID NO 81
<211> LENGTH: 21
<212> TYPE: PRT
<213> ORGANISM: Artificial sequence
<220> FEATURE:
<223> OTHER INFORMATION: Synthetic sequence

<400> SEQUENCE: 81

Ala Arg Thr Lys Gln Thr Ala Arg Lys Ser Thr Gly Gly Lys Ala Pro
1               5                   10                  15

Arg Lys Gln Leu Ala
```

20

<210> SEQ ID NO 82
<211> LENGTH: 21
<212> TYPE: PRT
<213> ORGANISM: Artificial sequence
<220> FEATURE:
<223> OTHER INFORMATION: Synthetic sequence

<400> SEQUENCE: 82

Ala Arg Thr Lys Gln Thr Ala Arg Lys Ser Thr Gly Gly Lys Ala Pro
1               5                   10                  15

Arg Lys Gln Leu Ala
            20

<210> SEQ ID NO 83
<211> LENGTH: 21
<212> TYPE: PRT
<213> ORGANISM: Artificial sequence
<220> FEATURE:
<223> OTHER INFORMATION: Synthetic sequence

<400> SEQUENCE: 83

Ala Arg Thr Lys Gln Thr Ala Arg Lys Ser Thr Gly Gly Lys Ala Pro
1               5                   10                  15

Arg Lys Gln Leu Ala
            20

<210> SEQ ID NO 84
<211> LENGTH: 21
<212> TYPE: PRT
<213> ORGANISM: Artificial sequence
<220> FEATURE:
<223> OTHER INFORMATION: Synthetic sequence

<400> SEQUENCE: 84

Ala Arg Thr Lys Gln Thr Ala Arg Lys Ser Thr Gly Gly Lys Ala Pro
1               5                   10                  15

Arg Lys Gln Leu Ala
            20

<210> SEQ ID NO 85
<211> LENGTH: 21
<212> TYPE: PRT
<213> ORGANISM: Artificial sequence
<220> FEATURE:
<223> OTHER INFORMATION: Synthetic sequence

<400> SEQUENCE: 85

Ala Arg Thr Lys Gln Thr Ala Arg Lys Ser Thr Gly Gly Lys Ala Pro
1               5                   10                  15

Arg Lys Gln Leu Ala
            20

<210> SEQ ID NO 86
<211> LENGTH: 21
<212> TYPE: PRT
<213> ORGANISM: Artificial sequence
<220> FEATURE:
<223> OTHER INFORMATION: Synthetic sequence

<400> SEQUENCE: 86

Ala Arg Thr Lys Gln Thr Ala Arg Lys Ser Thr Gly Gly Lys Ala Pro
1               5                   10                  15

Arg Lys Gln Leu Ala
        20

<210> SEQ ID NO 87
<211> LENGTH: 21
<212> TYPE: PRT
<213> ORGANISM: Artificial sequence
<220> FEATURE:
<223> OTHER INFORMATION: Synthetic sequence

<400> SEQUENCE: 87

Ala Arg Thr Lys Gln Thr Ala Arg Lys Ser Thr Gly Gly Lys Ala Pro
1               5                   10                  15

Arg Lys Gln Leu Ala
        20

<210> SEQ ID NO 88
<211> LENGTH: 21
<212> TYPE: PRT
<213> ORGANISM: Artificial sequence
<220> FEATURE:
<223> OTHER INFORMATION: Synthetic sequence

<400> SEQUENCE: 88

Ala Arg Thr Lys Gln Thr Ala Arg Lys Ser Thr Gly Gly Lys Ala Pro
1               5                   10                  15

Arg Lys Gln Leu Ala
        20

<210> SEQ ID NO 89
<211> LENGTH: 21
<212> TYPE: PRT
<213> ORGANISM: Artificial sequence
<220> FEATURE:
<223> OTHER INFORMATION: Synthetic sequence

<400> SEQUENCE: 89

Ala Arg Thr Lys Gln Thr Ala Arg Lys Ser Thr Gly Gly Lys Ala Pro
1               5                   10                  15

Arg Lys Gln Leu Ala
        20

<210> SEQ ID NO 90
<211> LENGTH: 21
<212> TYPE: PRT
<213> ORGANISM: Artificial sequence
<220> FEATURE:
<223> OTHER INFORMATION: Synthetic sequence

<400> SEQUENCE: 90

Ala Arg Thr Lys Gln Thr Ala Arg Lys Ser Thr Gly Gly Lys Ala Pro
1               5                   10                  15

Arg Lys Gln Leu Ala
        20

<210> SEQ ID NO 91
<211> LENGTH: 22
<212> TYPE: PRT
<213> ORGANISM: Artificial sequence
<220> FEATURE:
<223> OTHER INFORMATION: Synthetic sequence

<400> SEQUENCE: 91

Ala Arg Thr Lys Gln Thr Ala Arg Lys Ser Thr Gly Gly Lys Ala Pro
1               5                   10                  15

```
Arg Lys Gln Leu Ala Cys
            20

<210> SEQ ID NO 92
<211> LENGTH: 24
<212> TYPE: PRT
<213> ORGANISM: Artificial sequence
<220> FEATURE:
<223> OTHER INFORMATION: Synthetic sequence

<400> SEQUENCE: 92

Ala Arg Thr Lys Gln Thr Ala Arg Lys Ser Thr Gly Gly Lys Ala Pro
1               5                   10                  15

Arg Lys Gln Leu Ala Thr Lys Ala
            20

<210> SEQ ID NO 93
<211> LENGTH: 24
<212> TYPE: PRT
<213> ORGANISM: Artificial sequence
<220> FEATURE:
<223> OTHER INFORMATION: Synthetic sequence

<400> SEQUENCE: 93

Ala Arg Thr Lys Gln Thr Ala Arg Lys Ser Thr Gly Gly Lys Ala Pro
1               5                   10                  15

Arg Lys Gln Leu Ala Thr Lys Ala
            20

<210> SEQ ID NO 94
<211> LENGTH: 25
<212> TYPE: PRT
<213> ORGANISM: Artificial sequence
<220> FEATURE:
<223> OTHER INFORMATION: Synthetic sequence

<400> SEQUENCE: 94

Ala Arg Thr Lys Gln Thr Ala Arg Lys Ser Thr Gly Gly Lys Ala Pro
1               5                   10                  15

Arg Lys Gln Leu Ala Thr Lys Ala Ala
            20                  25

<210> SEQ ID NO 95
<211> LENGTH: 25
<212> TYPE: PRT
<213> ORGANISM: Artificial sequence
<220> FEATURE:
<223> OTHER INFORMATION: Synthetic sequence

<400> SEQUENCE: 95

Ala Arg Thr Lys Gln Thr Ala Arg Lys Ser Thr Gly Gly Lys Ala Pro
1               5                   10                  15

Arg Lys Gln Leu Ala Thr Lys Ala Ala
            20                  25

<210> SEQ ID NO 96
<211> LENGTH: 15
<212> TYPE: PRT
<213> ORGANISM: Artificial sequence
<220> FEATURE:
<223> OTHER INFORMATION: Synthetic sequence

<400> SEQUENCE: 96

Thr Lys Gln Thr Ala Arg Lys Ser Thr Gly Gly Lys Ala Pro Arg
```

<210> SEQ ID NO 97
<211> LENGTH: 15
<212> TYPE: PRT
<213> ORGANISM: Artificial sequence
<220> FEATURE:
<223> OTHER INFORMATION: Synthetic sequence

<400> SEQUENCE: 97

Thr Lys Gln Thr Ala Arg Lys Ser Thr Gly Gly Lys Ala Pro Arg
1               5                   10                  15

<210> SEQ ID NO 98
<211> LENGTH: 15
<212> TYPE: PRT
<213> ORGANISM: Artificial sequence
<220> FEATURE:
<223> OTHER INFORMATION: Synthetic sequence

<400> SEQUENCE: 98

Thr Lys Gln Thr Ala Arg Lys Ser Thr Gly Gly Lys Ala Pro Arg
1               5                   10                  15

<210> SEQ ID NO 99
<211> LENGTH: 11
<212> TYPE: PRT
<213> ORGANISM: Artificial sequence
<220> FEATURE:
<223> OTHER INFORMATION: Synthetic sequence

<400> SEQUENCE: 99

Lys Ser Thr Gly Gly Lys Ala Pro Arg Lys Gln
1               5                   10

<210> SEQ ID NO 100
<211> LENGTH: 19
<212> TYPE: PRT
<213> ORGANISM: Artificial sequence
<220> FEATURE:
<223> OTHER INFORMATION: Synthetic sequence

<400> SEQUENCE: 100

Gln Thr Ala Arg Lys Ser Thr Gly Gly Lys Ala Pro Arg Lys Gln Leu
1               5                   10                  15

Ala Ser Lys

<210> SEQ ID NO 101
<211> LENGTH: 25
<212> TYPE: PRT
<213> ORGANISM: Artificial sequence
<220> FEATURE:
<223> OTHER INFORMATION: Synthetic sequence

<400> SEQUENCE: 101

Ala Pro Arg Lys Gln Leu Ala Thr Lys Ala Ala Arg Lys Ser Ala Pro
1               5                   10                  15

Ala Thr Gly Gly Val Lys Lys Pro His
            20                  25

<210> SEQ ID NO 102
<211> LENGTH: 24
<212> TYPE: PRT
<213> ORGANISM: Artificial sequence
<220> FEATURE:
<223> OTHER INFORMATION: Synthetic sequence

<400> SEQUENCE: 102

Ala Thr Lys Ala Ala Arg Lys Ser Ala Pro Ala Thr Gly Gly Val Lys
1               5                   10                  15

Lys Pro His Arg Tyr Arg Pro Gly
            20

<210> SEQ ID NO 103
<211> LENGTH: 9
<212> TYPE: PRT
<213> ORGANISM: Artificial sequence
<220> FEATURE:
<223> OTHER INFORMATION: Synthetic sequence

<400> SEQUENCE: 103

Lys Ala Ala Arg Lys Ser Ala Pro Ala
1               5

<210> SEQ ID NO 104
<211> LENGTH: 12
<212> TYPE: PRT
<213> ORGANISM: Artificial sequence
<220> FEATURE:
<223> OTHER INFORMATION: Synthetic sequence

<400> SEQUENCE: 104

Lys Ala Ala Arg Lys Ser Ala Pro Ala Thr Gly Gly
1               5                   10

<210> SEQ ID NO 105
<211> LENGTH: 13
<212> TYPE: PRT
<213> ORGANISM: Artificial sequence
<220> FEATURE:
<223> OTHER INFORMATION: Synthetic sequence

<400> SEQUENCE: 105

Lys Ala Ala Arg Lys Ser Ala Pro Ala Thr Gly Gly Cys
1               5                   10

<210> SEQ ID NO 106
<211> LENGTH: 12
<212> TYPE: PRT
<213> ORGANISM: Artificial sequence
<220> FEATURE:
<223> OTHER INFORMATION: Synthetic sequence

<400> SEQUENCE: 106

Lys Ala Ala Arg Lys Ser Ala Pro Ala Thr Gly Gly
1               5                   10

<210> SEQ ID NO 107
<211> LENGTH: 12
<212> TYPE: PRT
<213> ORGANISM: Artificial sequence
<220> FEATURE:
<223> OTHER INFORMATION: Synthetic sequence

<400> SEQUENCE: 107

Lys Ala Ala Arg Lys Ser Ala Pro Ala Thr Gly Gly
1               5                   10

<210> SEQ ID NO 108
<211> LENGTH: 12
<212> TYPE: PRT
<213> ORGANISM: Artificial sequence

```
<220> FEATURE:
<223> OTHER INFORMATION: Synthetic sequence

<400> SEQUENCE: 108

Lys Ala Ala Arg Lys Ser Ala Pro Ala Thr Gly Gly
1               5                   10

<210> SEQ ID NO 109
<211> LENGTH: 12
<212> TYPE: PRT
<213> ORGANISM: Artificial sequence
<220> FEATURE:
<223> OTHER INFORMATION: Synthetic sequence

<400> SEQUENCE: 109

Lys Ala Ala Arg Lys Ser Ala Pro Ala Thr Gly Gly
1               5                   10

<210> SEQ ID NO 110
<211> LENGTH: 24
<212> TYPE: PRT
<213> ORGANISM: Artificial sequence
<220> FEATURE:
<223> OTHER INFORMATION: Synthetic sequence

<400> SEQUENCE: 110

Ala Thr Lys Ala Ala Arg Lys Ser Ala Pro Ser Thr Gly Gly Val Lys
1               5                   10                  15

Lys Pro His Arg Tyr Arg Pro Gly
            20

<210> SEQ ID NO 111
<211> LENGTH: 24
<212> TYPE: PRT
<213> ORGANISM: Artificial sequence
<220> FEATURE:
<223> OTHER INFORMATION: Synthetic sequence

<400> SEQUENCE: 111

Ala Thr Lys Ala Ala Arg Lys Ser Ala Pro Ser Thr Gly Gly Val Lys
1               5                   10                  15

Lys Pro His Arg Tyr Arg Pro Gly
            20

<210> SEQ ID NO 112
<211> LENGTH: 35
<212> TYPE: PRT
<213> ORGANISM: Artificial sequence
<220> FEATURE:
<223> OTHER INFORMATION: Synthetic sequence

<400> SEQUENCE: 112

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
            20                  25                  30

Gly Gly Val
        35

<210> SEQ ID NO 113
<211> LENGTH: 11
<212> TYPE: PRT
<213> ORGANISM: Artificial sequence
<220> FEATURE:
<223> OTHER INFORMATION: Synthetic sequence
```

<400> SEQUENCE: 113

Ser Thr Gly Gly Val Lys Lys Pro His Arg Tyr
1               5                   10

<210> SEQ ID NO 114
<211> LENGTH: 11
<212> TYPE: PRT
<213> ORGANISM: Artificial sequence
<220> FEATURE:
<223> OTHER INFORMATION: Synthetic sequence

<400> SEQUENCE: 114

Ser Thr Gly Gly Val Lys Lys Pro His Arg Tyr
1               5                   10

<210> SEQ ID NO 115
<211> LENGTH: 11
<212> TYPE: PRT
<213> ORGANISM: Artificial sequence
<220> FEATURE:
<223> OTHER INFORMATION: Synthetic sequence

<400> SEQUENCE: 115

Ser Thr Gly Gly Val Lys Lys Pro His Arg Tyr
1               5                   10

<210> SEQ ID NO 116
<211> LENGTH: 20
<212> TYPE: PRT
<213> ORGANISM: Artificial sequence
<220> FEATURE:
<223> OTHER INFORMATION: Synthetic sequence

<400> SEQUENCE: 116

Gly Thr Val Ala Leu Arg Glu Ile Arg Arg Tyr Gln Lys Ser Thr Glu
1               5                   10                  15

Leu Leu Ile Arg
            20

<210> SEQ ID NO 117
<211> LENGTH: 50
<212> TYPE: PRT
<213> ORGANISM: Artificial sequence
<220> FEATURE:
<223> OTHER INFORMATION: Synthetic sequence

<400> SEQUENCE: 117

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
            20                  25                  30

Gly Gly Val Lys Lys Pro His Arg Tyr Arg Pro Gly Thr Val Ala Leu
        35                  40                  45

Arg Glu
    50

<210> SEQ ID NO 118
<211> LENGTH: 32
<212> TYPE: PRT
<213> ORGANISM: Artificial sequence
<220> FEATURE:
<223> OTHER INFORMATION: Synthetic sequence

<400> SEQUENCE: 118

Thr Glu Leu Leu Ile Arg Lys Leu Pro Phe Gln Arg Leu Val Arg Glu
1               5                   10                  15

Ile Ala Gln Asp Phe Lys Thr Asp Leu Arg Phe Gln Ser Ala Ala Ile
                20                  25                  30

<210> SEQ ID NO 119
<211> LENGTH: 11
<212> TYPE: PRT
<213> ORGANISM: Artificial sequence
<220> FEATURE:
<223> OTHER INFORMATION: Synthetic sequence

<400> SEQUENCE: 119

Glu Ile Ala Gln Asp Phe Lys Thr Asp Leu Arg
1               5                   10

<210> SEQ ID NO 120
<211> LENGTH: 11
<212> TYPE: PRT
<213> ORGANISM: Artificial sequence
<220> FEATURE:
<223> OTHER INFORMATION: Synthetic sequence

<400> SEQUENCE: 120

Glu Ile Ala Gln Asp Phe Lys Thr Asp Leu Arg
1               5                   10

<210> SEQ ID NO 121
<211> LENGTH: 11
<212> TYPE: PRT
<213> ORGANISM: Artificial sequence
<220> FEATURE:
<223> OTHER INFORMATION: Synthetic sequence

<400> SEQUENCE: 121

Glu Ile Ala Gln Asp Phe Lys Thr Asp Leu Arg
1               5                   10

<210> SEQ ID NO 122
<211> LENGTH: 21
<212> TYPE: PRT
<213> ORGANISM: Artificial sequence
<220> FEATURE:
<223> OTHER INFORMATION: Synthetic sequence

<400> SEQUENCE: 122

Arg Leu Val Arg Glu Ile Ala Gln Asp Phe Lys Thr Asp Leu Arg Phe
1               5                   10                  15

Gln Ser Ser Ala Val
            20

<210> SEQ ID NO 123
<211> LENGTH: 21
<212> TYPE: PRT
<213> ORGANISM: Artificial sequence
<220> FEATURE:
<223> OTHER INFORMATION: Synthetic sequence

<400> SEQUENCE: 123

Arg Leu Val Arg Glu Ile Ala Gln Asp Phe Lys Thr Asp Leu Arg Phe
1               5                   10                  15

Gln Ser Ser Ala Val
            20

```
<210> SEQ ID NO 124
<211> LENGTH: 21
<212> TYPE: PRT
<213> ORGANISM: Artificial sequence
<220> FEATURE:
<223> OTHER INFORMATION: Synthetic sequence

<400> SEQUENCE: 124

Arg Leu Val Arg Glu Ile Ala Gln Asp Phe Lys Thr Asp Leu Arg Phe
1               5                   10                  15

Gln Ser Ser Ala Val
            20

<210> SEQ ID NO 125
<211> LENGTH: 21
<212> TYPE: PRT
<213> ORGANISM: Artificial sequence
<220> FEATURE:
<223> OTHER INFORMATION: Synthetic sequence

<400> SEQUENCE: 125

Arg Leu Val Arg Glu Ile Ala Gln Asp Phe Lys Thr Asp Leu Arg Phe
1               5                   10                  15

Gln Ser Ser Ala Val
            20

<210> SEQ ID NO 126
<211> LENGTH: 21
<212> TYPE: PRT
<213> ORGANISM: Artificial sequence
<220> FEATURE:
<223> OTHER INFORMATION: Synthetic sequence

<400> SEQUENCE: 126

Lys Arg Val Thr Ile Met Pro Lys Asp Ile Gln Leu Ala Arg Arg Ile
1               5                   10                  15

Arg Gly Glu Arg Ala
            20

<210> SEQ ID NO 127
<211> LENGTH: 136
<212> TYPE: PRT
<213> ORGANISM: Artificial sequence
<220> FEATURE:
<223> OTHER INFORMATION: Synthetic sequence

<400> SEQUENCE: 127

Met Ala Arg Thr Lys Gln Thr Ala Arg Lys Ser Thr Gly Gly Lys Ala
1               5                   10                  15

Pro Arg Lys Gln Leu Ala Thr Lys Val Ala Arg Lys Ser Ala Pro Ala
                20                  25                  30

Thr Gly Gly Val Lys Lys Pro His Arg Tyr Arg Pro Gly Thr Val Ala
            35                  40                  45

Leu Arg Glu Ile Arg Arg Tyr Gln Lys Ser Thr Glu Leu Leu Ile Arg
        50                  55                  60

Lys Leu Pro Phe Gln Arg Leu Met Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ser Tyr Leu Val Gly Leu Phe Glu Asp Thr Asn Leu Cys Val
            100                 105                 110

Ile His Ala Lys Arg Val Thr Ile Met Pro Lys Asp Ile Gln Leu Ala
```

Arg Arg Ile Arg Gly Glu Arg Ala
        130             135

<210> SEQ ID NO 128
<211> LENGTH: 7
<212> TYPE: PRT
<213> ORGANISM: Artificial sequence
<220> FEATURE:
<223> OTHER INFORMATION: Synthetic sequence

<400> SEQUENCE: 128

Ser Gly Arg Gly Lys Gly Gly
1               5

<210> SEQ ID NO 129
<211> LENGTH: 12
<212> TYPE: PRT
<213> ORGANISM: Artificial sequence
<220> FEATURE:
<223> OTHER INFORMATION: Synthetic sequence

<400> SEQUENCE: 129

Arg Gly Lys Gly Gly Lys Gly Leu Gly Lys Gly Ala
1               5                   10

<210> SEQ ID NO 130
<211> LENGTH: 21
<212> TYPE: PRT
<213> ORGANISM: Artificial sequence
<220> FEATURE:
<223> OTHER INFORMATION: Synthetic sequence

<400> SEQUENCE: 130

Ser Gly Arg Gly Lys Gly Gly Lys Gly Leu Gly Lys Gly Ala Lys
1               5                   10                  15

Arg His Arg Lys Val
            20

<210> SEQ ID NO 131
<211> LENGTH: 20
<212> TYPE: PRT
<213> ORGANISM: Artificial sequence
<220> FEATURE:
<223> OTHER INFORMATION: Synthetic sequence

<400> SEQUENCE: 131

Lys Gly Leu Gly Lys Gly Gly Ala Lys Arg His Arg Lys Val Leu Arg
1               5                   10                  15

Asp Asn Trp Cys
            20

<210> SEQ ID NO 132
<211> LENGTH: 30
<212> TYPE: PRT
<213> ORGANISM: Artificial sequence
<220> FEATURE:
<223> OTHER INFORMATION: Synthetic sequence

<400> SEQUENCE: 132

Ser Gly Arg Gly Lys Gly Gly Lys Gly Leu Gly Lys Gly Ala Lys
1               5                   10                  15

Arg His Arg Lys Val Leu Arg Asp Asn Gly Ser Gly Ser Lys
            20                  25                  30

<210> SEQ ID NO 133
<211> LENGTH: 20
<212> TYPE: PRT
<213> ORGANISM: Artificial sequence
<220> FEATURE:
<223> OTHER INFORMATION: Synthetic sequence

<400> SEQUENCE: 133

Ser Gly Arg Gly Lys Gly Gly Lys Gly Leu Gly Lys Gly Gly Ala Lys
1               5                   10                  15

Arg His Arg Lys
            20

<210> SEQ ID NO 134
<211> LENGTH: 20
<212> TYPE: PRT
<213> ORGANISM: Artificial sequence
<220> FEATURE:
<223> OTHER INFORMATION: Synthetic sequence

<400> SEQUENCE: 134

Ser Gly Arg Gly Lys Gly Gly Lys Gly Leu Gly Lys Gly Gly Ala Lys
1               5                   10                  15

Arg His Arg Lys
            20

<210> SEQ ID NO 135
<211> LENGTH: 20
<212> TYPE: PRT
<213> ORGANISM: Artificial sequence
<220> FEATURE:
<223> OTHER INFORMATION: Synthetic sequence

<400> SEQUENCE: 135

Ser Gly Arg Gly Lys Gly Gly Lys Gly Leu Gly Lys Gly Gly Ala Lys
1               5                   10                  15

Arg His Arg Lys
            20

<210> SEQ ID NO 136
<211> LENGTH: 20
<212> TYPE: PRT
<213> ORGANISM: Artificial sequence
<220> FEATURE:
<223> OTHER INFORMATION: Synthetic sequence

<400> SEQUENCE: 136

Ser Gly Arg Gly Lys Gly Gly Lys Gly Leu Gly Lys Gly Gly Ala Lys
1               5                   10                  15

Arg His Arg Lys
            20

<210> SEQ ID NO 137
<211> LENGTH: 20
<212> TYPE: PRT
<213> ORGANISM: Artificial sequence
<220> FEATURE:
<223> OTHER INFORMATION: Synthetic sequence

<400> SEQUENCE: 137

Ser Gly Arg Gly Lys Gly Gly Lys Gly Leu Gly Lys Gly Gly Ala Lys
1               5                   10                  15

Arg His Arg Lys
            20

```
<210> SEQ ID NO 138
<211> LENGTH: 20
<212> TYPE: PRT
<213> ORGANISM: Artificial sequence
<220> FEATURE:
<223> OTHER INFORMATION: Synthetic sequence

<400> SEQUENCE: 138

Lys Gly Leu Gly Lys Gly Gly Ala Lys Arg His Arg Lys Val Leu Arg
1               5                   10                  15

Asp Asn Trp Cys
            20

<210> SEQ ID NO 139
<211> LENGTH: 103
<212> TYPE: PRT
<213> ORGANISM: Artificial sequence
<220> FEATURE:
<223> OTHER INFORMATION: Synthetic sequence

<400> SEQUENCE: 139

Met Ser Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys
            20                  25                  30

Pro Ala Ile Arg Arg Leu Ala Arg Gly Gly Val Lys Arg Ile Ser
        35                  40                  45

Gly Leu Ile Tyr Glu Glu Thr Arg Gly Val Leu Lys Val Phe Leu Glu
    50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100

<210> SEQ ID NO 140
<211> LENGTH: 10
<212> TYPE: PRT
<213> ORGANISM: Artificial sequence
<220> FEATURE:
<223> OTHER INFORMATION: Synthetic sequence

<400> SEQUENCE: 140

Cys Lys Ala Thr Gln Ala Ser Gln Glu Tyr
1               5                   10

<210> SEQ ID NO 141
<211> LENGTH: 22
<212> TYPE: PRT
<213> ORGANISM: Artificial sequence
<220> FEATURE:
<223> OTHER INFORMATION: Synthetic sequence

<400> SEQUENCE: 141

Ala Arg Thr Lys Gln Thr Ala Arg Lys Ser Thr Gly Gly Lys Ala Pro
1               5                   10                  15

Arg Lys Gln Leu Ala Cys
            20

<210> SEQ ID NO 142
```

```
<211> LENGTH: 20
<212> TYPE: PRT
<213> ORGANISM: Artificial sequence
<220> FEATURE:
<223> OTHER INFORMATION: Synthetic sequence

<400> SEQUENCE: 142

Ala Arg Thr Lys Gln Thr Ala Arg Lys Ser Thr Gly Gly Lys Ala Pro
1               5                   10                  15

Arg Lys Trp Cys
            20

<210> SEQ ID NO 143
<211> LENGTH: 13
<212> TYPE: PRT
<213> ORGANISM: Artificial sequence
<220> FEATURE:
<223> OTHER INFORMATION: Synthetic sequence

<400> SEQUENCE: 143

Lys Ala Ala Arg Lys Ser Ala Pro Ala Thr Gly Gly Cys
1               5                   10

<210> SEQ ID NO 144
<211> LENGTH: 20
<212> TYPE: PRT
<213> ORGANISM: Artificial sequence
<220> FEATURE:
<223> OTHER INFORMATION: Synthetic sequence

<400> SEQUENCE: 144

Lys Gly Leu Gly Lys Gly Gly Ala Lys Arg His Arg Lys Val Leu Arg
1               5                   10                  15

Asp Asn Trp Cys
            20

<210> SEQ ID NO 145
<211> LENGTH: 136
<212> TYPE: PRT
<213> ORGANISM: Artificial sequence
<220> FEATURE:
<223> OTHER INFORMATION: Synthetic sequence

<400> SEQUENCE: 145

Met Ala Arg Thr Lys Gln Thr Ala Arg Lys Ser Thr Gly Gly Lys Ala
1               5                   10                  15

Pro Arg Lys Gln Leu Ala Thr Lys Val Ala Arg Lys Ser Ala Pro Ala
                20                  25                  30

Thr Gly Gly Val Lys Lys Pro His Arg Tyr Arg Pro Gly Thr Val Ala
            35                  40                  45

Leu Arg Glu Ile Arg Arg Tyr Gln Lys Ser Thr Glu Leu Leu Ile Arg
        50                  55                  60

Lys Leu Pro Phe Gln Arg Leu Met Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ser Tyr Leu Val Gly Leu Phe Glu Asp Thr Asn Leu Cys Val
                100                 105                 110

Ile His Ala Lys Arg Val Thr Ile Met Pro Lys Asp Ile Gln Leu Ala
            115                 120                 125

Arg Arg Ile Arg Gly Glu Arg Ala
        130                 135
```

```
<210> SEQ ID NO 146
<211> LENGTH: 10
<212> TYPE: PRT
<213> ORGANISM: Artificial sequence
<220> FEATURE:
<223> OTHER INFORMATION: Synthetic sequence

<400> SEQUENCE: 146

Gly Gly Gly Gly Ser Gly Gly Gly Gly Ser
1               5                   10

<210> SEQ ID NO 147
<211> LENGTH: 10
<212> TYPE: PRT
<213> ORGANISM: Artificial sequence
<220> FEATURE:
<223> OTHER INFORMATION: Synthetic sequence

<400> SEQUENCE: 147

Arg Arg Arg Arg Arg Arg Arg Arg Arg Arg
1               5                   10

<210> SEQ ID NO 148
<211> LENGTH: 28
<212> TYPE: PRT
<213> ORGANISM: Artificial sequence
<220> FEATURE:
<223> OTHER INFORMATION: Synthetic sequence

<400> SEQUENCE: 148

Ser Asn Arg Trp Leu Asp Val Lys Gly Gly Gly Gly Ser Gly Gly
1               5                   10                  15

Gly Gly Ser Arg Arg Arg Arg Arg Arg Arg Arg Arg
            20                  25

<210> SEQ ID NO 149
<211> LENGTH: 32
<212> TYPE: PRT
<213> ORGANISM: Artificial sequence
<220> FEATURE:
<223> OTHER INFORMATION: Synthetic sequence

<400> SEQUENCE: 149

Arg Arg Arg Arg Arg Arg Arg Arg Arg Gly Gly Gly Gly Ser Gly
1               5                   10                  15

Gly Gly Gly Ser Val Val Leu Lys Tyr Glu Lys Asp Ala Phe Lys Arg
            20                  25                  30

<210> SEQ ID NO 150
<211> LENGTH: 32
<212> TYPE: PRT
<213> ORGANISM: Artificial sequence
<220> FEATURE:
<223> OTHER INFORMATION: Synthetic sequence

<400> SEQUENCE: 150

Val Val Leu Lys Tyr Glu Lys Asp Ala Phe Lys Arg Gly Gly Gly Gly
1               5                   10                  15

Gly Ser Gly Gly Gly Gly Ser Arg Arg Arg Arg Arg Arg Arg Arg Arg
            20                  25                  30

<210> SEQ ID NO 151
<211> LENGTH: 26
<212> TYPE: PRT
```

```
<213> ORGANISM: Artificial sequence
<220> FEATURE:
<223> OTHER INFORMATION: Synthetic sequence

<400> SEQUENCE: 151

Arg Arg Arg Arg Arg Arg Arg Arg Arg Gly Gly Gly Gly Ser Gly Gly
1               5                   10                  15

Gly Gly Ser Glu Asn Leu Val Leu Asn Glu
            20                  25

<210> SEQ ID NO 152
<211> LENGTH: 26
<212> TYPE: PRT
<213> ORGANISM: Artificial sequence
<220> FEATURE:
<223> OTHER INFORMATION: Synthetic sequence

<400> SEQUENCE: 152

Glu Asn Leu Val Leu Asn Glu Gly Gly Gly Gly Ser Gly Gly Gly Gly
1               5                   10                  15

Ser Arg Arg Arg Arg Arg Arg Arg Arg Arg
            20                  25

<210> SEQ ID NO 153
<211> LENGTH: 29
<212> TYPE: PRT
<213> ORGANISM: Artificial sequence
<220> FEATURE:
<223> OTHER INFORMATION: Synthetic sequence

<400> SEQUENCE: 153

Arg Arg Arg Arg Arg Arg Arg Arg Arg Gly Gly Gly Gly Ser Gly Gly
1               5                   10                  15

Gly Gly Ser Pro Thr Gly Met Ile Arg Ile His Gln Met
            20                  25

<210> SEQ ID NO 154
<211> LENGTH: 25
<212> TYPE: PRT
<213> ORGANISM: Artificial sequence
<220> FEATURE:
<223> OTHER INFORMATION: Synthetic sequence

<400> SEQUENCE: 154

Arg Arg Arg Arg Arg Arg Arg Arg Arg Gly Gly Gly Gly Gly Ser Gly
1               5                   10                  15

Gly Gly Ser Ala Ala Gln Glu Glu
            20                  25

<210> SEQ ID NO 155
<211> LENGTH: 33
<212> TYPE: PRT
<213> ORGANISM: Artificial sequence
<220> FEATURE:
<223> OTHER INFORMATION: Synthetic sequence

<400> SEQUENCE: 155

Arg Arg Arg Arg Arg Arg Arg Arg Arg Gly Gly Gly Gly Ser Gly Gly
1               5                   10                  15

Gly Gly Ser Thr Ser Val Gly Lys Tyr Pro Asn Thr Gly Tyr Tyr Gly
            20                  25                  30

Asp
```

```
<210> SEQ ID NO 156
<211> LENGTH: 33
<212> TYPE: PRT
<213> ORGANISM: Artificial sequence
<220> FEATURE:
<223> OTHER INFORMATION: Synthetic sequence

<400> SEQUENCE: 156

Thr Ser Val Gly Lys Tyr Pro Asn Thr Gly Tyr Tyr Gly Asp Gly Gly
1               5                   10                  15

Gly Gly Ser Gly Gly Gly Ser Arg Arg Arg Arg Arg Arg Arg
            20                  25                  30

Arg

<210> SEQ ID NO 157
<211> LENGTH: 32
<212> TYPE: PRT
<213> ORGANISM: Artificial sequence
<220> FEATURE:
<223> OTHER INFORMATION: Synthetic sequence

<400> SEQUENCE: 157

Arg Arg Arg Arg Arg Arg Arg Arg Gly Gly Gly Gly Ser Gly Gly
1               5                   10                  15

Gly Gly Ser Asn Pro Lys Leu Thr Arg Met Leu Thr Phe Lys Phe Tyr
            20                  25                  30

<210> SEQ ID NO 158
<211> LENGTH: 32
<212> TYPE: PRT
<213> ORGANISM: Artificial sequence
<220> FEATURE:
<223> OTHER INFORMATION: Synthetic sequence

<400> SEQUENCE: 158

Asn Pro Lys Leu Thr Arg Met Leu Thr Phe Lys Phe Tyr Gly Gly Gly
1               5                   10                  15

Gly Ser Gly Gly Gly Ser Arg Arg Arg Arg Arg Arg Arg Arg
            20                  25                  30

<210> SEQ ID NO 159
<211> LENGTH: 10
<212> TYPE: PRT
<213> ORGANISM: Artificial sequence
<220> FEATURE:
<223> OTHER INFORMATION: Synthetic sequence

<400> SEQUENCE: 159

Lys Lys Lys Lys Lys Lys Lys Lys Lys Lys
1               5                   10

<210> SEQ ID NO 160
<211> LENGTH: 40
<212> TYPE: PRT
<213> ORGANISM: Artificial sequence
<220> FEATURE:
<223> OTHER INFORMATION: Synthetic sequence

<400> SEQUENCE: 160

Arg Arg Arg Arg Arg Arg Arg Arg Arg Gly Gly Gly Gly Ser Gly Gly
1               5                   10                  15

Gly Gly Ser Met Ile Ala Ser Gln Phe Leu Ser Ala Leu Thr Leu Val
            20                  25                  30

Leu Leu Ile Lys Glu Ser Gly Ala
```

35                  40

<210> SEQ ID NO 161
<211> LENGTH: 40
<212> TYPE: PRT
<213> ORGANISM: Artificial sequence
<220> FEATURE:
<223> OTHER INFORMATION: Synthetic sequence

<400> SEQUENCE: 161

Met Ile Ala Ser Gln Phe Leu Ser Ala Leu Thr Leu Val Leu Leu Ile
1               5                   10                  15

Lys Glu Ser Gly Ala Gly Gly Gly Ser Gly Gly Gly Gly Ser Arg
            20                  25                  30

Arg Arg Arg Arg Arg Arg Arg
        35                  40

<210> SEQ ID NO 162
<211> LENGTH: 33
<212> TYPE: PRT
<213> ORGANISM: Artificial sequence
<220> FEATURE:
<223> OTHER INFORMATION: Synthetic sequence

<400> SEQUENCE: 162

Arg Arg Arg Arg Arg Arg Arg Arg Gly Gly Gly Ser Gly Gly
1               5                   10                  15

Gly Gly Ser Glu Lys Phe Ile Leu Lys Val Arg Pro Ala Phe Lys Ala
            20                  25                  30

Val

<210> SEQ ID NO 163
<211> LENGTH: 24
<212> TYPE: PRT
<213> ORGANISM: Artificial sequence
<220> FEATURE:
<223> OTHER INFORMATION: Synthetic sequence

<400> SEQUENCE: 163

Arg Arg Arg Arg Arg Arg Thr Tyr Ser Cys His Phe Gly Pro Leu Thr
1               5                   10                  15

Trp Val Cys Lys Pro Gln Gly Gly
            20

<210> SEQ ID NO 164
<211> LENGTH: 24
<212> TYPE: PRT
<213> ORGANISM: Artificial sequence
<220> FEATURE:
<223> OTHER INFORMATION: Synthetic sequence

<400> SEQUENCE: 164

Thr Tyr Ser Cys His Phe Gly Pro Leu Thr Trp Val Cys Lys Pro Gln
1               5                   10                  15

Gly Gly Arg Arg Arg Arg Arg Arg
            20

<210> SEQ ID NO 165
<211> LENGTH: 18
<212> TYPE: PRT
<213> ORGANISM: Artificial sequence
<220> FEATURE:
<223> OTHER INFORMATION: Synthetic sequence

```
<400> SEQUENCE: 165

Arg Arg Arg Arg Arg Arg Thr His Arg Pro Pro Met Trp Ser Pro Val
1               5                   10                  15

Trp Pro

<210> SEQ ID NO 166
<211> LENGTH: 18
<212> TYPE: PRT
<213> ORGANISM: Artificial sequence
<220> FEATURE:
<223> OTHER INFORMATION: Synthetic sequence

<400> SEQUENCE: 166

Thr His Arg Pro Pro Met Trp Ser Pro Val Trp Pro Arg Arg Arg Arg
1               5                   10                  15

Arg Arg

<210> SEQ ID NO 167
<211> LENGTH: 21
<212> TYPE: PRT
<213> ORGANISM: Artificial sequence
<220> FEATURE:
<223> OTHER INFORMATION: Synthetic sequence

<400> SEQUENCE: 167

Ala Arg Thr Lys Gln Thr Ala Arg Lys Ser Thr Gly Gly Lys Ala Pro
1               5                   10                  15

Arg Lys Gln Leu Ala
            20

<210> SEQ ID NO 168
<211> LENGTH: 20
<212> TYPE: PRT
<213> ORGANISM: Artificial sequence
<220> FEATURE:
<223> OTHER INFORMATION: Synthetic sequence

<400> SEQUENCE: 168

Ser Gly Arg Gly Lys Gly Gly Lys Gly Leu Gly Lys Gly Gly Ala Lys
1               5                   10                  15

Arg His Arg Lys
            20

<210> SEQ ID NO 169
<211> LENGTH: 20
<212> TYPE: PRT
<213> ORGANISM: Artificial sequence
<220> FEATURE:
<223> OTHER INFORMATION: Synthetic sequence

<400> SEQUENCE: 169

Ser Gly Arg Gly Lys Gln Gly Gly Lys Ala Arg Ala Lys Ala Lys Thr
1               5                   10                  15

Arg Ser Ser Arg
            20

<210> SEQ ID NO 170
<211> LENGTH: 43
<212> TYPE: PRT
<213> ORGANISM: Artificial sequence
<220> FEATURE:
<223> OTHER INFORMATION: Synthetic sequence

<400> SEQUENCE: 170
```

-continued

```
Ser Asn Tyr Ser Ala Ala Asp Lys Ala Ala Asn Ala Ala Asp Asp Ala
1               5                   10                  15

Ala Glu Ala Ala Lys Glu Asn Ser Gly Gly Gly Gly Ser Gly Gly Gly
            20                  25                  30

Gly Ser Arg Arg Arg Arg Arg Arg Arg Arg Arg
        35                  40

<210> SEQ ID NO 171
<211> LENGTH: 33
<212> TYPE: PRT
<213> ORGANISM: Artificial sequence
<220> FEATURE:
<223> OTHER INFORMATION: Synthetic sequence

<400> SEQUENCE: 171

Arg Arg Arg Arg Arg Arg Arg Arg Arg Gly Gly Gly Gly Ser Gly Gly
1               5                   10                  15

Gly Gly Ser Glu Lys Phe Ile Leu Lys Val Arg Pro Ala Phe Lys Ala
            20                  25                  30

Val
```

What is claimed is:

1. A delivery molecule, comprising:

a targeting ligand comprising amino acid SEQ ID NO: 171 that specifically binds to cKit, the targeting ligand:

conjugated to a protein payload, a nucleic acid payload, and/or a charged polymer polypeptide domain, and configured to engage the long endosomal recycling pathway upon binding of the targeting ligand to a cell surface protein and subsequent endocytosis of the delivery molecule.

2. The delivery molecule of claim 1, wherein the targeting ligand is conjugated to a nucleic acid payload, and wherein the nucleic acid payload is an RNAi agent; optionally, wherein the RNAi agent is an siRNA molecule.

3. The delivery molecule of claim 1, wherein the targeting ligand is conjugated to the protein payload, nucleic acid payload, and/or charged polymer polypeptide domain via a linker.

4. The delivery molecule of claim 3, wherein the linker comprises the amino acid sequence SEQ ID NO:17.

5. The delivery molecule of claim 1, wherein the charged polymer polypeptide domain is selected from the group consisting of poly-arginine and poly-histidine.

* * * * *